United States Patent
Yeung et al.

(10) Patent No.: US 11,161,837 B2
(45) Date of Patent: Nov. 2, 2021

(54) BENZOFURAN DERIVATIVES FOR THE TREATMENT OF HEPATITIS C

(71) Applicant: BRISTOL-MYERS SQUIBB COMPANY, Princeton, NJ (US)

(72) Inventors: Kap-Sun Yeung, Madison, CT (US); John F. Kadow, Wallingford, CT (US); Rajesh Onkardas Bora, Bangalore (IN); Prakash Anjanappa, Bangalore (IN); Kumaravel Selvakumar, Bangalore (IN); Samayamunthula Venkata Satya Arun Kumar Gupta, Bangalore (IN)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 370 days.

(21) Appl. No.: 16/083,972

(22) PCT Filed: Mar. 17, 2017

(86) PCT No.: PCT/US2017/023045
§ 371 (c)(1),
(2) Date: Sep. 11, 2018

(87) PCT Pub. No.: WO2017/165233
PCT Pub. Date: Sep. 28, 2017

(65) Prior Publication Data
US 2020/0291002 A1  Sep. 17, 2020

Related U.S. Application Data

(60) Provisional application No. 62/311,026, filed on Mar. 21, 2016.

(51) Int. Cl.
| | | |
|---|---|---|
| C07D 405/12 | (2006.01) | |
| C07D 307/84 | (2006.01) | |
| C07D 413/12 | (2006.01) | |
| A61K 31/343 | (2006.01) | |
| A61K 31/4245 | (2006.01) | |
| A61K 31/506 | (2006.01) | |
| A61P 31/00 | (2006.01) | |
| A61P 31/14 | (2006.01) | |

(52) U.S. Cl.
CPC ............ C07D 405/12 (2013.01); A61P 31/00 (2018.01); A61P 31/14 (2018.01); C07D 307/84 (2013.01); C07D 413/12 (2013.01)

(58) Field of Classification Search
CPC .. C07D 307/84; C07D 405/12; C07D 413/12; A61P 31/14
See application file for complete search history.

(56) References Cited

U.S. PATENT DOCUMENTS

| | | | |
|---|---|---|---|
| 7,994,171 B2 | 8/2011 | Yeung et al. | |
| 8,048,887 B2 | 11/2011 | Yeung et al. | |
| 10,125,111 B2 | 11/2018 | Wang et al. | |
| 2018/0030019 A1 | 2/2018 | Wang et al. | |

FOREIGN PATENT DOCUMENTS

| | | | | |
|---|---|---|---|---|
| WO | WO 2010/030592 | * | 3/2010 | ........... C07D 307/84 |
| WO | 2011/112191 A1 | | 9/2011 | |
| WO | 2016/133948 A1 | | 8/2016 | |
| WO | 2016/133972 A1 | | 8/2016 | |

OTHER PUBLICATIONS

International Preliminary Report on Patentability received for PCT International Application No. PCT/US17/23045, dated Oct. 4, 2018, 8 Pages.
International Search Report received for PCT Patent International Application No. PCT/US17/23045., dated Apr. 28, 2017, 10 Pages.

* cited by examiner

*Primary Examiner* — Alicia L Otton
(74) *Attorney, Agent, or Firm* — Mintz Levin Cohn Ferris Glovsky and Popeo, P.C.

(57) ABSTRACT

The disclosure provides compounds of formula (I), including their salts, as well as compositions and methods of using the compounds. The compounds have activity against hepatitis C virus (HCV) and may be useful in treating those infected with HCV.

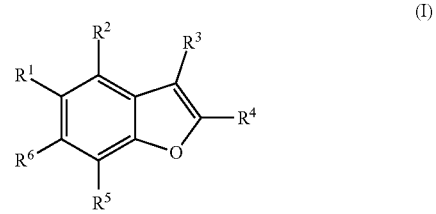

(I)

13 Claims, No Drawings

BENZOFURAN DERIVATIVES FOR THE TREATMENT OF HEPATITIS C

CROSS REFERENCE TO RELATED APPLICATION

This application claims priority to U.S. Provisional Patent Application Ser. No. 62/311,026, filed Mar. 21, 2016, which is incorporated by reference in its entirety.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

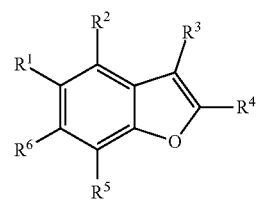

where:

$R^1$ is phenyl or pyridinyl and is substituted with 0-3 substituents selected from the group consisting of halo, alkyl, cycloalkyl, haloalkyl, alkoxy, or haloalkoxy, and wherein the phenyl or pyridinyl is also substituted with 1 CON($R^9$)($R^{10}$) substituent;

$R^2$ is hydrogen, halo, alkyl, or alkoxy;

$R^3$ is CON($R^7$)($R^8$);

$R^4$ is phenyl that is independently substituted with 0-2 halo, alkyl, or alkoxy or is para substituted with X—$Ar^1$;

$R^5$ is hydrogen, nitro, halo, alkyl, or alkoxy;

$R^6$ is hydrogen, alkyl, haloalkyl, alkoxy, haloalkoxy, or N($R^{14}$)($R^{15}$);

$R^7$ is alkyl;

$R^8$ is hydrogen;

$R^9$ is

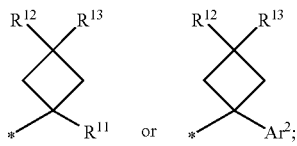

$R^{10}$ is hydrogen;
$R^{11}$ is alkyl;
$R^{12}$ and $R^{13}$ are independently hydrogen, halo, hydroxy, alkoxy, or haloalkoxy, or taken together are carbonyl;
$R^{14}$ is hydrogen, alkyl, or haloalkyl;
$R^{15}$ is hydrogen, alkyl, haloalkyl, or alkylsulfonyl;
$Ar^1$ is phenyl or para-halophenyl;
$Ar^2$ is phenyl, pyridinyl, pyrazinyl, pyrimidinyl, pyrazolyl, isoxazolyl, isothiazolyl, imidazolyl, oxazolyl, thiazolyl, oxadiazolyl, thiadiazolyl, triazolyl, or tetrazolyl; and
X is —O— or —NH—;
or a pharmaceutically acceptable salt thereof.

Another aspect of the invention is a compound of formula I where $R^1$ is phenyl substituted with 0-3 substituents selected from the group consisting of halo, alkyl, cycloalkyl, haloalkyl, alkoxy, and haloalkoxy, and wherein the phenyl is also substituted with 1 $CON(R^9)(R^{10})$ substituent; $R^2$ is hydrogen or halo; $R^3$ is $CON(R^7)(R^8)$; $R^4$ is phenyl that is independently substituted with 0-1 halo; $R^5$ is hydrogen; $R^6$ is hydrogen, alkyl, haloalkyl, alkoxy, haloalkoxy, or $N(R^{14})(R^{15})$; $R^7$ is alkyl; $R^8$ is hydrogen; $R^9$ is

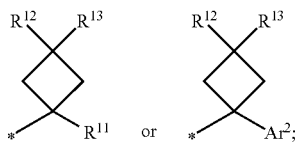

$R^{10}$ is hydrogen; $R^{11}$ is alkyl; $R^{12}$ and $R^{13}$ are independently hydrogen, halo, hydroxy, alkoxy, or haloalkoxy, or taken together are carbonyl; $R^{14}$ is alkyl, or haloalkyl; $R^{15}$ is hydrogen or alkylsulfonyl; and $Ar^2$ is pyrimidinyl or oxadiazolyl; or a pharmaceutically acceptable salt thereof.

Another aspect of the invention is a compound of formula I where $R^1$ is phenyl substituted with 0-3 substituents selected from the group consisting of halo, alkyl, and alkoxy, and wherein the phenyl is also substituted with 1 $CON(R^9)(R^{10})$ substituent; $R^2$ is hydrogen or fluoro; $R^3$ is $CON(R^7)(R^8)$; $R^4$ is phenyl that is independently substituted with 0-1 fluoro; $R^5$ is hydrogen; $R^6$ is hydrogen, alkyl, haloalkyl, alkoxy, haloalkoxy, or $N(R^7)(R^8)$; $R^7$ is alkyl; $R^8$ is hydrogen; $R^9$ is

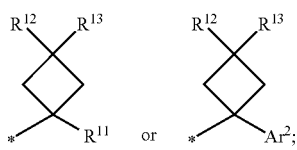

$R^{10}$ is hydrogen; $R^{11}$ is alkyl; $R^{12}$ and $R^{13}$ are independently hydrogen, halo, hydroxy, alkoxy, or haloalkoxy, or taken together are carbonyl; $R^{14}$ is alkyl, or haloalkyl; $R^{15}$ is hydrogen or alkylsulfonyl; and $Ar^2$ is pyrimidinyl or oxadiazolyl; or a pharmaceutically acceptable salt thereof.

Another aspect of the invention is a compound of formula I where $R^1$ is phenyl substituted with 0-3 substituents selected from the group consisting of halo, alkyl, and alkoxy, and wherein the phenyl is also substituted with 1 $CON(R^9)(R^{10})$ substituent.

Another aspect of the invention is a compound of formula I where $R^2$ is hydrogen or halo.

Another aspect of the invention is a compound of formula I where $R^3$ is $CON(R^7)(R^8)$; $R^7$ is methyl, and $R^8$ is hydrogen.

Another aspect of the invention is a compound of formula I where $R^9$ is

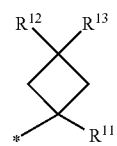

and $R^{11}$ is alkyl.

Another aspect of the invention is a compound of formula I where $R^9$ is

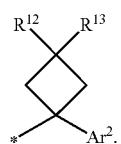

Another aspect of the invention is a compound of formula I where $R^{14}$ is haloalkyl and $R^{15}$ is hydrogen or where $R^{14}$ is alkyl and $R^{15}$ is alkylsulfonyl.

Another aspect of the invention is a compound of formula I where $Ar^2$ is pyrimidinyl or oxadiazolyl.

Another aspect of the invention is a compound of formula I where $Ar^1$ is phenyl or pyridinyl substituted with 1 $CON(R^4)(R^5)$ and also with 0-3 substituents selected from cyano, halo, alkyl, haloalkyl, alkoxy, and haloalkoxy.

Another aspect of the invention is a compound of formula I where $Ar^1$ is phenyl or pyridinyl substituted with 1 $CON(R^4)(R^5)$ and also with 0-3 substituents selected from cyano, halo, deuterated alkyl, and deuterated alkoxy.

Another aspect of the invention is a compound of formula I where $Ar^1$ is phenyl or pyridinyl substituted with 1 $CON(R^4)(R^5)$ and with 1 deuterated alkoxy substituent.

Another aspect of the invention is a compound of formula I where $Ar^2$ is pyrimidinyl, oxadiazolyl, thiadiazolyl, or imidazopyridinyl.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $Ar^1$ $Ar^2$, and X can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." Ethylene means ethanediyl or —CH$_2$CH$_2$—; propylene means propanediyl or —CH$_2$CH$_2$CH$_2$—; butylene means butanediyl or —CH$_2$CH$_2$CH$_2$CH$_2$—; pentylene means pentanediyl or —CH$_2$CH$_2$CH$_2$CH$_2$CH$_2$—. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucuronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixirs, and solutions. Compositions are made using common formulation techniques, and conventional excipients (such as binding and wetting agents) and vehicles (such as water and alcohols) are generally used for compositions. See, for example, Remington's Pharmaceutical Sciences, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |

TABLE 1-continued

| Brand Name | Physiological Class | Type of Inhibitor or Target | Source Company |
|---|---|---|---|
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immuno-modulator | immune modulator | Maxim Pharmaceuticals Inc., San Diego, CA |
| CellCept | Immuno-suppressant | HCV IgG immuno-suppressant | F. Hoffmann-La Roche LTD, Basel, Switzerland |
| Civacir | Immuno-suppressant | HCV IgG immuno-suppressant | Nabi Biopharmaceuticals Inc., Boca Raton, FL |
| Albuferon - α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/ α1-thymosin | Regene Rx Biopharma. Inc., Bethesda, MD/ SciClone Pharmaceuticals Inc, San Mateo, CA |
| Rebetron | Interferon | IFN-α2b/ ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead (formerly from Pharmasset) |
| PSI-7977 sofosbuvir | Antiviral | Nucleotide NS5B Polymerase Inhibitor | Gilead (formerly from Pharmasset) |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |
| asunaprevir | Antiviral | serine protease inhibitor | Bristol-Myers Squibb |
| BMS-791325 | Antiviral | NS5B Polymerase Inhibitor | Bristol-Myers Squibb |

TABLE 1-continued

| Brand Name | Physiological Class | Type of Inhibitor or Target | Source Company |
|---|---|---|---|
| daclatasvir | Antiviral | HCV NS5A replication complex inhibitor | Bristol-Myers Squibb |
| GS-5885 | Antiviral | HCV NS5A replication complex inhibitor | Gilead |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "hr" for hours; "rt" or "RT" for room temperature, and "Rt" for retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine; TEA for triethylamine; DCM for dichloromethane Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "hr" for hour or hours, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Scheme 1.

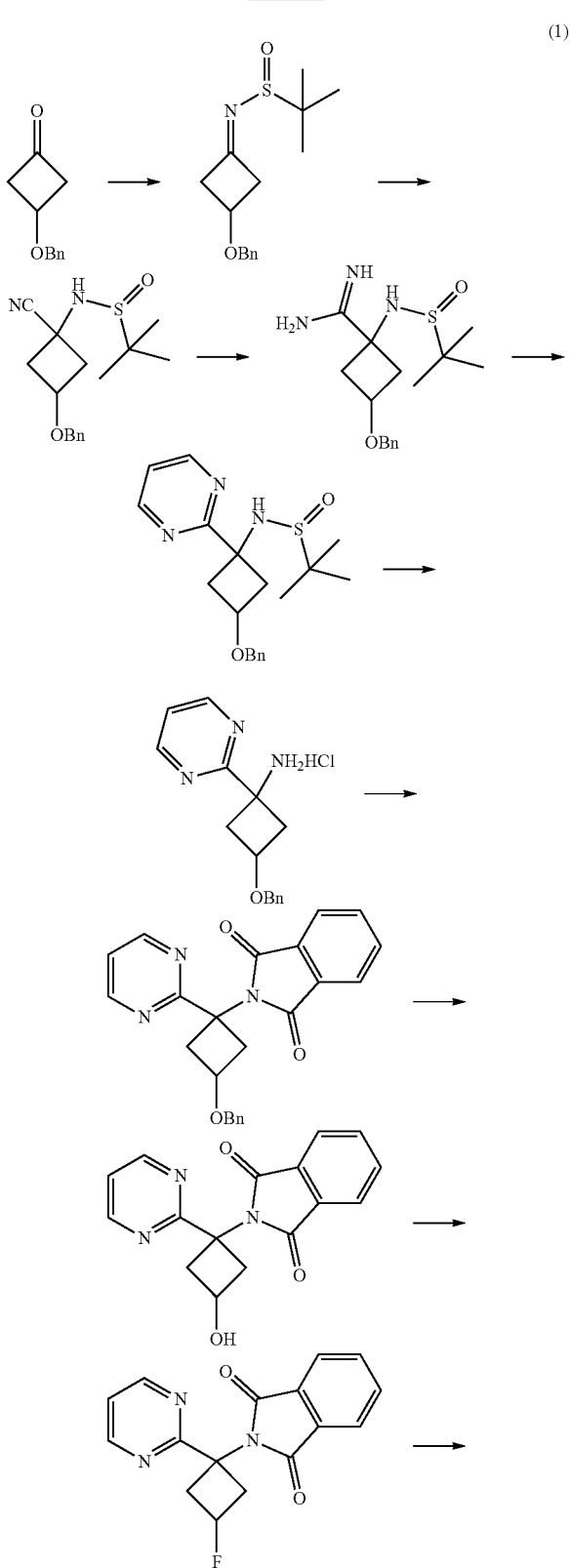

(1)

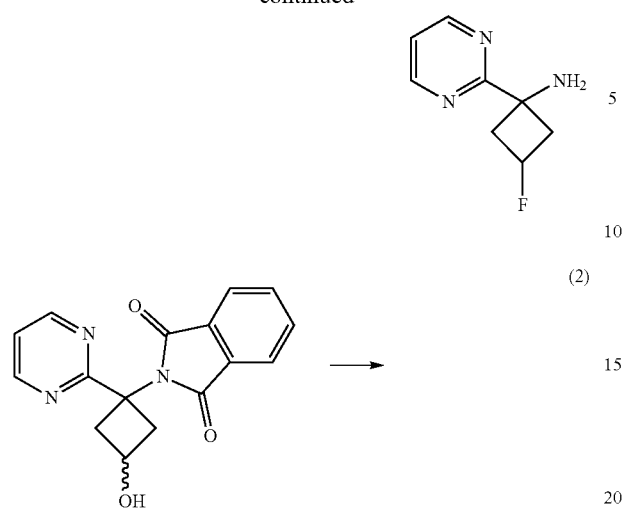
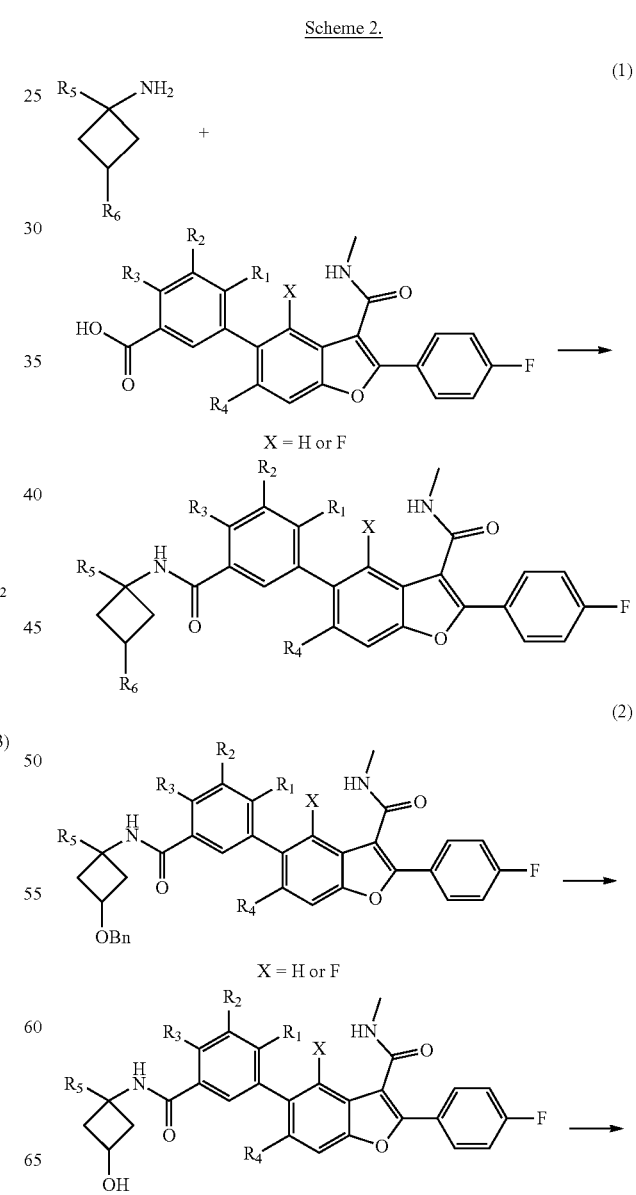
Scheme 2.

15
-continued
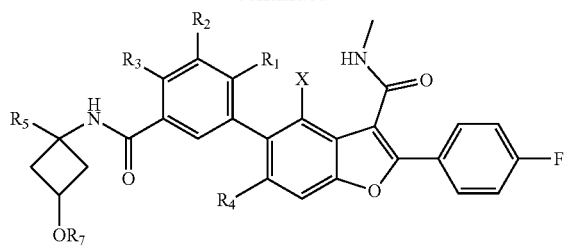
16
-continued
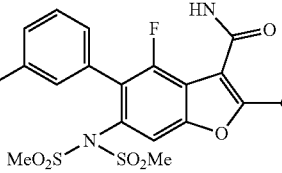
Scheme 3.
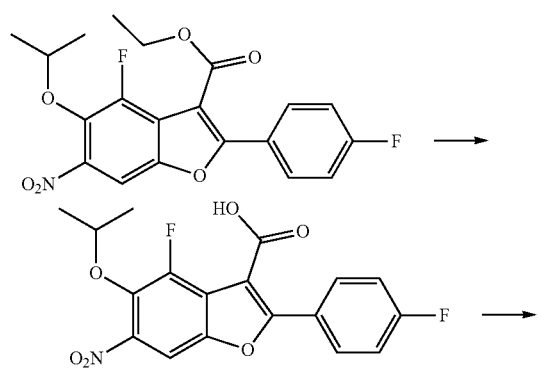
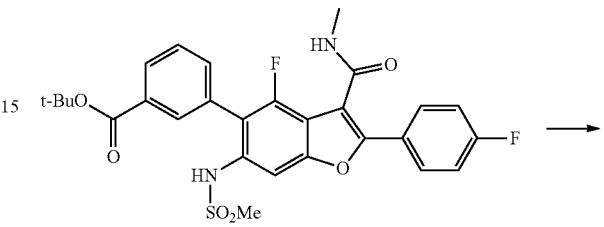
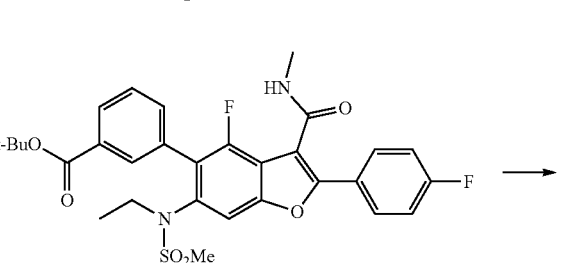
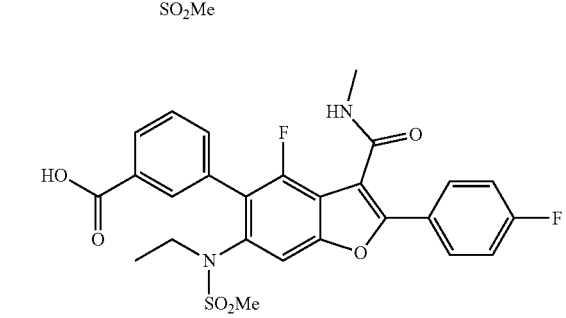
Scheme 4.
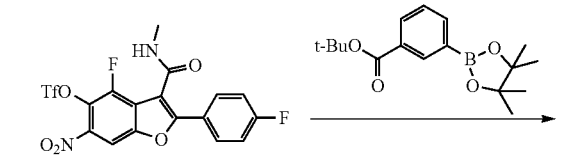
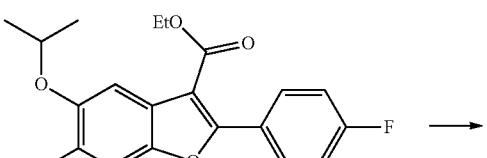
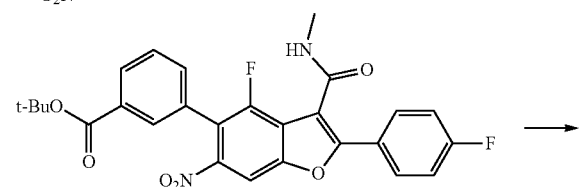
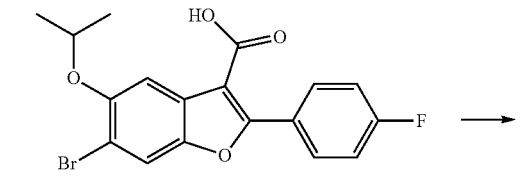
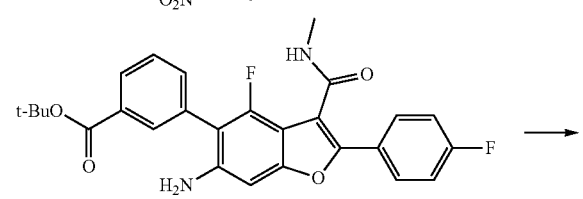
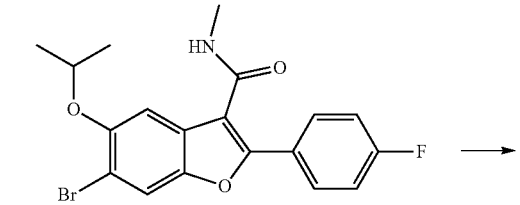

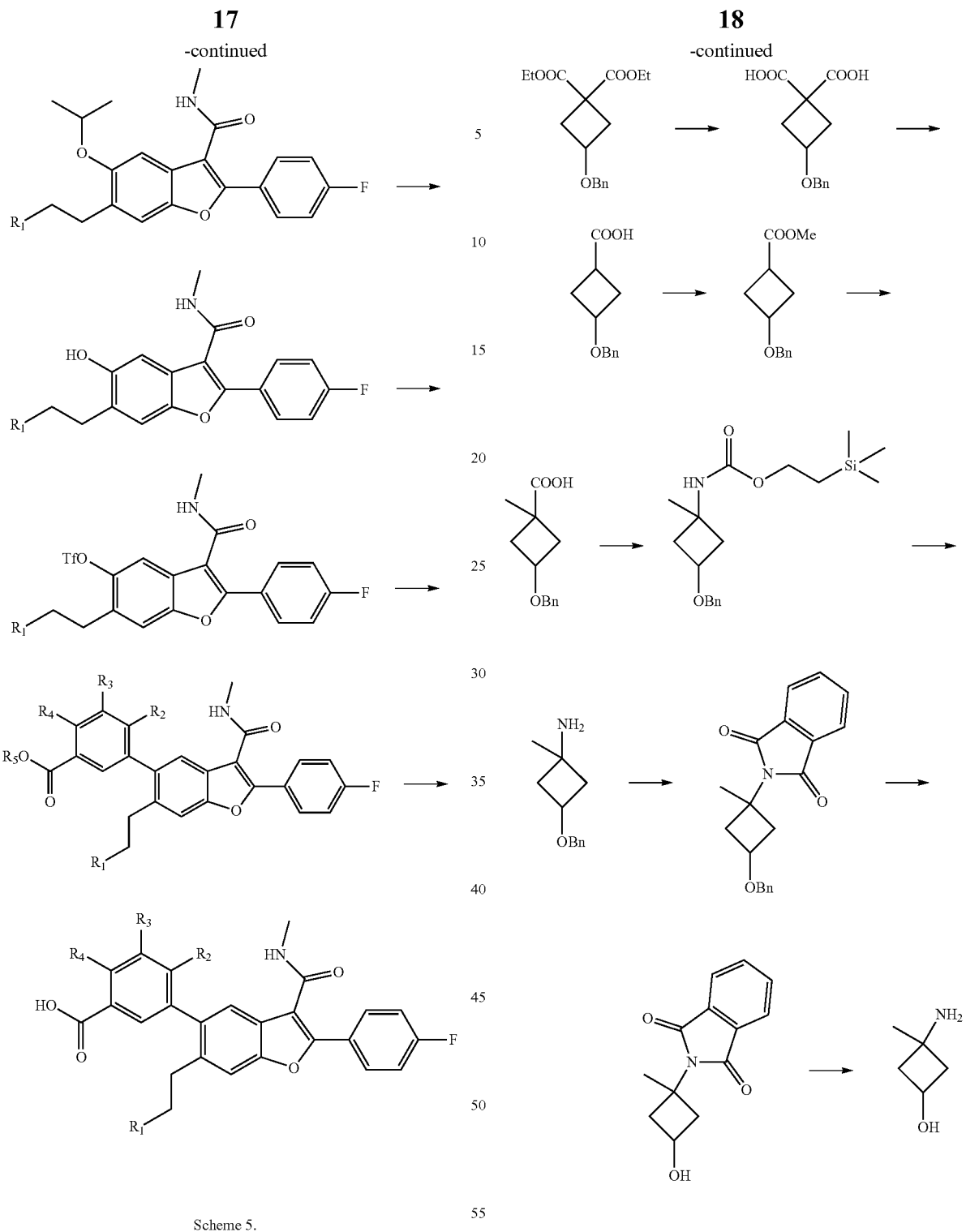
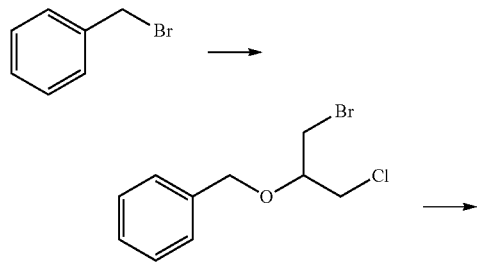
Scheme 5.
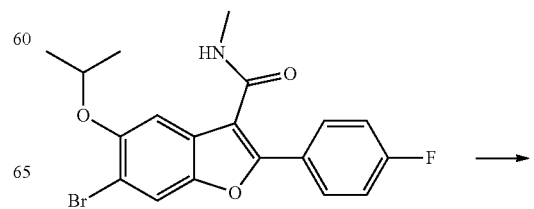
Scheme 6.

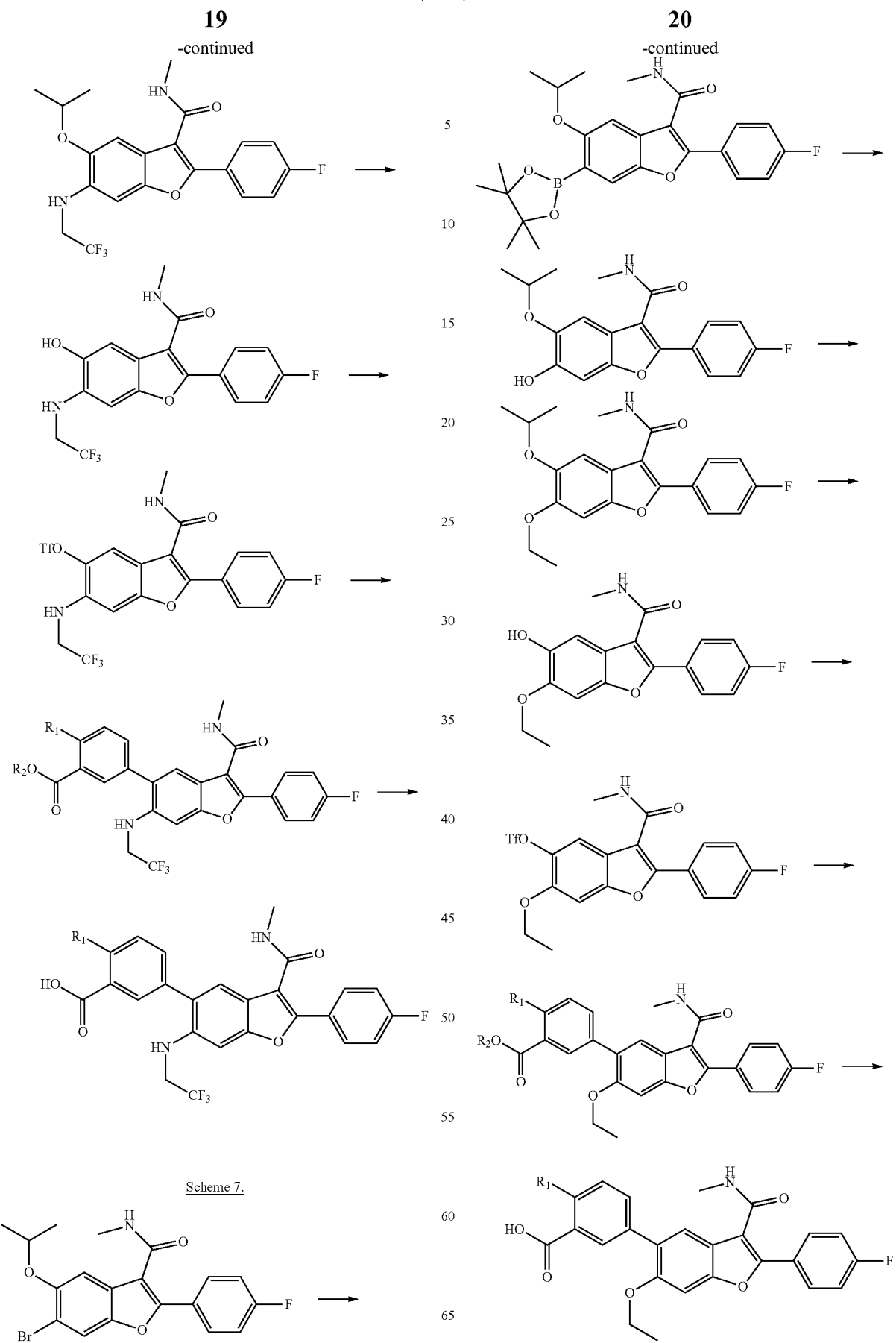
Scheme 7.

Preparation of Intermediates

N-(3-(Benzyloxy)cyclobutylidene)-2-methylpropane-2-sulfinamide

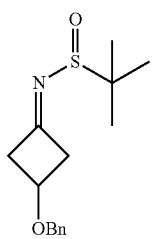 [SMILES: CC(C)(C)S(=O)N=C1CC(OCc2ccccc2)C1]

To a mixture of 3-(benzyloxy)cyclobutanone (3 g, 17.02 mmol) in THF (90 mL) at room temperature was added 2-methylpropane-2-sulfinamide (4.13 g, 34.0 mmol) followed by titanium(IV) isopropoxide (4.99 mL, 17.02 mmol). The reaction mixture was then heated to and stirred at 60° C. in a sealed tube for 10 hr (hours). After completion of the reaction, the reaction mixture was diluted with water and extracted with ethyl acetate (100 ml×2). The white suspension obtained was passed through a pad of celite, and the combined organic extracts were dried over sodium sulphate and concentrated. The crude product was purified by Combiflash using a mixture of 4:6 ethyl aceate/n-hexane as an eluent, and the desired fractions were evaporated to obtain the product in 2.8 g (58.9%) as a mixture of isomers. $^1$H NMR (400 MHz, CDCl$_3$) δ 1.16-1.34 (m, 18H), 3.08-3.36 (m, 6H), 3.40-3.52 (m, 1H), 3.52-3.85 (m, 1H), 4.25-4.38 (m, 2H), 4.38-4.57 (m, 4H), 7.17-7.42 (m, 10H).

N-(3-(benzyloxy)-1-cyanocyclobutyl)-2-methylpropane-2-sulfinamide

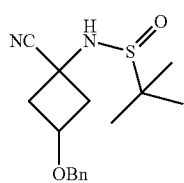 [SMILES: CC(C)(C)S(=O)NC1(C#N)CC(OCc2ccccc2)C1]

To a mixture of N-(3-(benzyloxy)cyclobutylidene)-2-methylpropane-2-sulfinamide (2.8 g, 10.02 mmol) in dichloromethane (90 mL) at r.t. was added trimethylsilylcyanide (2.69 ml, 20.04 mmol) dropwise followed by titanium (IV) isopropoxide (2.202 ml, 7.52 mmol). The reaction mixture was then stirred at ambient temperature for 14 hr. After completion of the reaction, the mixture was diluted with dichloromethane (200 ml) and water (50 ml). The resulting white suspension was passed through a pad of celite and the organic extract concentrated to obtain the desired product, which was sufficiently pure for use in the next step without any purification. Yield 2.4 g (78%). $^1$H NMR (400 MHz, CDCl$_3$) δ: 1.24 (d, J=4.25 Hz, 9H), 1.48-1.53 (d, J=4.25 Hz, 9H), 2.57 (dd, J=11.01, 7.25 Hz, 1H), 2.65-2.89 (m, 1H), 2.99-3.21 (m, 3H), 3.41-3.74 (m, 3H), 4.10-4.32 (m, 2H), 4.37-4.60 (m, 4H), 7.15-7.46 (m, 10H).

3-(Benzyloxy)-1-(1,1-dimethylethylsulfinamido)cyclobutanecarboximidamide

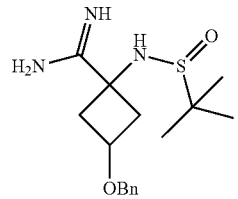 [SMILES: CC(C)(C)S(=O)NC1(C(=N)N)CC(OCc2ccccc2)C1]

To a mixture of N-(3-(benzyloxy)-1-cyanocyclobutyl)-2-methylpropane-2-sulfinamide (1 g, 3.26 mmol) in methanol (10 mL) was added N-acetyl-L-(+)-cysteine (0.533 g, 3.26 mmol) followed by ammonium acetate (1.258 g, 16.32 mmol). The reaction mixture was stirred at 70° C. for 16 hr. Additional amounts of ammonium acetate (1.258 g, 16.32 mmol) and N-acetyl-L-(+)-cysteine (0.533 g, 3.26 mmol) were added, and the mixture was stirred for a further 10 hr. Heating was then stopped and the solvent evaporated under vacuum. The product was taken for the next step without isolation and purification.

LCMS: (ES+) m/z=324 (M+H)$^+$.
Column: PUROSPHER@star RP-18 (4×55) mm, 3 μm
Buffer: 20 mM NH$_4$OAc in water
Mobile (M) phase A: Buffer+MeCN (90+10)
Mobile (M) phase B: Buffer+MeCN (10+90)
Flow: 2.5 ml/min

| Time (min.): | 0 | 2 | 2.5 | 3 |
|---|---|---|---|---|
| % B: | 0 | 100 | 100 | 0 |

RetentionTime (Rt)=1.168 min
(All LCMS, analytical HPLC and preparative HPLC gradient time in min.)

N-(3-(Benzyloxy)-1-(pyrimidin-2-yl)cyclobutyl)-2-methylpropane-2-sulfinamide

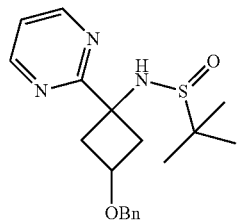 [SMILES: CC(C)(C)S(=O)NC1(c2ncccn2)CC(OCc2ccccc2)C1]

To a mixture of 3-(benzyloxy)-1-(1,1-dimethylethylsulfinamido)cyclobutanecarboximidamide (crude 1 g, assumed 3.09 mmol, prepared as above) in methanol (10 ml) was added N,N-dimethylamino-2-propen-3-al (0.619 ml, 6.18 mmol) and sodium methoxide (3.98 g, 15.46 mmol). The resulting reaction mixture was heated to and stirred at 75° C. for 24 hr. After completion of the reaction, the mixture was concentrated and the residue dissolved in ethyl acetate (100 ml) and then water (15 ml) was added to it. The organic layer was separated, dried over sodium sulphate and concentrated to give the crude compound. This was further purified by Combiflash using a mixture of 1:9 MeOH/CHCl₃ as an eluent to obtain the desired product. Yield 350 mg, (28.3%).
¹H NMR (400 MHz, CDCl₃) δ: 1.14-1.28 (s, 9H), 2.57-2.73 (m, 2H), 2.84-3.00 (m, 1H), 3.02-3.22 (m, 1H), 4.31-4.56 (m, 3H), 7.17 (s, 1H), 7.23-7.43 (m, 6H), 8.66-8.82 (m, 2H).
LCMS: (ES+) m/z=360 (M+H)⁺.
Column: PUROSPHER@star RP-18 (4×55) mm, 3 m
Buffer: 20 mM NH₄OAc in water
M phase A: Buffer+MeCN (90+10)
M phase B: Buffer+MeCN (10+90)
Flow: 2.5 ml/min

| Time (min.): | 0 | 2 | 2.5 | 3 |
|---|---|---|---|---|
| % B: | 0 | 100 | 100 | 0 |

Rt=1.531 min

3-(Benzyloxy)-1-(pyrimidin-2-yl)cyclobutanamine Hydrochloride

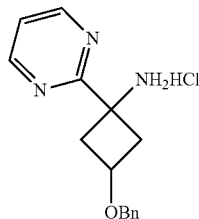

A mixture of N-(3-(benzyloxy)-1-(pyrimidin-2-yl)cyclobutyl)-2-methylpropane-2-sulfinamide (0.350 g, 0.974 mmol) in a solution of HCl (4M, 15 ml, 0.974 mmol) in dioxane was stirred at room temperature for 3 hr. The reaction mixture was then concentrated to remove the organic solvent and the crude product was triturated with diethyl ether to give 3-(benzyloxy)-1-(pyrimidin-2-yl)cyclobutanamine as a hydrochloride salt. Yield: 280 mg (84%).
LCMS: (ES+) m/z=256 (M+H)⁺.
Column: ZORBAX Eclipse plus C18 (4.6×100 mm), 5 m
M phase A: 20 mM NH₄OAc in 90% H₂O, 10% MeCN
M phase B: 20 mM NH₄OAc in 10% H₂O, 90% MeCN
Flow: 1.5 ml/min

| Time (min.): | 0 | 6 | 8 | 10 |
|---|---|---|---|---|
| % B: | 0 | 100 | 100 | 0 |

Rt=1.213 min

2-(3-(Benzyloxy)-1-(pyrimidin-2-yl)cyclobutyl)isoindoline-1,3-dione

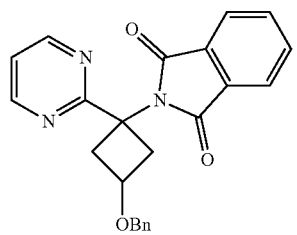 [SMILES: O=C1c2ccccc2C(=O)N1C1(c2ncccn2)CC(OCc2ccccc2)C1]

To a mixture of 3-(benzyloxy)-1-(pyrimidin-2-yl)cyclobutanamine hydrochloride (0.280 g, 0.960 mmol) in dioxane (15 mL) was added N,N-diisopropylethylamine (DIPEA) (0.838 mL, 4.80 mmol) followed by phthalic anhydride (0.213 g, 1.439 mmol). The reaction mixture was heated and stirred in a sealed tube for 10 hr. After completion of the reaction, the reaction mixture was concentrated, and ethyl acetate (25 ml) was added to it. The mixture was washed with water (10 ml) and then brine, and the organic layer dried over sodium sulphate to give a crude product which was further purified by Combiflash using a mixture of 1:9 MeOH/CHCl₃ as an eluent to give the isomeric mixture product as a white solid. Yield: 0.16 g (43.3%). ¹H NMR (400 MHz, DMSO-d₆) δ: 2.82-3.02 (m, 4H), 3.08-3.23 (m, 3H), 3.62-3.76 (m, 2H), 4.32-4.39 (m, 1H), 4.43-4.54 (m, 3H), 4.67 (s, 1H), 7.26-7.49 (m, 10H), 7.78-7.93 (m, 8H), 8.81-8.81 (m, 6H).

2-(3-Hydroxy-1-(pyrimidin-2-yl)cyclobutyl)isoindoline-1,3-dione

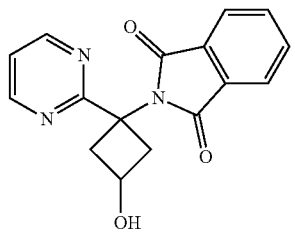 [SMILES: O=C1c2ccccc2C(=O)N1C1(c2ncccn2)CC(O)C1]

To a mixture of 2-(3-(benzyloxy)-1-(pyrimidin-2-yl)cyclobutyl)isoindoline-1,3-dione (0.160 g, 0.415 mmol) in dichloromethane (DCM) (2 mL) at −78° C. was added boron trichloride (1.245 mL, 1.245 mmol). The mixture was then stirred at room temperature for 8 hr. After completion of the reaction, the mixture was quenched with water and extracted with DCM (25 ml×2). The combined organic extracts were dried over sodium sulphate, filtered, and concentrated. The crude product was triturated with (5%) n-hexane:diethyl ether to give the desired compound which was then used in the next step without further purification. Yield: 0.1 g (68%).
LCMS: (ES+) m/z=296 (M+H)⁺.
Column: ZORBAX SB C18 (4.6×50) mm, 5 m
M phase A: 10% MeOH-90% H₂O-0.1% TFA
M phase B: 90% MeOH-10% H₂O-0.1% TFA
Flow: 5 ml/min

| Time (min.): | 0 | 2 | 3 |
|---|---|---|---|
| % B: | 0 | 100 | 0 |

Rt=1.244 min

2-(3-Fluoro-1-(pyrimidin-2-yl)cyclobutyl)isoindoline-1,3-dione

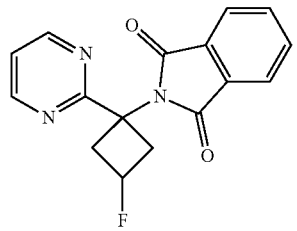 [SMILES: O=C1c2ccccc2C(=O)N1C1(c2ncccn2)CC(F)C1]

To a mixture of 2-(3-hydroxy-1-(pyrimidin-2-yl)cyclobutyl)isoindoline-1,3-dione (0.220 g, 0.745 mmol) in dry DCM (2 mL) at 0° C. was added DAST ((diethylamino)sulfur trifluoride) (0.217 mL, 1.639 mmol), and the reaction was stirred at ambient temperature for 12 hr. After completion, the reaction mixture was quenched with an aqueous solution of NaHCO$_3$ and extracted with DCM (15 ml×2), and the organic layer separated. The organic layer was washed with brine, dried over sodium sulphate and concentrated to give the crude compound. This was further purified by Combiflash using a mixture of 2:8 ethyl acetate/n-hexane as an eluent. Yield: 0.1 g (45.2%). $^1$H NMR (400 MHz, CDCl$_3$) δ: 3.09-3.30 (m, 2H) 3.35-3.51 (m, 2H) 5.54-5.77 (m, 1H) 7.13 (t, J=4.88 Hz, 1H) 7.65-7.79 (m, 2H) 7.87 (dd, J=5.50, 3.00 Hz, 2H) 8.62 (d, J=5.00 Hz, 2H). $^{19}$F NMR (376.6 MHz, CDCl$_3$) δ: −162.52.

3-Fluoro-1-(pyrimidin-2-yl)cyclobutanamine

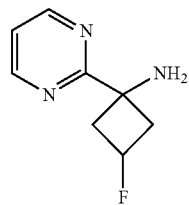 [SMILES: NC1(c2ncccn2)CC(F)C1]

To a mixture of 2-(3-fluoro-1-(pyrimidin-2-yl)cyclobutyl)isoindoline-1,3-dione (0.05 g, 0.168 mmol) in ethanol (0.5 ml) was added hydrazine hydrate (5.28 µl, 0.168 mmol, 99%) and the reaction mixture was refluxed for 4 hr. After white solid precipitated out, the heating was discontinued and the reaction mixture filtered. The filtrate was concentrated to give the amine, which was used for the next step without further purification. Yield: 20 mg (71%).

LCMS: (ES+) m/z=168 (M+H)$^+$.
Column: PUROSPHER@star RP-18 (4×55) mm, 3 m
Buffer: 20 mM NH$_4$OAc IN water
M phase A: Buffer+MeCN (90+10)
M phase B: Buffer+MeCN (10+90)
Flow: 2.5 ml/min

| Time (min.): | 0 | 2 | 2.5 | 3 |
|---|---|---|---|---|
| % B: | 0 | 100 | 100 | 0 |

Rt=0.524 min

2-(3-Oxo-1-(pyrimidin-2-yl)cyclobutyl)isoindoline-1,3-dione

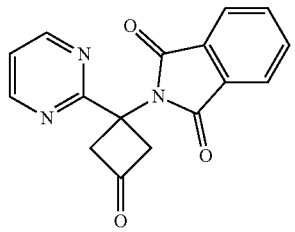 [SMILES: O=C1CC(c2ncccn2)(N2C(=O)c3ccccc3C2=O)C1]

To a stirred solution of 2-(3-hydroxy-1-(pyrimidin-2-yl)cyclobutyl)isoindoline-1,3-dione (150 mg, 0.508 mmol) in DCM (10 ml) in a 25 ml RBF (round bottomed flask) was added DMP (Dess-Martin periodinane) reagent (280 mg, 0.660 mmol). The resulting mixture was stirred at room temperature for 2 hr, during which time solids precipitated out. After completion of the reaction, the crude mixture was filtered, and the filtrate was washed with 10% NaHCO$_3$ solution and separated. The organic layer was concentrated after drying over Na$_2$SO$_4$ to obtain the crude compound. It was then purified by Combiflash by using 15% ethyl acetate in n-hexane as an eluent. The desired fractions were concentrated to give the product as a pale yellow solid. Yield: 90 mg (60%). $^1$H NMR (400 MHz, CDCl$_3$) δ: 3.97-4.09 (m, 2H), 4.14-4.24 (m, 2H), 7.16 (t, J=4.89 Hz, 1H), 7.74-7.82 (m, 2H), 7.89-7.97 (m, 2H), 8.63 (d, J=4.77 Hz, 2H).

LCMS: (ES+) m/z=294 (M+H)$^+$.
Column: PUROSPHER@star RP-18 (4×55) mm, 3 m
Buffer: 20 mM NH$_4$OAc IN water
M phase A: Buffer+ACN (90+10) (ACN=acetonitrile; M phase=Mobile phase)
M phase B: Buffer+ACN (10+90)
Flow: 2.5 ml/min

| Time (min.): | 0, | 2, | 2.5, | 3 |
|---|---|---|---|---|
| % B: | 0, | 100, | 100, | 0 |

Rt: 1.52 min

2-(3,3-Difluoro-1-(pyrimidin-2-yl)cyclobutyl)isoindoline-1,3-dione

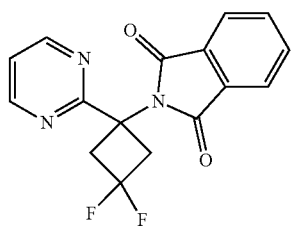 [SMILES: O=C1c2ccccc2C(=O)N1C1(c2ncccn2)CC(F)(F)C1]

To a stirred solution of 2-(3-oxo-1-(pyrimidin-2-yl)cyclobutyl)isoindoline-1,3-dione (90 mg, 0.307 mmol) in DCM (10 ml) in a 25 ml RBF was added DAST (0.161 ml, 1.228 mmol). The resulting mixture was stirred at room temperature overnight. After completion of the reaction, the mixture was diluted with additional amounts of dichloromethane (10 ml) and then washed with 10% aqueous NaHCO₃ solution. The organic layer was separated, dried over Na₂SO₄ and evaporated to obtain the crude compound. This was purified by Combiflash by using 15% ethyl acetate/n-hexane as an eluent. Yield: 25 mg (26%) ¹H NMR (400 MHz, CDCl₃) δ: 3.65-3.80 (m, 2H) 3.86-3.99 (m, 2H) 7.07-7.13 (m, 1H) 7.65-7.73 (m, 2H) 7.86-7.96 (m, 2H) 8.66 (d, J=4.75 Hz, 2H); ¹⁹F NMR (376.6 MHz, CDCl₃): −89.566.

3,3-Difluoro-1-(pyrimidin-2-yl)cyclobutanamine

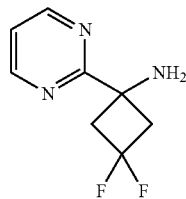 [SMILES: NC1(c2ncccn2)CC(F)(F)C1]

To a mixture of 2-(3,3-difluoro-1-(pyrimidin-2-yl)cyclobutyl)isoindoline-1,3-dione (30 mg, 0.095 mmol) in ethanol (1 mL) in a 5 ml sealed tube was added NH₂NH₂.H₂O (9.52 mg, 0.190 mmol). The resulting reaction mixture was heated to and stirred at 80° C. for 3 hr. Additional amounts of ethanol (3 ml) was added to the reaction mixture, and the mixture filtered to remove the white solid precipitates. The filtrate was concentrated under vacuum, triturated with n-hexane and dried under vacuum. The semi-solid product was used for the next step. Yield: 15 mg (85%).

LCMS: (ES+) m/z=186 (M+H)⁺.
Column: PUROSPHER@star RP-18 (4.6×30) mm, 3 m
Buffer: 20 mM NH₄OAc IN water
M phase A: Buffer+ACN (90+10)
M phase B: Buffer+ACN (10+90)
Flow: 2.5 ml/min
Time (min.): 0, 2, 2.5, 3
% B: 0, 100, 100, 0

| Time (min.): | 0, | 2, | 2.5, | 3 |
|---|---|---|---|---|
| % B: | 0, | 100, | 100, | 0 |

Rt: 0.83 min 3-(6-(N-ethylmethylsulfonamido)-4-fluoro-2-(4-fluorophenyl)-3-(methylcarbamoyl)benzofuran-5-yl)benzoic Acid

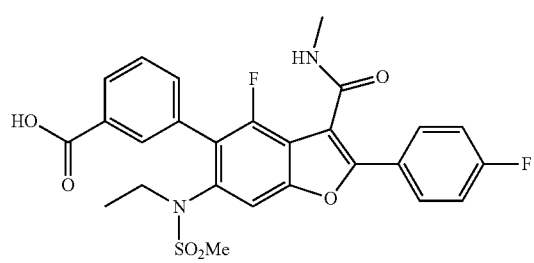 [SMILES: CCN(c1cc2oc(-c3ccc(F)cc3)c(C(=O)NC)c2c(F)c1-c1cccc(C(=O)O)c1)S(C)(=O)=O]

To a mixture of tert-butyl 3-(6-(N-ethylmethylsulfonamido)-4-fluoro-2-(4-fluorophenyl)-3-(methylcarbamoyl) benzofuran-5-yl)benzoate (0.150 g, 0.257 mmol, prepared according to Scheme 3) under ice-cold conditions was added TFA (2.5 mL), and the mixture stirred at r.t. for 3 hr. Aliquot of the reaction mixture was analyzed by LCMS, which showed the desired molecular mass with complete conversion. The reaction mixture was quenched with ice-cold water. The off white solid precipitated out was filtered and dried under suction to give the acid which was used for the next step without further purification (100 mg). LCMS: (ES+) m/z=529.27 (M+H)⁺. Buffer: 10 mM Ammonium Acetate pH-5 adjusted with HCOOH. Mobile phase A: Buffer:ACN (95:5); Mobile phase B: Buffer:ACN (5:95). Rt min: 0.70, Wavelength: 220 nm.

5-(6-(N-ethylmethylsulfonamido)-4-fluoro-2-(4-fluorophenyl)-3-(methylcarbamoyl)benzofuran-5-yl)-2-methoxybenzoic Acid

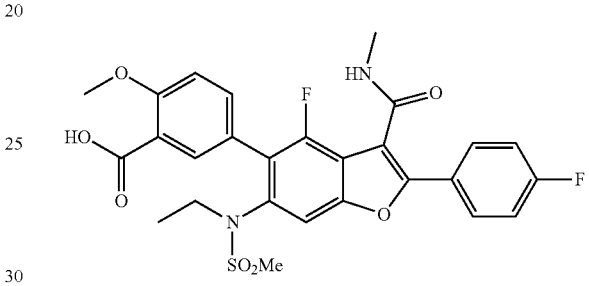

To a mixture of methyl 5-(6-(N-ethylmethylsulfonamido)-4-fluoro-2-(4-fluorophenyl)-3-(methyl carbamoyl)benzofuran-5-yl)-2-methoxybenzoate (150 mg, 0.262 mmol) in THF (2.5 mL) was added MeOH and NaOH. The mixture was stirred at 25° C. for 3 hr. The solvent was evaporated under vacuum, and the residue obtained was acidified with cold 1.5 N HCl. The off white solid precipitated out was filtered and dried, and used for the next step without further purification (100 mg). LCMS: (ES+) m/z=559.3 (M+H)⁺. Column: Acquity BEH C18 (2.1×50 mm) 1.7 μm, Mobile phase A: 5 mM Ammonium Acetate: ACN (95:5). Mobile phase B: 5 mM Ammonium Acetate: ACN (5:95). Method:% B: 0 min-5%; 1.1 min-95%; 1.7 min-95%. Flow: 0.8 ml/min. Rt min: 0.71, Wavelength: 220 nm.

6-Bromo-2-(4-fluorophenyl)-5-isopropoxybenzofuran-3-carboxylic Acid

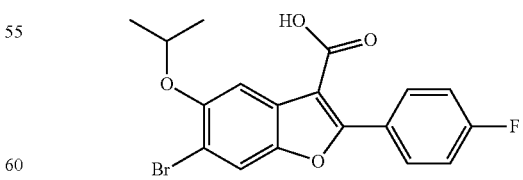

To a solution of ethyl 6-bromo-2-(4-fluorophenyl)-5-isopropoxybenzofuran-3-carboxylate (9.5 g, 22.55 mol) in a mixture of THF (60 ml) and methanol (60 ml) was added an aqueous solution of NaOH (33.8 mL, 67.7 mmol, 2N). The resulting mixture was heated to 80° C. for and stirred for 16 hours. After completion of the reaction, the volatiles were evaporated and the pH was adjusted to 1.0 with 1.5 N HCl. The solid thus precipitated was filtered and dried under vacuum to get 6-bromo-2-(4-fluorophenyl)-5-isopropoxy-benzofuran-3-carboxylic acid as a white solid product (8.9 g, 100%). $^1$H NMR (300 MHz, DMSO-$d_6$): δ ppm 8.15-8.09 (m, 2H), 7.99 (s, 1H), 7.64 (s, 1H), 7.40-7.33 (m, 2H), 4.62 (m, J=6.0 Hz, 1H), 1.34 (d, J=6.0 Hz, 6H). LCMS for mol. LCMS: (ES+) m/z observed=393 (M+H)$^+$, Column-ACQUITY UPLC BEH C18 (50×2.1 mm; 1.7 μm), M phase A: 5 mM Ammonium Acetate: ACN (95:5), M phase B: 5 mM Ammonium Acetate: ACN (5:95), Flow: 0.8 ml/min. Rt min: 1.10 min, wavelength: 220 nm.

| Time | % A | % B |
| --- | --- | --- |
| 0 | 95 | 5 |
| 1.1 | 5 | 95 |
| 1.7 | 95 | 5 |

6-Bromo-2-(4-fluorophenyl)-5-isopropoxy-N-methylbenzofuran-3-carboxamide

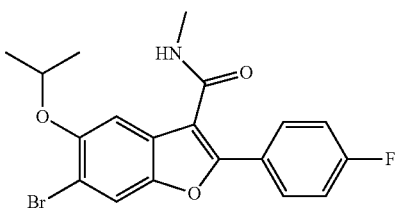 [SMILES: CNC(=O)c1c(-c2ccc(F)cc2)oc2cc(Br)c(OC(C)C)cc12]

To a stirred solution of 6-bromo-2-(4-fluorophenyl)-5-isopropoxybenzofuran-3-carboxylic acid (8.9 g, 22.63 mmol), DIPEA (11.86 mL, 67.9 mmol) and 2-(7-aza-1H-benzotriazole-1-yl)-1,1,3,3-tetramethyluronium hexafluorophosphate (HATU) (12.91 g, 34.0 mmol) in DMF (50 mL) at 0° C. was added methylamine hydrochloride (1.681 g, 24.90 mmol). The reaction was continued stirring at 25° C. for 4 hours. To the reaction mixture was added ice-cold water, the solid formed was filtered and dried under vacuum to obtain 6-bromo-2-(4-fluorophenyl)-5-isopropoxy-N-methylbenzofuran-3-carboxamide as a pale yellow solid (8.5 g, 92%). LCMS for mol. LCMS: (ES+) m/z observed=408.3 (M+H)$^+$, Column-ACQUITY UPLC BEH C8 (50×2.1 mm; 1.7 μm), M phase A: 5 mM Ammonium Acetate: ACN (95:5), M phase B: 5 mM Ammonium Acetate: ACN (5:95), Flow: 0.8 ml/min. Rt min: 1.18 min, wavelength: 220 nm.

| Time | % A | % B |
| --- | --- | --- |
| 0 | 95 | 5 |
| 1.1 | 5 | 95 |
| 1.7 | 5 | 95 |

2-(4-Fluorophenyl)-5-isopropoxy-N-methyl-6-(3,3,3-trifluoropropyl)benzofuran-3-carboxamide

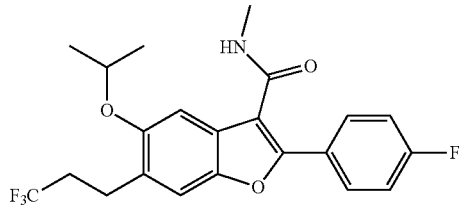 [SMILES: CNC(=O)c1c(-c2ccc(F)cc2)oc2cc(CCC(F)(F)F)c(OC(C)C)cc12]

A mixture of 6-bromo-2-(4-fluorophenyl)-5-isopropoxy-N-methylbenzofuran-3-carboxamide (0.5 g, 1.231 mmol), potassium 3,3,3-triflouoropropane-1-trifluoroborate (0.377 g, 1.846 mmol) and cesium carbonate (1.805 g, 5.54 mmol) in a toluene (10 mL)/water (1 mL) mixture in a 50 mL pressure tube was flushed with nitrogen, and then PdCl$_2$ (dppf).CH$_2$Cl$_2$ adduct (0.060 g, 0.074 mmol) was added to it. The mixture was degassed again for another 4 min, and then stirred at 90° C. for 16 hrs. After completion of the reaction, the mixture was passed through a celite bed and the filtrate was washed with water. The organic layer was dried over anhydrous Na$_2$SO$_4$ and concentrated. The residue obtained was purified by using Combi-flash with 35% ethyl acetate/n-hexane as a mobile phase to give 2-(4-fluorophenyl)-5-isopropoxy-N-methyl-6-(3,3,3-trifluoropropyl)benzofuran-3-carboxamide as a white solid product (500 mg, 96%). $^1$H NMR (400 MHz, DMSO-$d_6$): δ ppm 8.37 (d, J=4.6 Hz, 1H), 7.96-7.89 (m, 2H), 7.57 (s, 1H), 7.40-7.34 (m, 2H), 7.11 (s, 1H), 4.72-4.61 (m, 1H), 2.92-2.87 (m, 2H), 2.83 (d, J=4.6 Hz, 3H), 2.60-2.53 (m, 2H), 1.33 (d, J=6.0 Hz, 6H). LCMS: (ES+) m/z=424 (M+H)$^+$. Column: ACQUITY UPLC BEH C18 (50×2.1 mm; 1.7 μm). M phase A: 0.1% TFA in water. M phase B: Acetonitrile. Flow: 0.8 ml/min. Rt min: 1.13 min, wavelength: 220 nm.

2-(4-Fluorophenyl)-5-hydroxy-N-methyl-6-(3,3,3-trifluoropropyl)benzofuran-3-carboxamide

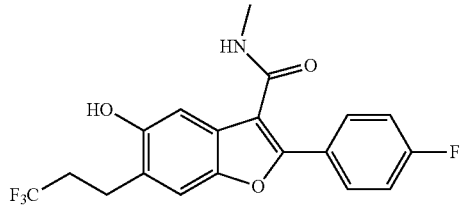

A solution of 2-(4-fluorophenyl)-5-isopropoxy-N-methyl-6-(3,3,3-trifluoropropyl)benzofuran-3-carboxamide (0.5 g, 1.181 mmol) in DCM (10 mL) was cooled to −50° C., and then was added dropwise with boron trichloride (3.54 mL, 3.54 mmol). The reaction mixture was stirred at 0° C. for 3 hours. The volatiles were removed under vacuum and the residue diluted with ice-cold water. The solid obtained was filtered, dried under suction to give 2-(4-fluorophenyl)-5-hydroxy-N-methyl-6-(3,3,3-trifluoropropyl)benzofuran-3-carboxamide as a pale yellow solid (420 mg, 93%). LCMS: (ES+) m/z=382 (M+H)$^+$. Column-ACQUITY UPLC BEH C18 (50×2.1 mm; 1.7 μm). M phase A: 0.1% TFA in water, M phase B: Acetonitrile. Flow: 0.8 ml/min. Rt min: 0.94 min, wavelength: 220 nm.

2-(4-Fluorophenyl)-3-(methylcarbamoyl)-6-(3,3,3-trifluoropropyl)benzofuran-5-yl trifluoromethanesulfonate

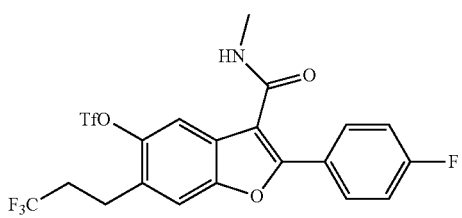 [SMILES: CNC(=O)c1c(-c2ccc(F)cc2)oc2cc(CCC(F)(F)F)c(O)cc12]

To a solution of 2-(4-fluorophenyl)-5-hydroxy-N-methyl-6-(3,3,3-trifluoropropyl)benzofuran-3-carboxamide (0.42 g, 1.101 mmol) in pyridine (4 mL) at 25° C. was added DMAP (0.067 g, 0.551 mmol). The mixture was cooled to 0° C., and trifluoromethanesulfonyl anhydride (0.558 mL, 3.30 mmol) was added dropwise to the mixture. The reaction mixture was stirred at room temperature for 3 hours. After completion of the reaction, the mixture was diluted with water and extracted with ethyl acetate (3×100 ml). The organic layer was dried over anhydrous $Na_2SO_4$ and concentrated to get 2-(4-fluorophenyl)-3-(methylcarbamoyl)-6-(3,3,3-trifluoropropyl)benzofuran-5-yl-trifluoro methanesulfonate as a brown colored product (500 mg, 88%). LCMS: (ES+) m/z=514.4 $(M+H)^+$. Column-ACQUITY UPLC BEH C8 (50×2.1 mm; 1.7 m), M phase A: 5 mM Ammonium Acetate: ACN (95:5), M phase B: 5 mM Ammonium Acetate: ACN (5:95), Flow: 0.8 ml/min. Rt min: 1.23 min, wavelength: 220 nm.

tert-Butyl 3-(2-(4-fluorophenyl)-3-(methylcarbamoyl)-6-(3,3,3-trifluoropropyl)benzofuran-5-yl)benzoate

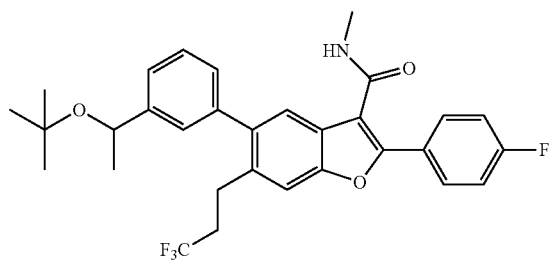 [SMILES: CNC(=O)c1c(-c2ccc(F)cc2)oc2cc(CCC(F)(F)F)c(-c3cccc(C(C)OC(C)(C)C)c3)cc12]

A mixture of 2-(4-fluorophenyl)-3-(methylcarbamoyl)-6-(3,3,3-trifluoropropyl)benzofuran-5-yl trifluoromethanesulfonate (0.42 g, 0.818 mmol), (3-(tert-butoxycarbonyl)phenyl)boronic acid (0.218 g, 0.982 mmol) and cesium carbonate (0.800 g, 2.454 mmol) in a 1,4-dioxane (20 mL)/Water (1 mL) mixture was degassed for 5 min. Tetrakis(triphenyl)phosphinepalladium(0) (0.047 g, 0.041 mmol) was added to the mixture, which was then degassed again for 5 min. The resulting mixture was stirred at 90° C. for 16 hrs. It was then passed through a celite bed and the bed washed with EtOAc (50 mL). The filtrate was washed with water, dried over anhydrous $Na_2SO_4$ and concentrated. The residue obtained was purified by column chromatography using Combi-flash with 11% ethyl acetate/n-hexane as a mobile phase to give tert-butyl 3-(2-(4-fluorophenyl)-3-(methylcarbamoyl)-6-(3,3,3-trifluoropropyl)benzofuran-5-yl)benzoate as a white solid product (300 mg, 67.7%). $^1H$ NMR (400 MHz, DMSO-$d_6$): δ ppm 8.44 (d, J=4.6 Hz, 1H), 8.03-7.95 (m, 3H), 7.86 (t, J=1.5 Hz, 1H), 7.82 (s, 1H), 7.69-7.61 (m, 2H), 7.46 (s, 1H), 7.44-7.38 (m, 2H), 2.92-2.87 (m, 2H), 2.83 (d, J=4.6 Hz, 3H), 2.60-2.53 (m, 2H), 1.57 (s, 9H). LCMS: (ES+) m/z=542.2 $(M+H)^+$. Column-ACQUITY UPLC BEH C8 (50×2.1 mm; 1.7 m), M phase A: 5 mM Ammonium Acetate: ACN (95:5), M phase B: 5 mM Ammonium Acetate: ACN (5:95), Flow: 0.8 ml/min. Rt min: 1.38 min, wavelength: 220 nm.

3-(2-(4-Fluorophenyl)-3-(methylcarbamoyl)-6-(3,3,3-trifluoropropyl)benzofuran-5-yl)benzoic Acid

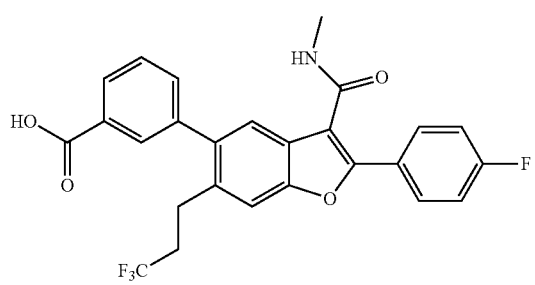 [SMILES: CNC(=O)c1c(-c2ccc(F)cc2)oc2cc(CCC(F)(F)F)c(-c3cccc(C(=O)O)c3)cc12]

To a mixture of tert-butyl 3-(2-(4-fluorophenyl)-3-(methylcarbamoyl)-6-(3,3,3-trifluoropropyl) benzo furan-5-yl) benzoate (0.28 g, 0.517 mmol) in DCM (2 mL) was added TFA (0.040 mL, 0.517 mmol). The resulting mixture was stirred at 25° C. for 2 hours. The TFA was removed under vacuum, and the solid washed with hexane (3×10 ml) to get 3-(2-(4-fluorophenyl)-3-(methyl carbamoyl)-6-(3,3,3-trifluoropropyl)benzofuran-5-yl)benzoic acid as a white solid (250 mg, 100%). $^1H$ NMR (400 MHz, DMSO-$d_6$): δ ppm 13.03 (bs, 1H), 8.47-8.42 (m, 1H), 8.05-7.97 (m, 3H), 7.92 (t, J=1.5 Hz, 1H), 7.82 (s, 1H), 7.70-7.60 (m, 2H), 7.47 (s, 1H), 7.44-7.37 (m, 2H), 2.91-2.86 (m, 2H), 2.81 (d, J=4.6 Hz, 3H), 2.49-2.43 (m, 2H). LCMS: (ES+) m/z=486.1 $(M+H)^+$. Column-ACQUITY UPLC BEH C18 (50×2.1 mm; 1.7 m). M phase A: 0.1% TFA in water, M phase B: Acetonitrile. Flow: 0.8 ml/min. Rt min: 1.08 min, wavelength: 220 nm.

2-(4-Fluorophenyl)-5-isopropoxy-N-methyl-6-propylbenzofuran-3-carboxamide

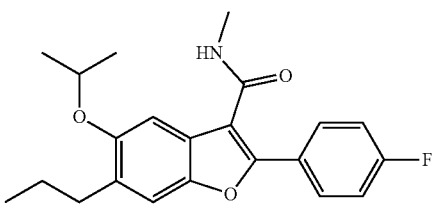 [SMILES: CCCc1cc2oc(-c3ccc(F)cc3)c(C(=O)NC)c2cc1OC(C)C]

A mixture of 6-bromo-2-(4-fluorophenyl)-5-isopropoxy-N-methylbenzofuran-3-carboxamide (5.0 g, 12.31 mmol), n-propyl boronic acid (1.623 g, 18.46 mmol) and cesium carbonate (12.03 g, 36.9 mmol) in a toluene (2 mL)/water (0.2 mL) mixture was degassed for 5 min. $PdCl_2(dppf)$. $CH_2Cl_2$ adduct (0.603 g, 0.738 mmol) was added to the mixture which was then degassed once again for 5 min. The resulting reaction mixture was stirred at 90° C. for 16 hrs. After completion of the reaction, it was cooled and filtered through a celite bed, and the bed washed thoroughly with ethyl acetate. The combined organic mixture was washed water, dried over $Na_2SO_4$, filtered and concentrated. The residue was purified by column chromatography using Combiflash with 12% ethyl acetate/n-hexane as a mobile phase to obtain 2-(4-fluorophenyl)-5-isopropoxy-N-methyl-6-propylbenzofuran-3-carboxamide as a white solid product (2.8 g, 61.6%). $^1$H NMR (400 MHz, $CDCl_3$) δ ppm 7.84-7.89 (m, 2H), 7.25-7.26 (m, 1H), 7.25 (s, 1H), 7.14-7.19 (m, 2H), 5.75 (bs, 1H), 4.61 (m, 1H), 2.99 (d, J=4.8 Hz, 3H), 2.69 (t, J=8.0 Hz, 2H), 1.65 (qd, J=7.2, 8.4 Hz, 2H), 1.36 (d, J=3.6 Hz, 6H), 0.99-0.94 (t, 7.2 Hz, 3H). LCMS: (ES+) m/z=370 (M+H)$^+$. Column-ACQUITY UPLC BEH C8 (50×2.1 mm; 1.7 m), M phase A: 5 mM Ammonium Acetate: ACN (95:5), M phase B: 5 mM Ammonium Acetate: ACN (5:95), Flow: 0.8 ml/min. Rt min: 1.34 min, wavelength: 220 nm.

| Time | % A | % B |
| --- | --- | --- |
| 0 | 95 | 5 |
| 1.1 | 5 | 95 |
| 1.7 | 5 | 95 |

2-(4-Fluorophenyl)-5-hydroxy-N-methyl-6-propyl-benzofuran-3-carboxamide

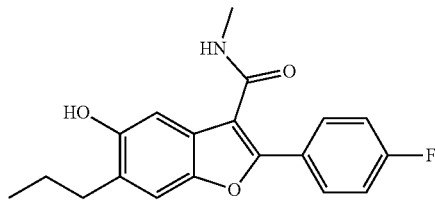 [SMILES: CCCc1cc2oc(-c3ccc(F)cc3)c(C(=O)NC)c2cc1O]

To a solution of 2-(4-fluorophenyl)-5-isopropoxy-N-methyl-6-propylbenzofuran-3-carboxamide (2.8 g, 7.58 mmol) in DCM (30 mL) cooled to −50° C. was added boron trichloride (22.74 mL, 22.74 mmol, 1M in DCM) dropwise. The mixture was then stirred at 0° C. for 3 hours. The volatiles were removed and the residue quenched with ice-cold water. The solid thus separated was filtered and dried to obtain 2-(4-fluorophenyl)-5-hydroxy-N-methyl-6-propylbenzofuran-3-carboxamide as a pale yellow solid (2.45 g, 99%). $^1$H NMR (400 MHz, DMSO-$d_6$): δ ppm 9.32 (s, 1H), 8.36 (q, J=3.2 Hz, 1H), 7.94-7.88 (m, 2H), 7.38-7.30 (m, 3H), 6.99 (s, 1H), 6.51 (bs, 1H), 2.81 (d, J=4.6 Hz, 3H), 2.59 (t, J=7.6 Hz, 2H), 1.60-1.63 (m, 2H), 0.92 (t, J=7.6 Hz, 3H). LCMS: (ES+) m/z=328.4 (M+H)$^+$. Column-ACQUITY UPLC BEH C8 (50×2.1 mm; 1.7 μm), M phase A: 5 mM Ammonium Acetate: ACN (95:5), M phase B: 5 mM Ammonium Acetate: ACN (5:95), Flow: 0.8 ml/min. Rt min: 1.05 min, wavelength: 220 nm.

| Time | % A | % B |
| --- | --- | --- |
| 0 | 95 | 5 |
| 1.1 | 5 | 95 |
| 1.7 | 5 | 95 |

2-(4-Fluorophenyl)-3-(methylcarbamoyl)-6-propyl-benzofuran-5-yl Trifluromethanesulfonate

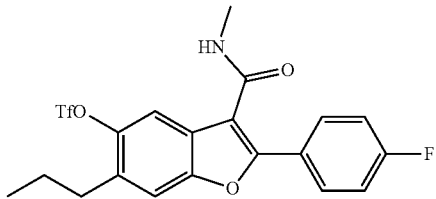 [SMILES: CCCc1cc2oc(-c3ccc(F)cc3)c(C(=O)NC)c2cc1OS(=O)(=O)C(F)(F)F]

To a solution of 2-(4-fluorophenyl)-5-hydroxy-N-methyl-6-propylbenzofuran-3-carboxamide (2.45 g, 7.48 mmol) in pyridine (10 mL) at 25° C. was added DMAP (0.091 g, 0.748 mmol). The mixture was cooled to 0° C. and triflic anhydride (3.16 mL, 18.71 mmol) was added dropwise. The brown colored reaction mixture was stirred at 25° C. for 3 hr. The reaction mixture was diluted with water and extracted with ethyl acetate (3×100 ml). The organic extract was dried over $Na_2SO_4$ and concentrated to give 2-(4-fluorophenyl)-3-(methylcarbamoyl)-6-propylbenzofuran-5-yl trifluoromethanesulfonate as a white solid product (2.9 g, 84%). LCMS: (ES+) m/z=460.4 (M+H)$^+$. Column-ACQUITY UPLC BEH C8 (50×2.1 mm; 1.7 m), M phase A: 5 mM Ammonium Acetate: ACN (95:5), M phase B: 5 mM Ammonium Acetate: ACN (5:95), Flow: 0.8 ml/Min. Rt min: 1.27 min, wavelength: 220 nm.

| Time | % A | % B |
| --- | --- | --- |
| 0 | 95 | 5 |
| 1.1 | 5 | 95 |
| 1.7 | 5 | 95 | tert-Butyl 2-fluoro-5-(2-(4-fluorophenyl)-3-(methyl-cabamoyl)-6-propylbenzofuran-5-yl)benzoate

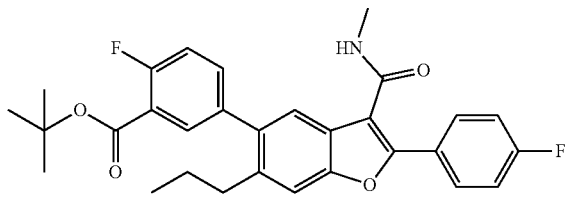 [SMILES: CCCc1cc2oc(-c3ccc(F)cc3)c(C(=O)NC)c2cc1-c1ccc(F)c(C(=O)OC(C)(C)C)c1]

A mixture of 2-(4-fluorophenyl)-3-(methylcarbamoyl)-6-propylbenzofuran-5-yl trifluoromethanesulfonate (1.0 g, 2.177 mmol), tert-butyl 2-fluoro-5-(4,4,5,5-tetramethyl-1,3,2dioxaborolan-2-yl)benzoate (0.842 g, 2.61 mmol) and potassium phosphate, dibasic (1.137 g, 6.53 mmol) in dioxane (25 mL)/water (1 mL) mixture was degassed for 5 min. $PdCl_2$(dppf).$CH_2Cl_2$ (0.107 g, 0.131 mmol) was added to the mixture, which was again degassed for 5 min. The resulting reaction mixture was stirred at 90° C. for 16 hrs. After completion of the reaction, the mixture was passed through celite and the celite bed washed with EtOAc (50 ml). The obtained filtrate was washed with water. The separated organic layer was dried over $Na_2SO_4$, filtered and evaporated under vacuum. The residue was purified through Combiflash with 30% ethyl acetate/n-hexane as a mobile phase to obtain tert-butyl 2-fluoro-5-(2-(4-fluorophenyl)-3-(methylcabamoyl)-6-propylbenzofuran-5-yl)benzoate as a pale brown solid product (600 mg, 54.5%). LCMS: (ES+) m/z=506 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min. Rt min: 1.44 min, wavelength: 220 nm.

| Time | % A | % B |
|------|-----|-----|
| 0    | 98  | 2   |
| 1.0  | 2   | 98  |
| 1.6  | 2   | 98  |

2-Fluoro-5-(2-(4-fluorophenyl)-3-(methylcabamoyl)-6-propylbenzofuran-5-yl)benzoic Acid

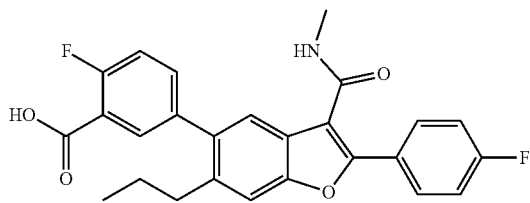 [SMILES: CCCc1cc2oc(-c3ccc(F)cc3)c(C(=O)NC)c2cc1-c1ccc(F)c(C(=O)O)c1]

In a 50 mL round bottomed flask, a mixture of tert-butyl 2-fluoro-5-(2-(4-fluorophenyl)-3-(methylcarbamoyl)-6-propylbenzofuran-5-yl)benzoate (0.6 g, 1.187 mmol) in TFA (0.914 mL, 11.87 mmol) was stirred at 25° C. for 2 hours. The reaction was monitored by TLC to check the absence of starting material. The TFA was then removed under vacuum, and the solid washed with hexane (3×10 ml) to obtain 2-fluoro-5-(2-(4-fluorophenyl)-3-(methylcabamoyl)-6-propylbenzofuran-5-yl)benzoic acid as a white solid product (450 mg, 84%). LCMS: (ES+) m/z=450.2 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min. Rt min: 1.23 min, wavelength: 220 nm.

| Time | % A | % B |
|------|-----|-----|
| 0    | 98  | 2   |
| 1.0  | 2   | 98  |
| 1.6  | 2   | 98  |

Methyl 5-2-(4-fluorophenyl)-3-(methylcarbamoyl)-6-propylbenzofuran-5-yl)-2-methoxybenzoate

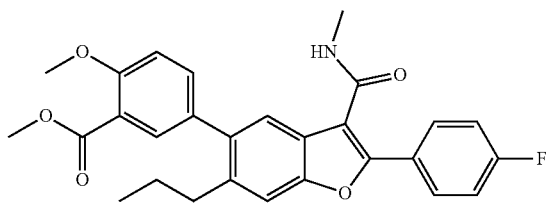 [SMILES: CCCc1cc2oc(-c3ccc(F)cc3)c(C(=O)NC)c2cc1-c1ccc(OC)c(C(=O)OC)c1]

A mixture of 2-(4-fluorophenyl)-3-(methylcarbamoyl)-6-propylbenzofuran-5-yl trifluoromethanesulfonate (0.65 g, 1.415 mmol), (4-methoxy-3-(methoxycarbonyl)phenyl)boronic acid (0.357 g, 1.698 mmol) and cesium carbonate (1.383 g, 4.24 mmol) in dioxane (20 mL)/water (1 mL) mixture was degassed for 5 min. To this mixture was added tetrakis(triphenylphosphine)palladium(0) (0.082 g, 0.071 mmol), and the mixture degassed again for 5 min. This reaction mixture was stirred at 90° C. for 4 hours. After completion of the reaction, it was passed through a celite bed and the bed was washed with EtOAc (50 ml). The combined organic mixture was washed with water, dried over Na$_2$SO$_4$ and concentrated. The residue obtained was purified by Combiflash with 22% ethyl acetate/n-hexane as a mobile phase to obtain methyl 5-2-(4-fluorophenyl)-3-(methylcarbamoyl)-6-propylbenzofuran-5-yl)-2-methoxybenzoate as a pale brown solid product (400 mg, 59.5%). $^1$H NMR (400 MHz, DMSO-d$_6$): δ ppm 8.41 (m, 1H), 8.02-7.96 (m, 2H), 7.63-7.59 (m, 2H), 7.53 (dd, J=2.4, 8.5 Hz, 1H), 7.41-7.35 (m, 3H), 7.25 (d, J=8.7 Hz, 1H), 3.89 (s, 3H), 3.80 (s, 3H), 2.80 (d, J=4.6 Hz, 3H), 2.65-2.59 (m, 2H), 1.52-1.44 (m, 2H), 0.78 (t, J=7.3 Hz, 3H). LCMS: (ES+) m/z=476.2 (M+H)$^+$. Column-ACQUITY UPLC BEH C18 (50×2.1 mm; 1.7 m). M phase A: 0.1% TFA in water. M phase B: Acetonitrile. Flow: 0.8 ml/min. Rt min: 1.15 min, wavelength: 220 nm.

| Time | % A | % B |
|------|-----|-----|
| 0    | 98  | 2   |
| 1.0  | 2   | 98  |
| 1.6  | 2   | 98  |

5-2-(4-Fluorophenyl)-3-(methylcarbamoyl)-6-propylbenzofuran-5-yl)-2-methoxybenzoic Acid

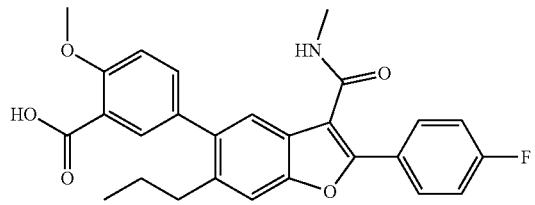 [SMILES: CCCc1cc2oc(-c3ccc(F)cc3)c(C(=O)NC)c2cc1-c1ccc(OC)c(C(=O)O)c1]

To a solution of methyl 5-(2-(4-fluorophenyl)-3-(methylcarbamoyl)-6-propylbenzofuran-5-yl)-2-methoxybenzoate (0.4 g, 0.841 mmol) in THF (3 mL) in methanol (3 mL), a 3M aqueous solution of NaOH (0.841 mL, 2.52 mmol) was added and the mixture then stirred at 25° C. for 5 hours. The volatiles were removed under vacuum, and the residue acidified to pH 2. The solid was filtered and dried to give 5-2-(4-fluorophenyl)-3-(methylcarbamoyl)-6-propylbenzofuran-5-yl)-2-methoxybenzoic acid as a yellow solid (350 mg, 90%). $^1$H NMR (400 MHz, DMSO-d$_6$): δ ppm 12.8 (bs, 1H), 8.41 (d, J=4.6 Hz, 1H), 8.00-7.97 (m, 2H), 7.63-7.57 (m, 2H), 7.48 (dd, J=2.4, 8.5 Hz, 1H), 7.41-7.35 (m, 3H), 7.22 (d, J=8.7 Hz, 1H), 3.89 (s, 3H), 2.81 (d, J=4.6 Hz, 3H), 2.65-2.60 (m, 2H), 1.52-1.45 (m, 2H), 0.78 (t, J=7.3 Hz, 3H). LCMS: (ES+) m/z=462.2 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min. Rt min: 1.24 min, wavelength: 220 nm.

| Time | % A | % B |
| --- | --- | --- |
| 0 | 98 | 2 |
| 1.0 | 2 | 98 |
| 1.6 | 2 | 98 |

Methyl 5-(2-(4-fluorophenyl)-3-(methylcarbamoyl)-6-propylbenzofuran-5-yl)-2-methoxy-4-methylbenzoate

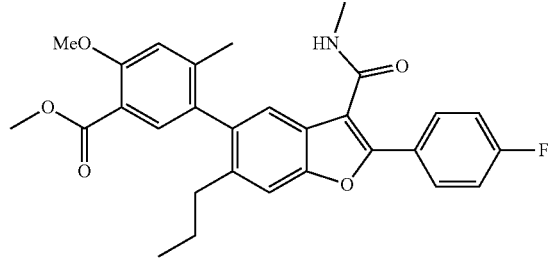 [SMILES: CCCc1cc2oc(-c3ccc(F)cc3)c(C(=O)NC)c2cc1-c1cc(C(=O)OC)c(OC)cc1C]

To a mixture of 2-(4-fluorophenyl)-3-(methylcarbamoyl)-6-propylbenzofuran-5-yl trifluoro methanesulfonate (0.850 g, 1.850 mmol) in dioxane (10 mL) and water (1.250 mL) was added methyl 2-methoxy-4-methyl-5-(4,4,5,5-tetramethyl-1,3,2-dioxaborolan-2-yl)benzoate (0.708 g, 2.313 mmol), cesium carbonate (1.808 g, 5.55 mmol). The reaction mixture was then degassed using argon for 10 min prior to the addition of tetrakis(triphenylphosphine)palladium(0) (0.214 g, 0.185 mmol). The mixture was heated to and stirred at 100° C. 12 hr. The reaction mixture was then diluted with ethyl acetate and filtered through a celite pad. The combined organic filtrates was dried over sodium sulphate and concentrated. The crude product was recrystalized from pet. ether:diethyl ether to give a pale yellow solid (0.6 g, Yield: 67%). LCMS: (ES+) m/z=490.5 (M+H)+. Column: Acquity BEH C18 (2.1×50 mm) 1.7 µm, Mobile phase A: 5 mM Ammonium Acetate:ACN (95:5). Mobile phase B: 5 mM Ammonium Acetate:ACN (5:95). Method: % B: 0 min-5%; 1.1 min-95%; 1.7 min-95%. Flow: 0.8 ml/min. Rt min: 1.31, Wavelength: 220 nm.

5-(2-(4-Fluorophenyl)-3-(methylcarbamoyl)-6-propylbenzofuran-5-yl)-2-methoxy-4-methylbenzoic Acid

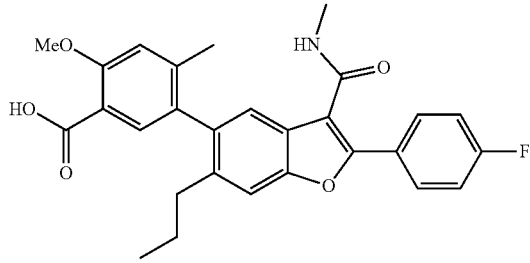 [SMILES: CCCc1cc2oc(-c3ccc(F)cc3)c(C(=O)NC)c2cc1-c1cc(C(=O)O)c(OC)cc1C]

To a mixture of methyl 5-(2-(4-fluorophenyl)-3-(methylcarbamoyl)-6-propylbenzofuran-5-yl)-2-methoxy-4-methylbenzoate (0.6 g, 1.226 mmol) in THF (10 mL) and methanol (1.250 mL) was added NaOH (5 mL, 1.226 mmol), the reaction mixture was then stirred at 25° C. for 12 hr. The mixture was then concentrated, and the residue obtained was dissolved in water and washed with diethyl ether. The aqueous layer was then acidified with 1.5N HCl. The white solid precipitated out was filtered and dried under suction. This product was taken to the next step without further purification (0.25 g). LCMS: (ES+) m/z=476.5 (M+H)+. Column: Acquity BEH C18 (2.1×50 mm) 1.7 µm, Mobile phase A: 5 mM Ammonium Acetate:ACN (95:5). Mobile phase B: 5 mM Ammonium Acetate:ACN (5:95). Method: % B: 0 min-5%:1.1 min-95%:1.7 min-95%. Flow: 0.8 ml/min. Rt min: 1.14, Wavelength: 220 nm.

Methyl 5-(2-(4-fluorophenyl)-3-(methylcarbamoyl)-6-(3,3,3-trifluoropropyl)benzofuran-5-yl)-2-methoxy-4-methylbenzoate

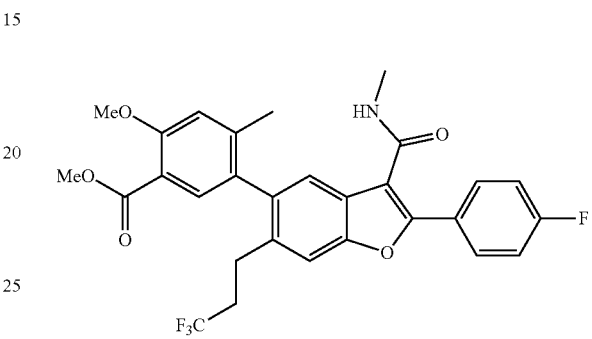

To a mixture of 2-(4-fluorophenyl)-3-(methylcarbamoyl)-6-(3,3,3-trifluoropropyl)benzofuran-5-yl trifluoromethanesulfonate (0.5 g, 0.974 mmol) in a dioxane (10 mL)/water (1.25 mL) mixture was added methyl 2-methoxy-4-methyl-5-(4,4,5,5-tetramethyl-1,3,2-dioxaborolan-2-yl)benzoate (0.373 g, 1.217 mmol) and cesium carbonate (0.952 g, 2.92 mmol). The reaction mixture was degassed by using argon for 10 min prior to the addition of tetrakis(triphosphine) palladium(0) (0.113 g, 0.097 mmol). The mixture was heated at 100° C. for 12 hr. The mixture was then diluted with ethyl acetate and filtered through a celite pad to remove inorganic salts. The organic mixture was dried over anhydrous sodium sulphate and concentrated. The crude product was purified by Combiflash using a snap-24 g column and pet. ether/ethyl acetate as an eluent. (Yield: 0.4 g, 88%, pale yellow solid). LCMS: (ES+) m/z=544.6 (M+H)+. Column: Acquity BEH C18 (2.1×50 mm) 1.7 µm, Mobile phase A: 5 mM Ammonium Acetate:ACN (95:5). Mobile phase B: 5 mM Ammonium Acetate:ACN (5:95). Method: % B: 0 min-5%:1.1 min-95%:1.7 min-95%. Flow: 0.8 ml/min. Rt min: 1.19, Wavelength: 220 nm.

5-(2-(4-Fluorophenyl)-3-(methylcarbamoyl)-6-(3,3,3-trifluoropropyl)benzofuran-5-yl)-2-methoxy-4-methylbenzoic Acid

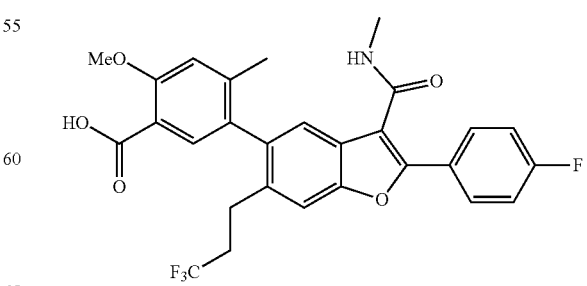

To a mixture of methyl 5-(2-(4-fluorophenyl)-3-(methylcarbamoyl)-6-(3,3,3-trifluoropropyl) benzofuran-5-yl)-2- methoxy-4-methylbenzoate (0.6 g, 1.104 mmol) in THF (10 mL) and methanol (1.25 mL) was added aqueous NaOH (5 mL, 1.104 mmol). The reaction mixture was then stirred at 25° C. for 12 hr. The volatiles were removed under vacuum, and the residue obtained was dissolved in water and washed with diethyl ether. The aqueous layer was then acidified with 1.5N HCl. The white solid precipitates were filtered, dried under suction, and taken to the next step without further purification (Yield: 0.25 g, white solid). LCMS: (ES+) m/z observed=531.2 (M+H)+. Column: ZORBAX SB AQ (4.6× 50) mm, 3.5 micron. Mobile phase A:0.1% HCOOH in Water. Mobile phase B: ACN. FLOW: 1.0 ml/min. Rt min: 4.91, Wavelength: 220 nm.

tert-Butyl 2-fluoro-5-(2-(4-fluorophenyl)-3-(methyl-carbamoyl)-6-(3,3,3-trifluoropropyl)benzofuran-5-yl)benzoate

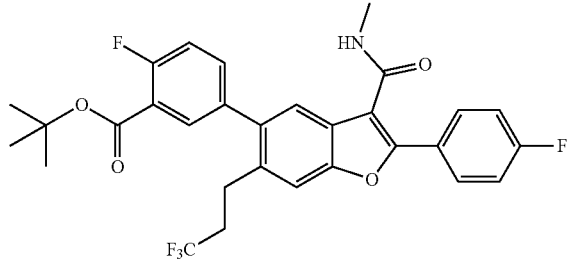 [SMILES: CNC(=O)c1c(-c2ccc(F)cc2)oc2cc(CCC(F)(F)F)c(-c3ccc(F)c(C(=O)OC(C)(C)C)c3)cc12]

To a mixture of 2-(4-fluorophenyl)-3-(methylcarbamoyl)-6-(3,3,3-trifluoropropyl)benzofuran-5-yl trifluoromethanesulfonate (0.7 g, 1.364 mmol) in dioxane (10 mL) and water (2.500 mL) was added tert-butyl 2-fluoro-5-(4,4,5,5-tetramethyl-1,3,2-dioxaborolan-2-yl)benzoate (0.420 g) and cesium carbonate (1.333 g, 4.09 mmol). The reaction mixture was then degassed for 10 min by using argon prior to the addition of tetrakis(triphenylphosphine)palladium(0) (0.158 g, 0.136 mmol). The mixture was stirred at 100° C. for 12 hours. The reaction mixture was then diluted with ethyl acetate and filtered through a celite pad to remove inorganic components. The organic filtrate was dried over sodium sulphate and concentrated (0.35 g, pale yellow solid).

2-Fluoro-5-(2-(4-fluorophenyl)-3-(methylcarbamoyl)-6-(3,3,3-trifluoropropyl)benzofuran-5-yl)benzoic Acid

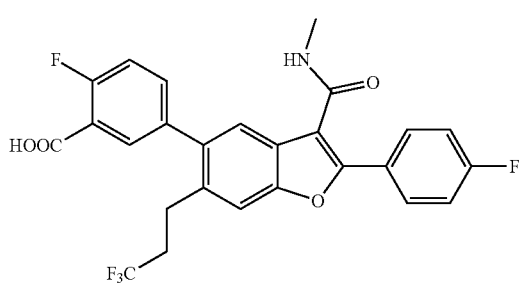 [SMILES: CNC(=O)c1c(-c2ccc(F)cc2)oc2cc(CCC(F)(F)F)c(-c3ccc(F)c(C(=O)O)c3)cc12]

A mixture of tert-butyl 2-fluoro-5-(2-(4-fluorophenyl)-3-(methylcarbamoyl)-6-(3,3,3-trifluoropropyl)benzofuran-5-yl)benzoate (0.4 g, 0.715 mmol) and TFA (2.5 mL) was stirred at room temperature for 4 hours. The reaction mixture was then concentrated and the residue obtained was dissolved in water. The white solid precipitated out was filtered and dried under suction, and was used for the next step without further purification (Yield: 0.35 g, white solid). LCMS: (ES+) m/z=504.5 (M+H)+. Buffer: 10 mM Ammonium Acetate pH 5 adjusted with HCOOH. Mobile phase A: Buffer:ACN (95:5); Mobile phase B: Buffer:ACN (5:95). Column: Acquity BEH C18 (2.1×50 mm) 1.7 μm. Rt min: 0.90, Wavelength: 220 nm.

(((1-Bromo-3-chloropropan-2-yl)oxy)methyl)benzene

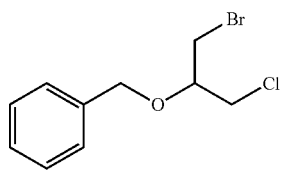 [SMILES: ClCC(CBr)OCc1ccccc1]

In a flask fitted with a condenser, a mixture consisting of benzyl bromide (193 ml, 1621 mmol), 2-(chloromethyl)oxirane (150 g, 1621 mmol) and mercury(II) chloride (4.40 g, 16.21 mmol) was heated with stirring at 150° C. for 12 hrs. The reaction mixture was diluted with diethyl ether and washed with water (1000 ml). The organic extract was dried over sodium sulphate and concentrated to give as a pale yellow liquid. The crude compound was purified by column chromatography using silica gel 60×120 mesh size and 8:2 pet. ether/ethyl acetate as an eluent to afford the title compound as a pale yellow liquid (yield: 100 g, 23.4%). 1H NMR (400 MHz, CHLOROFORM-d) δ ppm=7.37-7.29 (m, 5H), 4.73 (s, 2H), 3.87-3.80 (m, 1H), 3.73-3.71 (m, 2H), 3.63-3.53 (m, 2H).

Diethyl 3-(benzyloxy)cyclobutane-1,1-dicarboxylate

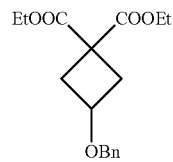 [SMILES: CCOC(=O)C1(C(=O)OCC)CC(OCc2ccccc2)C1]

Diethyl malonate (72.3 mL, 474 mmol) was added to a mixture of (((1-bromo-3-chloropropan-2-yl)oxy)methyl)benzene (50 g, 190 mmol) in ethanol (500 mL) at room temperature. Sodium ethoxide (177 mL, 474 mmol) was then added dropwise to the mixture. The reaction mixture was heated and refluxed for 10 hours. The mixture was filtered and the solvent in the filtrate was removed by distillation under reduced pressure at 10 mbar. The crude product was purified by Combiflash chromatography using a 40 g silica gel column and pet. ether/ethylacetate (7:3) as an eluent to afford the title compound as a pale yellow liquid. Yield: 55 g, 95%. 1H NMR (400 MHz, CHLOROFORM-d) δ=7.40-7.28 (m, 5H), 4.27-4.09 (m, 4H), 4.07-4.00 (m, 2H), 3.71 (t, J=7.7 Hz, 1H), 2.84-2.75 (m, 2H), 2.59-2.49 (m, 2H), 1.32-1.19 (m, 6H).

3-(Benzyloxy)cyclobutane-1,1-dicarboxylic Acid

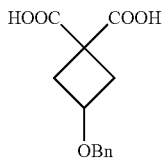

To a mixture of diethyl 3-(benzyloxy)cyclobutane-1,1-dicarboxylate (55 g, 180 mmol) in ethanol (400 mL) was added slowly and dropwise a solution of potassium hydroxide (50.4 g, 898 mmol) in water (105 mL). The reaction mixture was heated to reflux for 45 min., and then cooled to room temperature. The mixture was concentrated and the residue obtained diluted with water (10 ml), acidified to pH 2 with conc. HCl. The mixture was then extracted with MTBE (100 mL×2), dried over $Na_2SO_4$, and concentrated to give the crude diacid as a yellow oil. Yield: 30 g, 64%. $^1$H NMR (400 MHz, CHLOROFORM-d) δ=7.38-7.25 (m, 5H), 4.45 (s, 2H), 4.21 (m, 1H), 2.89-2.81 (m, 2H), 2.66-2.58 (m, 2H).

3-(Benzyloxy)cyclobutanecarboxylic Acid

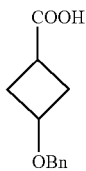

A mixture of 3-(benzyloxy)cyclobutane-1,1-dicarboxylic acid (30 g, 120 mmol) in pyridine (150 mL) was stirred at 125° C. for 12 hrs. The reaction mixture was concentrated, diluted with toluene (10 mL) and washed with 1.5N HCl (5 mL). The organic layer was dried over $Na_2SO_4$, concentrated and purified by Combiflash using 120 g column and 6:4 pet ether/ethyl acetate as an eluent to isolate the product as a pale yellow oil (15 g, 60.7% yield). $^1$H NMR (400 MHz, CHLOROFORM-d) δ=7.40-7.26 (m, 5H), 4.43 (d, J=5.0 Hz, 2H), 4.35-4.26 (m, 0.5H), 4.00-3.90 (m, 0.5H), 3.14-3.04 (m, 0.5H), 2.73-2.62 (m, 0.5H), 2.59-2.48 (m, 2H), 2.39-2.24 (m, 2H).

Methyl 3-(benzyloxy)cyclobutanecarboxylate

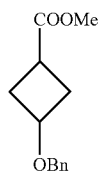

To a mixture of 3-(benzyloxy)cyclobutanecarboxylic acid (15 g, 72.7 mmol) in a mixture of methanol (30 mL) and dichloroethane (15 mL) was added a few drops of sulfuric acid (1.938 mL, 36.4 mmol). The reaction mixture was refluxed for 10 hours. The mixture was concentrated, and the residue obtained was dissolved in ethyl acetate and washed with 5% $Na_2CO_3$. The organic layer was separated, dried over $Na_2SO_4$, concentrated and purified by Combiflash using a snap-40 g silica gel column and 6:4 pet. ether ethyl acetate as an element to obtain the product as a pale yellow oil (10 g, 62.4% yield). $^1$H NMR (300 MHz, CHLOROFORM-d) δ=7.42-7.26 (m, 5H), 4.45 (d, J=3.1 Hz, 2H), 4.35-4.25 (m, 0.5H), 4.05-3.91 (m, 0.5H), 3.70 (s, 3H), 3.16-2.94 (m, 0.5H), 2.70-2.60 (m, 0.5H), 2.60-2.45 (m, 2H), 2.39-2.19 (m, 2H).

Methyl 3-(benzyloxy)-1-methylcyclobutanecarboxylate

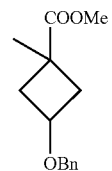

To a mixture of LDA (10.21 mL, 20.43 mmol) in THF (10 mL) at −78° C. was added methyl 3-(benzyloxy)cyclobutanecarboxylate (3 g, 13.62 mmol) in THF (10 mL) dropwise, and the mixture was stirred at same temperature for 30 min. Iodomethane (0.937 mL, 14.98 mmol) was then added slowly to the mixture at −78° C. The mixture was brought to room temperature and kept stirring another 30 min. The reaction mixture was quenched with sat. $NH_4Cl$ and extracted with ethyl acetate. The organic layer was dried over sodium sulphate, concentrated to obtain the crude methylated compound. This was further purified by Combiflash using a snap-40 g silica gel column and 6:4 pet. ether/ethyl acetate. The product was isolated as a colorless liquid (1.8 g, 56.4% yield). $^1$H NMR (400 MHz, CHLOROFORM-d) δ=7.38-7.27 (m, 5H), 4.44-4.38 (m, 2H), 4.18-4.05 (m, 1H), 3.72-3.65 (m, 3H), 2.78-2.69 (m, 1.3H), 2.51-2.43 (m, 0.7H), 2.25-2.16 (m, 0.7H), 1.99-1.91 (m, 1.3H), 1.41 and 1.36 (s, 3H).

3-(Benzyloxy)-1-methylcyclobutanecarboxylic Acid

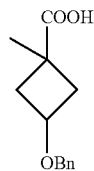

To a mixture of methyl 3-(benzyloxy)-1-methylcyclobutanecarboxylate (1.3 g, 5.55 mmol) in methanol (10 mL) and Water (2.500 mL) at room temperature was added NaOH (0.444 g, 11.10 mmol). The mixture was stirred at room temperature 12 hours. The reaction mixture was concentrated and washed with diethyl ether. The aqueous layer was then acidified with 1.5N HCl, and extracted with DCM. The organic layer was then dried over sodium sulphate and concentrated to give as Ig of the product as a colorless viscous liquid (82% Yield). $^1$H NMR (400 MHz, CHLOROFORM-d) δ=7.39-7.26 (m, 5H), 4.42 (m, 2H), 4.23-4.05

2-(Trimethylsilyl)ethyl (3-(benzyloxy)-1-methylcyclobutyl)carbamate

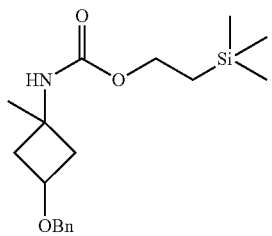

To a mixture of 3-(benzyloxy)-1-methylcyclobutanecarboxylic acid (2.8 g, 12.71 mmol), in toluene (30 mL) at room temperature was added triethylamine (7.09 mL, 50.8 mmol), followed by diphenylphosphoryl azide (3.44 mL, 15.25 mmol) slowly.

The reaction mixture was heated to and stirred at 45° C. for 2h. The temperature was then raised to 70° C. and 2-2-(trimethylsilyl)ethanol (5.47 mL, 38.1 mmol) was added dropwise to the mixture. The reaction mixture was then stirred at the same temperature for another 8 hours. The mixture was concentrated and the residue purified by Combiflash using a snap-40 g silica gel column and 8:2 pet. ether:ethylacetate to provide the product as a pale yellow liquid in 2.2 g (51.6% Yield). $^1$H NMR (400 MHz, CHLOROFORM-d) δ=7.35-7.24 (m, 5H), 4.40 (m, 2H), 4.80 and 4.65 (brs, 1H), 4.20-4.10 (m, 3H), 2.6 (brm, 1.3H), 2.50-2.40 (m, 0.7H), 2.20-2.20 (br m, 0.7H), 2.00-2.10 (m, 1.3H), 1.42 and 1.38 (s, 3H), 0.98-0.94 (m, 2H), 0.03 (s, 9H).

3-(Benzyloxy)-1-methylcyclobutanamine

A mixture of 2-(trimethylsilyl)ethyl (3-(benzyloxy)-1-methylcyclobutyl)carbamate (2.2 g, 6.56 mmol) and TFA (20 mL) was stirred at room temperature for 3 hours. An aliquot of the reaction mixture was submitted for LC/MS analysis for the formation of desired product. The reaction mixture was then concentrated and stripped with toluene. The 3-(benzyloxy)-1-methylcyclobutanamine TFA salt was used for the next step without further purification (Yield: 1.2 g, 96%). LCMS: (ES+) m/z=192.0 (M+H)$^+$, Column: Ascentis Express C8 (50×2.1 mm; 2.7 um), Buffer: 10 mM Ammonium Formate in Water, M phase A: Buffer+ACN (90+10), M phase B: Buffer+ACN (10+90), Flow: 1.0 ml/min, Rt min: 1.44, Wavelength: 254 nm.

2-(3-(Benzyloxy)-1-methylcyclobutyl)isoindoline-1,3-dione

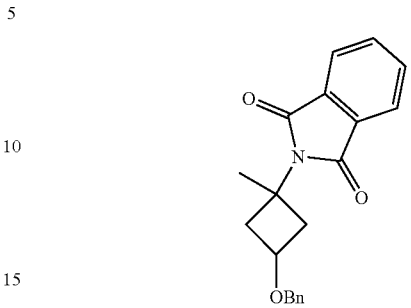

To a mixture of 3-(benzyloxy)-1-methylcyclobutanamine (1.2 g, 6.27 mmol) in toluene (8 mL) was added triethylamine (4.37 mL, 31.4 mmol) and phthalic anhydride (1.394 g, 9.41 mmol). The mixture was heated to and stirred at 125° C. for 8 hours. The reaction mixture was then concentrated, and the residue purified by Combiflash using a snap-24 g silica gel column and pet ether: ethyl acetate to isolate the product as a white solid in (1.3 g, 64.1% Yield). $^1$H NMR (400 MHz, CHLOROFORM-d) δ=7.84-7.75 (m, 2H), 7.73-7.63 (m, 2H), 7.44-7.27 (m, 5H), 4.47-4.41 (m, 2H), 4.20-4.10 (m, 0.6H), 4.09-3.97 (m, 0.4H), 3.14-3.03 (m, 1.3H), 2.94-2.80 (m, 0.7H), 2.64-2.54 (m, 0.7H), 2.52-2.44 (m, 1.3H), 1.71 and 1.49 (s, 3H).

2-(3-Hydroxy-1-methylcyclobutyl)isoindoline-1,3-dione

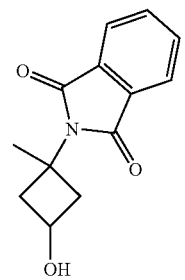 [SMILES: CC1(N2C(=O)c3ccccc3C2=O)CC(O)C1]

To a mixture of 2-(3-(benzyloxy)-1-methylcyclobutyl)isoindoline-1,3-dione (1.3 g, 4.02 mmol) in DCM (20 mL) at −78° C. was added boron trichloride (12.06 mL, 12.06 mmol). The reaction mixture was then brought to ambient temperature and stirred at the temperature for 5 hours. The mixture was concentrated, and the residue diluted with DCM and washed with water. The organic layer was dried over sodium sulphate and concentrated to get a white solid, which was further washed with pet. ether and filtered. The product was as used for the next step without further purification (0.996 g, 85% Yield). LCMS: (ES−) m/z=232.0 (M−H), Buffer: 10 mM AmmoniumAcetate pH-5 adjusted with HCOOH, Mobile phase A: Buffer:ACN (95:5), Mobile phase B: Buffer:ACN (5:95), Gradient Time-% B: 0 min-5%:1.1 min-95%:1.7 min-95%, Rt min: 0.69, Wavelength: 254 nm.

3-Amino-3-methylcyclobutanol

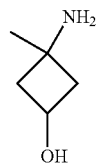

A mixture of 2-(3-hydroxy-1-methylcyclobutyl)isoindoline-1,3-dione (0.2 g, 0.857 mmol) and hydrazine (0.067 mL, 2.144 mmol) was dissolved in ethanol (1 mL) and heated to 90° C. The reaction mixture was stirred at same temperature for 1 hour and then filtered. The filtrate was concentrated to a semi solid which was used for the next step without further purification (0.07 g).

2-(4-Fluorophenyl)-5-isopropoxy-N-methyl-6-((2,2,-trifluoroethyl)amino)benzofuran-3-carboxamide

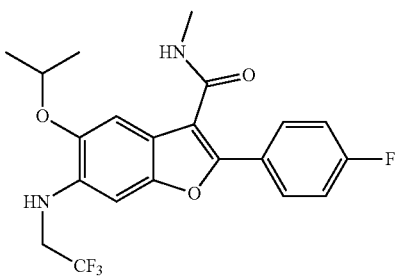 [SMILES: CNC(=O)c1c(-c2ccc(F)cc2)oc2cc(NCC(F)(F)F)c(OC(C)C)cc12]

A solution of 6-bromo-2-(4-fluorophenyl)-5-isopropoxy-N-methylbenzofuran-3-carboxamide (1.0 g, 2.462 mmol) and sodium t-amylate (1.355 g, 12.31 mmol) in dioxane (25 mL) in a 50 ml pressure tube was degasified for 10 minutes. After the addition of Brettphos precatalyst (0.197 g, 0.246 mmol), the mixture was degasified again for 5 min, and then 2,2,2-trifluoroethylamine (0.979 mL, 12.31 mmol) was added to it. The resulting reaction mixture was stirred at 90° C. for 2 hours. The reaction mixture was diluted with ethyl acetate and washed with 1N HCl, followed by water and brine. The solvent was removed and the residue purified by Combiflash using 32% ethyl acetate/hexane as an eluant to give 2-(4-fluorophenyl)-5-isopropoxy-N-methyl-6-((2,2,2,-trifluoroethyl)amino)benzofuran-3-carboxamide as a white solid product (850 mg, 81%). $^1$H NMR (400 MHz, CHLOROFORM-d) δ=7.83-7.78 (m, 2H), 7.18-7.12 (t, J=8.8 Hz, 2H), 6.81 (s, 1H), 5.74 (br. s., 1H), 4.89 (t, J=7.1 Hz, 1H), 4.64 (td, J=6.0, 12.1 Hz, 1H), 3.87-3.76 (m, 2H), 2.97 (d, J=4.9 Hz, 3H), 1.38 (d, J=6 Hz, 6H). LCMS: (ES+) m/z=425.1 (M+H)$^+$, Column-ACQUITY UPLC BEH C18 (50×2.1 mm; 1.7 m). M phase A: 0.1% TFA in water. M phase B: Acetonitrile. Flow: 0.8 ml/min. Rt min: 1.07 min, wavelength: 220 nm.

2-(4-Fluorophenyl)-5-hydroxy-N-methyl-6-((2,2,2,-trifluoroethyl)amino)benzofuran-3-carboxamide

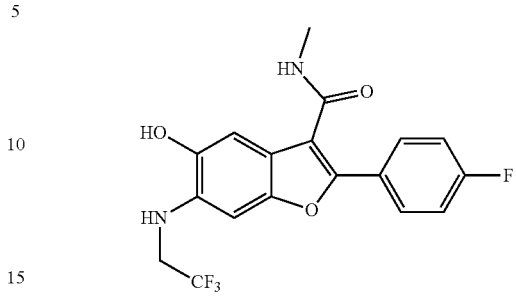

To a solution of 2-(4-fluorophenyl)-5-isopropoxy-N-methyl-6-((2,2,2-trifluoroethyl)amino)benzofuran-3-carboxamide (0.85 g, 2.003 mmol) in DCM (2 mL) at −50° C. was added boron trichloride (6.0 mL, 6.0 mmol, 1M in DCM) dropwise. The reaction mixture was slowly allowed to stir at 25° C. for 4 hours. The solvent was removed under vacuum and ice-cold water was added to the residue. The solid formed was filtered and dried under suction to get 2-(4-fluorophenyl)-5-hydroxy-N-methyl-6-((2,2,2,-trifluoroethyl)amino)benzofuran-3-carboxamide as a white solid product (700 mg, 91%). $^1$H NMR (400 MHz, DMSO-d$_6$) δ=9.69 (s, 1H), 8.31-8.27 (t, J=10 Hz, 1H), 7.88-7.82 (m, 2H), 7.35-7.27 (m, 2H), 6.99 (s, 1H), 6.88-6.87 (d, J=5.6 Hz, 1H), 5.61 (t, J=7.0 Hz, 1H), 4.09-4.01 (t, J=16.4 Hz, 2H), 2.80 (d, J=4.6 Hz, 3H). LCMS: (ES+) m/z=383.1 (M+H)$^+$, Column-ACQUITY UPLC BEH C8 (50×2.1 mm; 1.7 m), M phase A: 5 mM Ammonium Acetate: ACN (95:5), M phase B: 5 mM Ammonium Acetate: ACN (5:95), Flow: 0.8 ml/min. Rt min: 0.96 min, wavelength: 220 nm.

2-(4-Fluorophenyl)-3-(methylcarbamoyl)-6-((2,2,2,-trifluoroethyl)amino)benzofuran-5-yltrifluoromethanesulfonate

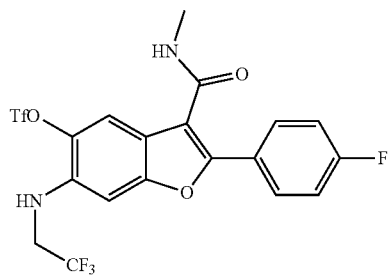 [SMILES: CNC(=O)c1c(-c2ccc(F)cc2)oc2cc(NCC(F)(F)F)c(OS(=O)(=O)C(F)(F)F)cc12]

To a solution of 2-(4-fluorophenyl)-5-hydroxy-N-methyl-6-((2,2,2-trifluoroethyl)amino)benzofuran-3-carboxamide (0.8 g, 2.093 mmol) in DCM (100 mL) was added TEA (0.583 mL, 4.19 mmol) dropwise. The mixture was cooled to 0° C. and then 1,1,1-trifluoro-N-phenyl-N-(trifluoromethyl)sulfonyl methanesulfonamide (0.748 g, 2.093 mmol) was added portionwise to it. The reaction was stirred at 25° C. for 16 hours. To the reaction mixture was added water (100 ml), and the resulting mixture extracted with ethyl acetate (3×50 ml). The organic layer was separated, dried over Na$_2$SO$_4$ and concentrated to obtain 2-(4-fluorophenyl)-3-(methylcarbamoyl)-6-((2,2,2,-trifluoroethyl)amino)benzofuran-5-yltrifluoromethanesulfonate as an off white solid product (500 mg, 46.5%). LCMS: (ES+) m/z=515.1

(M+H)+, Column-ACQUITY UPLC BEH C18 (50×2.1 mm; 1.7 μm). M phase A: 0.1% TFA in water. M phase B: Acetonitrile. Flow: 0.8 ml/min. Rt min: 1.05 min, wavelength: 220 nm.

Methyl 5-(2-(4-fluorophenyl)-3-(methylcarbamoyl)-6-((2,2,2-trifluoroethyl)amino)benzofuran-5-yl)-2-methoxybenzoate

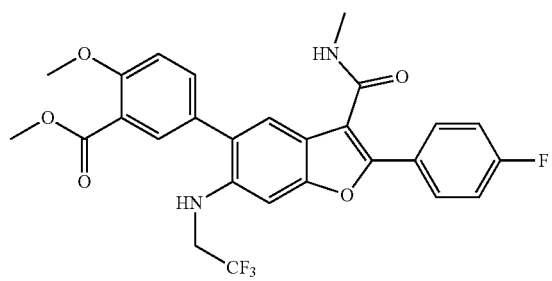 [SMILES: CNC(=O)c1c(-c2ccc(F)cc2)oc2cc(NCC(F)(F)F)c(-c3ccc(OC)c(C(=O)OC)c3)cc12]

A solution of 2-(4-fluorophenyl)-3-(methylcarbamoyl)-6-((2,2,2-trifluoroethyl)amino)benzofuran-5-yl trifluoromethanesulfonate (0.3 g, 0.583 mmol), methyl 2-methoxy-5-(4,4,5,5-tetramethyl-1,3,2-dioxaborolan-2-yl)benzoate (0.204 g, 0.700 mmol) and cesium carbonate (0.570 g, 1.750 mmol) in a mixture of dioxane (5 mL)/water (0.5 mL) was degasified for 5 min.

Tetrakis(triphenylphosphine)palladium(0) (0.034 g, 0.029 mmol) was added to the mixture, which was then degasified again for 5 min. The resulting reaction mixture was heated at 90° C. for 5 hrs. The mixture was passed through a celite bed and the celite washed with EtOAc (100 ml). The filtrate was washed with water, and the organic layer was dried over Na$_2$SO$_4$, filtered and concentrated. The residue was purified by Combi-flash silica gel column chromatography using 25% ethyl acetate/n-hexane as a mobile phase to obtain methyl 5-(2-(4-fluorophenyl)-3-(methylcarbamoyl)-6-((2,2,2-trifluoroethyl)amino)benzofuran-5-yl)-2-methoxybenzoate as a white solid product (220 mg, 71.1%). $^1$H NMR (400 MHz, DMSO-d$_6$) δ ppm 8.34-8.31 (d, J=1.6, 1H), 7.94-7.91 (m, 2H), 7.66 (d, J=2.4 Hz, 1H), 7.57-7.53 (m, 1H), 7.37-7.28 (m, 3H), 7.21-7.18 (m, 2H), 5.33 (t, J=6.8 Hz, 1H), 4.07-3.98 (m, 2H), 3.89 (s, 3H), 3.80 (s, 3H), 2.79 (s, 3H). LCMS: (ES+) m/z=531.1 (M+H)+, Column-ACQUITY UPLC BEH C18 (50×2.1 mm; 1.7 μm). M phase A: 0.1% TFA in water, M phase B: Acetonitrile. Flow: 0.8 ml/min. Rt min: 1.02 min, wavelength: 220 nm.

5-(2-(4-Fluorophenyl)-3-(methylcarbamoyl)-6-((2,2,2-trifluoroethyl)amino)benzofuran-5-yl)-2-methoxybenzoic Acid

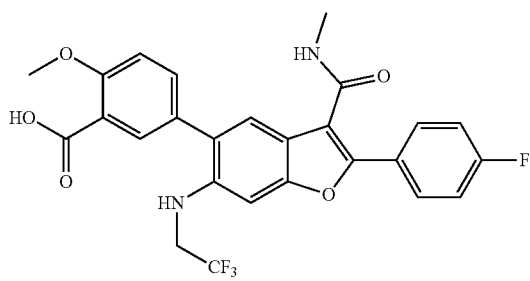 [SMILES: CNC(=O)c1c(-c2ccc(F)cc2)oc2cc(NCC(F)(F)F)c(-c3ccc(OC)c(C(=O)O)c3)cc12]

To a mixture of methyl 5-(2-(4-fluorophenyl)-3-(methylcarbamoyl)-6-((2,2,2-trifluoroethyl)amino)benzofuran-5-yl)-2-methoxybenzoate (0.21 g, 0.396 mmol) in THF (4 mL) in a 50 ml RB flask was added NaOH (1.188 mL, 1.188 mmol), and the mixture stirred at 25° C. for 4 hrs. The volatiles were removed under vacuum, and the residue acidified to pH 2. The solid was filtered and dried to obtain 5-(2-(4-fluorophenyl)-3-(methylcarbamoyl)-6-((2,2,2-trifluoroethyl)amino)benzofuran-5-yl)-2-methoxybenzoic acid as a yellow solid (180 mg, 88%). LCMS: (ES+) m/z=517.1 (M+H)+, Column-ACQUITY UPLC BEH C18 (50×2.1 mm; 1.7 μm). M phase A: 0.1% TFA in water, M phase B: Acetonitrile. Flow: 0.8 ml/Min. Rt min: 0.95 min, wavelength: 220 nm.

tert-Butyl 3-(2-(4-fluorophenyl)-3-(methylcarbamoyl)-6-((2,2,2,-trifluoroethyl)amino)benzofuran-5-yl)benzoate

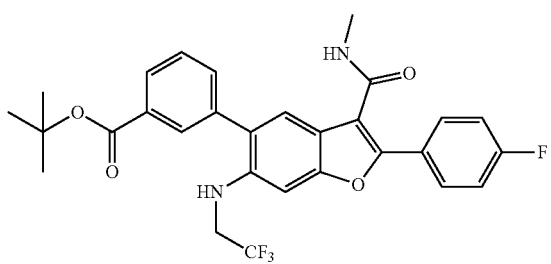 [SMILES: CNC(=O)c1c(-c2ccc(F)cc2)oc2cc(NCC(F)(F)F)c(-c3cccc(C(=O)OC(C)(C)C)c3)cc12]

A solution of 2-(4-fluorophenyl)-3-(methylcarbamoyl)-6-((2,2,2-trifluoroethyl)amino)benzofuran-5-yl trifluoromethanesulfonate (0.12 g, 0.233 mmol), tert-butyl 3-(4,4,5,5-tetramethyl-1,3,2-dioxaborolan-2-yl)benzoate (0.071 g, 0.233 mmol) and cesium carbonate (0.190 g, 0.583 mmol) in a dioxane (4 mL)/water (0.5 mL) mixture was degasified for 5 min.

Tetrakis(triphenylphosphine)palladium(0) (0.013 g, 0.012 mmol) was added to the mixture, which was then degasified again for 5 min. The resulting reaction mixture was stirred at 90° C. for 4 hrs. The reaction mixture was passed through a celite bed, and the celite washed with EtOAc (100 ml). The filtrate was washed with water, and the organic layer separated, dried over Na$_2$SO$_4$ and then concentrated. The residue was purified by Combiflash using 25% ethyl acetate/n-hexane as a mobile phase to obtain tert-butyl 3-(2-(4-fluorophenyl)-3-(methylcarbamoyl)-6-((2,2,2,-trifluoroethyl)amino)benzofuran-5-yl)benzoate as a white solid product (100 mg, 79%). $^1$H NMR (300 MHz, CHLOROFORM-d) δ=8.04 (s, 2H), 7.95-7.91 (m, 2H), 7.57-7.51 (m, 3H), 7.19 (t, J=8.7 Hz, 1H), 6.96 (s, 1H), 5.83 (s, 1H), 4.21-4.14 (m, 1H), 3.84-3.78 (m, 1H), 3.00 (d, J=4.9 Hz, 3H), 1.63 (s, 9H). LCMS: (ES+) m/z=543.2 (M+H)+, Column-ACQUITY UPLC BEH C18 (50×2.1 mm; 1.7 m). M phase A: 0.1% TFA in water. M phase B: Acetonitrile. Flow: 0.8 ml/min. Rt min: 1.15 min, wavelength: 220 nm.

3-(2-(4-Fluorophenyl)-3-(methylcarbamoyl)-6-((2,2,2,-trifluoroethyl)amino)benzofuran-5-yl)benzoic Acid

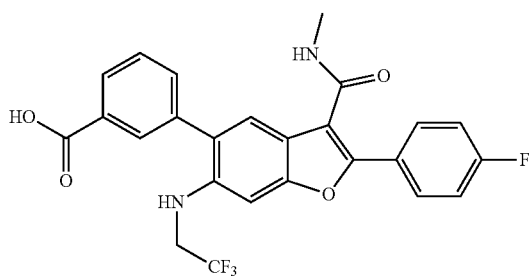 [SMILES: CNC(=O)c1c(-c2ccc(F)cc2)oc2cc(NCC(F)(F)F)c(-c3cccc(C(=O)O)c3)cc12]

A mixture of tert-butyl 3-(2-(4-fluorophenyl)-3-(methylcarbamoyl)-6-((2,2,2-trifluoroethyl)amino)benzofuran-5-yl)benzoate (0.1 g, 0.184 mmol) in TFA (1 mL) in a 50 ml RB flask was stirred at 25° C. for 2 hours. The reaction was monitored by TLC to check for the absence of starting material. The TFA was then removed under vacuum, and the solid residue washed with hexane (3×10 ml) to obtain 3-(2-(4-fluorophenyl)-3-(methylcarbamoyl)-6-((2,2,2,-trifluoroethyl)amino)benzofuran-5-yl)benzoic acid as a white solid product (85 mg, 95%). $^1$H NMR (400 MHz, DMSO-$d_6$) δ=13.00 (s, 1H) 8.35-8.30 (m, 1H), 8.01-7.91 (m, 3H), 7.65 (d, J=1.4 Hz, 2H), 7.35 (t, J=8.7 Hz, 2H), 7.25-7.21 (m, 2H), 5.37 (s, 1H), 4.06-4.00 (m, 2H), 2.79-2.77 (d, J=4.4, 3H). LCMS: (ES+) m/z=487.1 (M+H)$^+$, Column-ACQUITY UPLC BEH C18 (50×2.1 mm; 1.7 m). M phase A: 0.1% TFA in water. M phase B: Acetonitrile. Flow: 0.97 ml/min. Rt min: 1.15 min, wavelength: 220 nm.

2-(4-Fluorophenyl)-5-isopropoxy-N-methyl-6-(4,4,5,5-tetramethyl-1,3,2-dioxaborolan-2-yl)benzofuran-3-carboxamide

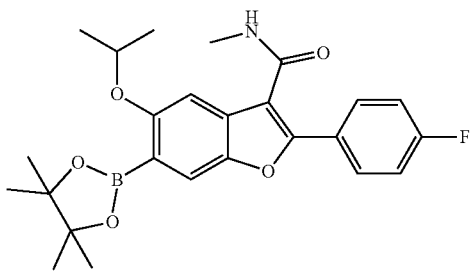 [SMILES: CNC(=O)c1c(-c2ccc(F)cc2)oc2cc(B3OC(C)(C)C(C)(C)O3)c(OC(C)C)cc12]

To a mixture of 6-bromo-2-(4-fluorophenyl)-5-isopropoxy-N-methylbenzofuran-3-carboxamide (4.0 g, 9.85 mmol) and bis(pinacolato)diboron (3.75 g, 14.77 mmol) in dioxane (100 mL) in a 250 ml round-bottomed flask was added potassium acetate (2.416 g, 24.62 mmol) and the mixture degassed for 5 min. PdCl$_2$(dppf)-CH$_2$Cl$_2$ adduct (0.402 g, 0.492 mmol) was added to the mixture, which was then degassed again for 5 min. The resulting reaction mixture was stirred at 90° C. for 12 hours. The TLC analysis showed formation of product. The reaction mixture was filtered through a celite bed, and the celite bed washed with EtOAc (50) ml. The organic layer was then dried over Na$_2$SO$_4$, filtered and concentrated. The crude product was purified by Combiflash silica gel column chromatography using 30% EtOAc in Petroleum ether as an eluant to give 2-(4-fluorophenyl)-5-isopropoxy-N-methyl-6-(4,4,5,5-tetramethyl-1,3,2-dioxaborolan-2-yl)benzofuran-3-carboxamide as a white solid. Yield: 3.6 g (81%). LCMS: (ES+) m/z=454 (M+H)$^+$. Column-ACQUITY UPLC BEH C18 (50×2.1 mm; 1.7 m). M phase A: 0.1% TFA in water, M phase B: Acetonitrile. Flow: 0.8 ml/min., Rt min: 1.14, wavelength: 220 nm., and gradient:

| Time | % A | % B |
|---|---|---|
| 0 | 98 | 2 |
| 1.0 | 2 | 98 |
| 1.6 | 2 | 98 |

2-(4-Fluorophenyl)-6-hydroxy-5-isopropoxy-N-methylbenzofuran-3-carboxamide

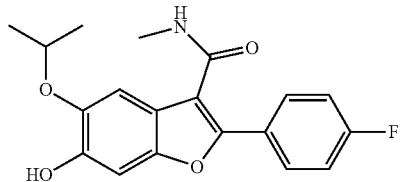 [SMILES: CNC(=O)c1c(-c2ccc(F)cc2)oc2cc(O)c(OC(C)C)cc12]

To a solution of 2-(4-fluorophenyl)-5-isopropoxy-N-methyl-6-(4,4,5,5-tetramethyl-1,3,2-dioxa borolan-2-yl) benzofuran-3-carboxamide (3.6 g, 7.94 mmol) in ethyl acetate (80 mL) was added hydrogen peroxide (24.34 mL, 238 mmol) dropwise and slowly for 15 min. Then the reaction was stirred at 25° C. for 12 hours. The TLC showed formation of product. The aqueous layer was separated. Aqueous sodium thiosulphate was added slowly to the ethyl acetate layer under cooling condition. After quenching the organic layer was separated. The aqueous layer was extracted with (2×100 ml) ethyl acetate, and the organic layer separated. The combined organic layers were concentrated under reduced pressure at 40° C. to obtain a pale yellow liquid. The crude product was purified by Combiflash silica gel column chromatography using 25% EtOAc in Petroleum ether as an eluant to give 2-(4-fluorophenyl)-6-hydroxy-5-isopropoxy-N-methyl-benzofuran-3-carboxamide as a pale yellow solid. Yield: 1.2 g (44%). $^1$H NMR (400 MHz, CHLOROFORM-d) δ=7.83-7.78 (m, 2H), 7.34 (s, 1H), 7.19-7.13 (m, 2H), 7.09-7.07 (m, 1H), 5.99 (s, 1H), 5.77-5.71 (m, 1H), 4.68 (spt, J=6.1 Hz, 1H), 2.97 (d, J=4.9 Hz, 3H), 1.42-1.38 (m, 6H). LCMS: (ES+) m/z=344.1 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min., Rt min: 0.90, wavelength: 220 nm., and gradient:

| Time | % A | % B |
|---|---|---|
| 0 | 98 | 2 |
| 1.0 | 2 | 98 |
| 1.6 | 2 | 98 |

6-Ethoxy-2-(4-fluorophenyl)-5-isopropoxy-N-methylbenzofuran-3-carboxamide

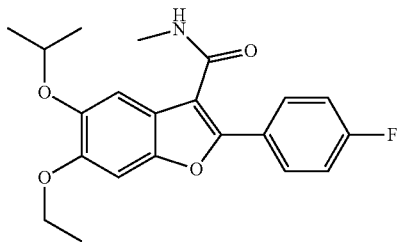 [SMILES: CCOc1cc2oc(-c3ccc(F)cc3)c(C(=O)NC)c2cc1OC(C)C]

To a solution of 2-(4-fluorophenyl)-6-hydroxy-5-isopropoxy-N-methylbenzofuran-3-carboxamide (1.2 g, 3.49 mmol) in DMF (5 mL) was added cesium carbonate (1.708 g, 5.24 mmol) followed by ethyl iodide (0.282 mL, 3.49 mmol). The reaction mixture was then stirred at 25° C. for 12 hours. The reaction mixture was quenched with water and extracted with ethyl acetate (2×100 ml). The combined organic extracts were dried over $Na_2SO_4$, filtered and concentrated to give 6-ethoxy-2-(4-fluorophenyl)-5-isopropoxy-N-methyl-benzofuran-3-carboxamide as a pale yellow solid. Yield: 1.1 g (85%). $^1$H NMR (400 MHz, CHLOROFORM-d) δ ppm=7.87 (dd, J=5.4, 8.9 Hz, 2H), 7.34 (s, 1H), 7.15 (t, J=8.8 Hz, 2H), 7.04 (s, 1H), 5.78 (bs, 1H), 4.51-4.45 (m, 1H), 4.11 (q, J=7.0 Hz, 2H), 3.00 (d, J=4.7 Hz, 3H), 1.53-1.49 (m, 3H), 1.36 (d, J=6 Hz, 6H). LCMS: (ES+) m/z=372.4 (M+H)$^+$. Column-ACQUITY UPLC BEH C8 (50×2.1 mm; 1.7 m). Buffer: 10 mM Ammonium Acetate pH-5 adjusted with HCOOH, M phase A: Buffer: MeCN (95:5). M phase B: Buffer: MeCN (5:95). Flow: 0.8 ml/min., Rt min: 1.11, wavelength: 220 nm., and gradient:

| Time | % A | % B |
| --- | --- | --- |
| 0 | 95 | 5 |
| 1.1 | 5 | 95 |
| 1.7 | 5 | 95 |

6-Ethoxy-2-(4-fluorophenyl)-5-hydroxy-N-methylbenzofuran-3-carboxamide

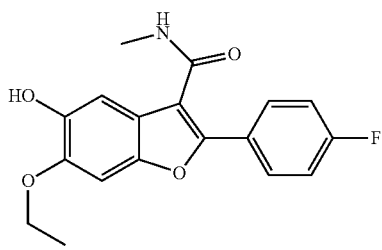 [SMILES: CCOc1cc2oc(-c3ccc(F)cc3)c(C(=O)NC)c2cc1O]

To a solution of 6-ethoxy-2-(4-fluorophenyl)-5-isopropoxy-N-methylbenzofuran-3-carboxamide (1.1 g, 2.96 mmol) in DCM (50 mL) at −78° C. was added boron trichloride (8.89 mL, 8.89 mmol) dropwise. The reaction mixture was slowly allowed to stir at 0° C. for 3 hours, and then quenched with ice-cold water at the same temperature. The mixture was extracted with DCM (2×100 ml). The combined organic extracts were dried over $Na_2SO_4$, filtered and concentrated to give 6-ethoxy-2-(4-fluorophenyl)-5-hydroxy-N-methylbenzofuran-3-carboxamide as a pale yellow solid. Yield: 0.95 g (97%). LCMS: (ES+) m/z=330.1 (M+H)$^+$. Column-ACQUITY UPLC BEH C18 (50×2.1 mm; 1.7 m). M phase A: 0.1% TFA in water. M phase B: Acetonitrile. Flow: 0.8 ml/min., Rt min: 0.86, wavelength: 220 nm., and gradient:

| Time | % A | % B |
| --- | --- | --- |
| 0 | 98 | 2 |
| 1.0 | 2 | 98 |
| 1.6 | 2 | 98 |

6-Ethoxy-2-(4-fluorophenyl)-3-(methylcarbamoyl)benzofuran-5-yl trifluoromethanesulfonate

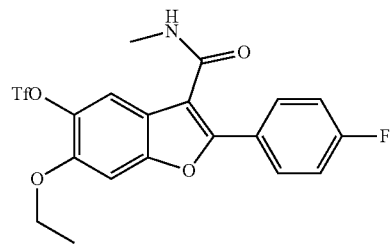 [SMILES: CCOc1cc2oc(-c3ccc(F)cc3)c(C(=O)NC)c2cc1OS(=O)(=O)C(F)(F)F]

To a solution of 6-ethoxy-2-(4-fluorophenyl)-5-hydroxy-N-methylbenzofuran-3-carboxamide (0.95 g, 2.88 mmol) in DMF (12 mL) was added DMAP (1.057 g, 8.65 mmol) and then 1,1,1-trifluoro-N-phenyl-N-(trifluoromethyl)sulfonylmethanesulfonamide (1.134 g, 3.17 mmol) portionwise. The reaction was stirred at 25° C. for 12 hours. The reaction mixture was quenched with ice-cold water, the solid formed was filtered and dried under suction to give 6-ethoxy-2-(4-fluorophenyl)-3-(methylcarbamoyl)benzofuran-5-yl trifluoromethanesulfonate as a white solid. Yield: 1.2 g (90%). LCMS: (ES+) m/z=462.2 (M+H)$^+$. Column-ACQUITY UPLC BEH C8 (50×2.1 mm; 1.7 m). M phase A: 5 mM Ammonium Acetate: MeCN (95:5). M phase B: 5 mM Ammonium Acetate: MeCN (5:95). Flow: 0.8 ml/m., Rt min: 1.18, wavelength: 220 nm., and gradient:

| Time | % A | % B |
| --- | --- | --- |
| 0 | 95 | 5 |
| 1.1 | 5 | 95 |
| 1.7 | 5 | 95 | tert-Butyl 3-(6-ethoxy-2-(4-fluorophenyl)-3-(methylcarbamoyl) benzofuran-5-yl)benzoate

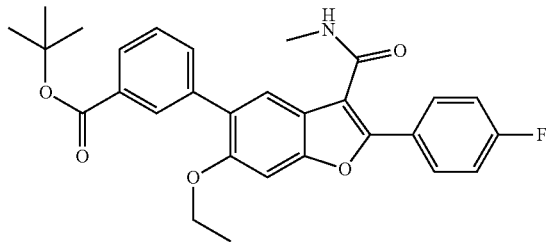 [SMILES: CCOc1cc2oc(-c3ccc(F)cc3)c(C(=O)NC)c2cc1-c1cccc(C(=O)OC(C)(C)C)c1]

A solution of 6-ethoxy-2-(4-fluorophenyl)-3-(methylcarbamoyl)benzofuran-5-yl trifluoro methanesulfonate (0.3 g, 0.650 mmol), tert-butyl 3-(4,4,5,5-tetramethyl-1,3,2-dioxaborolan-2-yl) benzoate (0.170 g, 0.559 mmol) and cesium carbonate (0.530 g, 1.626 mmol) in a DMF (5 mL)/water (0.5 mL) mixture was degasified for 5 min. To the mixture was added tetrakis(triphenylphosphine)palladium(0) (0.038 g, 0.033 mmol), and the mixture was degasified once again for 5 min. The resulting reaction mixture was stirred at 110° C. for 3 hrs. The reaction mixture was passed through a celite bed and the bed was washed with EtOAc (100 ml). The filtrate was washed with water, dried over $Na_2SO_4$ and concentrated. The residue was purified by Combi-flash with 25% ethyl acetate/n-hexane as a mobile phase to get tert-butyl 3-(6-ethoxy-2-(4-fluorophenyl)-3-(methylcarbamoyl) benzofuran-5-yl)benzoate as a white solid product (310 mg, 97%). $^1$H NMR (400 MHz, $CDCl_3$) δ ppm=8.17 (t, J=1.5 Hz, 1H), 8.02 (s, 1H), 7.98-7.91 (m, 2H), 7.71-7.64 (m, 1H), 7.48-7.42 (m, 2H), 7.21-7.14 (m, 2H), 7.12 (s, 1H), 5.85 (bs, 1H), 4.09 (q, J=7.0 Hz, 2H), 3.02-2.99 (m, 3H), 1.57 (d, J=8.2 Hz, 9H), 1.41-1.36 (t, J=6.8, 3.0 Hz, 3). LCMS: (ES+) m/z=490.2 (M+H)$^+$. Column-ACQUITY UPLC BEH C18 (50×2.1 mm; 1.7 m). M phase A: 0.1% TFA in water. M phase B: Acetonitrile. Flow: 0.8 ml/min. Rt min: 1.20 min, wavelength: 220 nm.

3-(6-Ethoxy-2-(4-fluorophenyl)-3-(methylcarbamoyl)benzofuran-5-yl)benzoic Acid

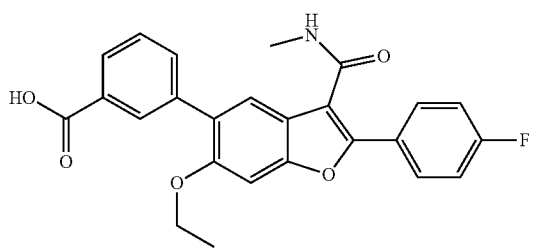 [SMILES: CCOc1cc2oc(-c3ccc(F)cc3)c(C(=O)NC)c2cc1-c1cccc(C(=O)O)c1]

A brown solution of tert-butyl 3-(6-ethoxy-2-(4-fluorophenyl)-3-(methylcarbamoyl)benzofuran-5-yl)benzoate (0.31 g, 0.633 mmol) in TFA (2 mL) in a 50 ml RB flask was stirred at 25° C. for 1 hour. The reaction was monitored by TLC to check the absence of starting material. The TFA was removed under vacuum, and the solid washed with hexane (3×10 ml) to get 3-(6-ethoxy-2-(4-fluorophenyl)-3-(methylcarbamoyl)benzofuran-5-yl)benzoic acid as a white solid product (270 mg, 98%). $^1$H NMR (300 MHz, DMSO-$d_6$) δ ppm 8.45-8.41 (m, 1H), 8.14 (s, 1H), 8.00-7.92 (m, 3H), 7.79 (d, J=8.0 Hz, 1H), 7.60-7.47 (m, 3H), 7.38 (t, J=8.9 Hz, 2H), 4.15 (q, J=6.9 Hz, 2H), 2.82 (d, J=4.7 Hz, 3H), 1.30 (t, J=6.9 Hz, 3H). LCMS: (ES+) m/z=434.2 (M+H)$^+$. Column-ACQUITY UPLC BEH C18 (50×2.1 mm; 1.7 μm). M phase A: 0.1% TFA in water. M phase B: Acetonitrile. Flow: 0.8 ml/min. Rt min: 0.96 min, wavelength: 220 nm.

3-(Benzyloxy)-1-(1,1-dimethylethylsulfinamido)-N'-hydroxycyclobutanecarboximidamide

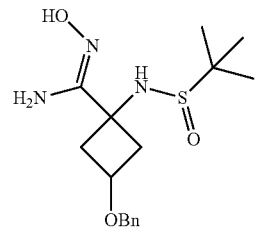 [SMILES: CC(C)(C)S(=O)NC1(/C(N)=N/O)CC(OCc2ccccc2)C1]

To a solution of N-(3-(benzyloxy)-1-cyanocyclobutyl)-2-methylpropane-2-sulfinamide (2.8 g, 9.14 mmol) in ethanol (50 ml) was added $K_2CO_3$ (5.04 g, 36.6 mmol) and followed by $NH_2OH.HCl$ (1.261 g, 18.28 mmol). The resulting orange coloured suspension was stirred at rt for 15 hr. After completion of the reaction, the mixture was filtered through a cake of celite and washed thoroughly with MeOH. The combined filtrates were concentrated to get 3-(benzyloxy)-1-(1,1-dimethylethylsulfinamido)-N'-hydroxycyclobutanecarboximidamide as a pale yellow solid (4.4 g, 48%). $^1$H NMR (400 MHz, DMSO-$d_6$) δ ppm 9.29-9.26 (m, 1H), 7.37-7.27 (m, 5H), 6.6-6.7 (2, bs, 1H), 5.76-5.73 (m, 2H), 5.21-5.16 (m, 2H), 3.80-3.75 (m, 1H), 2.97-2.90 (m, 1H), 2.69-2.62 (m, 1H), 2.28-2.22 (m, 1H), 2.07-2.01 (m, 1H), 1.12 (s, 9H); LCMS: (ES+) m/z=340 (M+H)$^+$, Column-ACQUITY UPLC BEH C18 (50×2.1 mm; 1.7 m), M phase (=Mobile phase) A: 0.1% TFA in water, M phase B: Acetonitrile, Flow: 0.8 ml/min, Rt (retention time) min: 0.67, wavelength: 220 nm.

| Time | % A | % B |
|---|---|---|
| 0.0 | 98 | 2 |
| 1.0 | 2 | 98 |
| 1.6 | 2 | 98 |

(All LCMS, analytical HPLC and preparative HPLC gradient time in min.)

N-(3-(Benzyloxy)-1-(1,2,4-oxadiazol-3-yl)cyclobutyl)-2-methylpropane-2-sulfinamide

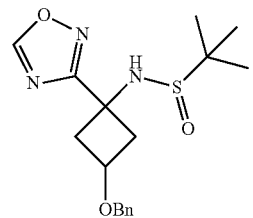 [SMILES: CC(C)(C)S(=O)NC1(c2ncon2)CC(OCc2ccccc2)C1]

To a solution of 3-(benzyloxy)-1-(1,1-dimethylethylsulfinamido)-N'-hydroxycyclobutanecarboximidamide (1.5 g, 4.42 mmol) in AcOH (20 ml) was added triethoxymethane (2.62 g, 17.68 mmol). The resulting mixture was stirred at room temperature for 5 hr. After completion of reaction, the mixture was evaporated under vacuum and the crude compound purified by Combiflash silica gel column chromatography using 60% EtOAc/n-hexane to obtain N-(3-(benzyloxy)-1-(1,2,4-oxadiazol-3-yl)cyclobutyl)-2-methylpropane-2-sulfinamide as a white solid (1.3 g, 84%). $^1$H NMR (400 MHz, CHLOROFORM-d): δ ppm 8.68 (s, 1H), 7.35-7.26 (m, 5H), 4.46 (s, 2H), 4.17-4.11 (m, 1H), 3.18-3.11 (m, 1H), 3.02-2.95 (m, 1H), 2.89-2.78 (m, 1H), 2.69-2.62 (m, 1H), 1.22 (s, 9H); LCMS: (ES+) m/z=350.3 (M+H)$^+$, Column-ACQUITY UPLC BEH C18 (50×2.1 mm; 1.7 μm), M phase A: 0.1% TFA in water, M phase B: Acetonitrile, Flow: 0.8 ml/min, Rt min: 0.85, wavelength: 220 nm.

| Time | % A | % B |
| --- | --- | --- |
| 0.0 | 98 | 2 |
| 1.0 | 2 | 98 |
| 1.6 | 2 | 98 |

3-(Benzyloxy)-1-(1,2,4-oxadiazol-3-yl)cyclobutan-amine

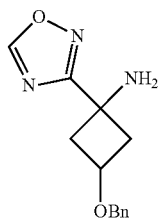 [SMILES: NC1(c2ncon2)CC(OCc2ccccc2)C1]

A mixture of N-(3-(benzyloxy)-1-(1,2,4-oxadiazol-3-yl)cyclobutyl)-2-methylpropane-2-sulfinamide (300 mg, 0.858 mmol) in a solution of HCl in dioxane (5 mL, 20.00 mmol, 4N) was stirred at room temperature for 2 hr. After completion of reaction, the mixture was evaporated under vacuum and the residue triturated with n-Hexane to obtain the hydrochloride salt of 3-(benzyloxy)-1-(1,2,4-oxadiazol-3-yl)cyclobutanamine as a pale yellow semi-solid product (0.78 mmol, 91%). LCMS: (ES+) m/z=246.4 (M+H)$^+$, Column-ACQUITY UPLC BEH C8 (50×2.1 mm; 1.7 μm), M phase A: 5 mM Ammonium Acetate: ACN (95:5), M phase B: 5 mM Ammonium Acetate: ACN (5:95), Flow: 0.8 ml/min, Rt min: 0.74, wavelength: 220 nm.

| Time | % A | % B |
| --- | --- | --- |
| 0.0 | 95 | 5 |
| 1.1 | 5 | 95 |
| 1.7 | 5 | 95 |

Example 1

5-(5-(3-(Benzyloxy)-1-(pyrimidin-2-yl)cyclobutyl-carbamoyl)-2-methylphenyl)-4-fluoro-2-(4-fluoro-phenyl)-N-methylbenzofuran-3-carboxamide

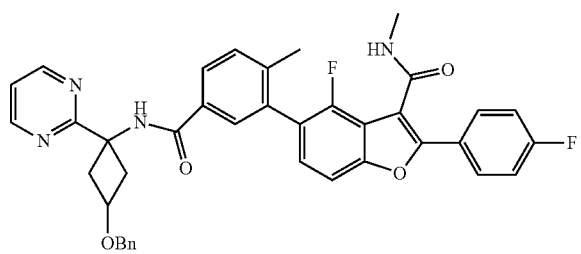 [SMILES: CNC(=O)c1c(-c2ccc(F)cc2)oc2ccc(-c3cc(C(=O)NC4(c5ncccn5)CC(OCc5ccccc5)C4)ccc3C)c(F)c12]

To a mixture of 3-(4-fluoro-2-(4-fluorophenyl)-3-(methylcarbamoyl)benzofuran-5-yl)-4-methylbenzoic acid (500 mg, 1.187 mmol), 3-(benzyloxy)-1-(pyrimidin-2-yl)cyclobutanamine HCl salt (303 mg, 1.187 mmol) and triethylamine (0.827 ml, 5.93 mmol) in DMF (15 ml) at 0° C. under nitrogen was added BOP reagent (787 mg, 1.780 mmol). The reaction mixture was stirred at r.t. overnight. The mixture was then diluted with water, extracted with EtOAc. The organic extract was washed with brine, dried over Na$_2$SO$_4$ and concentrated. The crude product was purified by chromatography using a silica (60-120) column and a mixture of MeOH in CHCl$_3$ as an eluent with the desired fractions collected at 2% MeOH in CHCl$_3$. Yield: 0.550 g (70.4%).

LCMS: (ES+) m/z=659.2 (M+H)$^+$.
Column: PUROSPHER@star RP-18 (4×55) mm, 3 μm
Mphase A: 20 mM NH$_4$OAc in 90% H$_2$O, 10% ACN
Mphase B: 20 mM NH$_4$OAc in 10% H$_2$O, 90% ACN
Flow: 2.5 ml/min

| Time (min.): | 0, | 2, | 2.5, | 3 |
| --- | --- | --- | --- | --- |
| % B: | 0, | 100, | 100, | 0 |

Time (min.): Rt min: 1.98, wavelength: 220 nm

Example 2

5-(5-(3-(Benzyloxy)-1-(pyrimidin-2-yl)cyclobutyl-carbamoyl)-3-fluoro-2-methylphenyl)-4-fluoro-2-(4-fluorophenyl)-N-methylbenzofuran-3-carboxamide

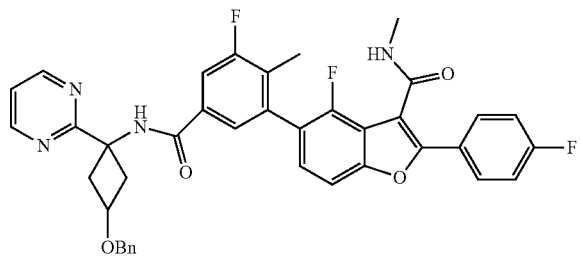 [SMILES: CNC(=O)c1c(-c2ccc(F)cc2)oc2ccc(-c3cc(C(=O)NC4(c5ncccn5)CC(OCc5ccccc5)C4)cc(F)c3C)c(F)c12]

To a mixture of 3-fluoro-5-(4-fluoro-2-(4-fluorophenyl)-3-(methylcarbamoyl)benzofuran-5-yl)-4-methyl benzoic acid (450 mg, 1.024 mmol) and 3-(benzyloxy)-1-(pyrimidin-2-yl)cyclobutanamine HCl salt (261 mg, 1.024 mmol) in DMF (12 mL) at room temperature was added TEA (0.714 mL, 5.12 mmol). The mixture was cooled to 0° C., and then BOP reagent (679 mg, 1.536 mmol) was added to the mixture. The reaction mixture was stirred at r.t. overnight.

The mixture was diluted with water and extracted with EtOAc. The organic extract was washed with brine, dried over Na$_2$SO$_4$ and concentrated. The crude product obtained was purified by chromatography using a silica (60-120) column and MeOH/CHCl$_3$ as eluent. The desired product was collected at 2% MeOH in CHCl$_3$. Yield: 400 mg (57.7%).

LCMS: (ES+) m/z=677.2 (M+H)$^+$.
Column: PUROSPHER@star RP-18 (4×55) mm, 3 μm
Buffer: 20 mM NH$_4$OAc IN water
M phase A: Buffer+ACN (90+10)
M phase B: Buffer+ACN (10+90)
Flow: 2.5 ml/min

| Time (min.): | 0, | 1.82, | 3.3, | 4 |
|---|---|---|---|---|
| % B: | 0, | 100, | 100, | 0 |

Time (min.): Rt min: 2.02, wavelength: 220 nm.

Example 3

5-(5-(3-(Benzyloxy)-1-(pyrimidin-2-yl)cyclobutyl-carbamoyl)-4-methoxy-2-methylphenyl)-4-fluoro-2-(4-fluorophenyl)-N-methylbenzofuran-3-carboxamide

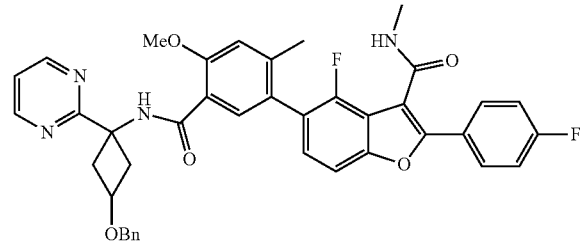 [SMILES: CNC(=O)c1c(-c2ccc(F)cc2)oc2ccc(-c3cc(C(=O)NC4(c5ncccn5)CC(OCc5ccccc5)C4)c(OC)cc3C)c(F)c12]

To a mixture of 5-(4-fluoro-2-(4-fluorophenyl)-3-(methylcarbamoyl)benzofuran-5-yl)-2-methoxy-4-methylbenzoic acid (500 mg, 1.108 mmol) and 3-(benzyloxy)-1-(pyrimidin-2-yl)cyclobutanamine HCl salt (283 mg, 1.108 mmol) in DMF (20 mL) at r.t. under a nitrogen atmosphere was added triethylamine (0.772 mL, 5.54 mmol). The mixture was cooled to 0° C., and BOP (735 mg, 1.661 mmol) reagent was added to the mixture. The reaction mixture was stirred at r.t. overnight. The mixture was diluted with water and extracted with EtOAc (25 ml×2). The combined organic extracts were washed with brine, dried over Na$_2$SO$_4$ and concentrated. The residue was purified by Combiflash silica gel column chromatography using MeOH/CHCl$_3$ as an eluent to give the final product Yield: 400 mg (52.4%).

LCMS: (ES+) m/z=689.2 (M+H)$^+$.
Column: PUROSPHER@star RP-18 (4×55) mm, 3 μm
Buffer: 20 mM NH$_4$OAc in water
M phase A: Buffer+ACN (90+10)
M phase B: Buffer+ACN (10+90)
Flow: 2.5 ml/min

| Time (min.): | 0, | 2, | 2.5, | 3 |
|---|---|---|---|---|
| % B: | 0, | 100 | 100 | 0 |

Time (min.): Rt min: 2.11, wavelength: 220 nm

Example 4

4-Fluoro-2-(4-fluorophenyl)-5-(4-hydroxy-5-(3-hydroxy-1-(pyrimidin-2-yl)cyclobutylcarbamoyl)-2-methylphenyl)-N-methylbenzofuran-3-carboxamide

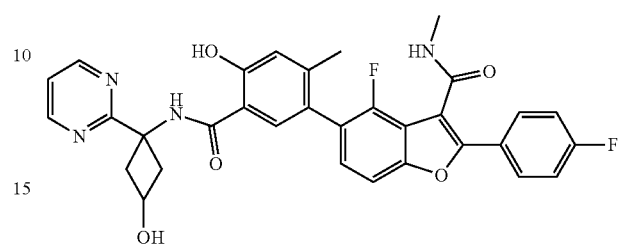

To a solution of 5-(5-(3-(benzyloxy)-1-(pyrimidin-2-yl)cyclobutylcarbamoyl)-4-methoxy-2-methylphenyl)-4-fluoro-2-(4-fluorophenyl)-N-methylbenzofuran-3-carboxamide (Example 3) (350 mg, 0.508 mmol) in DCM (20 mL) at −78° C. under nitrogen was charged a solution of trichloroborane in DCM (5.08 mL, 5.08 mmol). The mixture was allowed to warm to 0° C. and stirred at the same temperature for 4 hr. The reaction mixture was diluted with cold water and extracted with DCM (100 mL×3). The combined organic extracts were washed with brine wash, dried over Na$_2$SO$_4$ and concentrated. The residue was purified by Combiflash using a 12 g silica gel column and MeOH/CHCl$_3$ as an eluant. The desired fraction was collected at 5%. MeOH in CHCl$_3$. Yield: 200 mg (67.3%).

LCMS: (ES−) m/z=583.2 (M−H).
Column: PUROSPHER@star RP-18 (4×55) mm, 3 μm
Buffer: 20 mM NH$_4$OAc in water
Mphase A: Buffer+ACN (90+10)
Mphase B: Buffer+ACN (10+90)
Flow: 2.5 ml/min

| Time (min.): | 0, | 2, | 2.5, | 3 |
|---|---|---|---|---|
| % B: | 0, | 100, | 100, | 0 |

Time (min.): Rt min: 1.72, wavelength: 220 nm

Example 5a and Example 5b

4-Fluoro-2-(4-fluorophenyl)-5-(5-((3-hydroxy-1-(pyrimidin-2-yl)cyclobutyl)carbamoyl)-2-methylphenyl)-N-methylbenzofuran-3-carboxamide

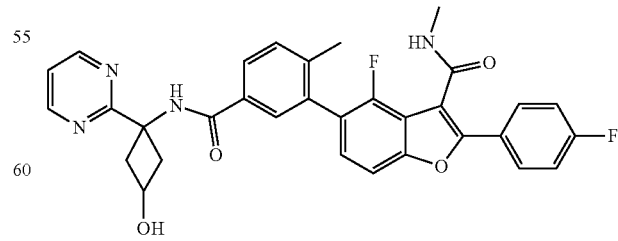

Isomer-I
Example 5a
Isomer-II
Example 5b

Trichloroborane (1.0M in CH₂Cl₂) (2.0 mL, 2.000 mmol) was added to a solution of 5-(5-(3-(benzyloxy)-1-(pyrimidin-2-yl)cyclobutylcarbamoyl)-2-methylphenyl)-4-fluoro-2-(4-fluorophenyl)-N-methylbenzofuran-3-carboxamide (Example 1) (60 mg, 0.091 mmol) and TBAI (tetrabutylammonium iodide) (12.82 mg) in dichloromethane (DCM) (10 mL) at −78° C. under nitrogen. The reaction mixture was allowed to stir at 0° C. for 4 hr. After completion of the reaction (monitored by TLC), the reaction mixture was quenched with ice-cooled water and the product extracted with DCM (20 mL×3). The combined organic layers were washed with brine, dried over Na₂SO₄ and concentrated under reduced pressure. The crude solid product obtained was purified by Prep (preparative) HPLC to afford the two isomers of 4-fluoro-2-(4-fluorophenyl)-5-(5-((3-hydroxy-1-(pyrimidin-2-yl)cyclobutyl)carbamoyl)-2-methylphenyl)-N-methylbenzofuran-3-carboxamide as white solids: Example 5a (Isomer-I), Yield: 8 mg, (15.44%). Example 5b (Isomer-II), Yield: 25 mg, (48.27%). PREPARATIVE HPLC: Column: Chiral pak IC (250×10) mm, 5, Mobile Phase: 0.1% TFA in water (A); THF+ACN=7:3 (B), Flow: 5.0 ml/min, Isocratic: A:B=65:35. Rt: 14.17 and 16.4 min.

Example 5a (Isomer-I) ¹H NMR (400 MHz, METHANOL-d₄) δ=8.76 (d, J=5.0 Hz, 2H), 7.98-7.93 (m, 2H), 7.88 (dd, J=2.0, 8.0 Hz, 1H), 7.82 (m, 1H), 7.55 (d, J=8.4 Hz, 1H), 7.45 (d, J=8.0 Hz, 1H), 7.34-7.26 (m, 4H), 4.59-4.52 (m, 1H), 3.02-2.96 (m, 2H), 2.96 (s, 3H), 2.88-2.82 (m, 2H), 2.28 (s, 3H). ¹⁹F NMR (376.6 MHz, METHANOL-d₄) δ: −112.29, −122.68. LCMS: (ES+) m/z=569.2 (M+H)⁺, Column-Purospher @star RP-18 (4×55) mm, 3 um, Buffer: 20 mM NH₄OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.63 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 9.03 min, Wavelength: 220 nm, Rt: 9.03 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 8.80 min, Wavelength: 220 nm, Rt: 8.80 min.

Example 5b (Isomer-II) ¹H NMR (400 MHz, METHANOL-d₄) δ=8.75 (d, J=4.8 Hz, 2H), 7.98-7.93 (m, 2H), 7.87 (dd, J=1.9, 7.9 Hz, 1H), 7.81 (d, J=2.0 Hz, 1H), 7.54 (d, J=8.5 Hz, 1H), 7.45 (d, J=8.0 Hz, 1H), 7.34-7.26 (m, 4H), 4.57 (quin, J=7.3 Hz, 1H), 3.22-3.16 (m, 2H), 2.96 (s, 3H), 2.62-2.55 (m, 2H), 2.28 (s, 3H). ¹⁹F NMR (376.6 MHz, METHANOL-d₄) δ: −112.28, −122.68. LCMS: (ES+) m/z=569.2 (M+H)⁺, Column-Purospher @star RP-18 (4×55) mm, 3 um, Buffer: 20 mM NH₄OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.64 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 9.06 min, Wavelength: 220 nm, Rt: 9.06 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 8.81 min, Wavelength: 220 nm, Rt: 8.81 min.

Example 6

4-Fluoro-2-(4-fluorophenyl)-N-methyl-5-(2-methyl-5-((3-oxo-1-(pyrimidin-2-yl)cyclobutyl)carbamoyl)phenyl)benzofuran-3-carboxamide

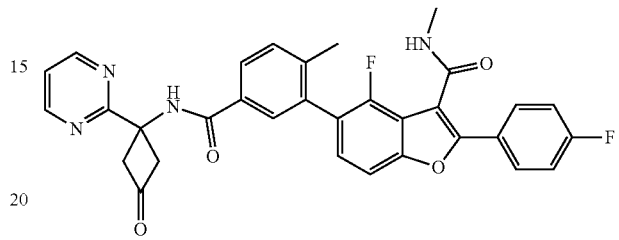

Dess-Martin periodinane (224 mg, 0.528 mmol) was added portion-wise to a stirred solution of 4-fluoro-2-(4-fluorophenyl)-5-(5-(3-hydroxy-1-(pyrimidin-2-yl)cyclobutylcarbamoyl)-2-methylphenyl)-N-methylbenzofuran-3-carboxamide (150 mg, 0.264 mmol) in DCM (25 mL) at ambient temperature under a nitrogen atmosphere. The reaction mixture was stirred at rt overnight. After completion of the reaction (monitored by TLC), the reaction mixture was filtered through a celite bed and the celite bed washed with DCM. The combined filtrates were washed with 10% NaHCO₃ solution, saturated brine solution, and dried over Na₂SO₄ and concentrated under reduced pressure. The crude product was purified by chromatography using a silica gel (60-120) column with 2% MeOH in CHCl₃ as an eluent to obtain 4-fluoro-2-(4-fluorophenyl)-N-methyl-5-(2-methyl-5-((3-oxo-1-(pyrimidin-2-yl)cyclobutyl)carbamoyl)phenyl)benzofuran-3-carboxamide as an off white solid. Yield: 100 mg, (67.11%). ¹H NMR (400 MHz, METHANOL-d₄) δ=8.80 (d, J=5.0 Hz, 2H), 7.98-7.91 (m, 3H), 7.86 (d, J=1.8 Hz, 1H), 7.55 (d, J=8.5 Hz, 1H), 7.49 (d, J=8.0 Hz, 1H), 7.38-7.26 (m, 4H), 3.91-3.74 (m, 4H), 2.96 (s, 3H), 2.30 (s, 3H). ¹⁹F NMR (376.6 MHz, METHANOL-d₄) δ: −112.26, −122.69. LCMS: (ES+) m/z=567.1 (M+H)⁺, Column-Acentis Express C18 (50×2.1 mm; 2.7 um), Buffer: 10 mM Ammonium Formate in Water pH 4.5, Mobile phase A: Buffer: ACN (98:2), Mobile phase B: Buffer:ACN (2:98), Gradient: Time (min)/% B: 0/0, 1.5/100, 3.2/100, Flow: 1.0 ml/min. Rt: 1.84 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 16.99 min, Wavelength: 220 nm, Rt: 16.99 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 10.08 min, Wavelength: 220 nm, Rt: 10.08 min.

Example 7

5-(5-((3,3-Dimethoxy-1-(pyrimidin-2-yl)cyclobutyl)carbamoyl)-2-methylphenyl)-4-fluoro-2-(4-fluorophenyl)-N-methylbenzofuran-3-carboxamide

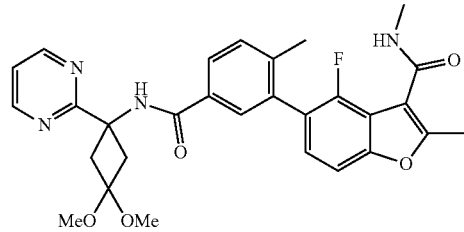

To a stirred solution of 4-fluoro-2-(4-fluorophenyl)-N-methyl-5-(2-methyl-5-(3-oxo-1-(pyrimidin-2-yl)cyclobutylcarbamoyl)phenyl)benzofuran-3-carboxamide (30 mg, 0.053 mmol) in MeOH (2.0 mL) and DCM (2.0 mL) at room temperature was added trimethoxymethane (11.24 mg, 0.106 mmol) followed by p-TsOH (2.014 mg, 10.59 mol). The reaction mixture was stirred at RT overnight. After completion of the reaction (monitored by TLC), the mixture was diluted with water and the product extracted with DCM (20 ml×3). The combined organic layers were washed with 10% NaHCO$_3$ solution, saturated brine solution, dried over Na$_2$SO$_4$ and concentrated under reduced pressure. The crude product was purified by chromatography using a silica gel (60-120) column with 1.5% MeOH in CHCl$_3$ as an eluent to obtained 5-(5-((3,3-dimethoxy-1-(pyrimidin-2-yl)cyclobutyl)carbamoyl)-2-methylphenyl)-4-fluoro-2-(4-fluorophenyl)-N-methylbenzofuran-3-carboxamide as a white solid. Yield: 25 mg, (77.06%). $^1$H NMR (400 MHz, METHANOL-d$_4$) δ=8.76 (d, J=5.0 Hz, 2H), 7.97-7.93 (m, 2H), 7.85 (dd, J=1.9, 7.9 Hz, 1H), 7.79 (d, J=2.0 Hz, 1H), 7.54 (d, J=8.3 Hz, 1H), 7.44 (d, J=8.0 Hz, 1H), 7.33-7.26 (m, 4H), 3.24 (s, 3H), 3.21 (s, 3H), 3.16-3.12 (m, 2H), 2.95 (s, 3H), 2.85-2.81 (m, 2H), 2.28 (s, 3H). $^{19}$F NMR (376.6 MHz, METHANOL-d$_4$) δ: −112.29, −122.67. LCMS for mol. LCMS: (ES−) m/z=611.2 (M−H), Column-PUROSPHER@star RP-18 (4×55) mm, 3 m, Buffer: 20 mM NH$_4$OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.82 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 10.37 min, Wavelength: 220 nm, Rt: 10.37 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 10.08 min, Wavelength: 220 nm, Rt: 10.08 min.

Example 8

5-(5-(3,3-Dimethoxy-1-(pyrimidin-2-yl)cyclobutylcarbamoyl)-3-fluoro-2-methylphenyl)-4-fluoro-2-(4-fluorophenyl)-N-methylbenzofuran-3-carboxamide To a stirred solution of 4-fluoro-5-(3-fluoro-2-methyl-5-(3-oxo-1-(pyrimidin-2-yl)cyclobutylcarbamoyl)phenyl)-2-(4-fluorophenyl)-N-methylbenzofuran-3-carboxamide (50 mg, 0.086 mmol) in MeOH (2.5 mL) and DCM (2.5 mL) at room temperature was added trimethoxymethane (18.15 mg, 0.171 mmol) followed by p-TsOH (3.25 mg, 0.017 mmol). The reaction mixture was stirred at RT overnight. After completion of the reaction (monitored by TLC), the mixture was diluted with water and the product extracted with DCM (25 mL×3). The combined organic extracts were washed with 10% NaHCO$_3$ solution, saturated brine solution, dried over Na$_2$SO$_4$ and concentrated under reduced pressure. The crude product was purified by chromatography using a silica gel (60-120) column and 2.0% MeOH in CHCl$_3$ as an eluent to obtain 5-(5-(3,3-dimethoxy-1-(pyrimidin-2-yl)cyclobutylcarbamoyl)-3-fluoro-2-methylphenyl)-4-fluoro-2-(4-fluorophenyl)-N-methylbenzofuran-3-carboxamide as a white solid. Yield: 35 mg, (64.9%). $^1$H NMR (400 MHz, CHLOROFORM-d) δ=8.72 (d, J=4.8 Hz, 2H), 8.02-7.95 (m, 2H), 7.54-7.48 (m, 2H), 7.40 (d, J=8.3 Hz, 1H), 7.21-7.10 (m, 5H), 6.19 (br. s, 1H), 3.24-3.18 (s, 3H; s, 3H; d, 2H), 3.03 (d, J=5.0 Hz, 3H), 2.75 (d, J=13.8 Hz, 2H), 2.15 (d, J=1.0 Hz, 3H). $^{19}$F NMR (376.6 MHz, CHLOROFORM-d) δ: −109.61, −114.00, −119.02. LCMS: (ES−) m/z=629.2 (M−H), Column-PUROSPHER@star RP-18 (4×55) mm, 3 m, Buffer: 20 mM NH$_4$OAc in water, Mobile phase A: Buffer: ACN (90:10), Mobile phase B: Buffer:ACN (10:90), Gradient: Time (min)/% B: 0/0, 2/100, 2.5/100, 3/0, Flow: 2.5 ml/min. Rt: 1.89 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 17.55 min, Wavelength: 220 nm, Rt: 17.55 min. HPLC Method: XBridge Phenyl (150×4.6 mm)

Example 9a and Example 9b

4-Fluoro-5-(3-fluoro-5-((3-hydroxy-1-(pyrimidin-2-yl)cyclobutyl)carbamoyl)-2-methylphenyl)-2-(4-fluorophenyl)-N-methylbenzofuran-3-carboxamide

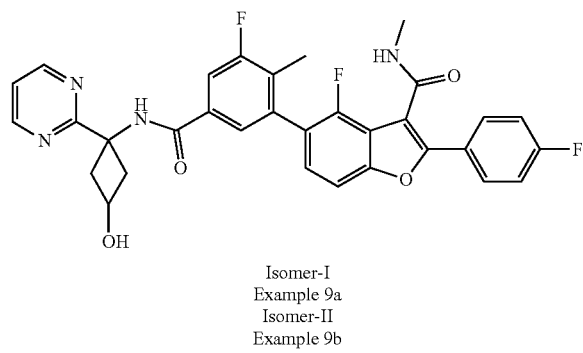 [SMILES: CNC(=O)c1c(-c2ccc(F)cc2)oc2ccc(-c3cc(C(=O)NC4(c5ncccn5)CC(O)C4)cc(F)c3C)c(F)c12]

Isomer-I
Example 9a
Isomer-II
Example 9b

Trichloroborane (1.0M in DCM) (5.17 ml, 5.17 mmol) was added to a solution of 5-(5-(3-(benzyloxy)-1-(pyrimidin-2-yl)cyclobutylcarbamoyl)-3-fluoro-2-methylphenyl)-4-fluoro-2-(4-fluorophenyl)-N-methylbenzofuran-3-carboxamide (Example 2) (350 mg, 0.517 mmol) and TBAI (19.10 mg, 0.052 mmol) in DCM (25 ml) at −78° C. under nitrogen. The reaction mixture was allowed to stir at 0° C. for 6 hr. After completion of the reaction (monitored by TLC), the reaction mixture was quenched with ice-cooled water and the product extracted with DCM (50 ml×3). The combined organic extracts were washed with saturated brine solution, dried over Na$_2$SO$_4$ and concentrated under reduced pressure. The crude product was purified via Combiflash chromatography using a 24 g silica column with 8% MeOH in CHCl$_3$ as an eluent to obtain the mixture of two isomers. The mixture was further purified by Prep HPLC to afford the two isomers of 4-fluoro-5-(3-fluoro-5-((3-hydroxy-1-(pyrimidin-2-yl)cyclobutyl)carbamoyl)-2-methylphenyl)-2-(4-fluorophenyl)-N-methylbenzofuran-3-carboxamide as white solids. Example 9a (Isomer-I), Yield: 10 mg, (3.30%). Example 9b (Isomer-II), Yield: 40 mg, (13.20%). PREPARATIVE HPLC: Column: Chiral pak IC (250×30) mm, 5 t, Mobile Phase: 0.1% TFA in water (A); ACN:THF=7:3 (B), Flow: 25 ml/min, Isocratic: A:B=60:40. Rt: 15.24 and 17.04 min.

Example 9a (Isomer-I) $^1$H NMR (400 MHz, METHANOL-d$_4$) δ=8.76 (d, J=4.8 Hz, 2H), 7.98-7.93 (m, 2H), 7.72-7.67 (m, 2H), 7.56 (d, J=8.5 Hz, 1H), 7.37-7.26 (m, 4H), 4.54 (quin, J=7.3 Hz, 1H), 3.68-3.64 (m, 1H), 3.02-2.97 (m, 2H), 2.96 (s, 3H), 2.88-2.81 (m, 2H), 2.20 (s, 3H). $^{19}$F NMR (376.6 MHz, METHANOL-d$_4$) δ: −112.16, −116.81, −122.54. LCMS: (ES+) m/z=587.2 (M+H)$^+$, Column-PUROSPHER@star RP-18 (4×55) mm, 3 m, Buffer: 20 mM NH$_4$OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.69 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.44 min, Wavelength: 220 nm, Rt: 9.44 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.17 min, Wavelength: 220 nm, Rt: 9.17 min.

Example 9b (Isomer-II) $^1$H NMR (400 MHz, METHANOL-d$_4$) δ=8.75 (d, J=5.0 Hz, 2H), 7.99-7.94 (m, 2H), 7.69 (t, J=4.4 Hz, 2H), 7.56 (d, J=8.3 Hz, 1H), 7.37-7.27 (m, 4H), 4.58 (quin, J=7.2 Hz, 1H), 3.19 (ddd, J=2.8, 7.3, 10.0 Hz, 2H), 2.96 (s, 3H), 2.60-2.54 (m, 2H), 2.20 (s, 3H). $^{19}$F NMR (376.6 MHz, METHANOL-d$_4$) δ: −112.17, −116.78, −122.56. LCMS: (ES+) m/z=587.2 (M+H)$^+$, Column-PUROSPHER@star RP-18 (4×55) mm, 3 m, Buffer: 20 mM NH$_4$OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.69 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 9.45 min, Wavelength: 220 nm, Rt: 9.45 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.16 min, Wavelength: 220 nm, Rt: 9.16 min.

Example 10a and Example 10b

4-Fluoro-2-(4-fluorophenyl)-5-(5-((3-methoxy-1-(pyrimidin-2-yl)cyclobutyl)carbamoyl)-2-methylphenyl)-N-methylbenzofuran-3-carboxamide

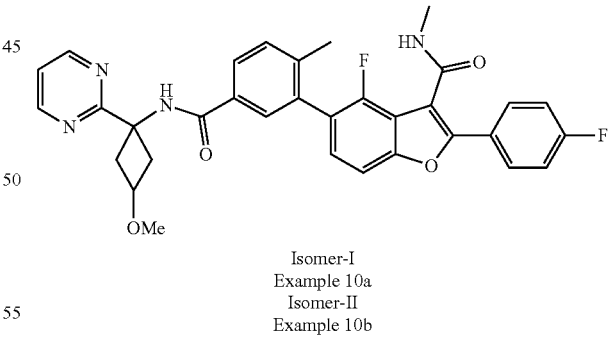

Isomer-I
Example 10a
Isomer-II
Example 10b

To a stirred solution of 4-fluoro-2-(4-fluorophenyl)-5-(5-(3-hydroxy-1-(pyrimidin-2-yl)cyclobutylcarbamoyl)-2-methylphenyl)-N-methylbenzofuran-3-carboxamide (100 mg, 0.176 mmol, isomeric mixture obtained from debenzylation of Example 1 using BCl$_3$/TBAI in DCM and purified by Combiflash with MeOH/CHCl$_3$ as eluent) in DCM (10 mL) at 0° C. under a nitrogen atmosphere was added trimethyloxonium tetrafluroborate (52.0 mg, 0.352 mmol). The reaction mixture was allowed to stir at room temperature overnight. After completion of the reaction (monitored by TLC), the mixture was diluted with water and the product extracted with DCM (20 mL×2). The combined organic extracts were washed with 10% NaHCO$_3$ solution, saturated brine solution, dried over Na$_2$SO$_4$ and concentrated under reduced pressure. The crude product was purified via Combiflash chromatography using a 12 g silica column with 4% MeOH in CHCl$_3$ as an eluent to obtain the mixture of two isomers. The mixture was further purified by Prep HPLC to afford the two isomers of 4-fluoro-2-(4-fluorophenyl)-5-(5-((3-methoxy-1-(pyrimidin-2-yl)cyclobutyl)carbamoyl)-2-methylphenyl)-N-methylbenzofuran-3-carboxamide as white solids.

Example 10a (Isomer-I), Yield: 2.85 mg, (2.78%). Example 10b (Isomer-II), Yield: 18.02 mg, (17.58%). PREPARATIVE HPLC: Column: Chiral pak IC (250×10) mm, 5 t, Mobile Phase: 0.1% TFA in water (A); ACN:THF=7:3 (B), Flow: 5 ml/min, Isocratic: A:B=60:40, Run time=30 min, Rt: 18.96 (Isomer-I) and 24.26 min (Isomer-II).

Example 10a (Isomer-I) $^1$H NMR (400 MHz, METHANOL-d$_4$) δ=8.76 (d, J=5.0 Hz, 2H), 7.99-7.93 (m, 2H), 7.88 (dd, J=1.8, 8.0 Hz, 1H), 7.82 (d, J=1.8 Hz, 1H), 7.54 (d, J=8.5 Hz, 1H), 7.45 (d, J=8.0 Hz, 1H), 7.35-7.26 (m, 4H), 4.26 (t, J=7.3 Hz, 1H), 3.40-3.30 (buried s, 3H), 2.99-2.92 (m, 2H), 2.97 (s, 3H), 2.89-2.82 (m, 2H), 2.29 (s, 3H). $^{19}$F NMR (376.6 MHz, METHANOL-d$_4$) δ: −112.29, −122.68. LCMS: (ES+) m/z=583.2 (M+H)$^+$, Column-PUROSPHER@star RP-18 (4×55) mm, 3 µm, Buffer: 20 mM NH$_4$OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.80 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 10.20 min, Wavelength: 220 nm, Rt: 10.20 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.65 min, Wavelength: 220 nm, Rt: 9.65 min.

Example 10b (Isomer-II) $^1$H NMR (400 MHz, CD$_3$OD) δ ppm=8.76 (d, J=5.02 Hz, 2H); 7.93-7.98 (m, 2H), 7.87 (dd, J=7.91, 1.88 Hz, 1H), 7.81 (d, J=1.76 Hz, 1H), 7.54 (d, J=8.53 Hz, 1H), 7.45 (d, J=8.03 Hz, 1H), 7.25-7.34 (m, 4H), 4.21-4.28 (m, 1H), 3.40-3.30 (buried s, 3H), 3.16-3.18 (m, 2H), 2.98 (s, 3H), 2.53-2.62 (m, 2H), 2.28 (s, 3H). $^{19}$F NMR (376.6 MHz, CD$_3$OD) δ: −112.30, −122.67. LCMS: (ES+) m/z=583.2 (M+H)$^+$, Column-PUROSPHER@star RP-18 (4×55) mm, 3 m, Buffer: 20 mM NH$_4$OAc in water, Mobile phase A: Buffer+ACN (90+10), Mobile phase B: Buffer+ACN (10+90), Gradient: Time (min)/% B: 0/0, 2/100, 2.5/100, 3/0, Flow: 2.5 ml/min. Rt: 1.81 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 10.24 min, Wavelength: 220 nm, Rt: 10.24 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.67 min, Wavelength: 220 nm, Rt: 9.67 min.

Example 11a and Example 11b

4-Fluoro-5-(3-fluoro-5-((3-methoxy-1-(pyrimidin-2-yl)cyclobutyl)carbamoyl)-2-methylphenyl)-2-(4-fluorophenyl)-N-methylbenzofuran-3-carboxamide

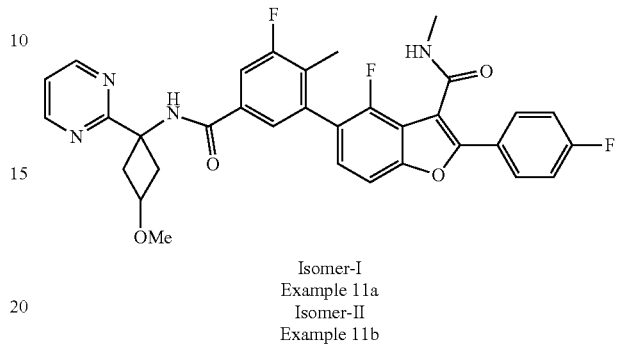

Isomer-I
Example 11a
Isomer-II
Example 11b

To a stirred solution of 4-fluoro-5-(3-fluoro-5-(3-hydroxy-1-(pyrimidin-2-yl)cyclobutylcarbamoyl)-2-methylphenyl)-2-(4-fluorophenyl)-N-methylbenzofuran-3-carboxamide (100 mg, 0.170 mmol, isomeric mixture obtained from debenzylation of Example 2 using BCl$_3$/TBAI in DCM and purified by Combiflash with MeOH/CHCl$_3$ as eluent) in DCM (10 mL) at 0° C. under a nitrogen atmosphere was added trimethyloxonium tetrafluroborate (50.4 mg, 0.341 mmol). The reaction mixture was allowed to stir at room temperature overnight. After completion of the reaction (monitored by TLC), the mixture was diluted with water and the product extracted with DCM (20 mL×3). The combined organic extracts were washed with 10% NaHCO$_3$ solution and saturated brine solution, dried over Na$_2$SO$_4$ and concentrated under reduced pressure. The crude product was purified via Combiflash chromatography using a 12 g silica column with 2% MeOH in CHCl$_3$ as an eluent to obtain the mixture of two isomers. The mixture was further purified by Prep HPLC to afford the two isomers of 4-fluoro-5-(3-fluoro-5-((3-methoxy-1-(pyrimidin-2-yl)cyclobutyl)carbamoyl)-2-methylphenyl)-2-(4-fluorophenyl)-N-methylbenzofuran-3-carboxamide as white solids. Example 11a (Isomer-I) Yield: 2.10 mg, (2.05%).

Example 11b (Isomer-II) Yield: 2.96 mg, (2.89%). PREPARATIVE HPLC: Column: Chiral pak IC (250×10) mm, 5, Mobile Phase: 0.1% TFA in water (A); ACN (B), Flow: 7 ml/min, Isocratic: A:B=40:60, Run time=25 min. Rt: 13.44 (Isomer-I) and 22.21 min (Isomer-II).

Example 11a (Isomer-I) $^1$H NMR (400 MHz, DMSO-d$_6$) δ=9.11 (s, 1H), 8.76 (d, J=4.8 Hz, 2H), 8.71 (d, J=4.8 Hz, 1H), 7.97-7.92 (m, 2H), 7.78 (d, J=10.5 Hz, 1H), 7.74 (s, 1H), 7.69 (d, J=8.5 Hz, 1H), 7.46-7.37 (m, 3H), 7.32 (t, J=4.8 Hz, 1H), 4.12 (quin, J=7.2 Hz, 1H), 3.19 (s, 3H), 2.87 (ddd, J=2.6, 7.0, 9.7 Hz, 2H), 2.81 (d, J=4.8 Hz, 3H), 2.70-2.63 (m, 2H), 2.13 (s, 3H). $^{19}$F NMR (376.6 MHz, DMSO-d$_6$) δ: −110.31, −115.11, −121.30. LCMS: (ES+) m/z=601.2 (M+H)$^+$, Column-PUROSPHER@star RP-18 (4×55) mm, 3 µm, Buffer: 20 mM NH$_4$OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.87 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 17.17 min, Wavelength: 220 nm, Rt: 17.17 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 15.71 min, Wavelength: 220 nm, Rt: 15.71 min.

Example 11b (Isomer-II) $^1$H NMR (400 MHz, DMSO-$d_6$) δ ppm=9.36 (s, 1H), 8.77 (d, J=4.77 Hz, 2H), 8.70 (d, J=4.77 Hz, 1H), 7.90-7.99 (m, 2H), 7.76 (d, J=10.8. 1H), 7.73 (s, 1H), 7.69 (d, J=8.28 Hz, 1H), 7.38-7.47 (m, 3H), 7.32-7.35 (m, 1H), 4.06-4.15 (m, 1H), 3.18 (s, 3H), 2.97-3.05 (m, 2H), 2.81 (d, J=4.77 Hz, 3H), 2.37-2.47 (m, 2H), 2.13 (s, 3H). $^{19}$F NMR (376.6 MHz, DMSO-$d_6$) δ: −110.32, −115.06, −121.30. LCMS: (ES+) m/z=601.2 (M+H)$^+$, Column-PUROSPHER@star RP-18 (4×55 mm, 3 m, Buffer: 20 mM NH$_4$OAc in water, Mobile phase A: Buffer+ACN (90+10), Mobile phase B: Buffer+ACN (10+90), Gradient: Time (min)/% B: 0/0, 2/100, 2.5/100, 3/0, Flow: 2.5 ml/min. Rt: 1.87 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 17.22 min, Wavelength: 220 nm, Rt: 17.22 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 15.73 min, Wavelength: 220 nm, Rt: 15.73 min.

Example 12a and 12b

4-Fluoro-2-(4-fluorophenyl)-5-(5-((3-hydroxy-1-(pyrimidin-2-yl)cyclobutyl)carbamoyl)-4-methoxy-2-methylphenyl)-N-methylbenzofuran-3-carboxamide

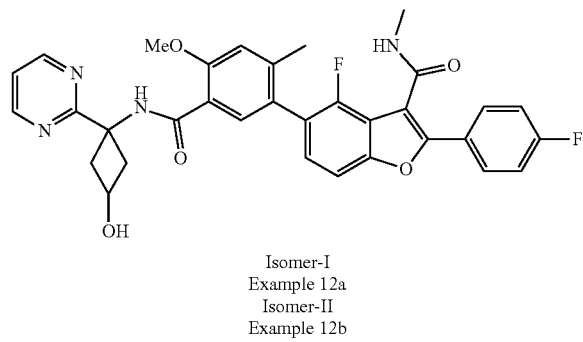 [SMILES: CNC(=O)c1c(-c2ccc(F)cc2)oc2ccc(-c3cc(C(=O)NC4(c5ncccn5)CC(O)C4)c(OC)cc3C)c(F)c12]

Isomer-I
Example 12a
Isomer-II
Example 12b

To a stirred solution of 4-fluoro-2-(4-fluorophenyl)-5-(4-hydroxy-5-(3-hydroxy-1-(pyrimidin-2-yl)cyclobutylcarbamoyl)-2-methylphenyl)-N-methylbenzofuran-3-carboxamide (Example 4) (150 mg, 0.257 mmol) in DMF (6.0 mL) at room temperature was added K$_2$CO$_3$ (70.9 mg, 0.513 mmol). The reaction mixture was cooled to 0° C., and iodomethane (54.6 mg, 0.385 mmol) was added to it. The reaction mixture was allowed stir at rt for 3 hr. After completion of the reaction (monitored by TLC), the mixture was diluted with water and the product extracted with EtOAc (20 mL×2). The combined organic extracts were washed with saturated brine solution, dried over Na$_2$SO$_4$ and concentrated under reduced pressure. The crude product was purified via Combiflash chromatography using a 12 g silica column with 4% MeOH in CHCl$_3$ as an eluent to obtain the mixture of two isomers. The mixture was further purified by Prep HPLC to afford the two isomers of 4-fluoro-2-(4-fluorophenyl)-5-(5-((3-hydroxy-1-(pyrimidin-2-yl)cyclobutyl)carbamoyl)-4-methoxy-2-methylphenyl)-N-methylbenzofuran-3-carboxamide as white solids. Example 12a (Isomer-I), Yield: 16.28 mg, (10.59%). Example 12b (Isomer-II), Yield: 25.46 mg, (16.57%). PREPARATIVE HPLC: Column: Symmetry C18 (300×19) mm, 7 t, Mobile Phase: 0.1% TFA in water (A); ACN (B), Flow: 20 ml/min, Rt: 20.68 and 27.34 min.

Example 12a Isomer-I $^1$H NMR (400 MHz, CHLOROFORM-d) δ=9.65 (s, 1H), 8.82 (d, J=5.0 Hz, 2H), 8.11 (s, 1H), 7.99 (dd, J=5.4, 8.9 Hz, 2H), 7.37 (d, J=8.5 Hz, 1H), 7.29-7.27 (m, 1H), 7.24-7.14 (m, 3H), 6.95 (s, 1H), 6.17 (br. s, 1H), 5.01 (br. s, 1H), 4.67 (br. s., 1H), 4.11 (s, 3H), 3.70-3.61 (m, 2H), 3.02 (d, J=5.0 Hz, 3H), 2.59 (dd, J=2.8, 14.3 Hz, 2H), 2.27 (s, 3H). $^{19}$F NMR (376.6 MHz, CHLOROFORM-d) δ: −110.01, −119.24. LCMS: (ES+) m/z=599.2 (M+H)$^+$, Column-PUROSPHER@star RP-18 (4×55) mm, 3 μm, Buffer: 20 mM NH$_4$OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.75 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 10.03 min, Wavelength: 220 nm, Rt: 10.03 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.28 min, Wavelength: 220 nm, Rt: 9.28 min.

Example 12b (Isomer-II) $^1$H NMR (400 MHz, CHLOROFORM-d) δ=10.46 (s, 1H), 8.81 (d, J=4.8 Hz, 2H), 8.16 (s, 1H), 8.03-7.97 (m, 2H), 7.38 (s, 1H), 7.25-7.21 (m, 2H), 7.17 (t, J=8.7 Hz, 2H), 6.97 (s, 1H), 6.18 (br. s, 1H), 5.06 (d, J=11.8 Hz, 1H), 4.48 (br. s, 1H), 4.13 (s, 3H), 3.24-3.11 (m, 4H), 3.02 (d, J=4.8 Hz, 3H), 2.28 (s, 3H). $^{19}$F NMR (376.6 MHz, CHLOROFORM-d) δ: −109.98, −119.29. LCMS: (ES+) m/z=599.2 (M+H)$^+$, Column-PUROSPHER@star RP-18 (4×55) mm, 3 m, Buffer: 20 mM NH$_4$OAC in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.69 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 9.57 min, Wavelength: 220 nm, Rt: 9.57 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.00 min, Wavelength: 220 nm, Rt: 9.00 min.

Example 13a and 13b

4-Fluoro-2-(4-fluorophenyl)-5-(4-methoxy-5-((3-methoxy-1-(pyrimidin-2-yl)cyclobutyl)carbamoyl)-2-methylphenyl)-N-methylbenzofuran-3-carboxamide

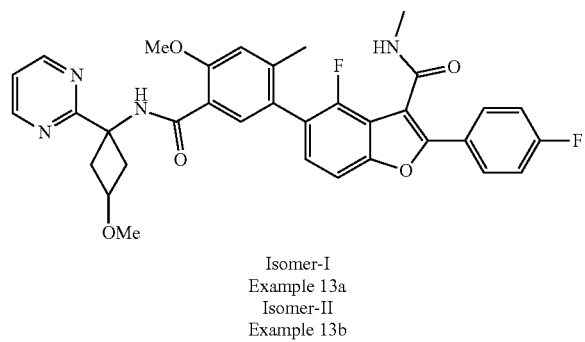

Isomer-I
Example 13a
Isomer-II
Example 13b

To a stirred solution of 4-fluoro-2-(4-fluorophenyl)-5-(5-(3-hydroxy-1-(pyrimidin-2-yl)cyclobutylcarbamoyl)-4-methoxy-2-methylphenyl)-N-methylbenzofuran-3-carboxamide (80 mg, 0.134 mmol, isomeric mixture obtained from Example 4 using iodomethane/$K_2CO_3$ in DMF and purified by Combiflash with MeOH/$CHCl_3$ as eluant and the desired fraction collected at 4% MeOH/$CHCl_3$) in DCM (10 mL) at 0° C. under a nitrogen atmosphere was added trimethyloxonium tetrafluroborate (39.5 mg, 0.267 mmol. The reaction mixture was allowed to stir at room temperature for overnight. After completion of the reaction (monitored by TLC), the mixture was diluted with water and the product extracted with DCM (20 mL×2). The combined organic extracts were washed with 10% $NaHCO_3$ solution and saturated brine solution, dried over $Na_2SO_4$ and concentrated under reduced pressure. The crude product was purified via Combiflash chromatography using a 12 g silica column with 2% MeOH in $CHCl_3$ as an eluent to obtain the mixture of two isomers. The mixture of was further purified by Prep HPLC to afford the two isomers of 4-fluoro-2-(4-fluorophenyl)-5-(4-methoxy-5-((3-methoxy-1-(pyrimidin-2-yl)cyclobutyl)carbamoyl)-2-methylphenyl)-N-methylbenzofuran-3-carboxamide as white solids.

Example 13a (Isomer-I) Yield: 6.70 mg, (8.18%).
Example 13b (Isomer-II) Yield: 11.56 mg, (14.11%). PREPARATIVE HPLC: Column: Chiral pak IC (250×10) mm, 5 t, Mobile Phase: 0.1% TFA in water (A); ACN:THF=70:30 (B), Flow: 6 ml/min, Isocratic: A:B=60:40, Run time=40 min. Rt: 23.38 (Isomer-I) and 31.77 min (Isomer-II).

Example 13a (Isomer-I) $^1$H NMR (400 MHz, CHLOROFORM-d) δ=9.27 (s, 1H), 8.77 (d, J=5.0 Hz, 2H), 8.08 (s, 1H), 8.01-7.96 (m, 2H), 7.35 (d, J=8.3 Hz, 1H), 7.21-7.13 (m, 4H), 6.95 (s, 1H), 6.16 (br. s, 1H), 4.50 (quin, J=7.0 Hz, 1H), 4.10 (s, 3H), 3.34 (s, 3H), 3.04-2.96 (m, 4H), 3.01 (s, 3H), 2.26 (s, 3H). $^{19}$F NMR (376.6 MHz, CHLOROFORM-d) δ: −110.01, 119.21. LCMS: (ES+) m/z=613.2 (M+H)$^+$, Column-PUROSPHER@star RP-18 (4×55) mm, 3 μm, Buffer: 20 mM $NH_4OAc$ in water, Mobile phase A: Buffer:ACN (90:10), Mobile phase B: Buffer: ACN (10:90), Gradient: Time (min)/% B: 0/0, 1.8/100, 3.3/100, 4/0, Flow: 2.5 ml/min. Rt: 1.76 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 17.74 min, Wavelength: 220 nm, Rt: 17.74 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 15.73 min, Wavelength: 220 nm, Rt: 15.73 min.

Example 13b (Isomer-II) $^1$H NMR (400 MHz, CDCl$_3$) δ ppm=9.13 (s, 1H), 8.73 (d, J=5.02 Hz, 2H), 8.06 (s, 1H), 7.98 (dd, J=8.91, 5.40 Hz, 2H), 7.34 (d, J=8.28 Hz, 1H), 7.07-7.22 (m, 4H), 6.93 (s, 1H), 6.17 (br. s, 1H), 4.25 (quin, J=6.90 Hz, 1H), 4.08 (s, 3H), 3.34 (s, 3H), 3.17 (ddd, J=9.98, 7.09, 2.76 Hz, 2H), 3.01 (d, J=4.77 Hz, 3H), 2.79 (ddd, J=9.91, 7.03, 2.64 Hz, 2H), 2.25 (s, 3H) $^{19}$F NMR (376.6 MHz, CDCl$_3$) δ: −110.07, −119.15. LCMS: (ES+) m/z=613.2 (M+H)$^+$, Column-PUROSPHER@star RP-18 (4×55) mm, 3 μm, Buffer: 20 mM $NH_4OAc$ in water, Mobile phase A: Buffer:ACN (90:10), Mobile phase B: Buffer:ACN (10:90), Gradient: Time (min)/% B: 0/0, 1.8/100, 3.3/100, 4/0, Flow: 2.5 ml/min. Rt: 1.79 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 18.11 min, Wavelength: 220 nm, Rt: 18.11 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 15.92 min, Wavelength: 220 nm, Rt: 15.92 min.

Example 14

5-(5-((3,3-Dimethoxy-1-(pyrimidin-2-yl)cyclobutyl)carbamoyl)-4-methoxy-2-methylphenyl)-4-fluoro-2-(4-fluorophenyl)-N-methylbenzofuran-3-carboxamide

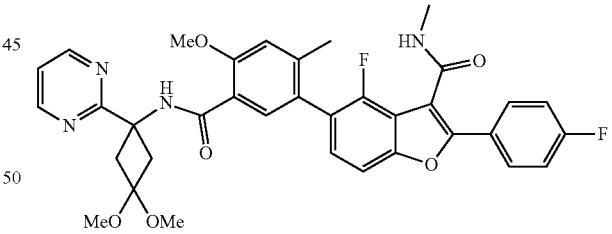

To a stirred solution of 4-fluoro-2-(4-fluorophenyl)-5-(4-methoxy-2-methyl-5-(3-oxo-1-(pyrimidin-2-yl)cyclobutylcarbamoyl)phenyl)-N-methylbenzofuran-3-carboxamide (25 mg, 0.042 mmol, prepared in a similar manner as Example 6) in MeOH (1.5 mL) and DCM (1.5 mL) at room temperature were added trimethoxymethane (8.89 mg, 0.084 mmol) followed by pTsOH (1.594 mg, 8.38 μmol). The reaction mixture was stirred at rt for overnight. After completion of the reaction (monitored by TLC), the mixture was diluted with water and the product extracted with DCM (20 mL×3). The combined organic extracts were washed with 10% $NaHCO_3$ solution and saturated brine solution, dried over $Na_2SO_4$ and concentrated under reduced pressure. The crude product was purified by chromatography using a silica(60-120) column with 2.0% MeOH in CHCl₃ as an eluent to obtain 5-(5-((3,3-dimethoxy-1-(pyrimidin-2-yl)cyclobutyl)carbamoyl)-4-methoxy-2-methylphenyl)-4-fluoro-2-(4-fluorophenyl)-N-methylbenzofuran-3-carboxamide as a white solid. Yield: 10.45 mg, (38.8%). $^1$H NMR (400 MHz, CHLOROFORM-d) δ=8.84 (s, 1H), 8.73 (d, J=4.8 Hz, 2H), 8.01-7.96 (m, 3H), 7.33 (d, J=8.5 Hz, 1H), 7.18-7.09 (m, 4H), 6.93 (s, 1H), 6.15 (br. s, 1H), 4.08 (s, 3H), 3.26 (s, 3H), 3.26-3.21 (m, 2H), 3.21 (s, 3H), 3.00 (d, J=4.8 Hz, 3H), 2.71 (d, J=13.8 Hz, 2H), 2.24 (s, 3H). $^{19}$F NMR (376.6 MHz, CHLOROFORM-d) δ: −110.05, −119.19. LCMS: (ES+) m/z=643.2 (M+H)⁺, Column-PUROSPHER@star RP-18 (4×55) mm, 3 m, Buffer: 20 mM NH₄OAc in water, Mobile phase A: Buffer: ACN (90:10), Mobile phase B: Buffer:ACN (10:90), Gradient: Time (min)/% B: 0/0, 2/100, 2.5/100, 3/0, Flow: 2.5 ml/min. Rt: 1.87 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 12/100, 15/100, Flow: 1.0 ml/min, Wavelength: 254 nm, Rt: 10.83 min, Wavelength: 220 nm, Rt: 10.83 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 12/100, 15/100, Flow: 1.0 ml/min, Wavelength: 254 nm, Rt: 9.97 min, Wavelength: 220 nm, Rt: 9.97 min.

Example 15

5-(5-((3,3-Difluoro-1-(pyrimidin-2-yl)cyclobutyl)carbamoyl)-2-methylphenyl)-4-fluoro-2-(4-fluorophenyl)-N-methylbenzofuran-3-carboxamide

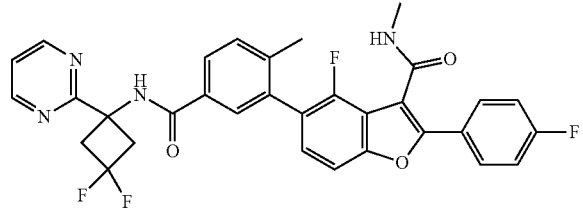 [SMILES: CNC(=O)c1c(-c2ccc(F)cc2)oc2ccc(-c3cc(C(=O)NC4(c5ncccn5)CC(F)(F)C4)ccc3C)c(F)c12]

To a mixture of 3-(4-fluoro-2-(4-fluorophenyl)-3-(methylcarbamoyl)benzofuran-5-yl)-4-methylbenzoic acid (25 mg, 0.059 mmol), 3,3-difluoro-1-(pyrimidin-2-yl)cyclobutanamine (15.38 mg, 0.083 mmol) in DMF (1 ml) in a 5 ml RBF (round bottomed flask) was added (benzotriazol-1-yloxy)tris(dimethylamino)phosphonium hexafluorophosphate (BOP) (26.2 mg, 0.059 mmol) and triethylamine (TEA) (0.025 ml, 0.178 mmol). The resulting reaction mixture was stirred at r.t. overnight. After the reaction was completed, ice-cold water was added to the mixture under stirring. The solid precipitated out was filtered and dried. It was then purified by Prep (=preparative) TLC using CHCl₃: MeOH (9:1) as a mobile phase. The desired fraction was evaporated and dried under vacuum to give 5-(5-((3,3-difluoro-1-(pyrimidin-2-yl)cyclobutyl)carbamoyl)-2-methylphenyl)-4-fluoro-2-(4-fluorophenyl)-N-methylbenzofuran-3-carboxamide as an off white solid. Yield: 7.0 mg (20%). $^1$H NMR (400 MHz, CD₃OD) δ ppm 2.26 (s, 3H) 2.95 (s, 3H) 3.22-3.27 (m, 2H), 3.49-3.60 (m, 2H), 7.27-7.34 (m, 4H), 7.45 (d, J=8.0, 1H), 7.53 (d, J=8.4 Hz 1H) 7.82-7.86 (m, 1H) 7.89-7.86 (m, 1H), 7.97 (m, 2H) 8.77 (d, J=4.8 Hz, 2H); $^{19}$F NMR (376.6 MHz, CD₃OD): −122.67, −112.29, −92.98 (d, J=196.2 Hz), −89.13 (d, J=196.2 Hz). LCMS: (ES+) m/z=589 (M+H)⁺, Column-Acentis Express C18 (50×2.1 mm; 2.7 u), Buffer: 10 mM Ammonium Formate in Water pH 4.5, Mobile phase A: Buffer: ACN (98:2), Mobile phase B: Buffer:ACN (2:98), Flow: 1.0 ml/min. Rt: 1.92 min, wavelength: 220 nm.

| Time | % A | % B |
|---|---|---|
| 0.0 | 100 | 0.0 |
| 1.7 | 0 | 100.0 |
| 3.4 | 0 | 100.0 |

HPLC Method: SUNFIRE (150×4.6 mm) 3.5 micron, SC/862, Buffer: 0.05% TFA in water pH 2.5 adjusted using dil NH₃, Mobile Phase A: Buffer:ACN (95:5), Mobile Phase B: ACN: Buffer (95:5), Flow: 1.0 ml/min, Time\% B: 0/10, 12/100, 15/100, Wavelength: 254 nm, Rt: 11.29 min, Wavelength: 220 nm, Rt: 11.29 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Flow: 1.0 ml/min, Time\% B: 0/10, 12/100, 15/100, Wavelength: 254 nm, Rt: 10.64 min, Wavelength: 220 nm, Rt: 10.64 min.

Example 16

4-Fluoro-5-(5-(3-fluoro-1-(pyrimidin-2-yl)cyclobutylcarbamoyl)-2-methylphenyl)-2-(4-fluorophenyl)-N-methylbenzofuran-3-carboxamide

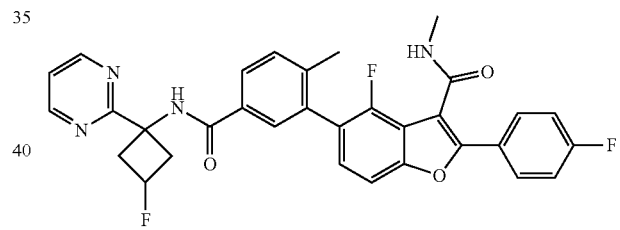

To a ice-cooled mixture of 3-(4-fluoro-2-(4-fluorophenyl)-3-(methylcarbamoyl)benzofuran-5-yl)-4-methyl benzoic acid (0.1 g, 0.237 mmol) in dry DMF (2 mL) was added 3-fluoro-1-(pyrimidin-2-yl)cyclobutanamine (0.048 g, 0.285 mmol) followed by triethylamine (TEA) (0.165 mL, 1.187 mmol) and (benzotriazol-1-yloxy)tris(dimethylamino)phosphonium hexafluorophosphate (BOP) (0.157 g, 0.356 mmol). The reaction mixture was left stirring at ambient temperature for 14 hr and then quenched with ice-cold water. The white thick solid precipitated was filtered, dried and purified by preparative HPLC. Yield: 20 mg, (15%). $^1$H NMR (400 MHz, DMSO-d₆) δ: 2.23 (s, 3H), 2.74-2.81 (m, 2H), 2.81 (d, J=4.4 Hz, 3H), 3.14 (m, 2H), 5.16-5.48 (m, 1H), 7.33-7.51 (m, 5H), 7.67 (d, J=8.53 Hz, 1H), 7.84 (d, J=1.76 Hz, 1H), 7.87-7.99 (m, 3H), 8.71 (q, J=4.35 Hz, 1H), 8.78 (d, J=4.77 Hz, 2H), 9.38 (s, 1H). $^{19}$F NMR (376.6 MHz, DMSO-d₆) δ: −164.40, −121.43, −110.41.

LCMS: (ES−) m/z=569.2 (M−H). Column-Puropsher @star RP-18 (4×55) mm, 3 um, Buffer: 20 mM NH₄OAc in water, Mobile phase A: Buffer:ACN (90:10), Mobile phase B: Buffer:ACN (10:90), Gradient: Time (min)/% B: 0/0, 2/100, 2.5/100, 3/0, Flow: 2.5 ml/min. Rt: 1.92 min, wavelength: 220 nm.

LCMS: (ES+) m/z=571 (M+H)⁺.
Column-Ascentis Express C18 (5×2.1 mm-2.7 m)
M phase A: 2% MeCN-98% H$_2$O-10 mM NH$_4$COOH
M phase B: 98% MeCN-2% H$_2$O-10 mM NH$_4$COOH
Flow=1 mL/min, Rt=1.969 min.

| Time | % A | % B |
|---|---|---|
| 0.0 | 100.0 | 0.0 |
| 1.5 | 0.0 | 100.0 |

HPLC Method: XBridge phenyl (150×4.6 mm) 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 16.67
Wavelength: 220 nm, Rt min: 16.67
HPLC Method: SUNFIRE C18 (4.6×150) mm, 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 18.90
Wavelength: 220 nm, Rt min: 18.90
Preparative HPLC method:
COLUMN: SUNFIRE C18 (150×4.6 mm; 3.5 micron)
Buffer: 0.05% TFA in water pH 2.5
Mobile phase A: Buffer: Acetonitrile(95:5)
Mobile phase B: Buffer: Acetonitrile(5:95)
Flow: 1.0 ml\min

| TIME(min) | % B |
|---|---|
| 0 | 10 |
| 25 | 100 |
| 30 | 100 |

Example 17

5-(5-((3,3-Difluoro-1-(pyrimidin-2-yl)cyclobutyl)carbamoyl)-3-fluoro-2-methylphenyl)-4-fluoro-2-(4-fluorophenyl)-N-methylbenzofuran-3-carboxamide

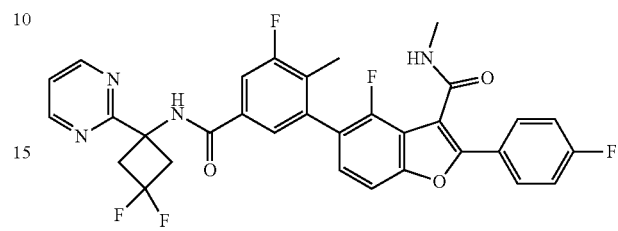

To a mixture of 3-fluoro-5-(4-fluoro-2-(4-fluorophenyl)-3-(methylcarbamoyl)benzofuran-5-yl)-4-methylbenzoic acid (25 mg, 0.057 mmol), 3,3-difluoro-1-(pyrimidin-2-yl)cyclobutanamine (20 mg, 0.108 mmol) in DMF (1 ml) in a 5 ml RBF was added BOP reagent (25.1 mg, 0.057 mmol) and TEA (0.032 ml, 0.228 mmol). The resulting mixture was stirred at rt for overnight. After the reaction was completed, ice-cold water was added to the reaction mixture under stirring. The solid precipitated out was filtered and dried. It was then purified by Prep TLC by using CHCl$_3$:MeOH (9:1) as a mobile phase. The desired fraction was evaporated and dried under vacuum to give 5-(5-((3,3-difluoro-1-(pyrimidin-2-yl)cyclobutyl)carbamoyl)-3-fluoro-2-methylphenyl)-4-fluoro-2-(4-fluorophenyl)-N-methylbenzofuran-3-carboxamide as an off white solid. Yield: 5.0 mg (15%). $^1$H NMR (400 MHz, DMSO-d$_6$) δ ppm 2.14 (s, 3H), 2.80 (d, J=4.77 Hz, 3H), 3.42-3.49 (m, 4H), 7.38-7.45 (m, 4H), 7.68 (d, 1H), 7.52-7.80 (m, 2H), 7.93-7.96 (m, 2H), 8.72-8.70 (m, 1H), 8.81 (d, J=5.02 Hz, 2H), 9.5 (s, 1H); $^{19}$F (376.6 MHz, DMSO-d$_6$): −121.312, −114.81, −110.29, −89.32 (d, J=192.4 Hz), −85.33 (d, J=192.8 Hz); LCMS: (ES+) m/z=607 (M+H)⁺, Column-Zorbax SBC18 (4.6×50 mm) 5u, Buffer: 0.1% TFA in Water, Mobile phase A: Buffer: MeOH (90:10), Mobile phase B: Buffer: MeOH (10:90), Flow: 5.0 ml/min. Rt: 1.97 min, wavelength: 220 nm.

| Time (min.): | % A | % B |
|---|---|---|
| 0 | 100 | 0 |
| 2.0 | 0 | 100 |
| 2.5 | 0 | 100 |
| 3.0 | 100 | 0 |

HPLC Method: SUNFIRE C18 (150×4.6 mm) 3.5 micron, Buffer: 0.05% TFA in water pH 2.5, Mobile Phase A: Buffer:ACN (95:5), Mobile Phase B: ACN: Buffer (95:5), Flow: 1.0 ml/min, Time\% B: 0/10, 25/100, 30/100, Wavelength: 254 nm, Rt: 19.27 min, Wavelength: 220 nm, Rt: 19.27 min. HPLC Method: XBridge Phenyl (150×4.6 mm) 3.5 micron, Buffer: 0.05% TFA in water pH 2.5 using dil NH$_3$, Mobile Phase A: Buffer:ACN (95:5), Mobile Phase B: Buffer:ACN (5:95), Flow: 1.0 ml/min, Time\% B: 0/10, 25/100, 30/100, Wavelength: 254 nm, Rt: 17.82 min, Wavelength: 220 nm, Rt: 17.82 min.

Example 18

5-(5-(3,3-Difluoro-1-(pyrimidin-2-yl)cyclobutylcarbamoyl)-4-methoxy-2-methylphenyl)-4-fluoro-2-(4-fluorophenyl)-N-methylbenzofuran-3-carboxamide

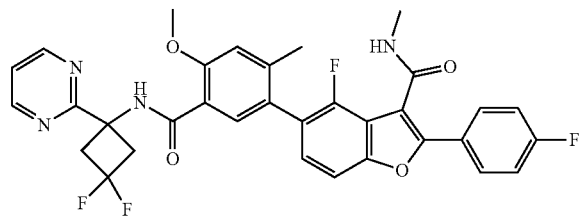 [SMILES: CNC(=O)c1c(-c2ccc(F)cc2)oc2ccc(-c3cc(C(=O)NC4(c5ncccn5)CC(F)(F)C4)c(OC)cc3C)c(F)c12]

To a mixture of 5-(4-fluoro-2-(4-fluorophenyl)-3-(methylcarbamoyl)benzofuran-5-yl)-2-methoxy-4-methylbenzoic acid (25 mg, 0.055 mmol) and 3,3-difluoro-1-(pyrimidin-2-yl)cyclobutanamine (12.31 mg, 0.066 mmol) in DMF (1 ml) in a 5 ml RBF was added (benzotriazol-1-yloxy)tris(dimethylamino)phosphonium hexafluorophosphate (24.48 mg, 0.055 mmol) and triethylamine (0.031 ml, 0.222 mmol). The resulting reaction mixture was stirred at r.t. overnight. After the reaction was completed, ice-cold water was added to the mixture under stirring. The solid precipitated out was filtered and dried. It was then purified by Prep TLC by using 1:9 MeOH/CHCl$_3$ as a mobile phase. The desired fraction was evaporated and dried under vacuum to give the product as an off white solid. Yield: 6.0 mg (17%). $^1$H NMR (400 MHz, DMSO-d$_6$) δ ppm 2.23 (s, 3H), 2.80 (d, J=4.77 Hz, 3H), 3.22-3.30 (m, 2H), 3.39-3.51 (m, 2H), 4.05 (s, 3H), 7.22 (s, 1H), 7.29 (dd, J=8.28, 7.28 Hz, 1H), 7.38-7.45 (s overlapped with m, 3H), 7.616 (d, J=8.4 Hz, 1H), 7.627 (s, 1H), 7.89-7.98 (m, 2H), 8.69 (q, J=4.43 Hz, 1H), 8.84 (d, J=5.02 Hz, 2H), 9.19 (s, 1H); $^{19}$F NMR (376.6 MHz, DMSO-d$_6$) δ: −121.52, −110.46, −88.63 (d, J=192 Hz), −86.32 (d, J=192 Hz).

LCMS: (ES+) m/z=619.2 (M+H)$^+$.
Column: PUROSPHER@star RP-18 (4×55) mm, 3 m
Buffer: 20 mM NH$_4$OAc IN water
M phase A: Buffer+ACN (90+10)
M phase B: Buffer+ACN (10+90)
Flow: 2.5 ml/min

| Time (min.): | 0, | 2, | 2.5, | 3 |
|---|---|---|---|---|
| % B: | 0, | 100, | 100, | 0 |

Rt: 2.016 min; Wavelength 220 nm
HPLC Method: XBridge phenyl (150×4.6 mm) 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 18.10
Wavelength: 220 nm, Rt min: 18.10

HPLC Method: SUNFIRE C18 (4.6×150) mm, 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 19.33
Wavelength: 220 nm, Rt min: 19.33

Example 19

4-Fluoro-5-(5-(3-fluoro-1-(pyrimidin-2-yl)cyclobutylcarbamoyl)-4-methoxy-2-methylphenyl)-2-(4-fluorophenyl)-N-methylbenzofuran-3-carboxamide

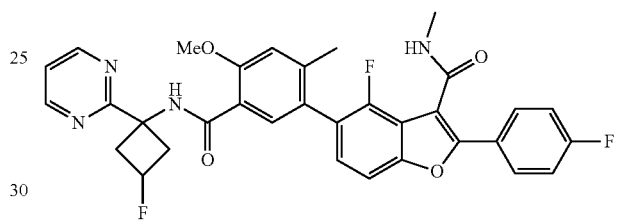

To a mixture of 5-(4-fluoro-2-(4-fluorophenyl)-3-(methylcarbamoyl)benzofuran-5-yl)-2-methoxy-4-methylbenzoic acid (0.05 g, 0.111 mmol) in DMF (2 ml) under ice-cooled conditions was added 3-fluoro-1-(pyrimidin-2-yl)cyclobutanamine (24.73 mg, 0.148 mmol), TEA (0.079 ml, 0.569 mmol) and BOP reagent (73 mg, 0.171 mmol). The reaction mixture was then stirred at ambient temperature for 12 hr. The reaction was quenched with ice-cold water, the white solid precipitated out was filtered and dried under suction. The crude product was then purified by prep HPLC. Yield: 18 mg, (25.5%). $^1$H NMR (400 MHz, DMSO-d$_6$) ppm: 2.25 (s, 3H), 2.80 (d, J=4.77 Hz, 3H), 2.88-3.03 (m, 2H), 3.21-3.28 (m, 2H), 4.09 (s, 3H), 5.31-5.49 (m, 1H), 7.24 (s, 1H), 7.31 (dd, J=8.28, 7.28 Hz, 1H), 7.36-7.48 (m, 3H), 7.63 (d, J=8.28 Hz, 1H), 7.76 (s, 1H), 7.88-7.98 (m, 2H), 8.70 (q, J=4.35 Hz, 1H), 8.88 (d, J=4.77 Hz, 2H), 9.59 (s, 1H). $^{19}$F NMR (376.6 MHz, DMSO-d$_6$) δ: −164.53, −121.52, −110.47.

LCMS: (ES+) m/z=601.2 (M+H)$^+$.
Column: PUROSPHER@star RP-18 (4×55) mm, 3 μm
Buffer: 20 mM NH$_4$OAc in water
M phase A: Buffer+ACN (90+10)
M phase B: Buffer+ACN (10+90)
Flow: 2.5 ml/min

| Time (min.): | 0 | 2 | 2.5 | 3 |
|---|---|---|---|---|
| % B: | 0 | 100 | 100 | 0 |

Rt min=2.011
HPLC Method: XBridge phenyl (150×4.6 mm) 3.5 micron
Buffer: 0.05% TFA in water pH 2.5
Mobile Phase A: Buffer:ACN (95:5)

Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 17.71
Wavelength: 220 nm, Rt min: 17.71
HPLC Method: SUNFIRE C18 (4.6×150) mm, 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 19.90
Wavelength: 220 nm, Rt min: 19.90

Example 20

4-Fluoro-5-(3-fluoro-5-(3-fluoro-1-(pyrimidin-2-yl)cyclobutylcarbamoyl)-2-methylphenyl)-2-(4-fluorophenyl)-N-methylbenzofuran-3-carboxamide

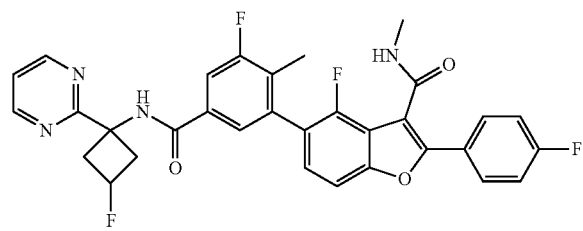 [SMILES: CNC(=O)c1c(-c2ccc(F)cc2)oc2ccc(-c3cc(C(=O)NC4(c5ncccn5)CC(F)C4)cc(F)c3C)c(F)c12]

To a mixture of 3-fluoro-5-(4-fluoro-2-(4-fluorophenyl)-3-(methylcarbamoyl)benzofuran-5-yl)-4-methylbenzoic acid (50 mg, 0.114 mmol) in DMF (2 ml) under ice-cooled conditions was added 3-fluoro-1-(pyrimidin-2-yl)cyclobutanamine (24.73 mg, 0.148 mmol), TEA (0.079 ml, 0.569 mmol) and BOP reagent (75 mg, 0.171 mmol). The reaction mixture was then stirred at ambient temperature for 12 hr. The reaction was quenched with ice-cold water. The white solid precipitated out was filtered and dried under suction. The crude product was then purified by prep. HPLC. Yield: 18 mg, (26.6%). $^1$H NMR (400 MHz, DMSO-$d_6$) δ: 2.14 (s, 3H), 2.70-2.80 (m, 2H), 2.81 (d, J=4.4 Hz, 3H), 3.09-3.22 (m, 2H), 5.26-5.44 (m, 1H), 7.36-7.45 (overlapping m, 4H), 7.70 (d, J=8.4 Hz, 1H), 7.75 (s, 1H), 7.78 (d, J=10.4 Hz, 1H), 7.90-7.97 (m, 2H), 8.69-8.73 (m, 1H), 8.78 (d, J=5.2 Hz, 2H), 9.48 (s, 1H). $^{19}$F NMR (376.6 MHz, DMSO-$d_6$) δ: −164.40, −121.30, −114.96, −110.30.
LCMS: (ES+) m/z=589.2 (M+H)$^+$.
Column: PUROSPHER@star RP-18 (4×55) mm, 3 μm
Buffer: 20 mM NH$_4$OAc in water
Mphase A: Buffer+ACN (90+10)
Mphase B: Buffer+ACN (10+90)
Flow: 2.5 ml/min

| Time (min.): | 0 | 2 | 2.5 | 3 |
|---|---|---|---|---|
| % B: | 0 | 100 | 100 | 0 |

Rt min: 1.948
HPLC Method: XBridge phenyl (150×4.6 mm) 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 17.25
Wavelength: 220 nm, Rt min: 17.25
HPLC Method: SUNFIRE C18 (4.6×150) mm, 3.5 micron
Buffer: 0.05% TFA in water pH 2.5
Mobile Phase A: Buffer:ACN (95:5)
Mobile Phase B: ACN: Buffer (95:5)
Flow: 1 ml/min

| Time | 0 | 25 | 30 |
|---|---|---|---|
| % B | 10 | 100 | 100 |

Wavelength: 254 nm, Rt min: 19.18
Wavelength: 220 nm, Rt min: 19.18

Example 21

5-(3-((3-(Difluoromethoxy)-1-(pyrimidin-2-yl)cyclobutyl)carbamoyl)phenyl)-6-(N-ethylmethylsulfonamido)-4-fluoro-2-(4-fluorophenyl)-N-methylbenzofuran-3-carboxamide

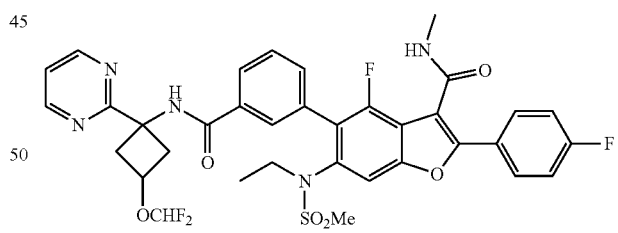

To a mixture of 3-(6-(N-ethylmethylsulfonamido)-4-fluoro-2-(4-fluorophenyl)-3-(methyl carbamoyl)benzofuran-5-yl)benzoic acid (0.07 g, 0.132 mmol) in DMF (0.5 mL) under ice cold conditions was added 3-(difluoromethoxy)-1-(pyrimidin-2-yl)cyclobutanamine (0.043 g, 0.199 mmol), followed by TEA (0.092 mL, 0.662 mmol) and BOP (0.088 g, 0.199 mmol). The reaction mixture was then stirred at ambient temperature for 12 hr. The mixture was diluted with ice cold water. The white solid precipitates were filtered and dried under suction. The crude product was purified by Preparative TLC using 1:9 methanol/chloroform (Yield: 10 mg, 10.2%, white solid). $^1$H NMR (400 MHz, DMSO-$d_6$): δ ppm=9.35 (s, 1H), 8.81 (d, J=4.8 Hz, 2H), 8.74 (d, J=4.8 Hz, 1H), 8.03-7.97 (m, 1H), 7.96-7.93 (m, 2H), 7.9 (s, 1H), 7.88 (s, 1H), 7.62-7.55 (m, 2H), 7.47-7.42 (t, 2H), 7.38 (t, J=4.8 Hz, 1H), 6.73 (t, J=75.6 Hz, 1H), 4.94 (t, J=7.3 Hz, 1H), 3.40-3.16 (hidden m, 2H), 3.16-3.08 (m, 2H), 3.01 (s, 3H), 2.79 (d, J=4.8 Hz, 3H), 2.74-2.66 (m, 2H), 0.95 (t, J=7.2 Hz, 3H). $^{19}$F NMR (376.6 MHz, DMSO-d$_6$): δ ppm: −81.71, −109.99, −118.62. LCMS: (ES+) m/z=726.47 (M+H)$^+$. Rt min: 1.02, Wavelength: 220 nm. Column: Acquity BEH C18 (2.1×50 mm) 1.7 µm, Mobile phase A: 5 mM Ammonium Acetate:ACN (95:5). Mobile phase B: 5 mM Ammonium Acetate:ACN (5:95). Method:% B: 0 min-5%:1.1 min-95%:1.7 min-95%. Flow: 0.8 ml/min. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 16.01. Wavelength: 220 nm, Rt min: 16.01. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 17.26. Wavelength: 220 nm, Rt min: 17.26.

Example 22

6-(N-ethylmethylsulfonamido)-4-fluoro-5-(3-((3-fluoro-1-(pyrimidin-2-yl)cyclobutyl)carbamoyl)phenyl)-2-(4-fluorophenyl)-N-methylbenzofuran-3-carboxamide

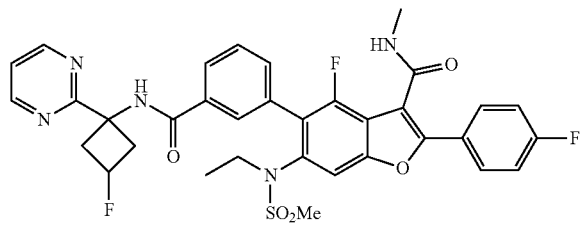

To a mixture of 3-(6-(N-ethylmethylsulfonamido)-4-fluoro-2-(4-fluorophenyl)-3-(methyl carbamoyl)benzofuran-5-yl)benzoic acid (0.04 g, 0.076 mmol) in DMF (0.5 mL) under ice cold conditions was added 3-fluoro-1-(pyrimidin-2-yl)cyclobutanamine (0.015 g, 0.091 mmol), followed by TEA (0.053 mL, 0.378 mmol) and then BOP (0.050 g, 0.114 mmol). The reaction mixture was then stirred at ambient temperature for 12 hr. The mixture was diluted with ice-cold water. The white solid precipitated out was filtered and dried under suction. The crude mixture was purified by prep HPLC using purospher@star RP-18 94×55 mm, water/MeOH/NH$_4$OAc (Yield: 5 mg, 9.65%, white solid). $^1$H NMR (400 MHz, METHANOL-d$_4$): δ ppm=8.77 (d, J=4.8 Hz, 2H), 8.05 (br s, 1H), 8.00-7.97 (m, 3H), 7.72 (s, 1H), 7.71 (m, 1H), 7.64-7.60 (m, 1H), 7.34-7.28 (m, 3H), 5.50-5.35 (d of quint, 1H), 3.35 (m, 1H), 3.30-3.20 (m, 3H), 3.00 (s, 3H), 2.96 (d, 3H), 2.95-2.86 (m, 2H), 1.05 (t, J=7.3 Hz, 3H). $^{19}$F: NMR (376.6 MHz, METHANOL-d$_4$): δ ppm −111.75, −120.01, −167.90. LCMS: (ES+) m/z=678.46 (M+H)$^+$. Column: Acquity BEH C18 (2.1×50 mm) 1.7 µm, Mobile phase A: 5 mM Ammonium Acetate: ACN (95:5). Mobile phase B: 5 mM Ammonium Acetate:ACN (5:95). Method:% B: 0 min-5%; 1.1 min-95%; 1.7 min-95%. Flow: 0.8 ml/min. Rt min: 0.99, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Time (min)/% B: 0/10, 25/100, 30/100, Flow: 1 ml/min. Wavelength: 254 nm, Rt min: 15.57. Wavelength: 220 nm, Rt min: 15.57. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/10, 25/100, 30/100, Flow: 1 ml/min. Wavelength: 254 nm, Rt min: 16.83. Wavelength: 220 nm, Rt min: 16.83.

Example 23

6-(N-ethylmethylsulfonamido)-2-(4-fluorophenyl)-5-(3-((3-hydroxy-1-(pyrimidin-2-yl)cyclobutyl)carbamoyl)phenyl)-N-methylbenzofuran-3-carboxamide

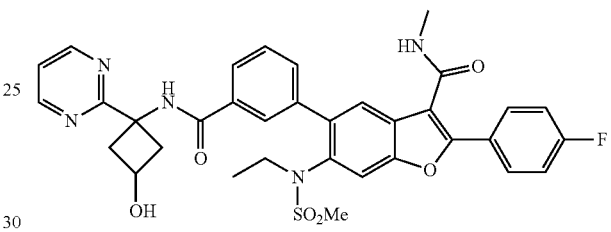

To a mixture of 3-(6-(N-ethylmethylsulfonamido)-2-(4-fluorophenyl)-3-(methylcarbamoyl) benzofuran-5-yl)benzoic acid (0.150 g, 0.284 mmol) in DMF (0.5 mL) under ice-cooled conditions was added 3-amino-3-(pyrimidin-2-yl)cyclobutanol (0.070 g, 0.426 mmol), followed by TEA (0.198 mL, 1.419 mmol) and then BOP (0.188 g, 0.426 mmol). The reaction was stirred at ambient temperature for 12 hr. The mixture was diluted with ice-cold water. The white solid precipitated out was filtered and dried under suction. The obtained product was used for the next step without further purification (80 mg). LCMS: (ES+) m/z=658.48 (M+H)$^+$. Mobile phase B: Acetonitrile, Mobile phase A: 0.1% TFA in water, Rt min: 0.95, Wavelength: 220 nm.

Example 24

5-(3-((3-(difluoromethoxy)-1-(pyrimidin-2-yl)cyclobutyl)carbamoyl)phenyl)-6-(N-ethylmethylsulfonamido)-2-(4-fluorophenyl)-N-methylbenzofuran-3-carboxamide

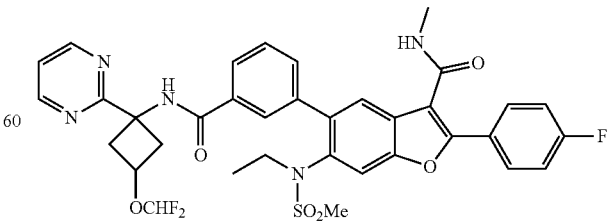

To a mixture of 6-(N-ethylmethylsulfonamido)-2-(4-fluorophenyl)-5-(3-((3-hydroxy-1-(pyrimidin-2-yl)cyclobutyl)

carbamoyl)phenyl)-N-methylbenzofuran-3-carboxamide (Example 23) (80 mg, 0.122 mmol) in acetonitrile (1 mL) was added copper(I) iodide (23.17 mg, 0.122 mmol) and heated to 50° C. To the mixture at the same temperature was then added 2-(fluorosulfonyl)difluoroacetic acid (0.017 mL, 0.182 mmol). The reaction was stirred at the same temperature for 2 hr. The mixture was quenched with saturated NaHCO$_3$, diluted with ethyl acetate (20 mL). The organic layer was separated and dried over sodium sulphate, and concentrated to give the crude product. The crude product was submitted for preparative HPLC (Yield: 6.1 mg, 7.09%, white solid). Preparative HPLC Method. Column: Inertsil ODS (19×250 mm) 5 m. Mobile phase A: 0.1% TFA (Aq.). Mobile phase B=Acetonitrile. Flow: 15 ml/min. Rt min: 13.97. $^1$H NMR (400 MHz, METHANOL-d$_4$): δ=8.79 (d, J=5.0 Hz, 2H), 8.51 (d, J=4.3 Hz, 1H), 8.12 (t, J=1.6 Hz, 1H), 8.05-7.99 (m, 2H), 7.93 (d, J=8.3 Hz, 1H), 7.82 (s, 1H), 7.80-7.74 (m, 1H), 7.75 (s, 1H), 7.64-7.55 (m, 1H), 7.35-7.26 (m, 3H), 6.42 (t, J=75.2 Hz, 1H), 5.06 (t, J=7.3 Hz, 1H), 3.30 (m, 1H), 3.28-3.18 (m, 3H), 3.09 (s, 3H), 2.97 (d, J=4.4 Hz, 3H), 2.90-2.84 (m, 2H), 1.02 (t, J=7.2 Hz, 3H). $^{19}$F $^1$H NMR (376.6 MHz, METHANOL-d$_4$) δ ppm: −84.16, −112.04. LCMS: (ES+) m/z=708.3 (M+H)$^+$. Column: Acentis Express C8 (50×2.1 mm; 2.7 μm). Buffer: 10 mM Ammonium formate in Water. M phase A: Buffer+ACN (90+10). M phase B: Buffer+ACN (10+90). Time (min)/% B: 0/0, 1.6/100, 3.2/100, 3.6/0, Flow: 1.0 ml/min. Time (min.): Rt min: 2.04, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/10, 25/100, 30/100, Flow: 1 ml/min. Wavelength: 254 nm, Rt min: 16.25. Wavelength: 220 nm, Rt min: 16.25. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/10, 25/100, 30/100, Flow: 1 ml/min. Wavelength: 254 nm, Rt min: 17.73. Wavelength: 220 nm, Rt min: 17.73.

Example 25

6-(N-ethylmethylsulfonamido)-5-(3-((3-fluoro-1-(pyrimidin-2-yl)cyclobutyl)carbamoyl)phenyl)-2-(4-fluorophenyl)-N-methylbenzofuran-3-carboxamide

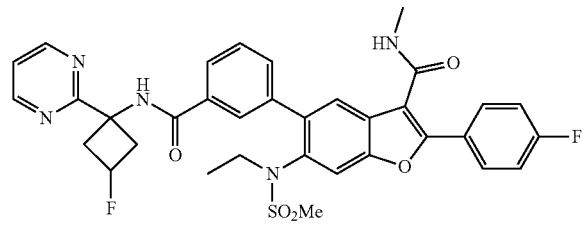

To a mixture of 3-(6-(N-ethylmethylsulfonamido)-2-(4-fluorophenyl)-3-(methylcarbamoyl) benzofuran-5-yl)benzoic acid (0.05 g, 0.098 mmol) in DMF (2 mL) under ice-cold conditions was added 3-fluoro-1-(pyrimidin-2-yl)cyclobutanamine (0.020 g, 0.118 mmol), followed by TEA (0.014 mL, 0.098 mmol) and then BOP (0.043 g, 0.098 mmol). The mixture was then stirred at ambient temperature for 12 hr. The mixture was diluted with ice-cold water. The white solid precipitated out was filtered and dried under suction. The crude product was purified by UPLC (t=0.97) to provide the product as a white solid (5.5 mg, 8.43%). Preparative HPLC Method. Column: Symmetry C8 (300× 19×7 m). Mobile phase A: 10 mM ammonium acetate. Mobile phase B=Acetonitrile. Flow: 17 mL/min. Rt min: 9.705. $^1$H NMR (400 MHz, DMSO-d$_6$): δ ppm=9.36 (s, 1H), 8.79 (d, J=4.8 Hz, 2H), 8.54-8.51 (m, 1H), 8.05-7.94 (m, 4H), 7.95 (s, 1H), 7.74 (d, J=8.0 Hz, 1H), 7.64 (s, 1H), 7.60-7.55 (m, 1H), 7.45-7.40 (m, 2H), 7.38 (t, J=4.8 Hz, 1H), 5.50-5.20 (m, 1H), 3.60-3.40 (br m, 2H), 3.22-3.13 (m, 2H), 3.09 (s, 3H), 2.86-2.72 (m, 2H), 2.83 (d, J=4.4 Hz, 3H), 0.92 (t, J=7.2 Hz, 3H). $^{19}$F NMR (376.6 MHz, DMSO-d$_6$): δ ppm: −110.32, −164.35. LCMS: (ES+) m/z=660.4 (M+H)$^+$. Column: Acquity BEH C18 (2.1×50 mm) 1.7 μm, Mobile phase A: 5 mM Ammonium Acetate: ACN (95:5), Mobile phase B: 5 mM Ammonium Acetate: ACN (5:95). Method: % B: 0 min-5%; 1.1 min-95%; 1.7 min-95%. Flow: 0.8 ml/min. Rt min: 0.96, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Flow: 1 ml/min. Wavelength: 254 nm, Rt min: 9.77. Wavelength: 220 nm, Rt min: 9.77. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Flow: 1 ml/min. Wavelength: 254 nm, Rt min: 10.30. Wavelength: 220 nm, Rt min: 10.30.

Example 26

6-(N-ethylmethylsulfonamido)-4-fluoro-5-(3-((3-fluoro-1-(pyrimidin-2-yl)cyclobutyl)carbamoyl)-4-methoxyphenyl)-2-(4-fluorophenyl)-N-methylbenzofuran-3-carboxamide

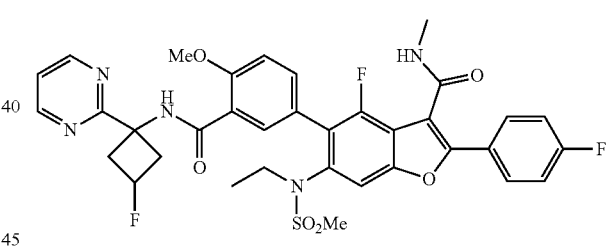

To a mixture of 5-(6-(N-ethylmethylsulfonamido)-4-fluoro-2-(4-fluorophenyl)-3-(methyl carbamoyl)benzofuran-5-yl)-2-methoxybenzoic acid (0.02 g, 0.036 mmol) in DMF (2 mL) under ice-cold conditions was added 3-fluoro-1-(pyrimidin-2-yl)cyclobutanamine (7.18 mg, 0.043 mmol), followed by TEA (4.99 μl, 0.036 mmol) and finally BOP (0.016 g, 0.036 mmol). The reaction was then stirred at ambient temperature for 12 hr. The mixture was diluted with ice-cold water, the solid thus precipitated out was filtered and dried under suction. The crude was submitted for preparative HPLC and afforded pure the product as a white solid. (2.4 mg, Yield: 9.28%). Preparative HPLC Method: Column: Symmetry C18 (250×19×7 μm) Mobile phase A: 0.1% TFA (Aq). Mobile phase B=Acetonitrile. Flow: 15 ml/min. Rt min: 16.79. $^1$H NMR (400 MHz, METHANOL-d$_4$): δ ppm=8.82 (d, J=5.0 Hz, 2H), 8.06-7.92 (m, 3H), 7.72-7.63 (m, 1H), 7.67 (s, 1H), 7.37 (t, J=4.8 Hz, 1H), 7.34-7.27 (m, 3H), 5.54-5.31 (m, 1H), 4.16 (s, 3H), 3.41-3.37 (m, 1H), 3.26-3.09 (m, 5H), 2.96 (br. s, 6H), 1.06 (t, J=7.2 Hz, 3H). $^{19}$F NMR (376.6 MHz, METHANOL-d$_4$): δ ppm: −111.84, −119.90, −168.16. LCMS: (ES+) m/z=708.2

(M+H)⁺. Column-ACE Excel 2 C18 (50×3.0 mm-2 µm). Mphase A: 2% ACN-98% H₂O-10 mM NH₄COOH. Mphase B: 98% ACN-2% H₂O-10 mM NH₄COOH, Flow=1.2 mL/min Rt min: 2.028, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Flow: 1 ml/min. Wavelength: 254 nm, Rt min: 16.24. Wavelength: 220 nm, Rt min: 16.24. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Flow: 1 ml/min. Wavelength: 254 nm, Rt min: 17.13. Wavelength: 220 nm, Rt min: 17.13.

Example 27

5-(3-((3-(Benzyloxy)-1-(pyrimidin-2-yl)cyclobutyl)carbamoyl)phenyl)-2-(4-fluorophenyl)-N-methyl-6-(3,3,3-trifluoropropyl)benzofuran-3-carboxamide

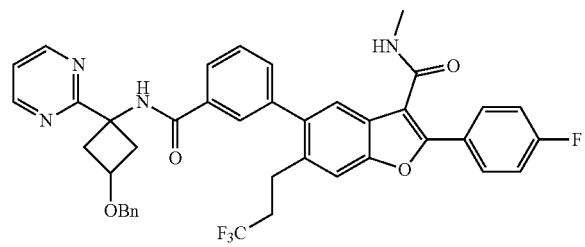 [SMILES: CNC(=O)c1c(-c2ccc(F)cc2)oc2cc(CCC(F)(F)F)c(-c3cccc(C(=O)NC4(c5ncccn5)CC(OCc5ccccc5)C4)c3)cc12]

A mixture of 3-(2-(4-fluorophenyl)-3-(methylcarbamoyl)-6-(3,3,3-trifluoropropyl)benzofuran-5-yl)benzoic acid (0.15 g, 0.309 mmol) and 3-(benzyloxy)-1-(pyrimidin-2-yl)cyclobutanamine (0.079 g, 0.309 mmol) in DMF (4 mL) to 0° C. was added DIPEA (0.108 mL, 0.618 mmol) followed by BOP (0.137 g, 0.309 mmol). The reaction mixture was stirred at 25° C. for 4 hours and then quenched with ice-cold water. The solid obtained was filtered, dried under suction and purified by column chromatography using Combiflash with 3% MeOH/chloroform as a mobile phase to get 5-(3-((3-(benzyloxy)-1-(pyrimidin-2-yl)cyclobutyl)carbamoyl)-4-fluorophenyl)-2-(4-fluorophenyl)-N-methyl-6-propylbenzofuran-3-carboxamide as a white solid (170 mg, 76%). LCMS: (ES+) m/z=723.3 (M+H)⁺. Column-ACQUITY UPLC BEH C18 (50×2.1 mm; 1.7 µm). M phase A: 0.1% TFA in water. M phase B: Acetonitrile. Flow: 0.8 ml/min. Rt min: 1.30 min, wavelength: 220 nm.

Example 28

2-(4-Fluorophenyl)-5-(3-((3-(hydroxy-1-(pyrimidin-2-yl)cyclobutyl)carbamoyl)phenyl)-N-methyl-6-(3,3,3-trifluoropropyl)benzofuran-3-carboxamide

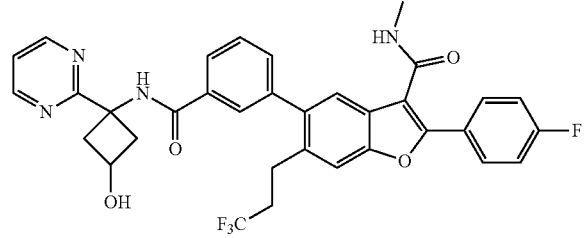 [SMILES: CNC(=O)c1c(-c2ccc(F)cc2)oc2cc(CCC(F)(F)F)c(-c3cccc(C(=O)NC4(c5ncccn5)CC(O)C4)c3)cc12]

5-(3-((3-(Benzyloxy)-1-(pyrimidin-2-yl)cyclobutyl)carbamoyl)phenyl)-2-(4-fluorophenyl)-N-methyl-6-(3,3,3-trifluoropropyl)benzofuran-3-carboxamide (Example 27) (0.12 g, 0.166 mmol) was dissolved in DCM (8 mL) in a 100 mL RB flask and cooled to −50° C. To this mixture was added dropwise boron trichloride (0.498 mL, 0.498 mmol). After addition, the reaction temperature was slowly brought to the 0° C. and the mixture stirred for 3 hours. After completion of the reaction, the volatiles were removed under vacuum, and the residue diluted with ice-cold water. The solid thus obtained was filtered and dried under suction to get 2-(4-fluorophenyl)-5-(3-((3-(hydroxy-1-(pyrimidin-2-yl)cyclobutyl)carbamoyl)phenyl)-N-methyl-6-(3,3,3-trifluoropropyl)benzofuran-3-carboxamide as a pale yellow solid (80 mg, 76%). LCMS: (ES+) m/z=633.3 (M+H)⁺. Column-ACQUITY UPLC BEH C18 (50×2.1 mm; 1.7 m). M phase A: 0.1% TFA in water. M phase B: Acetonitrile. Flow: 0.8 ml/min. Rt min: 1.16 min, wave length: 220 nm.

Example 29a and Example 29b 5-(3-((3-(Difluoromethoxy-1-(pyrimidin-2-yl)cyclobutyl)carbamoyl) phenyl)-2-(4-fluorophenyl)-N-methyl-6-(3,3,3-trifluoropropyl)benzofuran-3-carboxamide

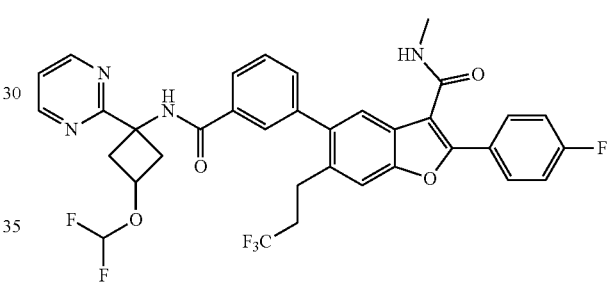

Isomer-I
Example 29a
Isomer-II
Example 29b

To a stirred solution of 2-(4-fluorophenyl)-5-(3-((3-hydroxy-1-(pyrimidin-2-yl)cyclobutyl)carbamoyl)phenyl)-N-methyl-6-(3,3,3-trifluoropropyl)benzofuran-3-carboxamide (Example 28) (0.07 g, 0.111 mmol) in acetonitrile (4 mL) in a 50 mL single necked round bottomed flask was added copper(I) iodide (0.021 g, 0.111 mmol). The resulting reaction mixture was heated to 50° C. and then 2-(fluorosulfonyl)difluoroacetic acid (0.020 g, 0.111 mmol) was added dropwise to it. After stirring at 50° C. for 2 hours, the reaction was cooled to 0° C. and quenched with 10% sodium bicarbonate solution and the mixture extracted with ethyl acetate. The organic layer separated was dried over anhyd. Na₂SO₄ and evaporated under vacuum. The crude product was submitted for reverse phase prep. HPLC purification to obtain the two isomers. PREPARATIVE HPLC METHOD Column: Chiral-IC250×19×5µ). M phase A: 0.2% DEA (diethylamine) in n-hexane. M phase B: ethanol. Flow: 16 mL/min. Time (min)/% B: 0/18.

Example 29a (Isomer-1) (12 mg, 15.89%). 1H NMR (400 MHz, DMSO-d₆): δ ppm 9.44 (s, 1H), 8.80 (d, J=4.9 Hz, 2H), 8.45 (d, J=4.6 Hz, 1H), 8.04-7.94 (m, 4H), 7.80 (s, 1H), 7.59 (s, 1H) 7.57 (s, 1H), 7.47 (s, 1H), 7.395-7.391 (d, J=1.6 Hz, 1H), 7.37-7.36 (t, J=4.8 Hz, 2H) 6.90-6.52 (t, J=72 Hz, 1H), 4.93-4.89 (t, J=7.2 Hz, 1H), 3.16-3.07 (m, 2H), 2.94-2.87 (m, 3H), 2.81 (d, J=4.6 Hz, 3H), 2.76-2.67 (m, 2H). ¹⁹F NMR (376.6 MHz, DMSO-d₆): δ ppm −64.95, −81.71, −110.77. LCMS: (ES+) m/z=683.2 (M+H)⁺. Column: Zorbax SB C18 (30×2.1 mm; 3.5 u). Buffer: 10 mM Ammonium Formate in Water pH 4.5. M phase A: Buffer+ACN (98+2). Mphase B: Buffer+ACN (2+98). Gradient: Time (min.): 0, 1.5, 2.2, 2.6, 3.0; % B: 6, 100, 100, 6, 6. Flow: 1.5 ml/min. Rt min: 1.64, wavelength: 220 nm.

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 20.93. Wavelength: 220 nm, Rt min: 20.93. HPLC Method: XBridge Phenyl (150×4.6 mm) 3.5 micron. Mobile Phase A: 0.05% TFA in water: Acetonitrile (95:5). Mobile Phase B: Acetonitrile: 0.05% TFA in water (95:5) Gradient: Time (min)/% B: 0/10, 25/100, 30/100, Flow: 1.0 ml/min. Wavelength: 254 nm. Rt min: 18.75. Wavelength: 220 nm. Rt min: 18.75.

Example 29b (Isomer-2) (5 mg, 6.62%). ¹H NMR (400 MHz METHANOL-d₄) δ ppm=8.79 (d, J=4.9 Hz, 2H), 8.02-7.96 (m, 3H), 7.93 (s, 1H) 7.67-7.56 (m, 4H), 7.36-7.25 (m, 3H), 6.61-6.23 (t, J=72 Hz, 1H), 5.02-4.98 (t, J=7.5 Hz, 1H), 3.17-3.05 (m, 3H), 3.04-2.97 (m, 2H), 2.95 (s, 3H), 2.40-2.30 (m, 2H). ¹⁹F NMR (376.6 MHz, METHANOL-d₄): δ ppm −68.19, −84.16, −112.59. LCMS: (ES+) m/z observed=682.7 (M+H)⁺. Column: XBridge C18 (50×2.1 mm) 2.5 m. Mobile phase-A: 10 mM Ammonium Hydrogen Carbonate. Mobile phase-B: ACN. Flow: 1.0 ml/min, Rt min: 2.18, wavelength: 220 nm.

| Time | % B | % A |
|---|---|---|
| 0 | 0 | 100 |
| 1.7 | 100 | 0 |
| 3.2 | 100 | 0 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 20.71. Wavelength: 220 nm, Rt min: 20.71. HPLC Method: XBridge Phenyl (150×4.6 mm) 3.5 micron. Mobile Phase A: 0.05% TFA in water: Acetonitrile (95:5). Mobile Phase B: Acetonitrile: 0.05% TFA in water (95:5) Gradient: Time (min)/% B: 0/10, 25/100, 30/100, Flow: 1.0 ml/min. Wavelength: 254 nm. Rt min: 18.62. Wavelength: 220 nm. Rt min: 18.62.

Example 30

5-(3-((3-(Benzyloxy)-1-(pyrimidin-2-yl)cyclobutyl)carbamoyl)-4-fluorophenyl)-2-(4-fluorophenyl)-N-methyl-6-propylbenzo furan-3-carboxamide

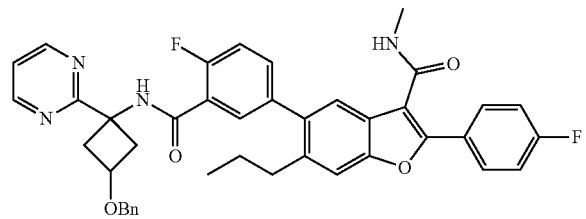 [SMILES: CCCc1cc2oc(-c3ccc(F)cc3)c(C(=O)NC)c2cc1-c1ccc(F)c(C(=O)NC2(c3ncccn3)CC(OCc3ccccc3)C2)c1]

To a solution of 2-fluoro-5-(2-(4-fluorophenyl)-3-(methylcarbamoyl)-6-propylbenzofuran-5-yl)benzoic acid (0.15 g, 0.334 mmol), DIPEA (0.117 mL, 0.667 mmol) and BOP (0.148 g, 0.334 mmol) reagent in DMF (4 mL) at 0° C. was added 3-(benzyloxy)-1-(pyrimidin-2-yl)cyclobutanamine (0.085 g, 0.334 mmol). The reaction mixture was stirred at 25° C. for 4 hours. The reaction mixture was diluted with water, the solid filtered and dried under suction. The crude product was purified by column chromatography using Combiflash with 3% MeOH/chloroform as a mobile phase to obtain 5-(3-((3-(benzyloxy)-1-(pyrimidin-2-yl)cyclobutyl)carbamoyl)-4-fluorophenyl)-2-(4-fluorophenyl)-N-methyl-6-propylbenzofuran-3-carboxamide as a white solid product (120 mg, 52.4%). LCMS: (ES+) m/z=687.3 (M+H)⁺. Column-ACQUITY UPLC BEH C18 (50×2.1 mm; 1.7 μm). M phase A: 0.1% TFA in water. M phase B: Acetonitrile. Flow: 0.8 ml/min. Rt min: 1.20 min, wavelength: 220 nm.

| Time | % A | % B |
|---|---|---|
| 0 | 98 | 2 |
| 1.0 | 2 | 98 |
| 1.6 | 2 | 98 |

Example 31

5-(4-Fluoro-3-((3-hydroxy)-1-(pyrimidin-2-yl)cyclobutyl)carbamoyl)phenyl)-2-(4-fluorophenyl)-N-methyl-6-propylbenzofuran-3-carboxamide

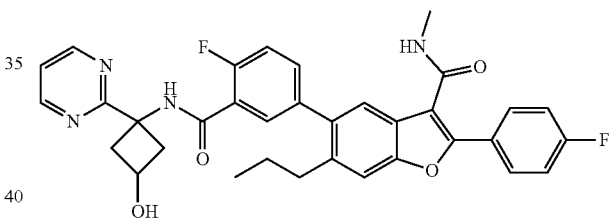

A solution of 5-(3-((3-(benzyloxy)-1-(pyrimidin-2-yl)cyclobutyl)carbamoyl)-4-fluorophenyl)-2-(4-fluorophenyl)-N-methyl-6-propylbenzofuran-3-carboxamide (Example 30) (0.12 g, 0.175 mmol) in DCM (8 mL) was cooled to −78° C. To this mixture was added boron trichloride (0.524 mL, 0.524 mmol, 1M in DCM) dropwise and slowly. The reaction mixture was maintained at 0° C. and under stirring for 3 hours. After completion of the reaction, the mixture was diluted with water and extracted with DCM. The organic layer thus separated was dried over anhydrous Na₂SO₄ and concentrated to give 5-(4-fluoro-3-((3-hydroxy)-1-(pyrimidin-2-yl)cyclobutyl)carbamoyl)phenyl)-2-(4-fluorophenyl)-N-methyl-6-propylbenzofuran-3-carboxamide as an off white solid product (80 mg, 77%). LCMS: (ES+) m/z=597.2 (M+H)⁺. Column: Zorbax SB C18 (30×2.1 mm; 3.5 u). Buffer: 10 mM Ammonium Formate in Water pH 4.5. M phase A: Buffer+ACN (98+2). M phase B: Buffer+ACN (2+98). Flow: 1.5 ml/min Rt min: 1.50 min, wavelength: 220 nm.

| Time | % A | % B |
|---|---|---|
| 0 | 94 | 6 |
| 1.5 | 0 | 100 |
| 2.2 | 0 | 100 |

-continued

| Time | % A | % B |
|---|---|---|
| 2.6 | 94 | 6 |
| 3.0 | 94 | 6 |

Example 32

5-(3-((3-(Difluoromethoxy)-1-(pyrimidin-2-yl)cyclobutyl)carbamoyl)-4-fluorophenyl)-2-(4-fluorophenyl)-N-methyl-6-propylbenzofuran-3-carboxamide

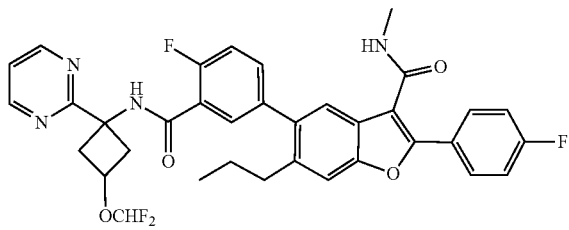 [SMILES: CCCc1cc2oc(-c3ccc(F)cc3)c(C(=O)NC)c2cc1-c1ccc(F)c(C(=O)NC2(c3ncccn3)CC(OC(F)F)C2)c1]

To a solution of 5-(4-fluoro-3-((3-hydroxy-1-(pyrimidin-2-yl)cyclobutyl)carbamoyl)phenyl)-2-(4-fluorophenyl)-N-methyl-6-propylbenzofuran-3-carboxamide (Example 31) (0.075 g, 0.126 mmol) in acetonitrile (4 mL) was added copper(I) iodide (0.024 g, 0.126 mmol). The resulting reaction mixture was heated to 50° C. To this reaction mixture was added 2-(fluorosulfonyl)difluoroacetic acid (0.022 g, 0.126 mmol) dropwise, and the mixture was stirred at 50° C. for 2 hours. It was then cooled to 50° C. and quenched with 10% sodium bicarbonate solution and extracted with ethyl acetate. The organic layer was dried over anhydrous Na₂SO₄, filtered and concentrated to obtain the crude product. It was purified by preparative HPLC to give 5-(3-((3-(difluoro methoxy)-1-(pyrimidin-2-yl)cyclobutyl)carbamoyl)-4-fluorophenyl)-2-(4-fluorophenyl)-N-methyl-6-propylbenzofuran-3-carboxamide as a white solid product (9 mg, 11.07%). ¹H NMR (400 MHz, DMSO-d₆): δ ppm 9.35 (d, J=1.6 Hz, 1H), 8.83 (d, J=5.2 Hz, 2H), 8.44 (q, J=4.4 Hz 4.3 Hz, 1H), 8.02-7.97 (m, 2H), 7.66 (s, 1H), 7.61 (dd, J=2.3, 6.9 Hz, 1H), 7.56-7.50 (m, 1H), 7.44-7.37 (m, 5H), 6.94-6.53 (t, J=72 Hz, 1H), 4.96-4.92 (m, 1H), 3.10-3.05 (m, 2H), 2.83-2.76 (m, 5H), 2.66-2.60 (m, 2H), 1.55-1.46 (m, 2H), 0.81 (t, J=7.3 Hz, 3H), ¹⁹F NMR (376.6 MHz, DMSO-d₆) δ ppm=−81.75, −110.955, −116.548. LCMS: (ES+) m/z=647.2 (M+H)⁺. Column: Zorbax SB C18 (30×2.1 mm; 3.5 um). Buffer: 10 mM Ammonium Formate in Water pH 4.5. phase A: Buffer+ACN (98+2). Mphase B: Buffer+ACN (2+98). Gradient Time (min)/% B: 0/6, 1.5/100, 2.2/100, 2.6/6, 3.0/6, Flow: 1.5 ml/min. Rt min: 1.73, wavelength: 220 nm. HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5), Gradient: Time (min)/% B: 0/10, 25/100, 30/100, Flow: 1.0 ml/min. Wavelength: 254 nm. Rt min: 23.20, Wavelength: 220 nm. Rt min: 23.20. HPLC Method: XBridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5), Gradient: Time (min)/% B: 0/10, 25/100, 30/100, Flow: 1.0 ml/min., Wavelength: 254 nm. Rt min: 19.98, Wavelength: 220 nm. Rt min: 19.98. PREPARATIVE HPLC METHOD: Column dimensions: sunfire C-18 (19*150) mm*5u. Mobile phase A: 10 mM Ammonium acetate pH-4.5 with AcOH. Mobile phase B: ACN. Flow: 16.0 ml/min, Rt: 19.47 min.

Example 33

5-(3-((3-(Difluoromethoxy)-1-(pyrimidin-2-yl)cyclobutyl)carbamoyl)phenyl)-2-(4-fluorophenyl)-N-methyl-6-propylbenzofuran-3-carboxamide

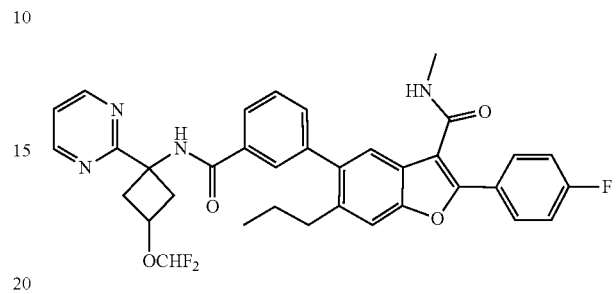

5-(3-((3-(difluoromethoxy)-1-(pyrimidin-2-yl)cyclobutyl)carbamoyl)phenyl)-2-(4-fluorophenyl)-N-methyl-6-propylbenzofuran-3-carboxamide (Example 33) was prepared in a similar manner as Example 32. ¹H NMR (300 MHz, CDCl₃): δ ppm 8.80 (d, J=5.2 Hz, 2H), 8.25 (s, 1H), 8.04-7.95 (m, 2H), 7.91-7.94 (m, 1H), 7.89 (s, 1H), 7.62 (s, 1H), 7.47 (s, 1H), 7.49-7.60 (m, 2H), 7.28-7.18 (m, 3H), 6.35 (t, J=74.3 Hz, 1H), 5.89 (br m, 1H), 5.19 (m, 1H), 3.66-3.59 (m, 2H), 3.02 (d, J=5.1 Hz, 3H), 3.01-2.96 (m, 2H), 2.66 (t, J=7.7 Hz, 2H), 1.57-1.49 (m, 2H), 0.85 (t, J=7.4 Hz, 3H), ¹⁹F NMR (376.6 MHz, CDCl₃) δ ppm=−82.65, −110.09. LCMS: (ES+) m/z=629.2 (M+H)⁺. Column: Acentis Express C18 (50×2.1 mm; 2.7 u). Buffer: 10 mM Ammonium Formate in Water pH 4.5. phase A: Buffer+ACN (98+2). Mphase B: Buffer+ACN (2+98). Gradient Time (min)/% B: 0/0, 1.6/100, 3.2/100, 3.6/0, Flow: 1.5 ml/min. Rt min: 2.18, wavelength: 220 nm. HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5), Gradient: Time (min)/% B: 0/10, 25/100, 30/100, Flow: 1.0 ml/min. Wavelength: 254 nm. Rt min: 21.96, Wavelength: 220 nm. Rt min: 21.96. HPLC Method: XBridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5), Gradient: Time (min)/% B: 0/10, 25/100, 30/100, Flow: 1.0 ml/min., Wavelength: 254 nm. Rt min: 18.79, Wavelength: 220 nm. Rt min: 18.79.

Example 34

5-(3-((3-(Benzyloxy)-1-(pyrimidin-2-yl)cyclobutyl)carbamoyl)-4-methoxyphenyl)-2-(4-fluorophenyl)-3-(methylcarbamoyl)-6-propylbenzofuran-3-carboxamide

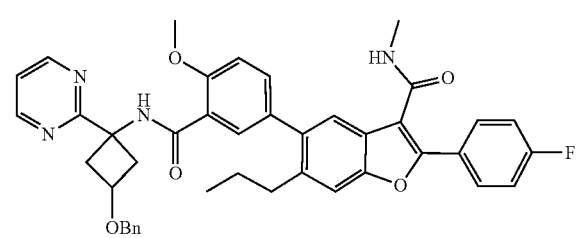 [SMILES: CCCc1cc2oc(-c3ccc(F)cc3)c(C(=O)NC)c2cc1-c1ccc(OC)c(C(=O)NC2(c3ncccn3)CC(OCc3ccccc3)C2)c1]

To a solution of 5-(2-(4-fluorophenyl)-3-(methylcarbamoyl)-6-propylbenzofuran-5-yl)-2-methoxybenzoic acid (0.2 g, 0.433 mmol), DIPEA (0.151 mL, 0.867 mmol) and BOP (0.192 g, 0.433 mmol) in DMF (4 mL) at 0° C. was added 3-(benzyloxy)-1-(pyrimidin-2-yl)cyclobutanamine (0.111 g, 0.433 mmol). The reaction mixture was stirred at 25° C. for 4 hours, and then diluted with water and filtered. The solid was dried and purified by Combiflash with 3% MeOH/chloroform as a mobile phase to give 5-(3-((3-(benzyloxy)-1-(pyrimidin-2-yl)cyclobutyl)carbamoyl)-4-methoxyphenyl)-2-(4-fluorophenyl)-3-(methylcarbamoyl)-6-propylbenzofuran-3-carboxamide as a white solid product (230 mg, 76%). LCMS: (ES+) m/z=699.4 (M+H)⁺. Column: Zorbax SB C18 (30×2.1 mm; 3.5 u). Buffer: 10 mM Ammonium Formate in Water pH 4.5. M phase A: Buffer+ACN (98+2). M phase B: Buffer+ACN (2+98) Flow: 1.5 ml/min, Rt min: 1.81 min, wavelength: 220 nm.

| Time | % A | % B |
|---|---|---|
| 0 | 94 | 6 |
| 1.5 | 0 | 100 |
| 2.2 | 0 | 100 |
| 2.6 | 94 | 6 |
| 3.0 | 94 | 6 |

Example 35

2-(4-Fluorophenyl)-5-(4-hydroxy-3-((3-hydroxy-1-(pyrimidin-2-yl)cyclobutyl)carbamoyl)phenyl)-N-methyl-6-propylbenzofuran-3-carboxamide

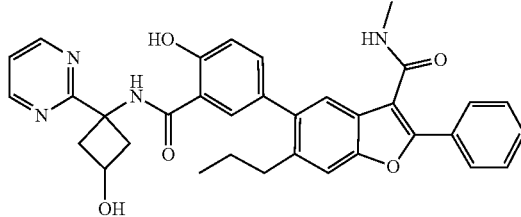

To a solution of 5-(3-((3-(benzyloxy)-1-(pyrimidin-2-yl)cyclobutyl)carbamoyl)-4-methoxyphenyl)-2-(4-fluorophenyl)-N-methyl-6-propylbenzofuran-3-carboxamide (Example 34) (0.23 g, 0.329 mmol) in DCM (8 mL) cooled to −78° C. was added boron trichloride (0.987 mL, 0.987 mmol) dropwise and slowly. The mixture was then stirred at 0° C. for 3 hours. The reaction was quenched with water (50 mL) and extracted with DCM (3×20 mL). The organic layer was dried over Na₂SO₄ and concentrated to give 2-(4-fluorophenyl)-5-(4-hydroxy-3-((3-hydroxy-1-(pyrimidin-2-yl)cyclobutyl)carbamoyl)phenyl)-N-methyl-6-propylbenzofuran-3-carboxamide as a pale yellow solid (160 mg, 82%). LCMS: (ES+) m/z=595.2 (M+H)⁺. Column-ACQUITY UPLC BEH C18 (50×2.1 mm; 1.7 m). M phase A: 0.1% TFA in water. M phase B: Acetonitrile. Flow: 0.8 ml/min. Rt min: 1.01 min, wavelength: 220 nm.

| Time | % A | % B |
|---|---|---|
| 0 | 98 | 2 |
| 1.0 | 2 | 98 |
| 1.6 | 2 | 98 |

Example 36

2-(4-fluorophenyl)-5-(3-((3-hydroxy-1-(pyrimidin-2-yl)cyclobutyl)carbamoyl)-4-methoxyphenyl)-N-methyl-6-propylbenzofuran-3-carboxamide

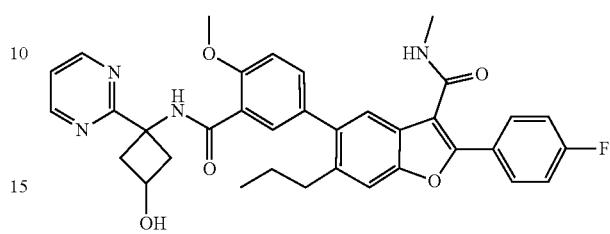

To a solution of 2-(4-fluorophenyl)-5-(4-hydroxy-3-((3-hydroxy-1-(pyrimidin-2-yl)cyclobutyl)carbamoyl)phenyl)-N-methyl-6-propylbenzofuran-3-carboxamide (Example 35) (0.14 g, 0.235 mmol) in DMF (0.5 mL) was added potassium carbonate (0.033 g, 0.235 mmol). The mixture was cooled to 0° C., and then methyl iodide (0.015 mL, 0.235 mmol) was added dropwise to it. The reaction mixture was then stirred at 25° C. for 2 hours. To the reaction mixture was added water (30 ml) and the mixture was extracted with ethyl acetate (3×20 ml). The organic layer was dried over Na₂SO₄ and concentrated to give 2-(4-fluorophenyl)-5-(3-((3-hydroxy-1-(pyrimidin-2-yl)cyclobutyl)carbamoyl)-4-methoxyphenyl)-N-methyl-6-propylbenzofuran-3-carboxamide as an off white solid (130 mg, 91%). LCMS: (ES+) m/z observed=608.9 (M+H)⁺. Column: Xbridge C18 (50×2.1 mm) 2.5 m, mobile phase A: 10 mM Ammonium Hydrogen Carbonate mobile phase B: ACN, Flow: 1.0 ml/min.

| Time | % B | % A |
|---|---|---|
| 0 | 0 | 100 |
| 1.7 | 100 | 0 |
| 3.2 | 100 | 0 |

Example 37

5-(3-((3-Difluoromethoxy)-1-(pyrimidin-2-yl)cyclobutyl)carbamoyl)-4-methoxyphenyl)-2-(4-fluorophenyl)-N-methyl-6-propylbenzofuran-3-carboxamide

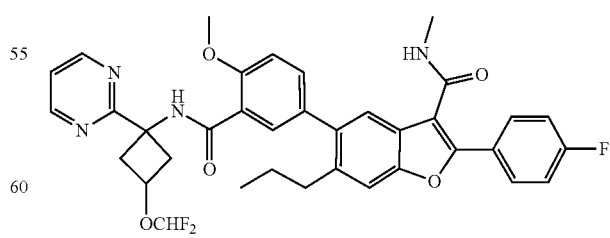

To a solution of 2-(4-fluorophenyl)-5-(3-((3-hydroxy-1-(pyrimidin-2-yl)cyclobutyl)carbamoyl)-4-methoxyphenyl)-N-methyl-6-propylbenzofuran-3-carboxamide (Example 36) (0.15 g, 0.246 mmol) in acetonitrile (4 mL) was added copper(I) iodide (0.047 g, 0.246 mmol). The resulting reaction mixture was heated to 50° C., and then 2-(fluorosulfonyl)difluoroacetic acid (0.044 g, 0.246 mmol) was added dropwise to it. The resulting reaction mixture was stirred at 50° C. for 2 hours. The reaction mixture was cooled to 0° C. and quenched with 10% sodium bicarbonate solution, and extracted with ethyl acetate. The organic extract was dried over $Na_2SO_4$ and concentrated to obtain the crude product, which was then purified by Preparative HPLC to give 5-(3-((3-difluoromethoxy)-1-(pyrimidin-2-yl)cyclobutyl)carbamoyl)-4-methoxyphenyl)-2-(4-fluorophenyl)-N-methyl-6-propylbenzofuran-3-carboxamide as a white solid product (14 mg, 8.62%). PREPARATIVE HPLC METHOD. Column: ymc trait (250×30×10 g). Mobile phase A: 10 mM Ammonium acetate pH-4.5 with AcOH. Mobile phase B: ACN. Flow: 15.0 ml/min. $^1$H NMR (400 MHz, Methanol-$d_4$): δ ppm 8.83 (d, J=4.9 Hz, 2H), 7.99-7.89 (m, 3H), 7.55-7.54 (d, 2.4 Hz, 2H), 7.51 (m, 1H) 7.45 (s, 1H), 7.3-7.23 (m, 3H), 6.64-6.25 (t, J=72 Hz, 1H), 5.15 (t, J=7.4 Hz, 1H), 4.16 (s, 3H), 3.16-3.12 (m, 4H), 2.94 (s, 3H), 2.71-2.66 (t, J=7.5, 2H), 1.57-1.49 (m, 2H), 0.84 (t, J=7.3 Hz, 3H). $^{19}$F NMR (376.6 MHz, Methanol-$d_4$): δ ppm −84.12, −112.96. LCMS: (ES+) m/z=659.2 (M+H)$^+$. Column: Zorbax SB C18 (30×2.1 mm; 3.5 um). Buffer: 10 mM Ammonium Formate in Water pH 4.5. M phase A: Buffer+ACN (98+2). M phase B: Buffer+ACN (2+98). Flow: 1.5 ml/min Rt min: 1.78, wavelength: 220 nm.

| Time | % A | % B |
|------|-----|-----|
| 0    | 94  | 6   |
| 1.5  | 0   | 100 |
| 2.2  | 0   | 100 |
| 2.6  | 94  | 6   |
| 3.0  | 94  | 6   |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile:0.05% TFA in Water (95:5). Gradient: Time (min)/% B: 0/10, 25/100, 30/100, Flow: 1.0 ml/min. Wavelength: 254 nm, Rt min: 23.36. Wavelength: 220 nm, Rt min: 23.36. HPLC Method: XBridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5). Gradient: Time (min)/% B: 0/10, 25/100, 30/100, Flow: 1.0 ml/min. Wavelength: 254 nm, Rt min: 20.61. Wavelength: 220 nm, Rt min: 20.61.

Example 38

2-(4-Fluorophenyl)-5-(5-((3-hydroxy-1-(pyrimidin-2-yl)cyclobutyl)carbamoyl)-4-methoxy-2-methylphenyl)-N-methyl-6-propylbenzofuran-3-carboxamide

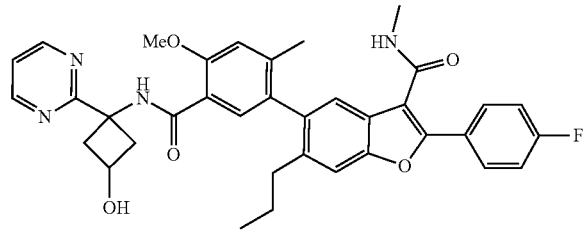 [SMILES: CCCc1cc2oc(-c3ccc(F)cc3)c(C(=O)NC)c2cc1-c1cc(C(=O)NC2(c3ncccn3)CC(O)C2)c(OC)cc1C]

To a mixture of 3-amino-3-(pyrimidin-2-yl)cyclobutanol (0.035 g, 0.210 mmol) and 5-(2-(4-fluorophenyl)-3-(methylcarbamoyl)-6-propylbenzofuran-5-yl)-2-methoxy-4-methylbenzoic acid (0.1 g, 0.210 mmol) in DMF (1 mL) under ice-cold condition was added TEA (0.147 mL, 1.052 mmol) and then BOP (0.140 g, 0.315 mmol). The reaction mixture was stirred at ambient temperature for 12 hr. The reaction was quenched with ice-cold water. The white solid precipitated was filtered and dried under suction. It was taken for the fluorination step without further purification (80 mg). LCMS: (ES+) m/z=623.7 (M+H)$^+$. Column: Acquity BEH C18 (2.1×50 mm) 1.7 μm, Mobile phase A: 5 mM Ammonium Acetate:ACN (95:5). Mobile phase B: 5 mM Ammonium Acetate:ACN (5:95). Method: % B: 0 min-5%:1.1 min-95%:1.7 min-95%. Flow: 0.8 ml/min. Rt min: 1.10, Wavelength: 220 nm.

Example 39

5-(5-((3-(Difluoromethoxy)-1-(pyrimidin-2-yl)cyclobutyl)carbamoyl)-4-methoxy-2-methylphenyl)-2-(4-fluorophenyl)-N-methyl-6-propylbenzofuran-3-carboxamide

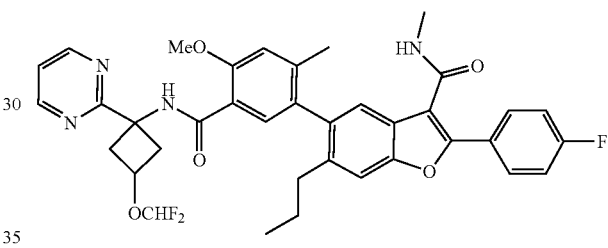

To a mixture of 2-(4-fluorophenyl)-5-(5-((3-hydroxy-1-(pyrimidin-2-yl)cyclobutyl)carbamoyl)-4-methoxy-2-methylphenyl)-N-methyl-6-propylbenzofuran-3-carboxamide (Example 38) (80 mg, 0.128 mmol) and copper(I) iodide (24.47 mg, 0.128 mmol) in acetonitrile (0.5 mL) at 45° C. was added 2-(fluorosulfonyl)difluoroacetic acid (0.018 mL, 0.193 mmol). The mixture was stirred at the same temperature for 12 hr. The reaction was quenched with sat. $NaHCO_3$, and diluted with ethyl acetate. The organic layer was separated, dried over $Na_2SO_4$, and then concentrated. The crude product was submitted for Prep-HPLC purification to afford a white solid product (7.52 mg, Yield: 8.61%). Preparative HPLC Method: Column: SUNFIRE C-18 (19*150) mm*5u. Mobile phase A: 10 mM ammonium acetate, Mobile phase B: Acetonitrile. Flow: 16 ml/min. Rt min: 14.622. $^1$H NMR (400 MHz, DMSO-$d_6$): δ ppm=9.59 (s, 1H), 8.90 (d, J=4.9 Hz, 2H), 8.39 (d, J=5.0 Hz, 1H), 7.99 (dd, J=5.5, 9.0 Hz, 2H), 7.68 (s, 1H), 7.63 (s, 1H), 7.49-7.45 (m, 1H), 7.39 (t, J=8.9 Hz, 2H), 7.27 (s, 1H), 7.20 (s, 1H), 6.76 (t, J=75.6 Hz, 1H), 4.99 (t, J=7.3 Hz, 1H), 4.09 (s, 3H), 3.18 (m, 2H), 2.96-2.89 (m, 2H), 2.79 (d, J=4.6 Hz, 3H), 2.46 (m, 1H), 2.38-2.27 (m, 1H), 2.09 (s, 3H), 1.45 (q, J=7.4 Hz, 2H), 0.76 (t, J=7.3 Hz, 3H). $^{19}$F NMR (376.6 MHz, DMSO-$d_6$): δ ppm: −81.66, −111.09. LCMS: (ES+) m/z=673.2 (M+H)$^+$. Column-Ascentis Express C18 (50×2.1 mm-2.7 μm). Mphase A: 10 mM $NH_4COOH$ in Water:ACN (98:02). Mphase B: 10 mM $NH_4COOH$ in Water:ACN (02:98), Gradient: Time (min)/% B: 0/10, 1.5/100, 3.2/100, Flow=1 mL/min. Rt min: 2.82, Wavelength: 220 nm.

HPLC Method: XBridge phenyl (4.6×150) mm, 3.5 micron. Buffer: 0.05% TFA in water pH 2.5, Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 20.81. Wavelength: 220 nm, Rt min: 20.81. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 24.09. Wavelength: 220 nm, Rt min: 24.09.

Example 40

2-(4-Fluorophenyl)-5-(5-((3-hydroxy-1-(pyrimidin-2-yl)cyclobutyl)carbamoyl)-4-methoxy-2-methylphenyl)-N-methyl-6-(3,3,3-trifluoropropyl)benzofuran-3-carboxamide

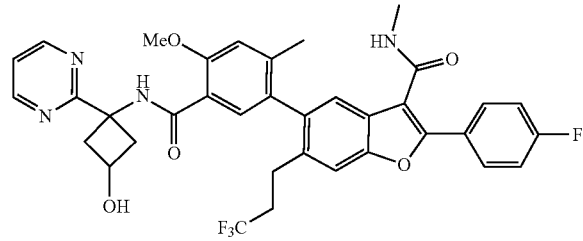 [SMILES: CNC(=O)c1c(-c2ccc(F)cc2)oc2cc(CCC(F)(F)F)c(-c3cc(C(=O)NC4(c5ncccn5)CC(O)C4)c(OC)cc3C)cc12]

To a mixture of 5-(2-(4-fluorophenyl)-3-(methylcarbamoyl)-6-(3,3,3-trifluoropropyl)benzofuran-5-yl)-2-methoxy-4-methylbenzoic acid (0.1 g, 0.189 mmol) and 3-amino-3-(pyrimidin-2-yl) cyclobutanol (0.031 g, 0.189 mmol) in DMF (0.5 mL) under ice-cold conditions was added TEA (0.132 mL, 0.944 mmol) and BOP (0.125 g, 0.283 mmol). The reaction mixture was stirred at same temperature for 12 hr. The reaction was quenched with ice-cold water. The pale yellow solid precipitated out was filtered and dried under suction. This product was taken to the next step (Yield: 80 mg, pale yellow solid). LCMS for mol. LCMS: (ES+) m/z=677.7 (M+H)$^+$. Column: Acquity BEH C18 (2.1×50 mm) 1.7 µm, Mobile phase A: 5 mM Ammonium Acetate: ACN (95:5). Mobile phase B: 5 mM Ammonium Acetate: ACN (5:95). Method: % B: 0 min-5%:1.1 min-95%:1.7 min-95%. Flow: 0.8 ml/min. Rt min: 1.10, Wavelength: 220 nm.

Example 41

5-(5-((3-(Difluoromethoxy)-1-(pyrimidin-2-yl)cyclobutyl)carbamoyl)-4-methoxy-2-methylphenyl)-2-(4-fluorophenyl)-N-methyl-6-(3,3,3-trifluoropropyl)benzofuran-3-carboxamide

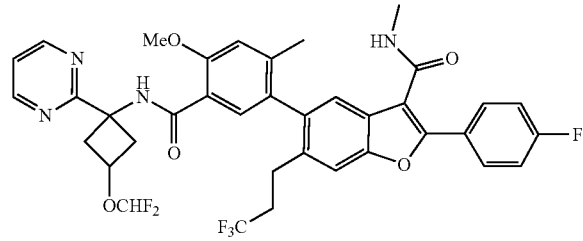

To 2-(4-fluorophenyl)-5-(5-((3-hydroxy-1-(pyrimidin-2-yl)cyclobutyl)carbamoyl)-4-methoxy-2-methylphenyl)-N-methyl-6-(3,3,3-trifluoropropyl)benzofuran-3-carboxamide (Example 40) (0.11 g, 0.163 mmol) and copper(I) iodide (0.031 g, 0.163 mmol) in acetonitrile (0.5 mL) at 45° C. was added 2-(fluorosulfonyl)difluoroacetic acid (0.023 mL, 0.244 mmol). The reaction mixture was stirred at the same temperature for 12 hr. The reaction was quenched with sat. NaHCO$_3$, and diluted with ethyl acetate (20 ml). The organic layer was separated, dried over Na$_2$SO$_4$, and concentrated. The crude product was submitted for Prep. HPLC. (Yield: 7.42 mg, 6.22%, white solid). Preparative HPLC Method: Column: Phenominex luna C18 (4.6×250) mm, 5 micron. Mobile phase A: 10 mM ammonium acetate; Mobile phase B: Acetonitrile; Flow: 16 ml/min Rt min: 16.61. $^1$H NMR (400 MHz, CDCl$_3$): δ ppm=9.53 (s, 1H), 8.78 (d, J=4.8 Hz, 2H), 8.03 (s, 1H), 8.06-7.95 (m, 2H), 7.46 (s, 1H), 7.41 (s, 1H), 7.24-7.13 (m, 3H), 6.94 (s, 1H), 6.30 (t, J=75.6 Hz, 1H), 5.87-5.86 (m, 1H), 5.11 (t, J=7.2 Hz, 1H), 4.12 (s, 3H), 3.35 (dd, J=6.9, 13.0 Hz, 2H), 3.15-3.05 (m, 2H), 3.00 (d, J=4.9 Hz, 3H), 2.83-2.72 (m, 1H), 2.71-2.59 (m, 1H), 2.25-2.13 (m, 2H), 2.12 (s, 3H). $^{19}$F NMR (376.6 MHz, CDCl$_3$): δ ppm −66.56, −82.49, −110.04. LCMS: (ES+) m/z=727.2 (M+H)$^+$. Rt min: 2.77, Wavelength: 220 nm. Column-Ascentis Express C18 (50×2.1 mm-2.7 µm). Mphase A: 10 mM NH$_4$COOH in Water:ACN (98:02). Mphase B: 10 mM NH$_4$COOH in Water:ACN (02:98). Gradient: Time (min)/% B: 0/0, 1.5/100, 3.2/100, Flow=1 mL/min. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 20.37. Wavelength: 220 nm, Rt min: 20.37. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Gradient: Time (min)/% B: 0/10, 25/100, 30/100, Flow: 1 ml/min. Wavelength: 254 nm, Rt min: 22.78. Wavelength: 220 nm, Rt min: 22.78.

Example 42

5-(3-((3-(Difluoromethoxy)-1-(pyrimidin-2-yl)cyclobutyl)carbamoyl)-4-fluorophenyl)-2-(4-fluorophenyl)-N-methyl-6-(3,3,3-trifluoropropyl)benzofuran-3-carboxamide

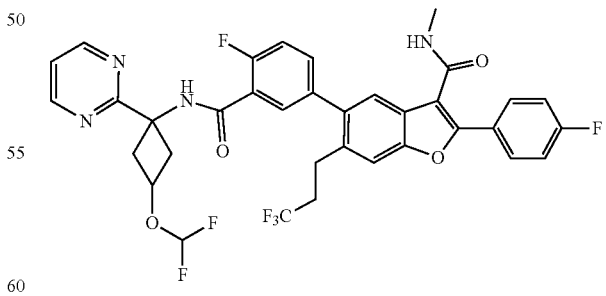

To a stirred solution of 2-fluoro-5-(2-(4-fluorophenyl)-3-(methylcarbamoyl)-6-(3,3,3-trifluoropropyl)benzofuran-5-yl)benzoic acid (50 mg, 0.099 mmol) and 3-(difluoromethoxy)-1-(pyrimidin-2-yl)cyclobutanamine (23.51 mg, 0.109 mmol) in DMF (5.0 mL) at room temperature under a N2 atmosphere was added DIPEA (0.052 mL, 0.298 mmol). The mixture was cooled to at 0° C., and BOP (65.9 mg, 0.149 mmol) reagent was added to it. The reaction mixture was allowed to stir at room temperature for 16 hr. After completion of the reaction, the mixture was diluted with water and the product extracted with EtOAc (25 ml×3). The combined organic extracts were washed with saturated brine solution, dried over $Na_2SO_4$ and concentrated under reduced pressure. The crude solid product was purified by Prep HPLC to obtained 5-(3-((3-(difluoromethoxy)-1-(pyrimidin-2-yl)cyclobutyl)carbamoyl)-4-fluorophenyl)-2-(4-fluorophenyl)-N-methyl-6-(3,3,3-trifluoropropyl)benzofuran-3-carboxamide as an off white solid. Yield: 15.00 mg, (21.47%). PREPARATIVE HPLC: Column: SUNFIRE C-18 (19*150) mm*5u, Mobile Phase: 10 mM Ammonium acetate in water pH 4.5 with acetic acid (A); ACN (B), Flow: 16 ml/min, Rt: 16.39 min. $^1$H NMR (400 MHz, CHLOROFORM-d) 6=8.79 (d, J=5.0 Hz, 2H), 8.63 (d, J=13.0 Hz, 1H), 8.12 (dd, J=2.5, 7.5 Hz, 1H), 8.00-7.95 (m, 2H), 7.61 (s, 1H), 7.47-7.42 (m, 1H), 7.42 (s, 1H), 7.25-7.16 (m, 4H), 6.31 (t, J=74.4 Hz, 1H), 5.83 (br. s, 1H), 5.17 (m, 1H), 3.52-3.45 (m, 2H), 3.07-3.02 (m, 2H), 3.00 (d, J=4.8 Hz, 3H), 2.95-2.90 (m, 2H), 2.24-2.16 (m, 2H). $^{19}$F NMR (376.6 MHz, CHLOROFORM-d) δ: −66.56, −82.64, −109.66, −114.58. LCMS: (ES+) m/z=701.2 (M+H)$^+$, Column-Acentis Express C18 (50×2.1 mm; 2.7 u), Buffer: 10 mM Ammonium Formate in Water, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.71 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 21.85 min, Wavelength: 220 nm, Rt: 21.85 min. HPLC Method: XBridge Phenyl (150×4.6 mm) 3.5 micron, Buffer: 0.05% TFA in water, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 19.27 min, Wavelength: 220 nm, Rt: 19.27 min.

Example 43

5-(3-((3-(Difluoromethoxy)-1-(pyrimidin-2-yl)cyclobutyl)carbamoyl)-4-methoxyphenyl)-2-(4-fluorophenyl)-N-methyl-6-(3,3,3-trifluoropropyl)benzofuran-3-carboxamide

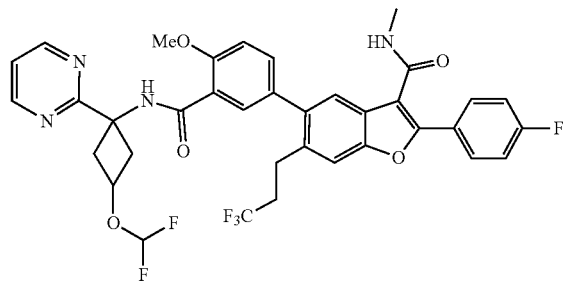 [SMILES: CNC(=O)c1c(-c2ccc(F)cc2)oc2cc(CCC(F)(F)F)c(-c3ccc(OC)c(C(=O)NC4(c5ncccn5)CC(OC(F)F)C4)c3)cc12]

To a stirred solution of 5-(2-(4-fluorophenyl)-3-(methylcarbamoyl)-6-(3,3,3-trifluoropropyl)benzofuran-5-yl)-2-methoxybenzoic acid (35 mg, 0.068 mmol) and 3-(difluoromethoxy)-1-(pyrimidin-2-yl)cyclobutanamine (16.07 mg, 0.075 mmol) in DMF (1.5 mL) at room temperature under a N2 atmosphere was added DIPEA (0.036 mL, 0.204 mmol). The mixture was cooled to 0° C., and to which was assed HATU (38.7 mg, 0.102 mmol). The reaction mixture was allowed to stir at room temperature for 16 hr. After completion of the reaction, the mixture was diluted with water and the product extracted with EtOAc (25 mL×3). The combined organic extracts were washed with saturated brine solution, dried over $Na_2SO_4$ and concentrated under reduced pressure. The crude solid product was purified by Prep HPLC to obtained 5-(3-((3-(difluoromethoxy)-1-(pyrimidin-2-yl)cyclobutyl)carbamoyl)-4-methoxyphenyl)-2-(4-fluorophenyl)-N-methyl-6-(3,3,3-trifluoropropyl)benzofuran-3-carboxamide as an off white solid. Yield: 36.00 mg, (74.20%). PREPARATIVE HPLC: Column: SUNFIRE C-18 (19*150) mm*5u, Mobile Phase: 10 mM Ammonium acetate in water pH 4.5 with acetic acid (A); ACN (B), Flow: 16 ml/min, Rt: 15.49 min. $^1$H NMR (400 MHz, DMSO-d$_6$) δ=9.62 (s, 1H), 8.89 (d, J=4.8 Hz, 2H), 8.45 (q, J=4.5 Hz, 1H), 8.02-7.97 (m, 2H), 7.85 (d, J=2.4 Hz, 1H), 7.78 (s, 1H), 7.56 (dd, J=2.4, 8.4 Hz, 1H), 7.47 (m, 1H), 7.42-7.37 (m, 3H), 7.32 (d, J=8.8 Hz, 1H), 6.76 (t, J=75.6 Hz, 1H), 4.99 (quin, J=7.1 Hz, 1H), 4.09 (s, 3H), 3.40-3.30 (hidden m, 2H), 3.20-3.13 (m, 2H), 2.99-2.88 (m, 4H), 2.81 (d, J=4.5 Hz, 3H). $^{19}$F NMR (376.6 MHz, DMSO-d$_6$) δ: −64.86, −81.68, −110.82. LCMS: (ES+) m/z=713.2 (M+H)$^+$, Column-Acentis Express C18 (50×2.1 mm; 2.7 u), Buffer: 10 mM Ammonium Formate in Water, Mobile phase A: Buffer: ACN (98:2), Mobile phase B: Buffer:ACN (2:98), Gradient: Time (min)/% B: 0/0, 1.5/100, 3.2/100, Flow: 1.0 ml/min. Rt: 2.73 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 22.16 min, Wavelength: 220 nm, Rt: 22.16 min. HPLC Method: XBridge Phenyl (150×4.6 mm) 3.5 micron, Buffer: 0.05% TFA in water, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 19.53 min, Wavelength: 220 nm, Rt: 19.53 min.

Example 44

2-(4-Fluorophenyl)-N-methyl-6-propyl-5-(3-((1-(pyrimidin-2-yl)-3-(trifluoromethoxy)cyclobutyl)carbamoyl)phenyl)benzofuran-3-carboxamide

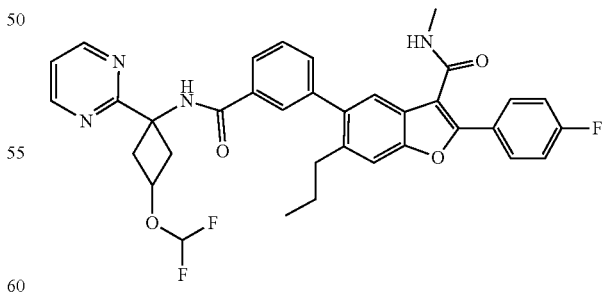

To a stirred solution of 3-(2-(4-fluorophenyl)-3-(methylcarbamoyl)-6-propylbenzofuran-5-yl)benzoic acid (30 mg, 0.070 mmol) and 1-(pyrimidin-2-yl)-3-(trifluoromethoxy) cyclobutanamine (17.84 mg, 0.076 mmol) in DMF (2.0 mL) at room temperature under a N2 atmosphere was added DIPEA (0.036 mL, 0.209 mmol). The mixture was cooled to 0° C., and to which was added HATU (39.7 mg, 0.104 mmol). The reaction mixture was allowed to stir at room temperature for 16 hr. After completion of the reaction, the mixture was diluted with water and the product extracted with EtOAc (25 mL×3). The combined organic extracts were washed with saturated brine solution, dried over $Na_2SO_4$ and concentrated under reduced pressure. The crude solid product was purified by Prep HPLC to obtained 2-(4-fluorophenyl)-N-methyl-6-propyl-5-(3-((1-(pyrimidin-2-yl)-3-(trifluoromethoxy)cyclobutyl)carbamoyl)phenyl) benzofuran-3-carboxamide as a white solid. Yield: 20.00 mg, (44.45%). PREPARATIVE HPLC: Column: SUNFIRE C-18 (19*150) mm*5u, Mobile Phase: 0.1% TFA (A); ACN (B), Flow: 16 ml/min, Rt: 17.47 min.

$^1$H NMR (400 MHz, CHLOROFORM-d) δ=8.78 (d, J=4.9 Hz, 2H), 8.24 (s, 1H), 8.01-7.97 (m, 2H), 7.93-7.89 (m, 1H), 7.87 (m, 1H), 7.60 (s, 1H), 7.55-7.50 (m, 2H), 7.45 (s, 1H), 7.25-7.24 (m, 1H), 7.21-7.16 (m, 2H), 5.87 (m, 1H), 5.22 (quin, J=7.1 Hz, 1H), 3.73-3.68 (m, 2H), 3.02-2.98 (m, 2H), 3.00 (d, J=4.8 Hz, 3H), 2.67-2.62 (m, 2H), 1.54-1.51 (m, 2H), 0.83 (t, J=7.3 Hz, 3H). $^{19}$F NMR (376.6 MHz, CHLOROFORM-d) δ: −59.20, −110.07. LCMS: (ES+) m/z=647.2 $(M+H)^+$, Column-Acentis Express C18 (50×2.1 mm; 2.7 u), Buffer: 10 mM Ammonium Formate in Water, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.20 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 24.48 min, Wavelength: 220 nm, Rt: 24.48 min. HPLC Method: XBridge Phenyl (150×4.6 mm) 3.5 micron, Buffer: 0.05% TFA in water, Mobile Phase A: Buffer:ACN (95:5), Mobile Phase B: Buffer: ACN (5:95), Gradient: Time (min)/% B: 0/10, 25/100, 30/100, Flow: 1.0 ml/min, Wavelength: 254 nm, Rt: 20.22 min, Wavelength: 220 nm, Rt: 20.22 min.

Example 45a and Example 45b 2-(4-Fluorophenyl)-N-methyl-5-(3-((1-(pyrimidin-2-yl)-3-(trifluoromethoxy)cyclobutyl)carbamoyl)phenyl)-6-(3,3,3-trifluoropropyl)benzofuran-3-carboxamide

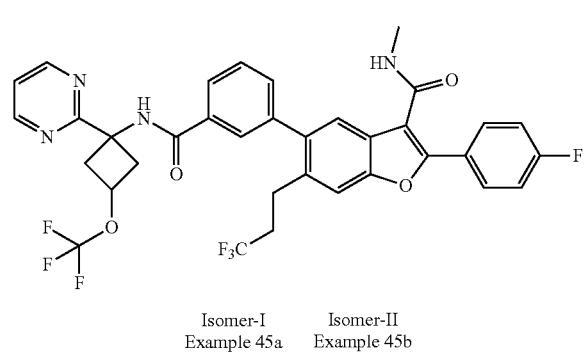 [SMILES: CNC(=O)c1c(-c2ccc(F)cc2)oc2cc(CCC(F)(F)F)c(-c3cccc(C(=O)NC4(c5ncccn5)CC(OC(F)(F)F)C4)c3)cc12]

Isomer-I  Isomer-II
Example 45a  Example 45b

To a stirred solution of 3-(2-(4-fluorophenyl)-3-(methylcarbamoyl)-6-(3,3,3-trifluoropropyl)benzofuran-5-yl)benzoic acid (30 mg, 0.062 mmol) and 1-(pyrimidin-2-yl)-3-(trifluoromethoxy)cyclobutanamine (15.85 mg, 0.068 mmol) in DMF (2.0 mL) at room under a N2 atmosphere temperature was added DIPEA (0.032 mL, 0.185 mmol). The mixture was cooled to 0° C., and HATU (35.2 mg, 0.093 mmol) was added to it. The reaction mixture was allowed to stir at room temperature for 16 hr. After completion of the reaction, the reaction mixture was diluted with water and the product extracted with EtOAc (20 mL×3). The combined organic extracts were washed with saturated brine solution, dried over $Na_2SO_4$ and concentrated under reduced pressure. The crude solid product obtained was purified by Prep HPLC to obtain the two isomers of 2-(4-fluorophenyl)-N-methyl-5-(3-((1-(pyrimidin-2-yl)-3-(trifluoromethoxy)cyclobutyl)carbamoyl)phenyl)-6-(3,3,3-trifluoropropyl)benzofuran-3-carboxamide as white solids. Example 45a (Isomer-I) Yield: 4.33 mg, (10.00%). Example 45b (Isomer-II) Yield: 6.46 mg, (14.92%). PREPARATIVE HPLC: Column: Chiralpak-IA (250×21) mm, 5u, Mobile Phase: 70% $CO_2$ (A); 30% (0.5% DEA (diethylamine) in Methanol) (B).

Example 45a (Isomer-I) $^1$H NMR (400 MHz, CHLOROFORM-d) δ=8.83 (d, J=4.9 Hz, 2H), 8.41 (s, 1H), 7.99-7.90 (m, 3H), 7.88-7.87 (m, 1H), 7.68 (s, 1H), 7.60-7.55 (m, 1H), 7.52-7.49 (m, 1H), 7.46 (s, 1H), 7.23-7.18 (m, 3H), 5.85 (br. m, 1H), 5.61 (quin, J=7.1 Hz, 1H), 3.30 (d, J=7.0 Hz, 4H), 3.00 (d, J=4.9 Hz, 3H), 2.98-2.94 (m, 2H), 2.28-2.20 (m, 2H). $^{19}$F NMR (376.6 MHz, CHLOROFORM-d) δ: −59.14, −66.49, −109.51. LCMS: (ES+) m/z=701.2 $(M+H)^+$, Column-Acentis Express C18 (50×2.1 mm; 2.7 u), Buffer: 10 mM Ammonium Formate in Water, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.14 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 22.92 min, Wavelength: 220 nm, Rt: 22.92 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 19.51 min, Wavelength: 220 nm, Rt: 19.51 min.

Example 45b (Isomer-II) $^1$H NMR (400 MHz, CHLOROFORM-d) δ=8.78 (d, J=4.9 Hz, 2H), 8.26 (s, 1H), 8.00-7.96 (m, 2H), 7.93-7.89 (m, 2H), 7.66 (s, 1H), 7.58-7.54 (m, 1H), 7.51-7.48 (m, 1H), 7.46 (s, 1H), 7.27-7.24 (m, 1H), 7.22-7.17 (m, 2H), 5.85 (br. m, 1H), 5.22 (quin, J=7.1 Hz, 1H), 3.75-3.68 (m, 2H), 3.01-2.94 (d, 3H overlapping with m, 4H), 2.26-2.19 (m, 2H). $^{19}$F NMR (376.6 MHz, CHLOROFORM-d) δ: −59.20, −66.48, −109.60. LCMS: (ES+) m/z=701.2 $(M+H)^+$, Column-Acentis Express C18 (50×2.1 mm; 2.7 u), Buffer: 10 mM Ammonium Formate in Water, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.13 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 23.21 min, Wavelength: 220 nm, Rt: 23.21 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 19.32 min, Wavelength: 220 nm, Rt: 19.32 min.

Example 46a and Example 46b 2-(4-Fluorophenyl)-5-(4-methoxy-2-methyl-5-((1-(pyrimidin-2-yl)-3-(trifluoromethoxy)cyclobutyl)carbamoyl)phenyl)-N-methyl-6-(3,3,3-trifluoropropyl)benzofuran-3-carboxamide

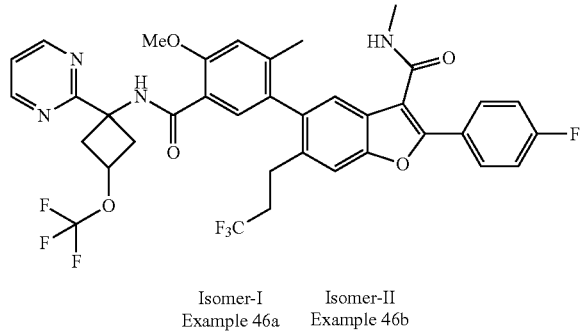 [SMILES: CNC(=O)c1c(-c2ccc(F)cc2)oc2cc(CCC(F)(F)F)c(-c3cc(C(=O)NC4(c5ncccn5)CC(OC(F)(F)F)C4)c(OC)cc3C)cc12]

Isomer-I  Isomer-II
Example 46a  Example 46b

To a stirred mixture of 5-(2-(4-fluorophenyl)-3-(methylcarbamoyl)-6-(3,3,3-trifluoropropyl)benzofuran-5-yl)-2-methoxy-4-methylbenzoic acid (35 mg, 0.066 mmol) and 1-(pyrimidin-2-yl)-3-(trifluoromethoxy)cyclobutanamine (16.96 mg, 0.073 mmol) in DMF (2.0 mL) at room temperature under a N2 atmosphere was added DIPEA (0.035 mL, 0.198 mmol). The mixture was cooled to 0° C., and HATU (37.7 mg, 0.099 mmol) was added to it. The reaction mixture was allowed to stir at room temperature for 16 hr. After completion of the reaction, the reaction mixture was diluted with water and the product extracted with EtOAc (20 mL×3). The combined organic extracts were washed with saturated brine solution, dried over Na$_2$SO$_4$ and concentrated under reduced pressure. The crude solid product obtained was purified by Prep HPLC to obtain the two isomers of 2-(4-fluorophenyl)-5-(4-methoxy-2-methyl-5-((1-(pyrimidin-2-yl)-3-(trifluoromethoxy)cyclobutyl)carbamoyl)phenyl)-N-methyl-6-(3,3,3-trifluoropropyl)benzofuran-3-carboxamide as white solids. Example 46a (Isomer-I) Yield: 10.60 mg, (21.53%). Example 46b (Isomer-II) Yield: 8.76 mg, (17.79%). PREPARATIVE HPLC: Column: YMC (150×4.6) 5u Mobile Phase: 10 mM NH$_4$OAc in water pH 4.6 with acetic acid (A); ACN (B), Flow: 1 ml/min, Rt: 17.37 and 17.72 min.

Example 46a (Isomer-I) $^1$H NMR (400 MHz, CHLOROFORM-d) δ=9.71 (s, 1H), 8.83 (d, J=4.9 Hz, 2H), 8.03-7.98 (s, 1H overlapped with m, 2H), 7.48 (s, 1H), 7.42 (s, 1H), 7.25-7.15 (m, 3H), 6.95 (s, 1H), 5.86 (br. d, J=4.8 Hz, 1H), 5.53-5.45 (m, 1H), 4.13 (s, 3H), 3.29-3.23 (m, 4H), 2.99 (d, J=4.9 Hz, 3H), 2.80-2.62 (m, 2H), 2.25-2.16 (m, 2H), 2.12 (s, 3H). $^{19}$F NMR (376.6 MHz, CHLOROFORM-d) δ: −59.14, −66.57, −109.95. LCMS: (ES+) m/z=745.2 (M+H)$^+$, Column-Acentis Express C18 (50×2.1 mm; 2.7 u), Buffer: 10 mM Ammonium Formate in Water pH 4.5, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.22 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/40, 25/100, 30/100, Flow: 1.2 ml/min, Wavelength: 254 nm, Rt: 19.41 min, Wavelength: 220 nm, Rt: 19.41 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/40, 25/100, 30/100, Flow: 1.0 ml/min, Wavelength: 254 nm, Rt: 15.35 min, Wavelength: 220 nm, Rt: 15.35 min.

Example 46b (Isomer-II) $^1$H NMR (400 MHz, CHLOROFORM-d) δ=9.57 (s, 1H), 8.78 (d, J=4.9 Hz, 2H), 8.05-8.00 (m, 2H), 8.03 (s, 1H), 7.46 (s, 1H), 7.41 (s, 1H), 7.24-7.15 (m, 3H), 6.94 (s, 1H), 5.89 (br. d, J=4.1 Hz, 1H), 5.21-5.12 (m, 1H), 4.12 (s, 3H), 3.47-3.42 (m, 2H), 3.13-3.06 (m, 2H), 3.00 (d, J=4.9 Hz, 3H), 2.82-2.61 (m, 2H), 2.23-2.14 (m, 2H), 2.12 (s, 3H). $^{19}$F NMR (376.6 MHz, CHLOROFORM-d) δ: −59.19, −66.57, −110.02. LCMS: (ES+) m/z=745.2 (M+H)$^+$, Column-Acentis Express C18 (50×2.1 mm; 2.7 u), Buffer: 10 mM Ammonium Formate in Water pH 4.5, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.25 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/40, 25/100, 30/100, Flow: 1.2 ml/min, Wavelength: 254 nm, Rt: 20.15 min, Wavelength: 220 nm, Rt: 20.15 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/40, 25/100, 30/100, Flow: 1.0 ml/min, Wavelength: 254 nm, Rt: 15.77 min, Wavelength: 220 nm, Rt: 15.77 min.

Example 47a and Example 47b 2-(4-Fluorophenyl)-5-(4-methoxy-3-((1-(pyrimidin-2-yl)-3-(trifluoromethoxy)cyclobutyl)carbamoyl)phenyl)-N-methyl-6-(3,3,3-trifluoropropyl)benzofuran-3-carboxamide

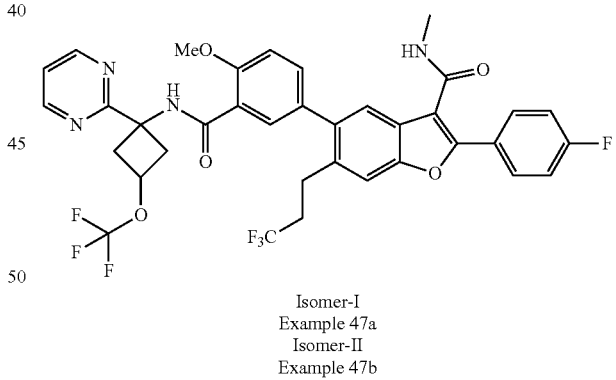

Isomer-I
Example 47a
Isomer-II
Example 47b

To a stirred mixture of 5-(2-(4-fluorophenyl)-3-(methylcarbamoyl)-6-(3,3,3-trifluoropropyl)benzofuran-5-yl)-2-methoxybenzoic acid (50 mg, 0.097 mmol) and 1-(pyrimidin-2-yl)-3-(trifluoromethoxy)cyclobutanamine (24.88 mg, 0.107 mmol) in DMF (4.0 mL) at room temperature under a N2 atmosphere was added DIPEA (0.051 mL, 0.291 mmol). The mixture was cooled to 0° C., and to which HATU (55.3 mg, 0.146 mmol) was added. The reaction mixture was allowed to stir at room temperature for 16 hr. After completion of the reaction, the reaction mixture was diluted with water and the product extracted with EtOAc (20 mL×3). The combined organic extracts were washed with saturated brine solution, dried over Na₂SO₄ and concentrated under reduced pressure. The crude product obtained was purified by Prep HPLC to obtained the two isomers of 2-(4-fluorophenyl)-5-(4-methoxy-3-((1-(pyrimidin-2-yl)-3-(trifluoromethoxy)cyclobutyl)carbamoyl)phenyl)-N-methyl-6-(3,3,3-trifluoropropyl)benzofuran-3-carboxamide as white solids. Example 47a (Isomer-I) Yield: 9.57 mg, (13.46%). Example 47b (Isomer-II) Yield: 14.48 mg, (21.40%). PREPARATIVE HPLC: Column: SUNFIRE C-18 (19*150) mm*5u, Mobile Phase: 10 mM NH₄OAc in water pH 4.6 with acetic acid (A); ACN (B), Flow: 16 ml/min, Rt: 13.00 and 16.06 min.

Example 47a (Isomer-I) ¹H NMR (400 MHz, CHLOROFORM-d) δ=9.73 (s, 1H), 8.83 (d, J=4.9 Hz, 2H), 8.18 (d, J=2.4 Hz, 1H), 8.01-7.97 (m, 2H), 7.60 (s, 1H), 7.46-7.40 (m, 1H), 7.41 (s, 1H), 7.24-7.16 (m, 3H), 7.11 (d, J=8.5 Hz, 1H), 5.87 (br. d, J=4.3 Hz, 1H), 5.49 (quin, J=7.1 Hz, 1H), 4.14 (s, 3H), 3.32-3.22 (m, 4H), 3.00 (d, J=4.9 Hz, 3H), 2.96-2.91 (m, 2H), 2.26-2.12 (m, 2H). ¹⁹F NMR (376.6 MHz, CHLOROFORM-d) δ: −59.14, −66.58, −109.87. LCMS: (ES+) m/z=731.2 (M+H)⁺, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.21 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 24.07 min, Wavelength: 220 nm, Rt: 24.07 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Wavelength: 220 nm, Rt: 20.34 min.

Example 47b (Isomer-II) ¹H NMR (400 MHz, CHLOROFORM-d) δ=9.61 (s, 1H), 8.79 (d, J=4.9 Hz, 2H), 8.22 (d, J=2.4 Hz, 1H), 8.02-7.97 (m, 2H), 7.58 (s, 1H), 7.45-7.40 (m, 1H), 7.40 (s, 1H), 7.24-7.15 (m, 3H), 7.10 (d, J=8.5 Hz, 1H), 5.88 (br. d, J=4.8 Hz, 1H), 5.18 (quin, J=7.1 Hz, 1H), 4.14 (s, 3H), 3.51-3.44 (m, 2H), 3.15-3.07 (m, 2H), 3.01 (d, J=4.9 Hz, 3H), 2.96-2.90 (m, 2H), 2.24-2.11 (m, 2H). ¹⁹F NMR (376.6 MHz, CHLOROFORM-d) δ: −59.19, −66.58, −109.87. LCMS: (ES+) m/z=731.2 (M+H)⁺, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.22 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 24.55 min, Wavelength: 220 nm, Rt: 24.55 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Wavelength: 220 nm, Rt: 20.42 min.

Example 48a and Example 48b 5-(4-Fluoro-3-((1-(pyrimidin-2-yl)-3-(trifluoromethoxy)cyclobutyl)carbamoyl)phenyl)-2-(4-fluorophenyl)-N-methyl-6-propylbenzofuran-3-carboxamide

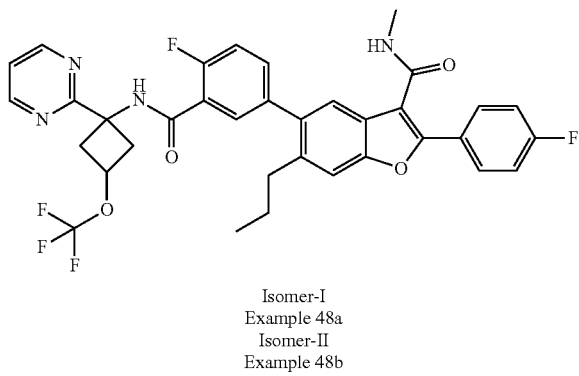 [SMILES: CCCc1cc2oc(-c3ccc(F)cc3)c(C(=O)NC)c2cc1-c1ccc(F)c(C(=O)NC2(c3ncccn3)CC(OC(F)(F)F)C2)c1]

Isomer-I
Example 48a
Isomer-II
Example 48b

To a stirred mixture of 2-fluoro-5-(2-(4-fluorophenyl)-3-(methylcarbamoyl)-6-propylbenzofuran-5-yl)benzoic acid (40 mg, 0.089 mmol) and 1-(pyrimidin-2-yl)-3-(trifluoromethoxy)cyclobutanamine (22.83 mg, 0.098 mmol) in DMF (4.0 mL) at room temperature under a N2 atmosphere was added DIPEA (0.047 mL, 0.267 mmol). The mixture was cooled to 0° C., and HATU (50.8 mg, 0.133 mmol) was added to it. The reaction mixture was allowed to stir at room temperature for 16 hr. After completion of the reaction, the reaction mixture was diluted with water and the product extracted with EtOAc (20 mL×3). The combined organic extracts were washed with saturated brine solution, dried over Na₂SO₄ and concentrated under reduced pressure. The crude solid product obtained was purified by Prep HPLC to obtain the two isomers of 5-(4-fluoro-3-((1-(pyrimidin-2-yl)-3-(trifluoromethoxy)cyclobutyl)carbamoyl)phenyl)-2-(4-fluorophenyl)-N-methyl-6-propylbenzofuran-3-carboxamide as white solids. Example 48a (Isomer-I) Yield: 12.78 mg, (21.60%). Example 48b (Isomer-II) Yield: 20.23 mg, (34.20%). PREPARATIVE HPLC: Column: SUNFIRE C-18 (19*150) mm*5u, Mobile Phase: 10 mM NH₄OAc in water pH 4.6 with acetic acid (A); ACN (B), Flow: 16 ml/min, Rt: 14.89 and 16.29 min.

Example 48a (Isomer-I) ¹H NMR (400 MHz, CHLOROFORM-d) δ=8.83 (d, J=4.9 Hz, 2H), 8.69 (d, J=12.4 Hz, 1H), 8.06 (dd, J=2.4, 7.6 Hz, 1H), 8.00-7.95 (m, 2H), 7.56 (s, 1H), 7.48-7.42 (m, 1H), 7.42 (s, 1H), 7.25-7.15 (m, 4H), 5.84 (br. d, J=4.6 Hz, 1H), 5.51 (quin, J=7.0 Hz, 1H), 3.29 (d, J=7.0 Hz, 4H), 2.99 (d, J=4.9 Hz, 3H), 2.65-2.59 (m, 2H), 1.53-1.47 (m, 2H), 0.83 (t, J=7.3 Hz, 3H). ¹⁹F NMR (376.6 MHz, CHLOROFORM-d) δ: −59.19, −110.06, −115.49. LCMS: (ES+) m/z=665.2 (M+H)⁺, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.23 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 25.06 min, Wavelength: 220 nm, Rt: 25.06 min. HPLC Method:

XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 20.33 min, Wavelength: 220 nm, Rt: 20.33 min.

Example 48b (Isomer-II) $^1$H NMR (400 MHz, CHLOROFORM-d) δ=8.79 (d, J=4.9 Hz, 2H), 8.60 (d, J=12.8 Hz, 1H), 8.10 (dd, J=2.4, 7.6 Hz, 1H), 8.01-7.97 (m, 2H), 7.54 (s, 1H), 7.47-7.42 (m, 1H), 7.42 (s, 1H), 7.24-7.15 (m, 4H), 5.85 (br. d, J=5.7 Hz, 1H), 5.21 (quin, J=7.1 Hz, 1H), 3.61-3.54 (m, 2H), 3.10-3.03 (m, 2H), 3.00 (d, J=4.9 Hz, 3H), 2.64-2.59 (m, 2H), 1.52-1.47 (m, 2H), 0.82 (t, J=7.3 Hz, 3H). $^{19}$F NMR (376.6 MHz, CHLOROFORM-d) δ: −59.22, −110.15, −115.49. LCMS: (ES+) m/z=665.2 (M+H)$^+$, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.26 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 25.79 min, Wavelength: 220 nm, Rt: 25.79 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 20.95 min, Wavelength: 220 nm, Rt: 20.95 min.

Example 49a and Example 49b 5-(4-Fluoro-3-((1-(pyrimidin-2-yl)-3-(trifluoromethoxy)cyclobutyl)carbamoyl)phenyl)-2-(4-fluorophenyl)-N-methyl-6-(3,3,3-trifluoropropyl)benzofuran-3-carboxamide

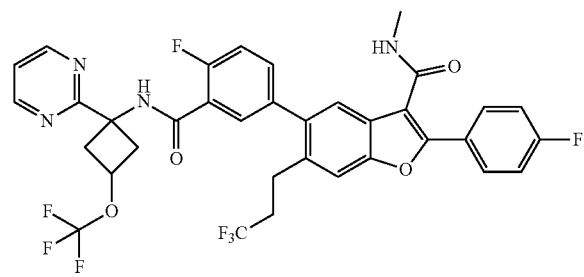

Isomer-I
Example 49a
Isomer-II
Example 49b

To a stirred solution of 2-fluoro-5-(2-(4-fluorophenyl)-3-(methylcarbamoyl)-6-(3,3,3-trifluoropropyl)benzofuran-5-yl)benzoic acid (60 mg, 0.119 mmol), 1-(pyrimidin-2-yl)-3-(trifluoromethoxy)cyclobutanamine (30.6 mg, 0.131 mmol) in DMF (5.0 mL) at room temperature under a N2 atmosphere was added DIPEA (0.062 mL, 0.358 mmol). The mixture was cooled to 0° C., and HATU (68.0 mg, 0.179 mmol) was added to it. The reaction mixture was allowed to stir at room temperature for 16 hr. After completion of the reaction, the reaction mixture was diluted with water and the product extracted with EtOAc (25 mL×3). The combined organic extracts were washed with saturated brine solution, dried over Na$_2$SO$_4$ and concentrated under reduced pressure. The crude solid product obtained was purified by Prep HPLC to obtain the two isomers of 5-(4-fluoro-3-((1-(pyrimidin-2-yl)-3-(trifluoromethoxy)cyclobutyl)carbamoyl)phenyl)-2-(4-fluorophenyl)-N-methyl-6-(3,3,3-trifluoropropyl)benzofuran-3-carboxamide as white solid. Example 49a (Isomer-I) Yield: 14.06 mg, (16.35%). Example 49b (Isomer-II) Yield: 29.15 mg, (33.80%). PREPARATIVE HPLC: Column: SUNFIRE C-18 (19*150) mm*5u, Mobile Phase: 10 mM NH$_4$OAc in water pH 4.6 with acetic acid (A); ACN (B), Flow: 16 ml/min, Rt: 8.23 and 13.39 min.

Example 49a (Isomer-I) $^1$H NMR (400 MHz, CHLOROFORM-d) δ=8.83 (d, J=4.9 Hz, 2H), 8.73 (d, J=12.5 Hz, 1H), 8.07 (dd, J=2.3, 7.5 Hz, 1H), 7.99-7.94 (m, 2H), 7.63 (s, 1H), 7.48-7.43 (m, 1H), 7.43 (s, 1H), 7.30-7.22 (m, 2H), 7.22-7.16 (m, 2H), 5.83 (br. d, J=4.0 Hz, 1H), 5.51 (quin, J=7.1 Hz, 1H), 3.32-3.25 (m, 4H), 2.99 (d, J=4.9 Hz, 3H), 2.96-2.90 (m, 2H), 2.27-2.15 (m, 2H). $^{19}$F NMR (376.6 MHz, CHLOROFORM-d) δ: −59.20, 66.57, −109.53, −114.53. LCMS: (ES+) m/z=719.0 (M+H)$^+$, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.65 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 23.42 min, Wavelength: 220 nm, Rt: 23.42 min. HPLC Method: XBridge Phenyl (150×4.6 mm) 3.5 micron, Buffer: 0.05% TFA in water, Mobile Phase A: Buffer:ACN (95:5), Mobile Phase B: Buffer: ACN (5:95), Gradient: Time (min)/% B: 0/10, 25/100, 30/100, Flow: 1.0 ml/min, Wavelength: 254 nm, Rt: 20.00 min, Wavelength: 220 nm, Rt: 20.00 min.

Example 49b (Isomer-II) $^1$H NMR (400 MHz, CHLOROFORM-d) δ=8.79 (d, J=4.9 Hz, 2H), 8.66 (d, J=12.8 Hz, 1H), 8.12 (dd, J=2.4, 7.5 Hz, 1H), 8.00-7.94 (m, 2H), 7.61 (s, 1H), 7.48-7.42 (m, 1H), 7.42 (s, 1H), 7.29-7.27 (m, 1H), 7.25-7.23 (m, 1H), 7.22-7.15 (m, 2H), 5.84 (br. d, J=4.6 Hz, 1H), 5.21 (quin, J=7.0 Hz, 1H), 3.62-3.55 (m, 2H), 3.06 (ddd, J=2.8, 7.5, 10.4 Hz, 2H), 3.00 (d, J=4.9 Hz, 3H), 2.96-2.90 (m, 2H), 2.26-2.13 (m, 2H). $^{19}$F NMR (376.6 MHz, CHLOROFORM-d) δ: −59.22, −66.57, −109.63, −114.55. LCMS: (ES+) m/z=719.0 (M+H)$^+$, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.70 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/10, 25/100, 30/100, Flow: 1.0 ml/min, Wavelength: 254 nm, Rt: 24.00 min, Wavelength: 220 nm, Rt: 24.00 min. HPLC Method: XBridge Phenyl (150×4.6 mm) 3.5 micron, Buffer: 0.05% TFA in water, Mobile Phase A: Buffer:ACN (95:5), Mobile Phase B: Buffer: ACN (5:95), Gradient: Time (min)/% B: 0/10, 25/100, 30/100, Flow: 1.0 ml/min, Wavelength: 254 nm, Rt: 20.28 min, Wavelength: 220 nm, Rt: 20.28 min.

Example 50a and Example 50b 2-(4-Fluorophenyl)-5-(4-methoxy-2-methyl-5-((1-(pyrimidin-2-yl)-3-(trifluoromethoxy)cyclobutyl)carbamoyl)phenyl)-N-methyl-6-propylbenzofuran-3-carboxamide

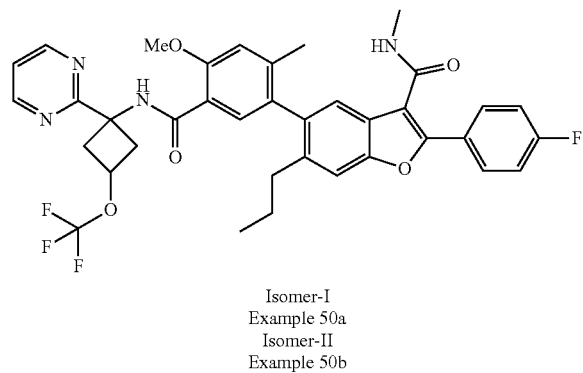 [SMILES: CCCc1cc2oc(-c3ccc(F)cc3)c(C(=O)NC)c2cc1-c1cc(C(=O)NC2(c3ncccn3)CC(OC(F)(F)F)C2)c(OC)cc1C]

Isomer-I
Example 50a
Isomer-II
Example 50b

To a stirred solution of 5-(2-(4-fluorophenyl)-3-(methylcarbamoyl)-6-propylbenzofuran-5-yl)-2-methoxy-4-methylbenzoic acid (50 mg, 0.105 mmol), 1-(pyrimidin-2-yl)-3-(trifluoromethoxy)cyclobutanamine (27.0 mg, 0.116 mmol) in DMF (5.0 mL) at room temperature under a N2 atmosphere was added DIPEA (0.055 mL, 0.315 mmol). The mixture was cooled to 0° C., and HATU (60.0 mg, 0.158 mmol) was added to it. The reaction mixture was allowed to stir at room temperature for 16 hr. After completion of the reaction, the reaction mixture was diluted with water and the product extracted with EtOAc (25 ml×3). The combined organic extracts were washed with saturated brine solution, dried over Na2SO4 and concentrated under reduced pressure. The crude solid product obtained was purified by Prep HPLC to obtain the two isomers of 2-(4-fluorophenyl)-5-(4-methoxy-2-methyl-5-((1-(pyrimidin-2-yl)-3-(trifluoromethoxy)cyclobutyl)carbamoyl)phenyl)-N-methyl-6-propylbenzofuran-3-carboxamide as white solids. Example 50a (Isomer-I) Yield: 11.68 mg, (16.08%). Example 50b (Isomer-II) Yield: 9.21 mg, (12.68%). PREPARATIVE HPLC: Column: SUNFIRE C-18 (19*150) mm*5u, Mobile Phase: 10 mM NH4OAc in water pH 4.6 with acetic acid (A); ACN (B), Flow: 16 ml/min, Rt: 11.31 and 11.98 min.

Example 50a (Isomer-I) $^1$H NMR (400 MHz, CHLOROFORM-d) δ=9.69 (s, 1H), 8.83 (d, J=4.9 Hz, 2H), 8.05-7.99 (m, 2H), 7.99 (s, 1H), 7.41 (d, J=5.8 Hz, 2H), 7.24-7.21 (m, 1H), 7.19-7.14 (m, 2H), 6.93 (s, 1H), 5.89 (br. d, J=4.9 Hz, 1H), 5.49 (quin, J=7.1 Hz, 1H), 4.12 (s, 3H), 3.33-3.23 (m, 4H), 2.99 (d, J=4.9 Hz, 3H), 2.51-2.34 (m, 2H), 2.11 (s, 3H), 1.52-1.46 (m, 2H), 0.81 (t, J=7.3 Hz, 3H). $^{19}$F NMR (376.6 MHz, CHLOROFORM-d) δ: −59.13, −110.48. LCMS: (ES+) m/z=691.2 (M+H)$^+$, Column-Kinetex C18 (50×2.1 mm-2.6 µm), Buffer: 10 mM Ammonium Formate, Mobile phase A: Buffer:ACN (98:2), Mobile phase B: Buffer:ACN (2:98), Gradient: Time (min)/% B: 0/0, 1.7/100, 3.2/100, Flow: 1.0 ml/min. Rt: 2.70 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/40, 25/100, 30/100, Flow: 1.2 ml/min, Wavelength: 254 nm, Rt: 21.44 min, Wavelength: 220 nm, Rt: 21.44 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 21.40 min, Wavelength: 220 nm, Rt: 21.40 min.

Example 50b (Isomer-II) $^1$H NMR (400 MHz, CHLOROFORM-d) δ=9.53 (s, 1H), 8.78 (d, J=4.9 Hz, 2H), 8.06-8.01 (m, 2H and s, 1H), 7.40 (d, J=10.7 Hz, 2H), 7.22 (t, J=4.8 Hz, 1H), 7.19-7.13 (m, 2H), 6.92 (s, 1H), 5.89 (br. d, J=4.7 Hz, 1H), 5.20-5.12 (m, 1H), 4.11 (s, 3H), 3.48-3.40 (m, 2H), 3.17-3.04 (m, 2H), 3.00 (d, J=4.9 Hz, 3H), 2.50-2.32 (m, 2H), 2.10 (s, 3H), 1.51-1.45 (m, 2H), 0.80 (t, J=7.3 Hz, 3H). $^{19}$F NMR (376.6 MHz, CHLOROFORM-d) δ: −59.19, −110.56. LCMS: (ES+) m/z=691.2 (M+H)$^+$, Column-Kinetex C18 (50×2.1 mm-2.6 m), Buffer: 10 mM Ammonium Formate, Mobile phase A: Buffer:ACN (98:2), Mobile phase B: Buffer:ACN (2:98), Gradient: Time (min)/% B: 0/0, 1.7/100, 3.2/100, Flow: 1.0 ml/min. Rt: 2.78 min, wavelength: 220 nm. HPLC Method: SUNFIRE (150×4.6 mm) 3.5 micron, Buffer: 0.05% TFA in water pH 2.5, Mobile Phase A: Buffer: ACN (95:5), Mobile Phase B: ACN: Buffer (95:5), Gradient: Time (min)/% B: 0/40, 25/100, 30/100, Flow: 1.2 ml/min, Wavelength: 254 nm, Rt: 22.35 min, Wavelength: 220 nm, Rt: 22.35 min. HPLC Method: XBridge Phenyl (150×4.6 mm) 3.5 micron, Buffer: 0.05% TFA in water pH 2.5, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 21.76 min, Wavelength: 220 nm, Rt: 21.76 min.

Example 51a and Example 51b 2-(4-Fluorophenyl)-5-(4-methoxy-3-((1-(pyrimidin-2-yl)-3-(trifluoromethoxy)cyclobutyl)carbamoyl)phenyl)-N-methyl-6-propylbenzofuran-3-carboxamide

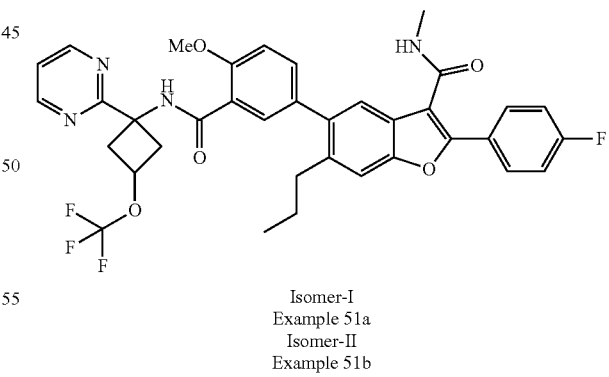

Isomer-I
Example 51a
Isomer-II
Example 51b

To a stirred solution of 5-(2-(4-fluorophenyl)-3-(methylcarbamoyl)-6-propylbenzofuran-5-yl)-2-methoxybenzoic acid (50 mg, 0.108 mmol), 1-(pyrimidin-2-yl)-3-(trifluoromethoxy)cyclobutanamine (27.8 mg, 0.119 mmol) in DMF (5.0 mL) under a N2 atmosphere at room temperature was added DIPEA (0.057 mL, 0.325 mmol). The mixture was cooled 0° C., and HATU (61.8 mg, 0.163 mmol) was added. The reaction mixture was allowed to stir at room temperature for 16 hr. After completion of the reaction, the reaction mixture was diluted with water and the product extracted with EtOAc (25 ml×3). The combined organic extracts were washed with saturated brine solution, dried over Na₂SO₄ and concentrated under reduced pressure. The crude solid product obtained was purified by Prep HPLC to obtain the two isomers of 2-(4-fluorophenyl)-5-(4-methoxy-3-((1-(pyrimidin-2-yl)-3-(trifluoromethoxy)cyclobutyl)carbamoyl)phenyl)-N-methyl-6-propylbenzofuran-3-carboxamide as white solids. Example 51a (Isomer-I) Yield: 16.36 mg, (22.12%). Example 51b (Isomer-II) Yield: 28.53 mg, (38.91%). PREPARATIVE HPLC: Column: Kromosil packed C-18 (19*250) mm, Mobile Phase: 10 mM NH₄OAc in water pH 4.6 with acetic acid (A); ACN (B), Flow: 16 ml/min, Rt: 11.68 and 13.98 min.

Example 51a (Isomer-I) ¹H NMR (400 MHz, CHLOROFORM-d) δ=9.69 (s, 1H), 8.83 (d, J=4.9 Hz, 2H), 8.18 (d, J=2.4 Hz, 1H), 8.03-7.98 (m, 2H), 7.53 (s, 1H), 7.44 (dd, J=2.4 Hz, 8.4 Hz, 1H), 7.40 (s, 1H), 7.25-7.21 (m, 1H), 7.20-7.14 (m, 2H), 7.08 (d, J=8.5 Hz, 1H), 5.88 (br. d, J=4.5 Hz, 1H), 5.49 (quin, J=7.1 Hz, 1H), 4.13 (s, 3H), 3.27 (d, J=7.1 Hz, 4H), 3.00 (d, J=4.9 Hz, 3H), 2.66-2.60 (m, 2H), 1.53-1.49 (m, 2H), 0.82 (t, J=7.3 Hz, 3H). ¹⁹F NMR (376.6 MHz, CHLOROFORM-d) δ: −59.13, −110.39. LCMS: (ES+) m/z=677.2 (M+H)⁺, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.37 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/40, 25/100, 30/100, Flow: 1.2 ml/min, Wavelength: 254 nm, Rt: 20.63 min, Wavelength: 220 nm, Rt: 20.63 min. HPLC Method: XBridge Phenyl (150×4.6 mm) 3.5 micron, Buffer: 0.05% TFA in water, Mobile Phase A: Buffer:ACN (95:5), Mobile Phase B: Buffer:ACN (5:95), Gradient: Time (min)/% B: 0/10, 25/100, 30/100, Flow: 1.0 ml/min, Wavelength: 254 nm, Rt: 20.69 min, Wavelength: 220 nm, Rt: 20.69 min.

Example 51b (Isomer-II) ¹H NMR (400 MHz, CHLOROFORM-d) δ=9.56 (s, 1H), 8.78 (d, J=4.9 Hz, 2H), 8.21 (d, J=2.4 Hz, 1H), 8.04-7.99 (m, 2H), 7.51 (s, 1H), 7.43 (dd, J=2.4 Hz, 8.4 Hz, 1H), 7.40 (s, 1H), 7.23 (t, J=4.9 Hz, 1H), 7.19-7.14 (m, 2H), 7.07 (d, J=8.5 Hz, 1H), 5.89 (br. d, J=4.7 Hz, 1H), 5.18 (quin, J=7.1 Hz, 1H), 4.12 (s, 3H), 3.49-3.42 (m, 2H), 3.15-3.08 (m, 2H), 3.00 (d, J=4.9 Hz, 3H), 2.65-2.60 (m, 2H), 1.53-1.48 (m, 2H), 0.81 (t, J=7.3 Hz, 3H). ¹⁹F NMR (376.6 MHz, CHLOROFORM-d) δ: −59.18, −110.47. LCMS: (ES+) m/z=677.2 (M+H)⁺, Column-Acentis Express C18 (50×2.1 mm; 2.7 u), Buffer: 10 mM Ammonium Formate, Mobile phase A: Buffer:ACN (98:2), Mobile phase B: Buffer:ACN (2:98), Gradient: Time (min)/% B: 0/0, 1.5/100, 3.2/100, Flow: 1.0 ml/min. Rt: 2.42 min, wavelength: 220 nm. HPLC Method: SUNFIRE (150×4.6 mm) 3.5 micron, Buffer: 0.05% TFA in water, Mobile Phase A: Buffer:ACN (95:5), Mobile Phase B: ACN: Buffer (95:5), Gradient: Time (min)/% B: 0/40, 25/100, 30/100, Flow: 1.2 ml/min, Wavelength: 254 nm, Rt: 21.48 min, Wavelength: 220 nm, Rt: 21.48 min. HPLC Method: XBridge Phenyl (150×4.6 mm) 3.5 micron, Buffer: 0.05% TFA in water, Mobile Phase A: Buffer:ACN (95:5), Mobile Phase B: Buffer: ACN (5:95), Gradient: Time (min)/% B: 0/10, 25/100, 30/100, Flow: 1.0 ml/min, Wavelength: 254 nm, Rt: 21.06 min, Wavelength: 220 nm, Rt: 21.06 min.

Example 52

2-(4-Fluorophenyl)-5-(5-((3-hydroxy-1-methylcyclobutyl)carbamoyl)-4-methoxy-2-methylphenyl)-N-methyl-6-(3,3,3-trifluoropropyl)benzofuran-3-carboxamide

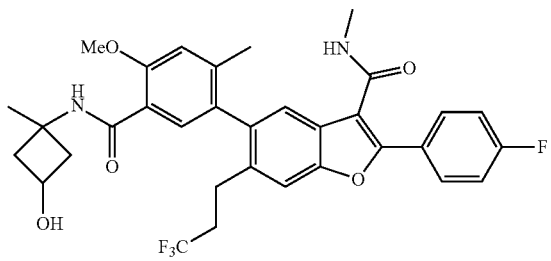 [SMILES: CNC(=O)c1c(-c2ccc(F)cc2)oc2cc(CCC(F)(F)F)c(-c3cc(C(=O)NC4(C)CC(O)C4)c(OC)cc3C)cc12]

To a mixture of 5-(2-(4-fluorophenyl)-3-(methylcarbamoyl)-6-(3,3,3-trifluoropropyl)benzofuran-5-yl)-2-methoxy-4-methylbenzoic acid (0.08 g, 0.151 mmol) and 3-amino-3-methylcyclobutanol (0.023 g, 0.227 mmol) in DMF (1 mL) under ice-cold conditions was added TEA (0.105 mL, 0.755 mmol) and BOP (0.100 g, 0.227 mmol). The reaction mixture was stirred at ambient temperature for 12 hr. The reaction was quenched with ice-cold water. The white solid precipitates were filtered and dried under suction. This product was as such taken to the next step (Yield: 60 mg, white solid). LCMS: (ES+) m/z=613.2 (M+H)⁺. Rt min: 2.57, Wavelength: 220 nm. Column-Ascentis Express C18 (50×2.1 mm-2.7 μm). Mphase A: 10 mM NH₄COOH in Water:ACN (98:02). Mphase B: 10 mM NH₄COOH in Water:ACN (02:98). Flow=1 mL/min.

Example 53a and Example 53b 5-(5-((3-(Difluoromethoxy)-1-methylcyclobutyl)carbamoyl)-4-methoxy-2-methylphenyl)-2-(4-fluorophenyl)-N-methyl-6-(3,3,3-trifluoropropyl)benzofuran-3-carboxamide

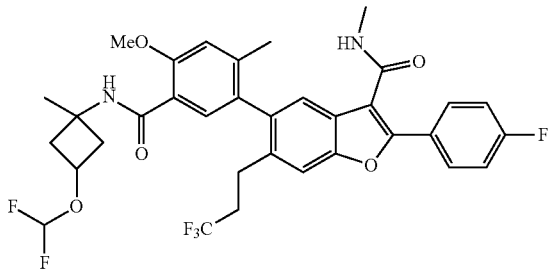

Isomer-I
Example 53a
Isomer-II
Example 53b

To a mixture of 2-(4-fluorophenyl)-5-(5-((3-hydroxy-1-methylcyclobutyl)carbamoyl)-4-methoxy-2-methylphenyl)-N-methyl-6-(3,3,3-trifluoropropyl)benzofuran-3-carboxamide (Example 52) (0.08 g, 0.131 mmol) and copper(I) iodide (0.012 g, 0.065 mmol) in acetonitrile (2 mL) at 50° C. was added 2-(fluorosulfonyl)difluoroacetic acid (0.021 mL, 0.196 mmol). The reaction mixture was stirred at same temperature for 4 hr. The reaction was quenched with sat. NaHCO₃, and diluted with ethyl acetate (10 mL). The organic layer was separated, dried over Na₂SO₄, and concentrated. The crude product was submitted for Prep-HPLC to separated the two isomers.

Example 53a (Isomer-1) (Yield: 2.85 mg, 3.26%, white solid) Preparative HPLC Method: Column: SUNFIRE C-18 (19*150) mm*5u. Mobile phase A: 10 mM ammonium acetate. Mobile phase B: Acetonitrile. Flow: 16 ml/min, Rt min: 18.60. ¹H NMR (300 MHz, DMSO-d₆): δ=8.41 (d, J=4.8 Hz, 1H), 8.27 (s, 1H), 8.04-7.91 (m, 2H), 7.78 (s, 1H), 7.54 (s, 1H), 7.40 (t, J=8.9 Hz, 2H), 7.30 (s, 1H), 7.15 (s, 1H), 6.63 (m, J=76 Hz, 1H), 4.59-4.54 (m, 1H), 3.97 (s, 3H), 2.80 (d, J=4.5 Hz, 3H), 2.77-2.58 (m, 4H), 2.39-2.50 (m, 4H), 2.07 (s, 3H), 1.43 (s, 3H). ¹⁹F NMR (376.6 MHz, DMSO-d₆): −64.80, −81.72, −110.86. LCMS: (ES+) m/z=663.2 (M+H)⁺, Rt min: 2.81, Wavelength: 220 nm, Column-Ascentis Express C18 (50×2.1 mm-2.7 m). Mphase A: 10 mM NH₄COOH in water: ACN (98:2). Mphase B: 10 mM NH₄COOH in Water:ACN (2:98). Gradient: Time (min)/% B: 0/0, 1.5/100, 3.2/100, Flow=1 mL/min. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN:Buffer (95:5). Gradient: Time (min)/% B: 0/10, 25/100, 30/100, Flow: 1 ml/min. Wavelength: 254 nm, Rt min: 19.30. Wavelength: 220 nm, Rt min: 19.30. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Gradient: Time (min)/% B: 0/10, 25/100, 30/100, Flow: 1 ml/min. Wavelength: 254 nm, Rt min: 23.28. Wavelength: 220 nm, Rt min: 23.28.

Example 53b (Isomer-2) Preparative HPLC Method. Column: SUNFIRE C-18 (19*150) mm*5u. Mobile phase A: 10 mM ammonium acetate. Mobile phase B: Acetonitrile. Flow: 16 ml/min. Rt min: 19.30. ¹H NMR (300 MHz, DMSO-d₆): δ ppm=8.42 (d, J=4.7 Hz, 1H), 8.16 (s, 1H), 8.03-7.91 (m, 2H), 7.78 (s, 1H), 7.52 (s, 1H), 7.45-7.35 (m, 2H), 7.29 (s, 1H), 7.15 (s, 1H), 6.63 (t, J=76 Hz, 1H), 4.73-4.65 (m, 1H), 3.97 (s, 3H), 2.79 (d, J=4.6 Hz, 3H), 2.73-2.69 (m, 6H), 2.18-2.08 (m, 2H), 2.07 (s, 3H), 1.50 (s, 3H). ¹⁹F NMR (376.6 MHz, DMSO-d₆): δ ppm: −64.79, −81.58, −110.85. LCMS: (ES+) m/z=663.2 (M+H)⁺. Rt min: 2.84, Wavelength: 220 nm. Column-Ascentis Express C18 (50×2.1 mm-2.7 μm). Mphase A: 10 mM NH₄COOH in Water:ACN (98:2). Mphase B: 10 mM NH₄COOH in Water:ACN (2:98). Gradient: Time (min)/% B: 0/0, 1.5/100, 3.2/100, Flow=1 mL/min. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN:Buffer (95:5). Gradient: Time (min)/% B: 0/10, 25/100, 30/100, Flow: 1 ml/min. Wavelength: 254 nm, Rt min: 19.47. Wavelength: 220 nm, Rt min: 19.47. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min Wavelength: 254 nm, Rt min: 23.53. Wavelength: 220 nm, Rt min: 23.53.

Example 54

2-(4-Fluorophenyl)-5-(3-((3-hydroxy-1-methylcyclobutyl)carbamoyl)phenyl)-N-methyl-6-propylbenzofuran-3-carboxamide

To a mixture of 3-(2-(4-fluorophenyl)-3-(methylcarbamoyl)-6-propylbenzofuran-5-yl)benzoic acid (0.12 g, 0.278 mmol) and 3-amino-3-methylcyclobutanol in DMF (2 mL) under ice-cold conditions was added TEA (0.194 mL, 1.391 mmol) and BOP (0.185 g, 0.417 mmol). The reaction mixture was stirred at ambient temperature for 12 hr. The reaction was quenched with ice-cold water. The white solid precipitated out was filtered and dried under suction. This product was taken as such to the next step (Yield: 80 mg, white solid). LCMS: (ES+) m/z=515.2 (M+H)⁺, Rt min: 2.50, Wavelength: 220 nm. Column-Ascentis Express C18 (50×2.1 mm-2.7 m). Mphase A: 10 mM NH₄COOH in Water:ACN (98:02). Mphase B: 10 mM NH₄COOH in Water:ACN (02:98). Flow=1 mL/min.

Example 55a and Example 55b 5-(3-((3-(Difluoromethoxy)-1-methylcyclobutyl) carbamoyl)phenyl)-2-(4-fluorophenyl)-N-methyl-6-propylbenzofuran-3-carboxamide

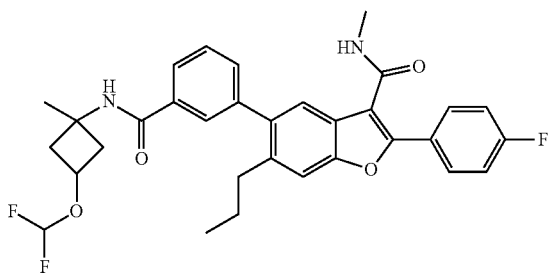

Isomer-I
Example 55a
Isomer-II
Example 55b

To a mixture of 2-(4-fluorophenyl)-5-(3-((3-hydroxy-1-methylcyclobutyl)carbamoyl)phenyl)-N-methyl-6-propylbenzofuran-3-carboxamide (Example 54) (0.08 g, 0.155 mmol) and copper(I) iodide (0.015 g, 0.078 mmol) in acetonitrile (2 mL) at 50° C. was added 2-(fluorosulfonyl) difluoroacetic acid (0.024 mL, 0.233 mmol). The reaction mixture was stirred at same temperature for 4 hr. The reaction was monitored by LC/MS. The reaction was quenched with cold sat. NaHCO₃, diluted with ethyl acetate (10 mL). The organic layer was separated, dried over Na₂SO₄, concentrated and submitted for Prep-HPLC purification to separate the two isomers, Example 55a (Isomer-I) and Example 55b (Isomer-II).

Example 55a (Isomer-I) (Yield: 2.38 mg, 2.66%, white solid) Preparative HPLC Method: Column: SUNFIRE C18 (250×4.6 mm) 3.5 t. Mobile phase A: 10 mM ammonium acetate. Mobile phase B: Acetonitrile. Flow: 16 ml/min. Rt min: 18.42. ¹H NMR (400 MHz, DMSO-d₆): δ ppm=8.70 (s, 1H), 8.41 (d, J=4.6 Hz, 1H), 8.04-7.97 (m, 2H), 7.90-7.87 (m, 1H) 7.81 (s, 1H), 7.65 (s, 1H), 7.57-7.46 (m, 2H), 7.41 (s, 1H), 7.41-7.36 (m, 2H), 6.62 (t, J=75.6 Hz 1H), 4.58 (t, J=7.2 Hz, 1H), 2.80 (d, J=4.4 Hz, 3H), 2.66-2.58 (m, 2H), 2.58-2.50 (m, 2H), 2.45-2.37 (m, 2H), 1.53-1.42 (m, 2H), 1.43 (s, 3H), 0.76 (t, J=7.3 Hz, 3H). ¹⁹F NMR (376.6 MHz, DMSO-d₆): δ ppm: −81.67, −110.00. LCMS: (ES+) m/z=565.2 (M+H)⁺. Rt min: 2.46, Wavelength: 220 nm. Column-Kinetex C18 (50×2.1 mm-2.6 m). Mphase A: 2% ACN-98% H₂O-10 mM NH₄COOH. Mphase B: 98% ACN-2% H₂O-10 mM NH₄COOH. Gradient: Time (min)/% B: 0/0, 1.7/100, 3.2/100, Flow=1 mL/min. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 19.42. Wavelength: 220 nm, Rt min: 19.42. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 22.97. Wavelength: 220 nm, Rt min: 22.97.

Example 55b (Isomer-II) (2.4 mg, 2.7%, white solid) Preparative HPLC Method: Column: SUNFIRE C18 (250×4.6 mm) 3.5. Mobile phase A: 10 mM ammonium acetate. Mobile phase B: Acetonitrile. Flow: 16 ml/min. Rt min: 18.70. ¹H NMR (400 MHz, DMSO-d₆): δ ppm=8.45 (s, 1H), 8.43-8.41 (m, 1H), 8.03-7.96 (m, 2H), 7.92-7.87 (m, 1H), 7.83 (s, 1H), 7.65 (s, 1H), 7.58-7.53 (m, 1H), 7.51-7.48 (m, 1H), 7.41 (s, 1H), 7.41-7.36 (m, 2H), 6.63 (t, J=75.6 Hz 1H), 4.70-4.64 (m, 1H), 2.94-2.85 (m, 2H), 2.79 (d, J=4.4 Hz, 3H), 2.65-2.58 (m, 2H), 2.17-2.07 (m, 2H), 1.52 (s, 3H), 1.50-1.43 (m, 2H), 0.77 (t, J=7.3 Hz, 3H). ¹⁹F NMR (376.6 MHz, DMSO-d₆): δ ppm: −81.54, −110.99. LCMS: (ES+) m/z=565.2 (M+H)⁺, Rt Min: 2.49, Wavelength: 220 nm. Column-Kinetex C18 (50×2.1 mm-2.6 μm). Mphase A: 2% ACN-98% H₂O-10 mM NH₄COOH. Mphase B: 98% ACN-2% H₂O-10 mM NH₄COOH. Gradient: Time (min)/% B: 0/0, 1.7/100, 3.2/100, Flow=1 mL/min. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN:Buffer (95:5). Gradient: Time (min)/% B: 0/10, 25/100, 30/100, Flow: 1 ml/min. Wavelength: 254 nm, Rt min: 19.63. Wavelength: 220 nm, Rt min: 19.63. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 25/100, 30/100, Flow: 1 ml/min. Wavelength: 254 nm, Rt min: 23.28. Wavelength: 220 nm, Rt min: 23.28.

Example 56

2-(4-Fluorophenyl)-5-(5-((3-hydroxy-1-methylcyclobutyl)carbamoyl)-4-methoxy-2-methylphenyl)-N-methyl-6-propylbenzofuran-3-carboxamide

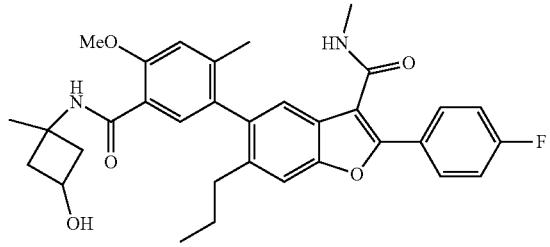 [SMILES: CCCc1cc2oc(-c3ccc(F)cc3)c(C(=O)NC)c2cc1-c1cc(C(=O)NC2(C)CC(O)C2)c(OC)cc1C]

To a mixture of 5-(2-(4-fluorophenyl)-3-(methylcarbamoyl)-6-propylbenzofuran-5-yl)-2-methoxy-4-methylbenzoic acid (0.25 g, 0.526 mmol), 3-amino-3-methylcyclobutanol (0.080 g, 0.789 mmol) in DMF (2 mL) under ice-cold conditions was added TEA (0.366 mL, 2.63 mmol) and BOP (0.349 g, 0.789 mmol). The reaction mixture was stirred at ambient temperature for 12 hours with the reaction progress monitored by LC/MS. After completion of the reaction, it was quenched with ice-cold water. The white solid thus precipitated out was filtered and dried under suction. This crude product was used for the fluorination without further purification (0.25 g, Yield: 46.8%). LCMS: (ES+) m/z=559 (M+H)⁺. Buffer: 10 mM Ammonium Acetate pH 5 adjusted with HCOOH, Column: Acquity BEH C18 (2.1×50 mm) 1.7 μm, Rt min: 1.09, Wavelength: 220 nm.

Example 57a and Example 57b 5-(5-((3-(Difluoromethoxy)-1-methylcyclobutyl)carbamoyl)-4-methoxy-2-methylphenyl)-2-(4-fluorophenyl)-N-methyl-6-propylbenzofuran-3-carboxamide

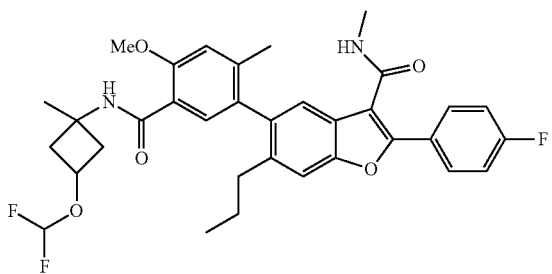

Isomer-I
Example 57a
Isomer-II
Example 57b

A mixture of 2-(4-fluorophenyl)-5-(5-((3-hydroxy-1-methylcyclobutyl)carbamoyl)-4-methoxy-2-methylphenyl)-N-methyl-6-propylbenzofuran-3-carboxamide (0.2 g, 0.358 mmol) and copper(I) iodide (0.034 g, 0.179 mmol) was dissolved in acetonitrile (2 mL). To this reaction mixture was added 2-(fluorosulfonyl)difluoroacetic acid (0.056 mL, 0.537 mmol), and the mixture was then and stirred at 50° C. for 4 hours. The reaction mixture was quenched with sat. NaHCO₃ and extracted with ethyl acetate (20 mL). The organic layer was separated, dried over Na₂SO₄, and concentrated. The crude product was further purified by preparative HPLC to give example 57a (Isomer-I) and Example 57b (Isomer-II) as white solids.

Example 57a (Isomer-I) ¹H NMR (400 MHz, DMSO-d₆): δ ppm: 8.40 (d, J=4.6 Hz, 1H), 8.28 (s, 1H), 8.02-7.94 (m, 2H), 7.63 (s, 1H), 7.53 (s, 1H), 7.43-7.35 (m, 2H), 7.26 (s, 1H), 7.12 (s, 1H), 6.62 (t, J=76 Hz, 1H), 4.58 (t, J=7.1 Hz, 1H), 3.97 (s, 3H), 2.78 (d, J=4.4 Hz, 3H), 2.55-2.45 (m, 1H), 2.45-2.30 (m, 5H), 2.06 (s, 3H), 1.49-1.38 (m, 2H), 1.43 (s, 3H), 0.76 (t, J=7.3 Hz, 3H). ¹⁹F (376.6 MHz, DMSO-d₆): δ ppm −81.69, −111.10. LCMS: (ES+) m/z=609.2 (M+H)⁺. Column-Ascentis Express C18 (50×2.1 mm-2.7 m). M phase A: 2% ACN-98% H₂O-10 mM NH₄COOH. M phase B: 98% ACN-2% H₂O-10 mM NH₄COOH. Gradient: Time (min)/% B: 0/0, 1.5/100, 3.2/100, Flow=1 mL/min. Rt min: 2.29, Wavelength: 220 nm. HPLC Method: XBridge phenyl (4.6×150) mm, 3.5 micron. Buffer: 0.05% TFA in water pH 2.5. Mobile Phase A: Buffer:ACN (95:5) and Mobile Phase B: ACN: Buffer (95:5). Gradient: Time (min)/% B: 0/10, 25/100, 30/100, Flow: 1 ml/min. In 254 nm wavelength Rt min: 20.27 and 220 nm wavelength: Rt min: 20.27. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/40, 25/100, 30/100, Flow: 1 ml/min. Wavelength: 254 nm, Rt min: 20.23 and Wavelength: 220 nm, Rt min: 20.23.

Example 57b (Isomer-II) ¹H NMR (400 MHz, DMSO-d₆): δ ppm 8.40 (d, J=4.6 Hz, 1H), 8.17 (s, 1H), 8.01-7.94 (m, 2H), 7.63 (s, 1H), 7.52 (s, 1H), 7.43-7.34 (m, 2H), 7.25 (s, 1H), 7.13 (s, 1H), 6.63 (t, J=6.9 Hz, 1H), 4.70 (t, J=76 Hz, 1H), 3.98 (s, 3H), 2.86-2.76 (m, 2H), 2.78 (d, J=4.8 Hz, 3H), 2.48-2.43 (m, 1H), 2.38-2.28 (m, 1H), 2.17-2.10 (m, 2H), 2.07 (s, 3H), 1.51 (s, 3H), 1.48-1.39 (m, 2H), 0.77 (t, J=7.3 Hz, 3H), ¹⁹F (376.6 MHz, DMSO-d₆): δ ppm: −81.56, −111.09. LCMS: (ES+) m/z=609.2 (M+H)⁺. Column-Ascentis Express C18 (50×2.1 mm-2.7 m). M phase A: 2% ACN-98% H₂O-10 mM NH₄COOH. M phase B: 98% ACN-2% H₂O-10 mM NH₄COOH. Time (min)/% B: 0/0, 1.5/100, 3.2/100, Flow=1 mL/min. Rt min: 2.31, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Time (min)/% B: 0/10, 25/100, 30/100, Flow: 1 ml/min. Wavelength: 254 nm, Rt min: 20.46. Wavelength: 220 nm, Rt min: 20.46. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/40, 25/100, 30/100, Flow: 1 ml/min. Wavelength: 254 nm, Rt min: 18.56 and Wavelength: 220 nm, Rt min: 18.56.

Example 58

2-(4-Fluorophenyl)-5-(3-((3-hydroxy-1-methylcyclobutyl)carbamoyl)phenyl)-N-methyl-6-(3,3,3-trifluoropropyl)benzofuran-3-carboxamide

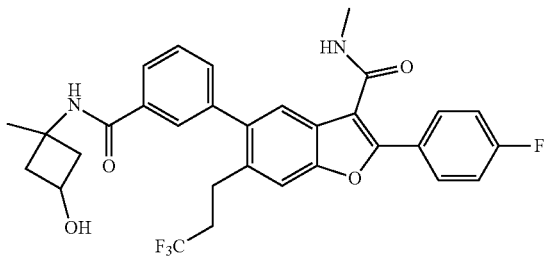 [SMILES: CNC(=O)c1c(-c2ccc(F)cc2)oc2cc(CCC(F)(F)F)c(-c3cccc(C(=O)NC4(C)CC(O)C4)c3)cc12]

To a RBF containing 3-(2-(4-fluorophenyl)-3-(methylcarbamoyl)-6-(3,3,3-trifluoropropyl)benzofuran-5-yl)benzoic acid (0.2 g, 0.412 mmol), 3-amino-3-methylcyclobutanol (0.063 g, 0.618 mmol) in DMF (2 mL) under ice-cold conditions was added TEA (0.287 mL, 2.060 mmol) and then BOP (0.273 g, 0.618 mmol). The reaction mixture was stirred at ambient temperature for 12 hours. The reaction mixture was quenched with ice-cold water. The white solid precipitated was filtered and dried (0.25 g, Yield: 60%). LCMS: (ES+) m/z=569.0 (M+H)⁺. Buffer: 10 mM AmmoniumAcetate pH −5 adjusted with HCOOH. Column: Acquity BEH C18 (2.1×50 mm) 1.7 m. Rt min: 1.03, Wavelength: 220 nm.

Example 59a and Example 59b 5-(3-((3-(Difluoromethoxy)-1-methylcyclobutyl)carbamoyl)phenyl)-2-(4-fluorophenyl)-N-methyl-6-(3,3,3-trifluoropropyl)benzofuran-3-carboxamide

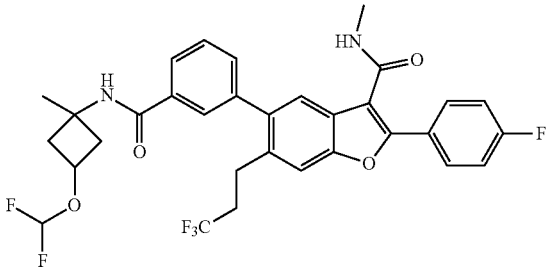

Isomer-I
Example 59a
Isomer-II
Example 59b

A mixture of 2-(4-fluorophenyl)-5-(3-((3-hydroxy-1-methylcyclobutyl)carbamoyl)phenyl)-N-methyl-6-(3,3,3-trifluoropropyl)benzofuran-3-carboxamide (0.22 g, 0.387 mmol) and copper (I) iodide (0.037 g, 0.193 mmol) was dissolved in acetonitrile (2 mL). To the mixture was added 2-(fluorosulfonyl)difluoroacetic acid (0.061 mL, 0.580 mmol), and the mixture was stirred at 50° C. for 4 hours with the reaction progress monitored by LCMS. The reaction mixture was then quenched with sat. NaHCO₃ and extracted with ethyl acetate (20 mL). The organic layer was separated, dried over Na₂SO₄ and concentrated. The obtained crude product was purified by Prep. HPLC to afford Example 59a (Isomer-I) and Example 59b (Isomer-II) as white solids.

Example 59a (Isomer-I) Preparative HPLC Method: Column KROMASIL PACKEDC-18 (19*250) mm; Mobile phase A: 10 mM Ammonium acetate pH-4.5 with AcOH, Mobile phase B: Acetonitrile. Flow: 15 ml/min. Rt min: 19.21. $^1$H NMR (400 MHz, DMSO-d₆): δ ppm 8.70 (s, 1H), 8.48-8.40 (m, 1H), 8.00 (dd, J=5.4, 9.0 Hz, 2H), 7.93-7.78 (m, 3H), 7.59-7.52 (m, 2H), 7.47 (s, 1H), 7.41 (t, J=8.9 Hz, 2H), 6.62 (t, J=76 Hz, 1H), 4.64-4.50 (m, 1H), 2.92-2.84 (m, 2H), 2.81 (d, J=4.6 Hz, 3H), 2.55-2.46 (m, 2H), 2.45-2.35 (m, 2H), 1.45 (s, 3H). $^{19}$F (376.6 MHz, DMSO-d₆): δ ppm: −64. 99, −81.69, −110.77. LCMS: (ES+) m/z=619.0 (M+H)⁺. Column-Ascentis Express C18 (50×2.1 mm-2.7 m). M phase A: 2% ACN-98% H₂O-10 mM NH₄COOH. M phase B: 98% ACN-2% H₂O-10 mM NH₄COOH. Gradient: Time (min)/% B: 0/0, 1.7/100, 3.4/100, Flow=1 mL/min. Rt min: 2.263, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Gradient: Time (min)/% B: 0/10, 12/100, 15/100, Flow: 1 mL/min, Wavelength: 254 nm, Rt min: 11.39. Wavelength: 220 nm, Rt min: 11.39. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Gradient: Time (min)/% B: 0/10, 25/100, 30/100, Flow: 1 mL/min. Wavelength: 254 nm, Rt min: 22.18. Wavelength: 220 nm, Rt min: 22.18.

Example 59b (Isomer-II) Preparative HPLC Method: Column KROMASIL PACKEDC-18 (19*250) mm. Mobile phase A: 10 mM Ammonium acetate pH-4.5 with AcOH and Mobile phase B: Acetonitrile. Flow: 15 mL/min. Rt min: 18.33. $^1$H NMR (400 MHz, DMSO-d₆): δ ppm 8.49-8.41 (m, 1H), 8.45 (s, 1H), 8.03-7.96 (m, 2H), 7.94-7.79 (m, 3H), 7.59-7.54 (m, 2H), 7.47 (s, 1H), 7.44-7.37 (m, 2H), 6.62 (t, J=76 Hz, 1H), 4.68 (quin., J=6.7 Hz, 1H), 2.91-2.83 (m, 4H), 2.81 (d, J=4.6 Hz, 3H), 2.55 (m, 2H), 2.17-2.07 (m, 2H), 1.52 (s, 3H). $^{19}$F (376.6 MHz, DMSO-d₆): δ ppm: −65.00, −81.59 and −110.76. LCMS: (ES+) m/z=619.0 (M+H)⁺. Column-Ascentis Express C18 (50×2.1 mm-2.7 μm). M phase A: 2% ACN-98% H₂O-10 mM NH₄COOH; M phase B: 98% ACN-2% H₂O-10 mM NH₄COOH; Gradient: Time (min)/% B: 0/0, 1.7/100, 3.4/100, Flow=1 mL/min. Rt Min: 2.287, Wavelength: 220 nm. HPLC Method: XBridge phenyl (4.6×150) mm, 3.5 micron. Buffer: 0.05% TFA in water pH 2.5. Mobile Phase A: Buffer:ACN (95:5) and Mobile Phase B: ACN: Buffer (95:5). Gradient: Time (min)/% B: 0/10, 12/100, 15/100, Flow: 1 mL/min, Wavelength: 254 nm, Rt min: 11.51 and Wavelength: 220 nm, Rt min: 11.51. HPLC Method: SUNFIRE C18 (4.6×150) mm, 3.5 micro/ Buffer: 0.05% TFA in water pH 2.5. Mobile Phase A: Buffer:ACN (95:5) and Mobile Phase B: ACN: Buffer (95:5). Gradient: Time (min)/% B: 0/10, 25/100, 30/100, Flow: 1 mL/min, Wavelength: 254 nm, Rt min: 22.51 and Wavelength: 220 nm, Rt min: 22.51.

Example 60

5-(4-Fluoro-3-((3-hydroxy-1-methylcyclobutyl)carbamoyl)phenyl)-2-(4-fluorophenyl)-N-methyl-6-propylbenzofuran-3-carboxamide

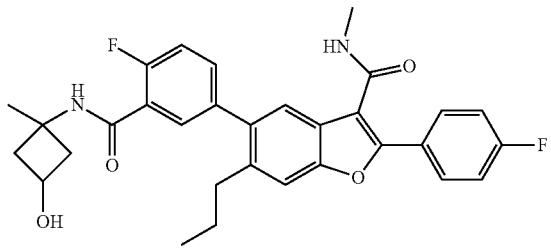 [SMILES: CCCc1cc2oc(-c3ccc(F)cc3)c(C(=O)NC)c2cc1-c1ccc(F)c(C(=O)NC2(C)CC(O)C2)c1]

2-Fluoro-5-(2-(4-fluorophenyl)-3-(methylcarbamoyl)-6-propylbenzofuran-5-yl)benzoic acid (0.18 g, 0.400 mmol) was dissolved in DMF (2 mL). To this mixture under ice-cold conditions was added TEA (0.279 mL, 2.002 mmol) and then BOP (0.266 g, 0.601 mmol). The reaction mixture was stirred at ambient temperature for 12 hours. The mixture was quenched with ice-cold water. The white solid thus precipitated out was filtered and dried under suction. This solid was used for the fluorination without further purification (0.15 g, Yield: 70%). LCMS: (ES+) m/z=533.2 (M+H)⁺. Column-Ascentis Express C18 (50×2.1 mm-2.7 m). M phase A: 2% ACN-98% H₂O-10 mM NH₄COOH. M phase B: 98% ACN-2% H₂O-10 mM NH₄COOH. Flow=1 mL/min and Rt min: 1.86, Wavelength: 220 nm.

Example 61a and 61b 5-(3-((3-(Difluoromethoxy)-1-methylcyclobutyl)carbamoyl)-4-fluorophenyl)-2-(4-fluorophenyl)-N-methyl-6-propylbenzofuran-3-carboxamide

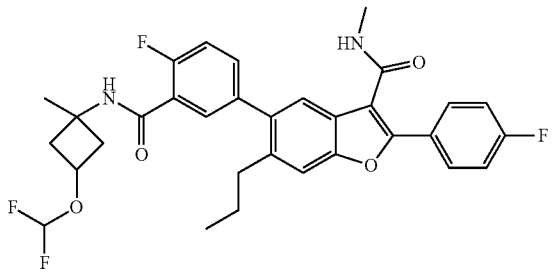

Isomer-I
Example 61a
Isomer-II
Example 61b 5-(3-((3-(Difluoromethoxy)-1-methylcyclobutyl)carbamoyl)-4-fluorophenyl)-2-(4-fluorophenyl)-N-methyl-6-propylbenzofuran-3-carboxamide was prepared as described above by stirring 5-(4-fluoro-3-((3-hydroxy-1-methylcyclobutyl)carbamoyl)phenyl)-2-(4-fluorophenyl)-N-methyl-6-propylbenzofuran-3-carboxamide with copper(I) iodide and 2-(fluorosulfonyl)difluoroacetic acid in acetonitrile (2 mL) at 50° C. for 4 hours. The crude product was submitted to Prep. HPLC purification to give Example 61a (Isomer-I) and Example 61b (Isomer-II) as white solids.

Example 61a (Isomer-I) $^1$H NMR (400 MHz, DMSO-$d_6$): δ ppm 0.79 (t, J=7.2 Hz, 3H), 1.44 (s, 3H), 1.49 (q, J=7.2 Hz, 2H), 2.40-2.49 (m, 2H), 2.59-2.64 (m, 2H), 2.81 (d, J=4.7 Hz, 3H), 2.50 (m, 2H), 4.56-4.60 (m, 1H), 6.63 (t, J=76 Hz, 1H), 7.37-7.42 (m, 4H), 7.46-7.52 (m, 2H), 7.64 (s, 1H), 7.97-8.02 (m, 2H), 8.44 (d, J=4.89 Hz, 1H), 8.65 (s, 1H). $^{19}$F (376.6 MHz, DMSO-$d_6$): δ ppm: −81.73, −110.96, −117.40. LCMS: (ES+) m/z observed=582.8 (M+H)$^+$. Column: ZORBAX SB AQ (4.6×50) mm, 3.5 micron. Mobile Phase A: 0.1% HCOOH in Water. Mobile Phase B: ACN. Time (min)/% B: 0/2, 1.5/20, 4.0/95, Flow-1.0 ml/min. Rt min: 4.97, Wavelength: 220 nm. HPLC Method: XBridge phenyl (4.6×150) mm, 3.5 micron. Buffer: 0.05% TFA in water pH 2.5. Mobile Phase A: Buffer:ACN (95:5) and Mobile Phase B: ACN: Buffer (95:5). Time (min)/% B: 0/10, 25/100, 30/100, Flow: 1 ml/min. Wavelength: 254 nm, Rt min: 21.24. Wavelength: 220 nm, Rt min: 21.24. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN: Buffer (95:5). Time (min)/% B: 0/40, 25/100, 30/100, Flow: 1.2 ml/min. Wavelength: 254 nm, Rt min: 18.01. Wavelength: 220 nm, Rt min: 18.01.

Example 61b (Isomer-II) $^1$H NMR (400 MHz, DMSO-$d_6$): δ ppm 0.79 (t, J=7.2 Hz, 3H) 1.43-1.52 (m, 2H), 1.51 (s, 3H), 2.08-2.13 (m, 2H), 2.58-2.62 (m, 2H), 2.81 (d, J=4.71 Hz, 3H), 2.80-2.84 (m, 2H), 4.69 (quin, J=6.87 Hz, 1H), 6.63 (t, J=76 Hz, 1H), 7.34-7.43 (m, 4H), 7.46-7.52 (m, 2H), 7.64 (s, 1H), 7.95-8.04 (m, 2H), 8.44 (d, J=4.71 Hz, 1H), 8.50 (s, 1H). $^{19}$F (376.6 MHz, DMSO-$d_6$): δ ppm: −81.69, −110.95, −117.55. LCMS: (ES+) m/z=583.2 (M+H)$^+$. Column-Kinetex C18 (50×2.1 mm-2.6 μm). M phase A: 2% ACN-98% H$_2$O-10 mM NH$_4$COOH. M phase B: 98% ACN-2% H$_2$O-10 mM NH$_4$COOH. Time (min)/% B: 0/0, 1.7/100, 3.2/100, Flow=1 mL/min. Rt Min 2.56, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN: Buffer (95:5). Time (min)/% B: 0/10, 25/100, 30/100, Flow: 1 ml/min. Wavelength: 254 nm, Rt min: 21.50. Wavelength: 220 nm, Rt min: 21.50. HPLC Method: SUNFIRE C18 (4.6×150) mm, 3.5 micron. Buffer: 0.05% TFA in water pH 2.5. Mobile Phase A: Buffer:ACN (95:5). Mobile Phase B: CAN: Buffer (95:5), Time (min)/% B: 0/40, 25/100, 30/100, Flow: 1.2 ml/min. Wavelength: 254 nm, Rt min: 18.43. Wavelength: 220 nm, Rt min: 18.43.

Example 62

5-(4-Fluoro-3-((3-hydroxy-1-methylcyclobutyl)carbamoyl)phenyl)-2-(4-fluorophenyl)-N-methyl-6-(3,3,3-trifluoropropyl)benzofuran-3-carboxamide

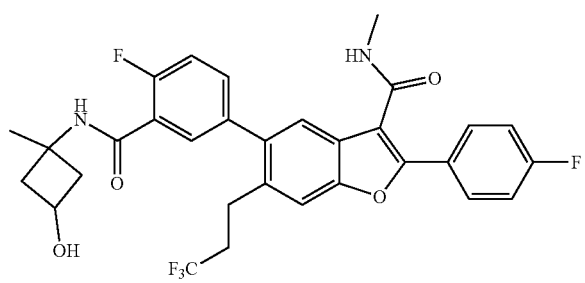 [SMILES: CNC(=O)c1c(-c2ccc(F)cc2)oc2cc(CCC(F)(F)F)c(-c3ccc(F)c(C(=O)NC4(C)CC(O)C4)c3)cc12]

To a mixture of 2-fluoro-5-(2-(4-fluorophenyl)-3-(methylcarbamoyl)-6-(3,3,3-trifluoropropyl) benzofuran-5-yl) benzoic acid (0.25 g, 0.497 mmol), 3-amino-3-methylcyclobutanol (0.075 g, 0.745 mmol) in DMF (2 mL) under ice cold conditions was added TEA (0.346 mL, 2.483 mmol) and then BOP (0.329 g, 0.745 mmol). The reaction was stirred at ambient temperature for 12 hr. The reaction mixture was quenched with ice-cold water. The white solid precipitated out was filtered, dried and used for the fluorination without further purification (0.25 g). LCMS: (ES+) m/z=587.3 (M+H)$^+$. Buffer: 10 mM Ammonium Acetate pH-5 adjusted with HCOOH. Mobile phase A: Buffer:ACN (95:5); Mobile phase B: Buffer:ACN (5:95). Acquity BEH C18 (2.1×50 mm) 1.7 μm. Rt min: 1.05, Wavelength: 220 nm.

Example 63a and Example 63b 5-(3-((3-(Difluoromethoxy)-1-methylcyclobutyl) carbamoyl)-4-fluorophenyl)-2-(4-fluorophenyl)-N-methyl-6-(3,3,3-trifluoropropyl)benzofuran-3-carboxamide

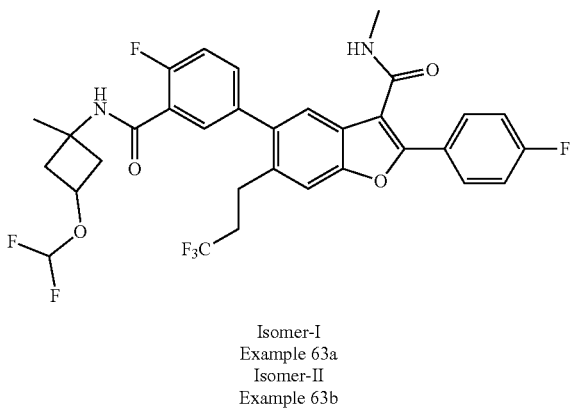 [SMILES: CNC(=O)c1c(-c2ccc(F)cc2)oc2cc(CCC(F)(F)F)c(-c3ccc(F)c(C(=O)NC4(C)CC(OC(F)F)C4)c3)cc12]

Isomer-I
Example 63a
Isomer-II
Example 63b

A mixture of 5-(4-fluoro-3-((3-hydroxy-1-methylcyclobutyl)carbamoyl)phenyl)-2-(4-fluoro phenyl)-N-methyl-6-(3,3,3-trifluoropropyl)benzofuran-3-carboxamide (0.25 g, 0.426 mmol) and copper(I) iodide (0.041 g, 0.213 mmol) was dissolved in acetonitrile (2 mL). To the mixture at 50° C. was added 2-(fluorosulfonyl)difluoroacetic acid (0.067 mL, 0.639 mmol). The reaction mixture was stirred at the same temperature for 4 hr. The reaction was quenched with sat. NaHCO$_3$, and the mixture diluted with ethyl acetate (20 mL). The organic layer was separated, dried over Na$_2$SO$_4$, and concentrated. The crude mixture was purified by prep HPLC to isolate Example 63a (Isomer-I) and Example 63b (Isomer-II).

Example 63a (Isomer-I) (Yield: 18.97 mg, 6.85%, white solid.) $^1$H NMR (400 MHz, DMSO-$d_6$): δ ppm 1.43 (s, 3H), 2.39-2.44 (m, 2H), 2.50-2.60 (m, 2H), 2.80 (d, J=4.8 Hz, 3H), 2.84-2.88 (m, 4H), 4.56 (m, 1H), 6.62 (t, J=76 Hz, 1H), 7.34-7.44 (m, 4H), 7.51-7.54 (m, 2H), 7.79 (s, 1H), 7.96-8.00 (m, 2H), 8.44 (m, 1H), 8.63 (s, 1H). $^{19}$F NMR (376.6 MHz, DMSO-$d_6$): δ ppm −64.89, −81.71, −110.74, −116.97. LCMS: (ES+) m/z=637.2 (M+H)$^+$. Method info: M phase A: 2% ACN-98% H$_2$O-10 mM NH$_4$COOH. M phase B: 98% ACN-2% H$_2$O-10 mM NH$_4$COOH, Flow=1 mL/min. Rt min: 2.37, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/10, 25/100, 30/100, Flow: 1 ml/min. Wavelength: 254 nm, Rt min: 19.67. Wavelength: 220 nm, Rt min: 19.67. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/40, 25/100, 30/100, Flow: 1.2 ml/min. Wavelength: 254 nm, Rt min: 17.43. Wavelength: 220 nm, Rt min: 17.43.

Example 63b (Isomer-II) $^1$H NMR (400 MHz, DMSO-$d_6$): δ ppm 1.50 (s, 3H), 2.08-2.13 (m, 2H), 2.50-2.60 (m, 2H), 2.81 (d, J=4.4 Hz, 3H), 2.81-2.88 (m, 4H), 4.68 (m, 1H), 6.63 (t, J=76 Hz, 1H), 7.35-7.44 (m, 4H), 7.50-7.58 (m, 2H), 7.79 (s, 1H), 7.96-8.00 (m, 2H), 8.44 (m, 1H), 8.49 (s, 1H). $^{19}$F-NMR: (376.6 MHz, DMSO-$d_6$): δ ppm −64.90, −81.71, −110.74, −117.10. LCMS: (ES+) m/z=637.2 (M+H)$^+$. Method info: M phase A: 2% ACN-98% H$_2$O-10 mM NH$_4$COOH. M phase B: 98% ACN-2% H$_2$O-10 mM NH$_4$COOH. Flow=1 mL/min. Rt Min: 2.35, Wavelength: 220 nm. HPLC Method: XBridge phenyl (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/10, 25/100, 30/100, Flow: 1 ml/min. Wavelength: 254 nm, Rt min: 19.49. Wavelength: 220 nm, Rt min: 19.49. HPLC Method: SUNFIRE C18 (4.6×150) mm, 3.5 micron. Buffer: 0.05% TFA in water pH 2.5. Mobile Phase A: Buffer:ACN (95:5). Mobile Phase B: ACN:Buffer (95:5). Time (min)/% B: 0/40, 25/100, 30/100, Flow: 1.2 ml/min. Wavelength: 254 nm, Rt min: 17.00. Wavelength: 220 nm, Rt min: 17.00.

Example 64a and Example 64b 5-(3-((3-(Difluoromethoxy)-1-(pyrimidin-2-yl)cyclobutyl)carbamoyl)-4-methoxyphenyl)-(2-(4-fluorophenyl)-N-methyl-6-((2,2,2-trifluoroethyl)amino) benzofuran-3-carboxamide

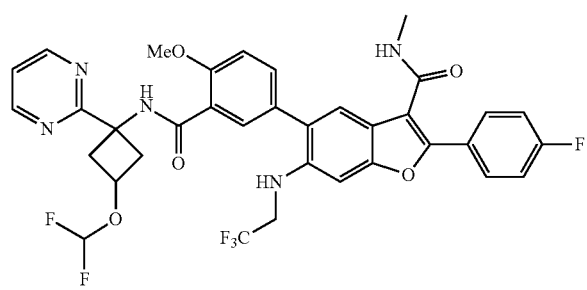

Isomer-I
Example 64a
Isomer-II
Example 64b

To a solution of 5-(2-(4-fluorophenyl)-3-(methylcarbamoyl)-6-((2,2,2-trifluoroethyl)amino)benzofuran-5-yl)-2-methoxybenzoic acid (0.15 g, 0.290 mmol), DIPEA (0.152 mL, 0.871 mmol) and HATU (0.133 g, 0.349 mmol) in DMF (4 mL) at 0° C. was added 3-(difluoromethoxy)-1-(pyrimidin-2-yl)cyclobutanamine (0.075 g, 0.349 mmol). The reaction was stirred at 25° C. for 4 hours. The mixture was diluted with ice-cold water, the solid filtered and dried under suction to obtain crude 5-(3-((3-(difluoromethoxy)-1-(pyrimidin-2-yl)cyclobutyl)carbamoyl)-4-methoxyphenyl)-(2-(4-fluorophenyl)-N-methyl-6-((2,2,2-trifluoroethyl)amino) benzofuran-3-carboxamide. The crude was submitted for reverse phase Prep. HPLC to obtain the two isomers, Example 64a (Isomer-I) and Example 64b (Isomer-II), using the Preparative HPLC Method: sunfire C18 (150×4.6 mm, 5u), Mobile phase A: 10 mM NH$_4$OAc in Water: ACN (90:10), Mobile phase B: ACN, Flow: 1.0 ml/min.

Example 64a (Isomer-I) (64 mg, 30.9%) white solid: $^1$H NMR (400 MHz, METHANOL-$d_4$) δ ppm 8.84 (d, J=4.8 Hz, 2H) 7.98 (d, J=2.4 Hz, 1H), 7.93-7.91 (m, 2H), 7.61 (dd, J=8.53, 2.38 Hz, 1H), 7.38 (t, J=4.8 Hz, 1H), 7.34 (d, J=8.8 Hz, 1H), 7.32 (s, 1H), 7.25-7.21 (m, 2H), 7.06 (s, 1H), 6.45 (t, J=74.8 Hz, 1H), 5.09 (m, 1H), 4.15 (s, 3H), 3.99-3.89 (m, 2H), 3.16-3.12 (d, 4H), 2.93 (s, 3H). $^{19}$F NMR (376.6 MHz, CD$_3$OD) δ: −73.18, −84.10, −113.87. LCMS: (ES+) m/z=714.2 (M+H)$^+$, Column-Acentis Express C18 (50×2.1 mm; 2.7 um), M phase A: 2% ACN-98% H$_2$O-10 mM NH$_4$COOH, M phase B: 98% ACN-2% H$_2$O-10 mM NH$_4$COOH, Gradient: Time (min)/% B: 0/0, 1.7/100, 3.4/100, Flow: 1 ml/min. Rt min: 2.30, wavelength: 254 nm. HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 20.84. Wavelength: 220 nm, Rt min: 20.84. HPLC Method: XBridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5). Gradient: Time (min)/% B: 0/10, 25/100, 30/100, Flow: 1.0 ml/min. Wavelength: 254 nm. Rt min: 18.72. Wavelength: 220 nm. Rt min: 18.72.

Example 64b (Isomer-II) (18 mg, 8.68%) white solid: $^1$H NMR (400 MHz, METHANOL-$d_4$) δ ppm 8.84 (d, J=4.4 Hz, 2H), 7.94-7.89 (overlapping m, 3H), 7.61 (dd, J=8.6, 2.4 Hz, 1H), 7.39-7.34 (overlapping m, 2H), 7.32 (s, 1H), 7.25-7.20 (m, 2H), 7.07 (s, 1H), 6.45 (t, J=75.2 Hz, 1H), 5.13 (m, 1H), 4.15 (s, 3H), 3.93 (q, J=9.31 Hz, 2H), 3.17-3.06 (m, 4H), 2.93 (s, 3H); $^{19}$F NMR (376.6 MHz, CD$_3$OD) δ: −73.19, −84.23, −113.86. LCMS: (ES+) m/z=714.2 (M+H)$^+$, Column-Acentis Express C18 (50×2.1 mm; 2.7 um), M phase A: 2% ACN-98% H$_2$O-10 mM NH$_4$COOH, M phase B: 98% ACN-2% H$_2$O-10 mM NH$_4$COOH, Gradient: Time (min)/% B: 0/0, 1.7/100, 3.4/100, Flow: 1 ml/min. Rt min: 2.28, wavelength: 220 nm. HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 20.34. Wavelength: 220 nm, Rt min: 20.34. HPLC Method: XBridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5). Gradient: Time (min)/% B: 0/10, 25/100, 30/100, Flow: 1.0 ml/min. Wavelength: 254 nm. Rt min: 18.40. Wavelength: 220 nm. Rt min: 18.40.

Example 65a and 65b 5-(3-((3-(Difluoromethoxy)-1-(pyrimidin-2-yl)cyclobutyl)carbamoyl)phenyl)-(2-(4-fluorophenyl)-N-methyl-6-((2,2,2,-trifluoroethyl)amino)benzofuran-3-carboxamide

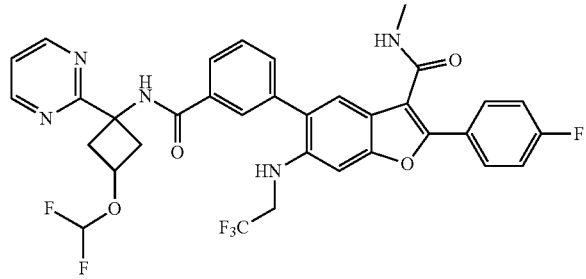

Isomer-I
Example 65a
Isomer-II
Example 65b

To a solution of 3-(2-(4-fluorophenyl)-3-(methylcarbamoyl)-6-((2,2,2-trifluoroethyl)amino)benzofuran-5-yl)benzoic acid (0.085 g, 0.175 mmol), DIPEA (0.092 mL, 0.524 mmol) and HATU (0.080 g, 0.210 mmol) in DMF (4 mL) at 0° C. was added 3-(difluoromethoxy)-1-(pyrimidin-2-yl)cyclobutanamine (0.045 g, 0.210 mmol). The reaction mixture was stirred at room temperature for 16 hours. The mixture was diluted with ice-cold water, the solid filtered and dried under suction. The crude material was purified by reverse phase Prep. HPLC to obtain the two isomers, Example 65a (Isomer-I) and Example 65b (Isomer-II). Preparative HPLC Method: COLUMN: CHIRALPAK IA (250× 4.6) mm, 5 micron, Mobile phase: 0.2% DEA (diethylamine) in hexane:ethanol (70:30), Flow: 1.0 ml\min; Rt min: 11.74. and 15.84 Wavelength: 254 nm; Rt min: 11.73 and 15.86 Wavelength: 220 nm.

Example 65a (Isomer-I) (12 mg, 10%) pale yellow solid: $^1$H NMR (400 MHz, METHANOL-$d_4$) δ ppm 8.79 (d, J=4.89 Hz, 2H) 8.00 (d, J=1.2 Hz, 1H) 7.97 (m, 3H) 7.66 (m, 2H) 7.40 (s, 1H) 7.34 (t, J=4.89 Hz, 1H) 7.24 (m, 2H) 7.12 (s, 1H) 6.43 (t, J=75.1 Hz, 1H) 5.00 (t, J=4.6 Hz, 1H) 3.96 (q, J=9.31 Hz, 2H) 3.08 (m, 4H) 2.94 (s, 3H). $^{19}$F NMR (376.6 MHz, METHANOL-$d_4$): δ ppm −73.17, −84.30, −113.77; LCMS: (ES+) m/z=684.8 (M+H)$^+$, Column-Acentis Express C18 (50×2.1 mm; 2.7 um), M phase A: 2% ACN-98% H$_2$O-10 mM NH$_4$COOH, M phase B: 98% ACN-2% H$_2$O-10 mM NH$_4$COOH, Gradient: Time (min)/% B: 0/0, 1.7/100, 3/100, 3.2/0, Flow: 1 ml/min. Rt min: 2.34, wavelength: 254 nm. HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 19.88. Wavelength: 220 nm, Rt min: 19.88 HPLC Method: XBridge Phenyl (150×4.6 mm) 3.5 micron SC/749. Mobile Phase A: 0.05% TFA in water: Acetonitrile (95:5). Mobile Phase B: 0.05% TFA in water (95:5) Gradient: Time (min)/% B: 0/10, 25/100, 30/100, Flow: 1.0 ml/min. Wavelength: 254 nm. Rt min: 17.80. Wavelength: 220 nm. Rt min: 17.80.

Example 65b (Isomer-II) (56 mg, 46.9%) pale yellow solid: $^1$H NMR (400 MHz, METHANOL-$d_4$) δ ppm 8.79 (d, J=4.89 Hz, 2H) 7.99 (d, J=1.2, 1H) 7.97 (m, 3H) 7.65 (m, 2H) 7.39 (s, 1H) 7.36 (t, J=4.89 Hz, 1H) 7.24 (m, 2H) 7.11 (s, 1H) 6.43 (t, J=75.1 Hz, 1H) 5.08 (t, J=4.6 Hz, 1H) 3.96 (q, J=9.31 Hz, 2H) 3.23 (m, 2H) 2.94 (s, 3H) 2.86 (m, 2H). $^{19}$F NMR (376.6 MHz, METHANOL-$d_4$): δ ppm −73.15, −84.14, −113.79; LCMS: (ES+) m/z=684.8 (M+H)$^+$, Column-Acentis Express C18 (50×2.1 mm; 2.7 um), M phase A: 2% ACN-98% H$_2$O-10 mM NH$_4$COOH, M phase B: 98% ACN-2% H$_2$O-10 mM NH$_4$COOH, Gradient: Time (min)/% B: 0/0, 1.7/100, 3/100, 3.2/0, Flow: 1 ml/min. Rt min: 2.35, wavelength: 254 nm. HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 20.06 Wavelength: 220 nm, Rt min: 20.06. HPLC Method: XBridge Phenyl (150×4.6 mm) 3.5 micron SC/749. Mobile Phase A: 0.05% TFA in water: Acetonitrile (95:5). Mobile Phase B: 0.05% TFA in water (95:5) Gradient: Time (min)/% B: 0/10, 25/100, 30/100, Flow: 1.0 ml/min. Wavelength: 254 nm. Rt min: 17.95. Wavelength: 220 nm. Rt min: 17.95.

Example 66a and Example 66b 5-(3-((3-(Difluoromethoxy)-1-(pyrimidin-2-yl)cyclobutyl)carbamoyl)-4-methoxyphenyl)-6-ethoxy-2-(4-fluorophenyl)-N-methylbenzofuran-3-carboxamide

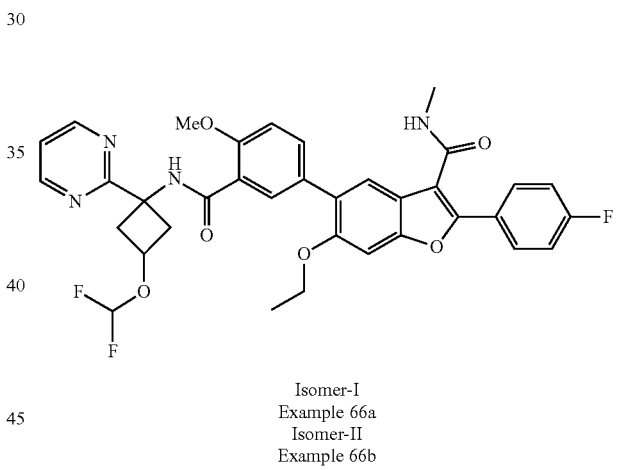

Isomer-I
Example 66a
Isomer-II
Example 66b

To a stirred solution of 5-(6-ethoxy-2-(4-fluorophenyl)-3-(methylcarbamoyl)benzofuran-5-yl)-2-methoxybenzoic acid (70 mg, 0.151 mmol) and 3-(difluoromethoxy)-1-(pyrimidin-2-yl)cyclobutanamine hydrochloride (38.0 mg, 0.151 mmol) in DMF (5.0 mL) at room temperature under a nitrogen atmosphere was added DIPEA (0.132 mL, 0.755 mmol). The mixture was cooled to 0° C., and 2-(7-aza-1H-benzotriazole-1-yl)-1,1,3,3-tetramethyluronium hexafluorophosphate (HATU) (86 mg, 0.227 mmol) was added to it. The reaction mixture was stirred at room temperature for 16 hr. After completion of the reaction, the mixture was diluted with cold water, stirred for 5 min and the solid filtered. The crude solid product obtained was purified by Prep HPLC to obtained the two isomers of 5-(3-((3-(difluoromethoxy)-1-(pyrimidin-2-yl)cyclobutyl)carbamoyl)-4-methoxyphenyl)-6-ethoxy-2-(4-fluorophenyl)-N-methylbenzofuran-3-carboxamide as white solids. Example 66a (Isomer-I) Yield: 18 mg, (17.85%); Example 66b (Isomer-II) Yield: 30 mg, (29.7%). PREPARATIVE HPLC: Column: SUNFIRE C-18

(19*150) mm*5u, Mobile Phase: 10 mM Ammonium acetate pH-4.5 with AcOH (mobile phase A): ACN (mobile phase B), Flow: 15 ml/min, Gradient: Time (min)/% B: 0/50, 10/75, 14/75, 15/100, Rt: 11.5 and 12.5 min.

Example 66a (Isomer-I) $^1$H NMR (400 MHz, DMSO-$d_6$) δ ppm=9.29 (s, 1H), 8.87 (d, J=4.9 Hz, 2H), 8.46-8.41 (m, 1H), 7.98-7.93 (m, 3H), 7.70 (dd, J=2.5, 8.6 Hz, 1H), 7.48-7.35 (m, 5H), 7.27 (d, J=8.7 Hz, 1H), 6.95-6.54 (t, J=75.6 Hz, 1H), 5.09 (quin, J=7.4 Hz, 1H), 4.14 (q, J=7.0 Hz, 2H), 4.05 (s, 3H), 3.06-2.95 (m, 4H), 2.83 (s, 3H), 1.31 (t, J=6.9 Hz, 3H). $^{19}$F NMR (376.6 MHz, DMSO-$d_6$) δ: −81.62, −111.53. LCMS: (ES+) m/z observed=660.8, 661.8 (M+H)$^+$, Column-Acentis Express C18 (50×2.1 mm; 2.7 um), Buffer: 10 mM Ammonium Formate in Water pH 4.5, Mobile phase A: Buffer:ACN (98:2), Mobile phase B: Buffer: ACN (2:98), Flow: 1.0 ml/min. Rt: 2.41 min, wavelength: 220 nm.

HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Flow: 1.0 ml/min, Wavelength: 254 nm, Rt: 20.88 min, Wavelength: 220 nm, Rt: 20.88 min. HPLC Method: XBridge Phenyl (150×4.6 mm) 3.5 micron SC/749, Buffer: 0.05% TFA in water pH 2.5, Mobile Phase A: Buffer:ACN (95:5), Mobile Phase B: Buffer:ACN (5:95), Flow: 1.0 ml/min, Wavelength: 254 nm, Rt: 18.45 min, Wavelength: 220 nm, Rt: 18.45 min.

LCMS

| Time | % A | % B |
| --- | --- | --- |
| 0.0 | 100 | 0 |
| 1.7 | 0 | 100 |
| 3.0 | 0 | 100 |
| 3.2 | 100 | 0 |

HPLC Method: SUNFIRE C18 (150×4.6 mm) 3.5 micron

| Time | B % |
| --- | --- |
| 0 | 10 |
| 25 | 100 |
| 30 | 100 |

HPLC Method: XBridge Phenyl (150×4.6 mm) 3.5 micron SC/749

| Time | B % |
| --- | --- |
| 0 | 10 |
| 25 | 100 |
| 30 | 100 |

Example 66b (Isomer-II) $^1$H NMR (400 MHz, DMSO-$d_6$) δ ppm=9.55 (s, 1H), 8.89 (d, J=4.9 Hz, 2H), 8.43 (q, J=4.6 Hz, 1H), 8.04 (d, J=2.4 Hz, 1H), 7.99-7.93 (m, 2H), 7.70 (dd, J=2.4, 8.6 Hz, 1H), 7.49-7.45 (m, 3H), 7.41-7.35 (m, 2H), 7.27 (d, J=8.8 Hz, 1H), 6.96-6.57 (t, J=75.6 Hz, 1H), 5.00 (t, J=7.2 Hz, 1H), 4.15 (q, J=6.9 Hz, 2H), 4.06 (s, 3H), 3.19-3.12 (m, 2H), 3.00-2.93 (m, 2H), 2.83 (d, J=4.6 Hz, 3H), 1.31 (t, J=6.9 Hz, 3H). $^{19}$F NMR (376.6 MHz, DMSO-$d_6$) δ: −81.67, −111.54. LCMS: (ES+) m/z observed=660.8, 661.8 (M+H)$^+$, Column-Acentis Express C18 (50×2.1 mm; 2.7 um), Buffer: 10 mM Ammonium Formate in Water pH 4.5, Mobile phase A: Buffer:ACN (98:2), Mobile phase B: Buffer: ACN (2:98), Flow: 1.0 ml/min. Rt: 2.69 min, wavelength: 220 nm. HPLC Method: SUNFIRE (150×4.6 mm) 3.5 micron, Buffer: 0.05% TFA in water pH 2.5, Mobile Phase A: Buffer:ACN (95:5), Mobile Phase B: ACN: Buffer (95:5), Flow: 1.0 ml/min, Wavelength: 254 nm, Rt: 21.47 min, Wavelength: 220 nm, Rt: 21.47 min. HPLC Method: XBridge Phenyl (150×4.6 mm) 3.5 micron SC/749, Buffer: 0.05% TFA in water pH 2.5, Mobile Phase A: Buffer:ACN (95:5), Mobile Phase B: Buffer: ACN (5:95), Flow: 1.0 ml/min, Wavelength: 254 nm, Rt: 18.80 min, Wavelength: 220 nm, Rt: 18.80 min.

LCMS

| Time | % A | % B |
| --- | --- | --- |
| 0.0 | 100 | 0 |
| 1.7 | 0 | 100 |
| 3.0 | 0 | 100 |
| 3.2 | 100 | 0 |

HPLC Method: SUNFIRE C18 (150×4.6 mm) 3.5 micron

| Time | B % |
| --- | --- |
| 0 | 10 |
| 25 | 100 |

HPLC Method: XBridge Phenyl (150×4.6 mm) 3.5 micron SC/749

| Time | B % |
| --- | --- |
| 0 | 10 |
| 25 | 100 |
| 30 | 100 |

Example 67a and Example 67b 5-(3-((3-(Difluoromethoxy)-1-(pyrimidin-2-yl)cyclobutyl) carbamoyl)phenyl)-6-ethoxy-2-(4-fluorophenyl)-N-methylbenzofuran-3-carboxamide

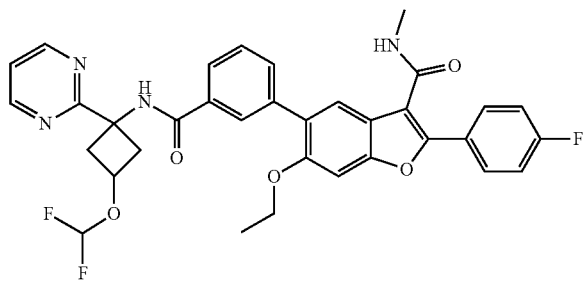

Isomer-I
Example 67a
Isomer-II
Example 67b

To a solution of 3-(6-ethoxy-2-(4-fluorophenyl)-3-(methylcarbamoyl)benzofuran-5-yl)benzoic acid (0.05 g, 0.115 mmol) and), DIPEA (0.060 mL, 0.346 mmol) and HATU (0.044 g, 0.115 mmol) in DMF (4 mL) at 0° C. was added 3-(difluoromethoxy)-1-(pyrimidin-2-yl)cyclobutanamine (0.030 g, 0.138 mmol). The reaction mixture was stirred at room temperature for 4 hours. The mixture was diluted with ice-cold water, the solid filtered and dried under suction to get crude 5-(3-((3-(difluoromethoxy)-1-(pyrimidin-2-yl)cyclobutyl)carbamoyl)phenyl)-6-ethoxy-2-(4-fluorophenyl)-N-methylbenzofuran-3-carboxamide. The crude product was submitted for preparative HPLC to obtain the two isomers, Example 67a (Isomer-I) and Example 67b (Isomer-II). Preparative HPLC Method: Column: Chiralcel OD-H (19*250) mm*5u. Mobile phase A: hexane (0.2% DEA). Mobile phase B: EtOH. Flow: 18 ml/min.

Example 67a (Isomer-I) (3 mg, 4.12%): $^1$H NMR (400 MHz, Methanol-$d_4$): δ ppm 8.80-8.79 (d, J=4.8, 2H), 8.10 (t, J=1.6 Hz, 1H), 7.96-7.92 (m, 2H), 7.90-7.88 (m, 1H), 7.79-7.76 (m, 1H), 7.63 (s, 1H), 7.54 (t, J=7.7 Hz, 1H), 7.34-7.32 (m, 2H), 7.28-7.22 (m, 2H), 6.62-6.24 (t, J=72, 1H), 4.95 (t, J=7.2 Hz, 1H), 4.16 (q, J=7.0 Hz, 2H), 3.15-3.05 (m, 4H), 2.96 (s, 3H), 1.38 (t, J=7.0 Hz, 3H). $^{19}$F NMR (376.6 MHz, METHANOL-$d_4$): δ ppm −84.24, −113.34. LCMS: (ES+) m/z=631.2 (M+H)$^+$. Column-Acentis Express C18 (50×2.1 mm; 2.7 um), Buffer: 10 mM Ammonium Formate in Water pH 4.5. phase A: Buffer+ACN (98+2). Mphase B: Buffer+ACN (2+98). Flow: 1.5 ml/min. Rt min: 2.24, wavelength: 220 nm.

| Time | % B | % A |
|---|---|---|
| 0 | 0 | 100 |
| 1.7 | 100 | 0 |
| 3.4 | 100 | 0 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 19.92. Wavelength: 220 nm, Rt min: 19.92. HPLC Method: XBridge Phenyl (150×4.6 mm) 3.5 micron SC/749. Mobile Phase A: 0.05% TFA in water: Acetonitrile (95:5). Mobile Phase B: ACN: 0.05% TFA in water (95:5) Gradient: Time (min)/% B: 0/10, 25/100, 30/100, Flow: 1.0 ml/min. Wavelength: 254 nm, Rt min: 17.78. Wavelength: 220 nm. Rt min: 17.78.

Example 67b (Isomer-II) (23 mg, 31.6%). $^1$H NMR (400 MHz, Methanol-$d_4$) δ ppm 8.80-8.79 (d, J=4.8, 2H), 8.10 (t, J=1.6 Hz, 1H), 7.97-7.93 (m, 2H), 7.92-7.87 (m, 1H), 7.80-7.75 (m, 1H), 7.63 (s, 1H), 7.54 (t, J=7.7 Hz, 1H), 7.36-7.33 (m, 2H), 7.28-7.23 (m, 2H), 6.61-6.24 (t, J=72 Hz, 1H), 5.06 (t, J=7.2 Hz, 1H), 4.16 (q, J=7.0 Hz, 2H), 3.27-3.14 (m, 2H), 2.96 (s, 3H), 2.93-2.85 (m, 2H), 1.39 (t, J=7.0 Hz, 3H). $^{19}$F NMR (376.6 MHz, METHANOL-$d_4$): δ ppm −84.11, −113.35. LCMS: (ES+) m/z=631.2 (M+H)$^+$. Column-Acentis Express C18 (50×2.1 mm; 2.7 um), Buffer: 10 mM Ammonium Formate in Water pH 4.5. M phase A: Buffer+ACN (98+2). M phase B: Buffer+ACN (2+98). Flow: 1 ml/min. Rt min: 2.25, wavelength: 220 nm.

| Time | % B | % A |
|---|---|---|
| 0 | 0 | 100 |
| 1.7 | 100 | 0 |
| 3.4 | 100 | 0 |

HPLC Method: COLUMN: SUNFIRE C18 (150×4.6 mm) 3.5 micron. Mobile Phase A: 0.05% TFA in Water: Acetonitrile (95:5). Mobile Phase B: Acetonitrile: 0.05% TFA in Water (95:5). Gradient: Time (min)/% B: 0/10, 25/100, 30/100, Flow: 1.0 ml/min. Wavelength: 254 nm, Rt min: 20.23. Wavelength: 220 nm, Rt min: 20.23. HPLC Method: XBridge Phenyl (150×4.6 mm) 3.5 micron SC/749. Mobile Phase A: 0.05% TFA in water: Acetonitrile (95:5). Mobile Phase B: Acetonitrile: 0.05% TFA in water (95:5) Gradient: Time (min)/% B: 0/10, 25/100, 30/100, Flow: 1.0 ml/min. Wavelength: 254 nm. Rt min: 17.92. Wavelength: 220 nm, Rt min: 17.92.

Example 68

5-(3-((3-(Benzyloxy)-1-(1,2,4-oxadiazol-3-yl)cyclobutyl) carbamoyl)phenyl)-6-ethoxy-2-(4-fluorophenyl)-N-methylbenzofuran-3-carboxamide

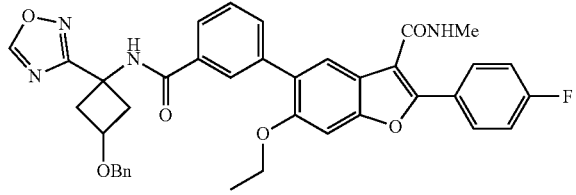

To a mixture of 3-(6-ethoxy-2-(4-fluorophenyl)-3-(methylcarbamoyl)benzofuran-5-yl)benzoic acid (200 mg, 0.461 mmol), 3-(benzyloxy)-1-(1,2,4-oxadiazol-3-yl)cyclobutan-amine hydrochloride (220 mg, 0.780 mmol) and DIPEA (N,N-diisopropylethylamine) (0.320 mL, 1.846 mmol) in DMF (8 mL) was added HATU (263 mg, 0.692 mmol). The resulting clear solution was stirred at room temperature for 18 hr. After completion of the reaction, it was quenched by the addition of ice-cold water, and the solid obtained was filtered and dried. It was then purified by Combiflash using 4% MeOH/CHCl$_3$ as a mobile phase to obtain 5-(3-((3-(benzyloxy)-1-(1,2,4-oxadiazol-3-yl)cyclobutyl)carbamoyl)phenyl)-6-ethoxy-2-(4-fluorophenyl)-N-methylbenzofuran-3-carboxamide (200 mg, 66%). LCMS: (ES+) m/z=661.5 (M+H)$^+$, Column-ACQUITY UPLC BEH C8 (50×2.1 mm; 1.7 m), M phase A: 5 mM Ammonium Acetate: ACN (95:5), M phase B: 5 mM Ammonium Acetate: ACN (5:95), Flow: 0.8 ml/min, Rt min: 1.17, wavelength: 220 nm.

| Time | % A | % B |
|---|---|---|
| 0.0 | 95 | 5 |
| 1.1 | 5 | 95 |
| 1.7 | 5 | 95 |

Example 69

6-Ethoxy-2-(4-fluorophenyl)-5-(3-((3-hydroxy-1-(1,2,4-oxadiazol-3-yl)cyclobutyl)carbamoyl)phenyl)-N-methylbenzofuran-3-carboxamide

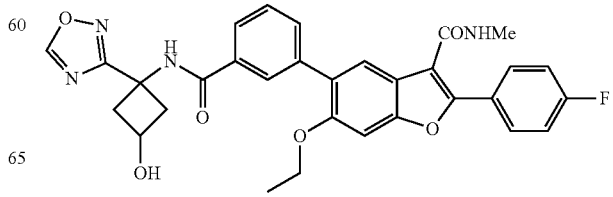

To a solution of 5-(3-((3-(benzyloxy)-1-(1,2,4-oxadiazol-3-yl)cyclobutyl)carbamoyl)phenyl)-6-ethoxy-2-(4-fluorophenyl)-N-methylbenzofuran-3-carboxamide (Example 68) (200 mg, 0.303 mmol) in DCM (dichloromethane) (4 mL) at −78° C. was added BCl₃ (1.0M in DCM) (1.211 mL, 1.211 mmol). After stirring for 15 min, the mixture was allowed to stir at room temperature for 1 hr. After completion of the reaction, the solvent was evaporated, and the crude residue was quenched with ice-cold water and extracted with ethyl acetate (10 ml×2). The combined organic extracts were dried over Na₂SO₄ and evaporated to give a crude product which was purified by using 3% MeOH/CHCl₃ as a mobile phase to obtain 6-ethoxy-2-(4-fluorophenyl)-5-(3-((3-hydroxy-1-(1,2,4-oxadiazol-3-yl)cyclobutyl)carbamoyl)phenyl)-N-methylbenzofuran-3-carboxamide as a buff colored solid (120 mg, 70%). ¹H NMR (400 MHz, DMSO-d₆): δ ppm 9.48 (s, 1H), 9.39 (s, 1H), 8.46-8.38 (m, 1H), 8.32 (s, 1H), 8.04 (s, 2H), 7.96 (d, J=3.5 Hz, 1H), 7.89-7.80 (m, 2H), 7.76-7.67 (m, 1H), 7.57-7.48 (m, 1H), 7.38 (t, J=8.8 Hz, 2H), 5.36-5.29 (m, 1H), 4.36-4.25 (m, 1H), 4.14 (d, J=7.0 Hz, 2H), 3.03-2.92 (m, 2H), 2.83 (d, J=4.5 Hz, 3H), 2.48-2.39 (m, 2H), 1.30 (t, J=7.0 Hz, 3H); LCMS: (ES+) m/z=571.1 (M+H)⁺, Column-ACQUITY UPLC BEH C18 (50×2.1 mm; 1.7 m), M phase A: 0.1% TFA in water, M phase B: Acetonitrile, Flow: 0.8 ml/min, Rt min: 0.90, wavelength: 220 nm.

| Time | % A | % B |
|------|-----|-----|
| 0.0 | 98 | 2 |
| 1.0 | 2 | 98 |
| 1.6 | 2 | 98 |

Example 70

5-(3-((3-(Difluoromethoxy)-1-(1,2,4-oxadiazol-3-yl)cyclobutyl)carbamoyl)phenyl)-6-ethoxy-2-(4-fluorophenyl)-N-methylbenzofuran-3-carboxamide

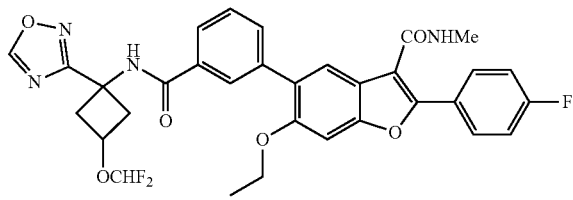

To a solution of 6-ethoxy-2-(4-fluorophenyl)-5-(3-((3-hydroxy-1-(1,2,4-oxadiazol-3-yl)cyclobutyl)carbamoyl)phenyl)-N-methylbenzofuran-3-carboxamide (Example 69) (120 mg, 0.210 mmol) in acetonitrile (10 mL) was added CuI(I) (40.4 mg, 0.210 mmol). The mixture was stirred at 50° C., and 2,2-difluoro-2-(fluorosulfonyl)acetic acid (37.5 mg, 0.210 mmol) was then added to the mixture at 50° C. After stirring for 2 hr, the solvent was evaporated. The residue was quenched with ice-cold water and filtered to give the crude product which was purified by preparative HPLC to obtain 5-(3-((3-(difluoromethoxy)-1-(1,2,4-oxadiazol-3-yl)cyclobutyl)carbamoyl)phenyl)-6-ethoxy-2-(4-fluorophenyl)-N-methylbenzofuran-3-carboxamide as a colorless solid (6 mg, 5%). Preparative HPLC method: Method: Preparative column dimensions: Sunfire C-18 (19*150 mm) 5u; Mobile phase A: 10 mM NH₄OAc in Water; Mobile phase B: Acetonitrile; Flow: 16.0 ml/min, Gradient: Time (min)\% B: 0/30, 10/60. ¹H NMR (400 MHz, METHANOL-d₄) δ 9.21 (s, 1H), 8.08 (s, 1H), 7.99-7.92 (m, 2H), 7.86 (d, J=7.8 Hz, 1H), 7.78 (d, J=7.8 Hz, 1H), 7.63 (s, 1H), 7.54 (t, J=7.7 Hz, 1H), 7.34 (s, 1H), 7.26 (t, J=8.8 Hz, 2H), 6.63-6.21 (t, J=74.8 Hz, 1H), 4.97 (t, J=7.2 Hz, 1H), 4.16 (q, J=7.0 Hz, 2H), 3.28-3.17 (m, 2H), 2.96 (s, 3H), 2.85-2.78 (m, 2H), 1.39 (t, J=7.0 Hz, 3H); ¹⁹F NMR (376.6 MHz, METHANOL-d₄) −84.54 and −113.34; LCMS: (ES+) m/z=621 (M+H)⁺, Method: Column-Ascentis Express C18 (50×2.1 mm-2.7 m), M phase A: 0.1% HCOOH in water, M phase B: ACN, Flow=1 mL/min, Rt=2.40 min.

| Time | % A | % B |
|------|-----|-----|
| 0.0 | 100 | 0 |
| 1.7 | 0 | 100 |
| 3.2 | 0 | 100 |

HPLC Method: SUNFIRE C18 (150×4.6 mm) 3.5 micron, Buffer: 0.05% TFA in water, Mobile Phase A: Buffer:ACN (95:5), Mobile Phase B: ACN: Buffer (95:5), Flow: 1.0 ml/min, Time\% B: 0/10, 25/100, 30/100, Wavelength: 254 nm, Rt: 19.10 min, Wavelength: 220 nm, Rt: 19.10 min. HPLC Method: XBridge Phenyl (150×4.6 mm) 3.5 micron SC/749, Buffer: 0.05% TFA in water pH 2.5, Mobile Phase A: Buffer:ACN (95:5), Mobile Phase B: Buffer:ACN (5:95), Flow: 1.0 ml/min, Time\% B: 0/10, 25/100, 30/100, Wavelength: 254 nm, Rt: 18.02 min, Wavelength: 220 nm, Rt: 18.02 min.

Biological Methods

HCVNS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl₂, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 µm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl₂ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCVNS5B RdRp Enzyme Assay.

An on-bead solid phase homogeneous assay was used in a 384-well format to assess NS5B inhibitors (WangY-K, Rigat K, Roberts S, and Gao M (2006) Anal Biochem, 359: 106-111). The biotinylated oligo $dT_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, polyA template, $^3$H-UTP, and RNAse inhibitor (Promega N2515)). Compounds were serially diluted 1:3 in DMSO and aliquoted into assay plates. Equal volumes (10 µL) of water, 3× reaction mix, and enzyme in 3× assay buffer (60 mM Hepes buffer, pH 7.5, 7.5 mM $MgCl_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 µM $^3$H-UTP (0.3 µCi), 1.6 U/µL RNAse inhibitor, 7 nM NS5B enzyme, 0.01 mg/mL BSA, 1 mM DTT, and 0.33 µg/µL beads, 20 mM Hepes buffer, pH 7.5, 2.5 mM $MgCl_2$, 2.5 mM KCl, and 0.1% DMSO.

Reactions were allowed to proceed from 4 to 24 hours at 30° C. For 24 hour reactions, enzyme and inhibitors were pre-incubated for 24 hours before adding template and primer. Reactions were terminated by the addition of 50 mM EDTA (10 µL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)^D)))$, where A and B denote minimal and maximal % inhibition, respectively, C is the $IC_{50}$, D is hill slope and x represents compound concentration.

Cell Lines.

The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 µL at a density of $2.4 \times 10^3$ cells/well) in DMEM containing 4% FBS (final DMSO concentration at 0.5%). After 3 days incubation at 37° C., cells were analyzed for *Renilla* Luciferase activity using the EnduRen substrate (Promega cat # E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration ($EC_{50}$) was calculated using the four-parameter logistic formula noted above.

To assess cytotoxicity of compounds, Cell Titer-Blue (Promega) was added to the EnduRen-containing plates and incubated for at least 4 h at 37° C. The fluorescence signal from each well was read using a Viewlux Imager. All $CC_{50}$ values were calculated using the four-parameter logistic formula.

1b enzyme and replicon data for the Examples are reported in Table 2.

| Example | Structure | $IC_{50}$ (µM) | $EC_{50}$ (µM) |
|---|---|---|---|
| Example 5a | 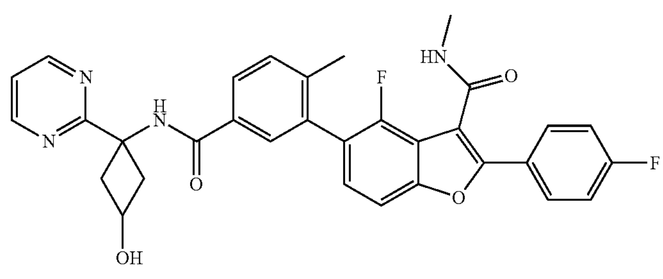 [SMILES: CNC(=O)c1c(-c2ccc(F)cc2)oc2ccc(-c3cc(C(=O)NC4(c5ncccn5)CC(O)C4)ccc3C)c(F)c12] | 1.28 | 3.86 |
| Example 5b | 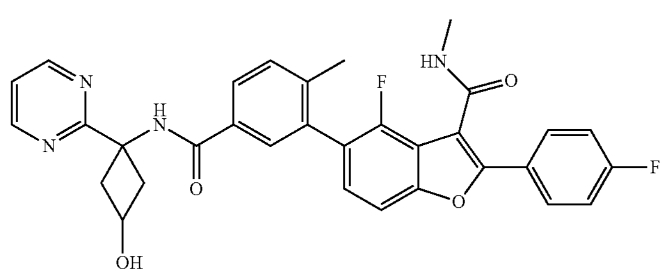 [SMILES: CNC(=O)c1c(-c2ccc(F)cc2)oc2ccc(-c3cc(C(=O)NC4(c5ncccn5)CC(O)C4)ccc3C)c(F)c12] | 0.23 | 1.19 |

-continued

| Example | Structure | IC$_{50}$ (μM) | EC$_{50}$ (μM) |
|---|---|---|---|
| Example 6 | 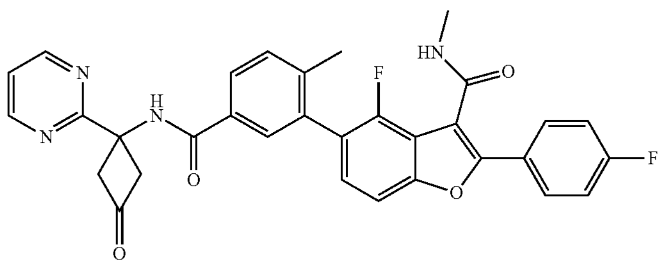 [SMILES: CNC(=O)c1c(-c2ccc(F)cc2)oc2ccc(-c3cc(C(=O)NC4(c5ncccn5)CC(=O)C4)ccc3C)c(F)c12] | 0.01 | 0.02 |
| Example 7 | 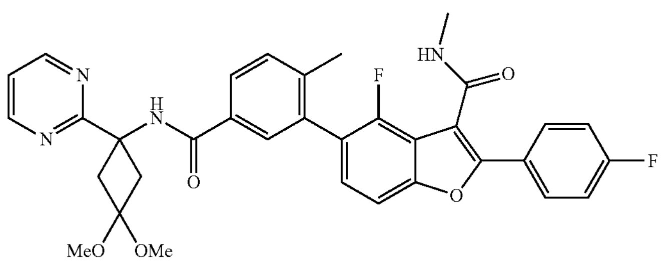 [SMILES: CNC(=O)c1c(-c2ccc(F)cc2)oc2ccc(-c3cc(C(=O)NC4(c5ncccn5)CC(OC)(OC)C4)ccc3C)c(F)c12] | 0.01 | 0.06 |
| Example 8 | 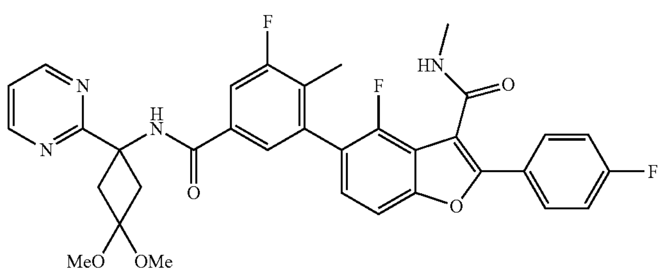 [SMILES: CNC(=O)c1c(-c2ccc(F)cc2)oc2ccc(-c3cc(C(=O)NC4(c5ncccn5)CC(OC)(OC)C4)cc(F)c3C)c(F)c12] | 0.04 | 0.02 |
| Example 9a | 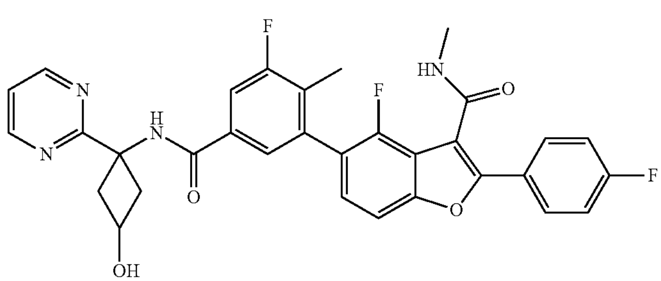 [SMILES: CNC(=O)c1c(-c2ccc(F)cc2)oc2ccc(-c3cc(C(=O)NC4(c5ncccn5)CC(O)C4)cc(F)c3C)c(F)c12] | 0.57 | 0.47 |
| Example 9b | 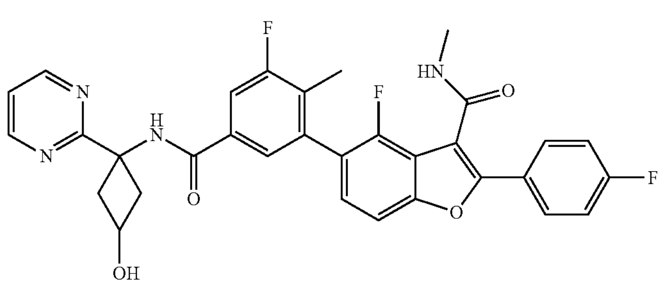 [SMILES: CNC(=O)c1c(-c2ccc(F)cc2)oc2ccc(-c3cc(C(=O)NC4(c5ncccn5)CC(O)C4)cc(F)c3C)c(F)c12] | 0.31 | 0.30 |

-continued

| Example | Structure | IC$_{50}$ (μM) | EC$_{50}$ (μM) |
|---|---|---|---|
| Example 10a | 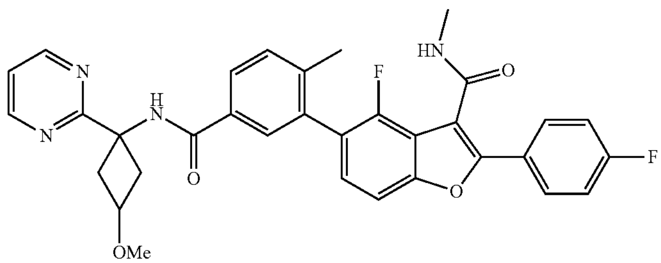 [SMILES: CNC(=O)c1c(-c2ccc(F)cc2)oc2ccc(-c3cc(C(=O)NC4(c5ncccn5)CC(OC)C4)ccc3C)c(F)c12] | 0.06 | 0.03 |
| Example 10b | 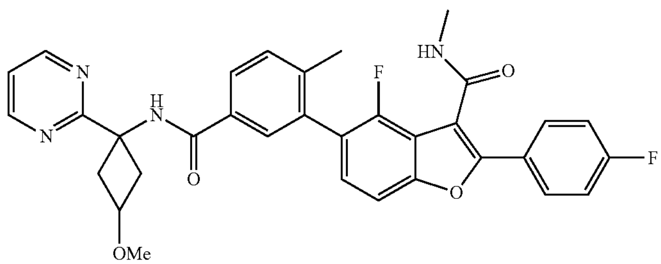 [SMILES: CNC(=O)c1c(-c2ccc(F)cc2)oc2ccc(-c3cc(C(=O)NC4(c5ncccn5)CC(OC)C4)ccc3C)c(F)c12] | 0.01 | 4.43E-03 |
| Example 11a | 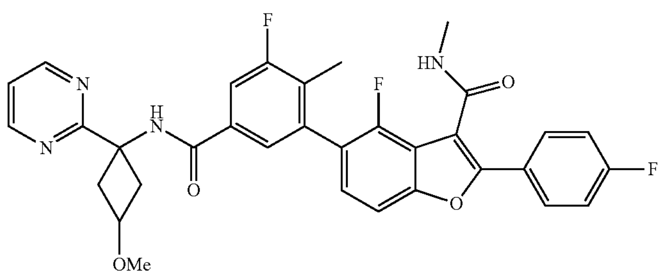 [SMILES: CNC(=O)c1c(-c2ccc(F)cc2)oc2ccc(-c3cc(C(=O)NC4(c5ncccn5)CC(OC)C4)cc(F)c3C)c(F)c12] | 0.09 | 0.04 |
| Example 11b | 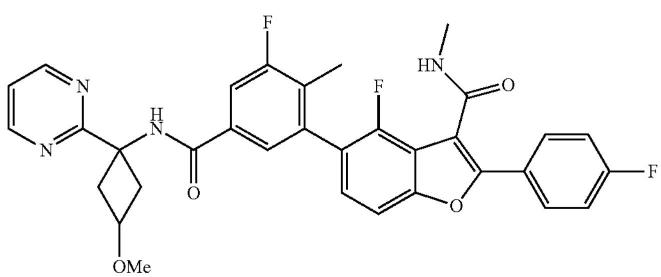 [SMILES: CNC(=O)c1c(-c2ccc(F)cc2)oc2ccc(-c3cc(C(=O)NC4(c5ncccn5)CC(OC)C4)cc(F)c3C)c(F)c12] | 0.03 | 4.56E-03 |
| Example 12a | 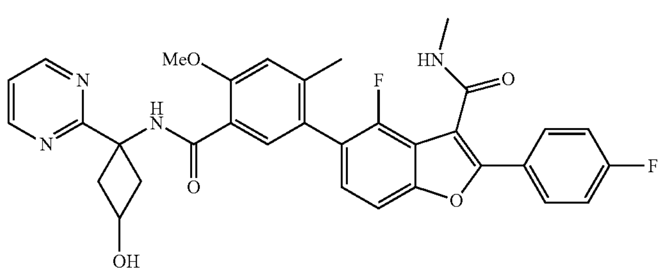 [SMILES: CNC(=O)c1c(-c2ccc(F)cc2)oc2ccc(-c3cc(C(=O)NC4(c5ncccn5)CC(O)C4)c(OC)cc3C)c(F)c12] | 0.76 | 0.43 |

-continued

| Example | Structure | IC$_{50}$ (μM) | EC$_{50}$ (μM) |
|---|---|---|---|
| Example 12b | 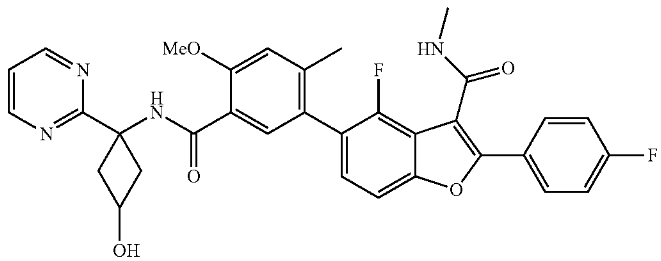 [SMILES: CNC(=O)c1c(-c2ccc(F)cc2)oc2ccc(-c3cc(C(=O)NC4(c5ncccn5)CC(O)C4)c(OC)cc3C)c(F)c12] | 0.21 | 0.14 |
| Example 13a | 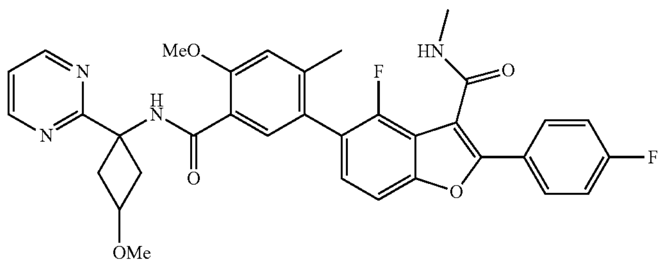 [SMILES: CNC(=O)c1c(-c2ccc(F)cc2)oc2ccc(-c3cc(C(=O)NC4(c5ncccn5)CC(OC)C4)c(OC)cc3C)c(F)c12] | 0.03 | 0.03 |
| Example 13b | 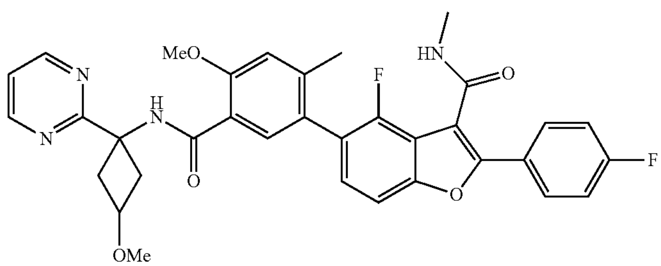 [SMILES: CNC(=O)c1c(-c2ccc(F)cc2)oc2ccc(-c3cc(C(=O)NC4(c5ncccn5)CC(OC)C4)c(OC)cc3C)c(F)c12] | 0.02 | 6.44E-03 |
| Example 14 | 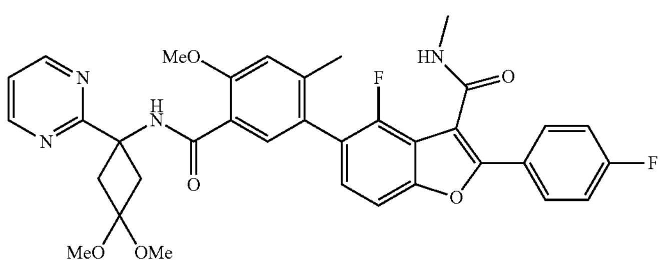 [SMILES: CNC(=O)c1c(-c2ccc(F)cc2)oc2ccc(-c3cc(C(=O)NC4(c5ncccn5)CC(OC)(OC)C4)c(OC)cc3C)c(F)c12] | 0.03 | 0.02 |
| Example 15 | 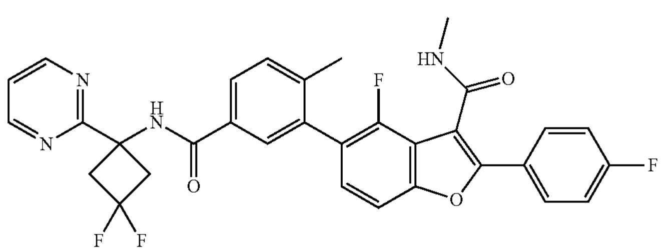 [SMILES: CNC(=O)c1c(-c2ccc(F)cc2)oc2ccc(-c3cc(C(=O)NC4(c5ncccn5)CC(F)(F)C4)ccc3C)c(F)c12] | 0.03 | 0.03 |

-continued

| Example | Structure | IC$_{50}$ (μM) | EC$_{50}$ (μM) |
|---|---|---|---|
| Example 16 | 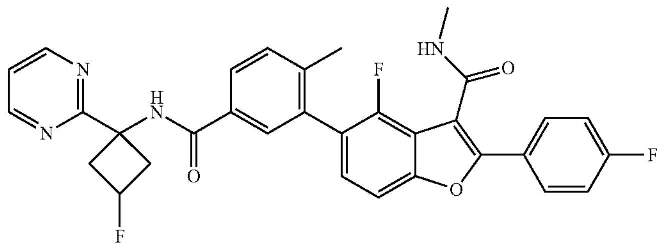 [SMILES: CNC(=O)c1c(-c2ccc(F)cc2)oc2ccc(-c3cc(C(=O)NC4(c5ncccn5)CC(F)C4)ccc3C)c(F)c12] | 0.03 | 6.62E-03 |
| Example 17 | 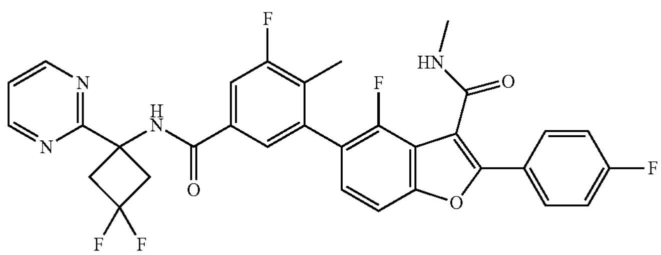 [SMILES: CNC(=O)c1c(-c2ccc(F)cc2)oc2ccc(-c3cc(C(=O)NC4(c5ncccn5)CC(F)(F)C4)cc(F)c3C)c(F)c12] | 0.25 | 0.01 |
| Example 18 | 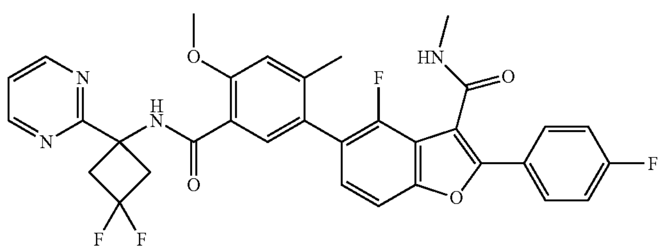 [SMILES: CNC(=O)c1c(-c2ccc(F)cc2)oc2ccc(-c3cc(C(=O)NC4(c5ncccn5)CC(F)(F)C4)c(OC)cc3C)c(F)c12] | 0.14 | 0.01 |
| Example 19 | 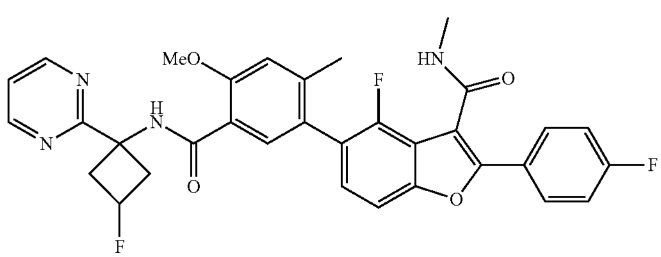 [SMILES: CNC(=O)c1c(-c2ccc(F)cc2)oc2ccc(-c3cc(C(=O)NC4(c5ncccn5)CC(F)C4)c(OC)cc3C)c(F)c12] | 0.12 | 5.26E-03 |
| Example 20 | 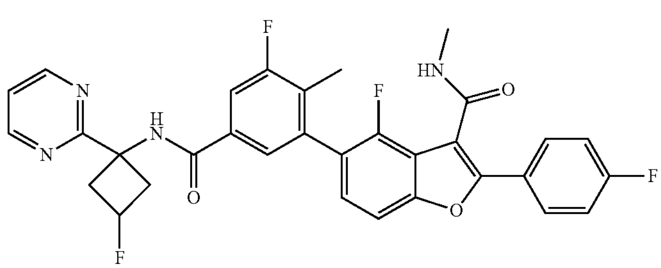 [SMILES: CNC(=O)c1c(-c2ccc(F)cc2)oc2ccc(-c3cc(C(=O)NC4(c5ncccn5)CC(F)C4)cc(F)c3C)c(F)c12] | 0.09 | 6.16E-03 |

| Example | Structure | IC$_{50}$ (μM) | EC$_{50}$ (μM) |
|---|---|---|---|
| Example 21 | 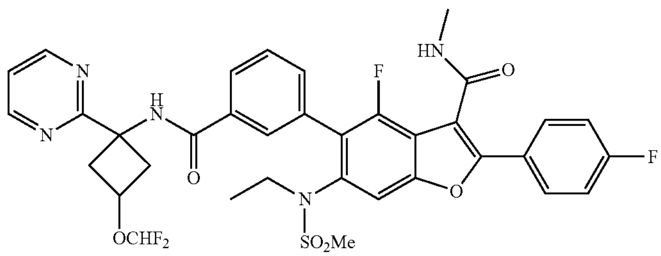 [SMILES: CCN(c1cc2oc(-c3ccc(F)cc3)c(C(=O)NC)c2c(F)c1-c1cccc(C(=O)NC2(c3ncccn3)CC(OC(F)F)C2)c1)S(C)(=O)=O] | | 2.23E-03 |
| Example 22 | 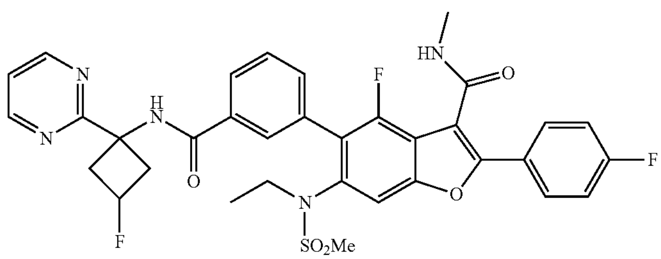 [SMILES: CCN(c1cc2oc(-c3ccc(F)cc3)c(C(=O)NC)c2c(F)c1-c1cccc(C(=O)NC2(c3ncccn3)CC(F)C2)c1)S(C)(=O)=O] | | 4.94E-03 |
| Example 24 | 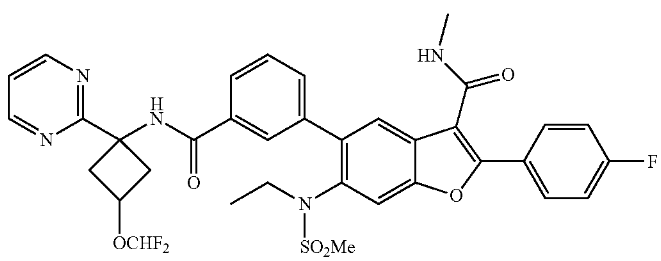 [SMILES: CCN(c1cc2oc(-c3ccc(F)cc3)c(C(=O)NC)c2cc1-c1cccc(C(=O)NC2(c3ncccn3)CC(OC(F)F)C2)c1)S(C)(=O)=O] | | 2.20E-03 |
| Example 25 | 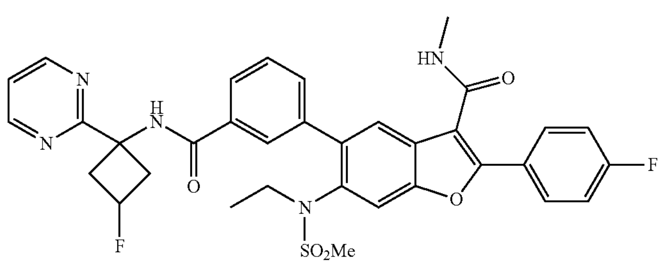 [SMILES: CCN(c1cc2oc(-c3ccc(F)cc3)c(C(=O)NC)c2cc1-c1cccc(C(=O)NC2(c3ncccn3)CC(F)C2)c1)S(C)(=O)=O] | 1.37E-03 | 5.29E-03 |
| Example 26 | 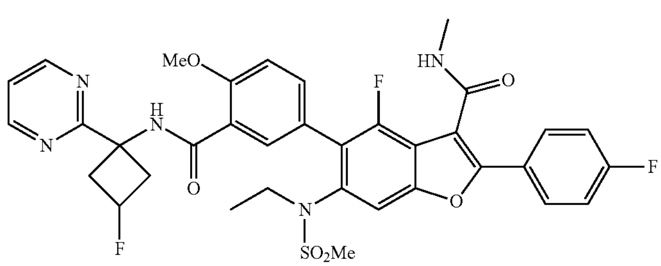 [SMILES: CCN(c1cc2oc(-c3ccc(F)cc3)c(C(=O)NC)c2c(F)c1-c1ccc(OC)c(C(=O)NC2(c3ncccn3)CC(F)C2)c1)S(C)(=O)=O] | | 2.25E-03 |

-continued

| Example | Structure | IC$_{50}$ (μM) | EC$_{50}$ (μM) |
|---|---|---|---|
| Example 29a | 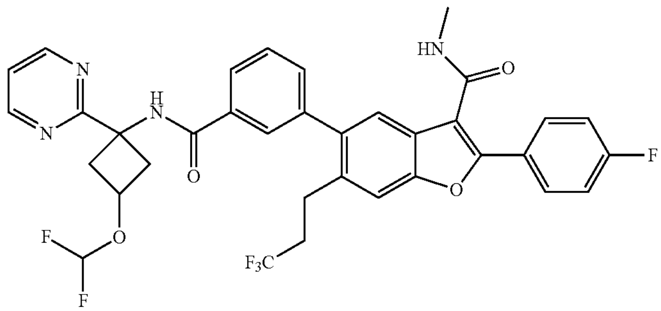 [SMILES: CNC(=O)c1c(-c2ccc(F)cc2)oc2cc(CCC(F)(F)F)c(-c3cccc(C(=O)NC4(c5ncccn5)CC(OC(F)F)C4)c3)cc12] | 6.14E-03 | 4.07E-03 |
| Example 29b | 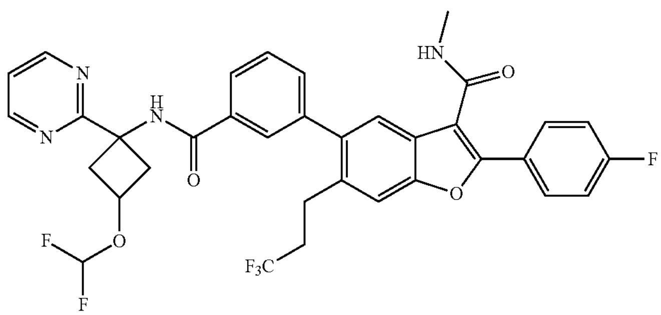 [SMILES: CNC(=O)c1c(-c2ccc(F)cc2)oc2cc(CCC(F)(F)F)c(-c3cccc(C(=O)NC4(c5ncccn5)CC(OC(F)F)C4)c3)cc12] | | 0.03 |
| Example 32 | 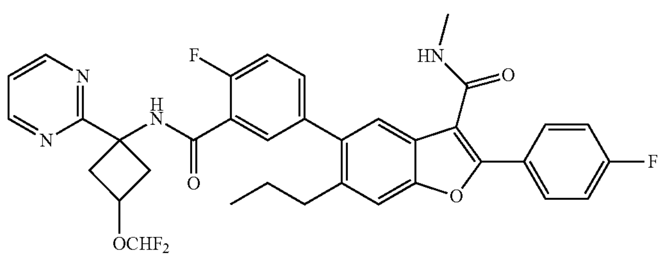 [SMILES: CCCc1cc2oc(-c3ccc(F)cc3)c(C(=O)NC)c2cc1-c1ccc(OC)c(C(=O)NC2(c3ncccn3)CC(OC(F)F)C2)c1] | | 9.02E-03 |
| Example 33 | 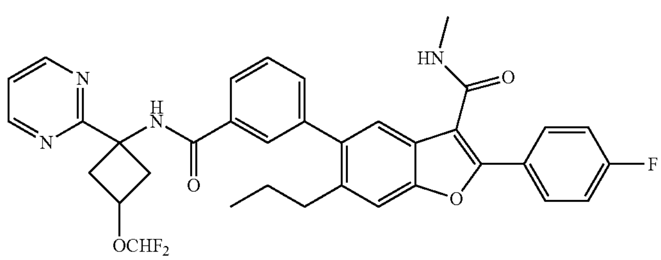 | | 4.55E-03 |
| Example 37 | 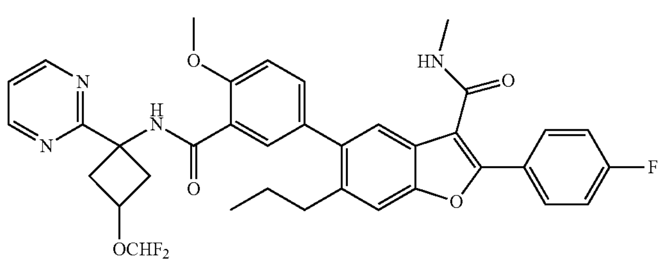 | | 6.08E-03 |

-continued

| Example | Structure | IC$_{50}$ (μM) | EC$_{50}$ (μM) |
|---|---|---|---|
| Example 39 | 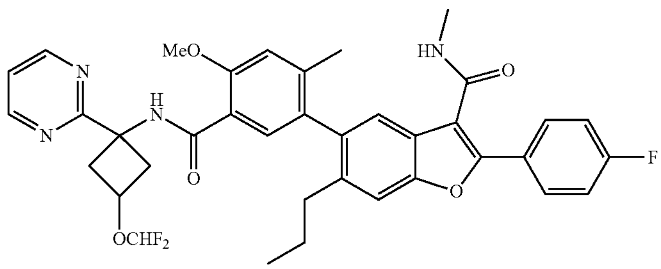 [SMILES: CCCc1cc2oc(-c3ccc(F)cc3)c(C(=O)NC)c2cc1-c1cc(C(=O)NC2(c3ncccn3)CC(OC(F)F)C2)c(OC)cc1C] | | 0.02 |
| Example 41 | 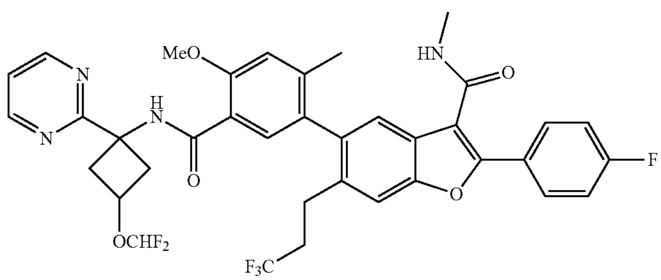 [SMILES: CNC(=O)c1c(-c2ccc(F)cc2)oc2cc(CCC(F)(F)F)c(-c3cc(C(=O)NC4(c5ncccn5)CC(OC(F)F)C4)c(OC)cc3C)cc12] | | 0.02 |
| Example 42 | 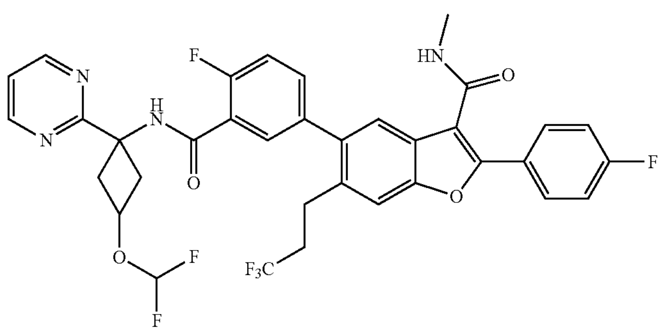 [SMILES: CNC(=O)c1c(-c2ccc(F)cc2)oc2cc(CCC(F)(F)F)c(-c3ccc(F)c(C(=O)NC4(c5ncccn5)CC(OC(F)F)C4)c3)cc12] | 7.60E-03 | 5.73E-03 |
| Example 43 | 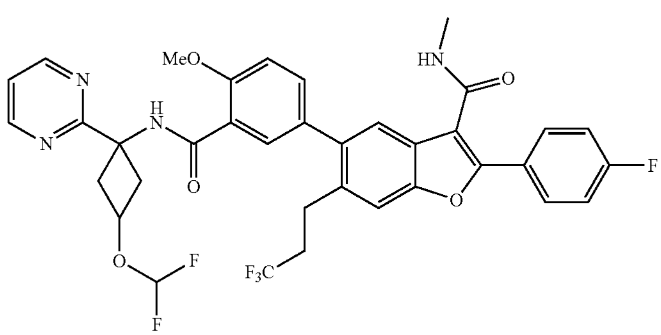 [SMILES: CNC(=O)c1c(-c2ccc(F)cc2)oc2cc(CCC(F)(F)F)c(-c3ccc(OC)c(C(=O)NC4(c5ncccn5)CC(OC(F)F)C4)c3)cc12] | 0.01 | 5.60E-03 |

| Example | Structure | IC$_{50}$ (μM) | EC$_{50}$ (μM) |
|---|---|---|---|
| Example 44 | 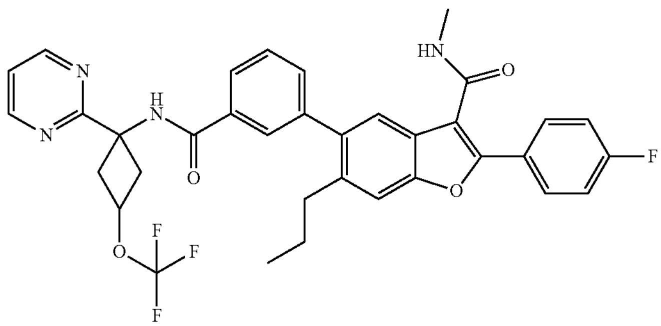 [SMILES: CCCc1cc2oc(-c3ccc(F)cc3)c(C(=O)NC)c2cc1-c1cccc(C(=O)NC2(c3ncccn3)CC(OC(F)(F)F)C2)c1] | 5.87E-03 | 9.51E-03 |
| Example 45a | 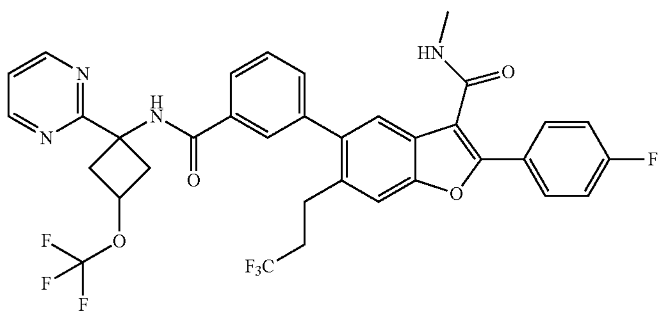 [SMILES: CNC(=O)c1c(-c2ccc(F)cc2)oc2cc(CCC(F)(F)F)c(-c3cccc(C(=O)NC4(c5ncccn5)CC(OC(F)(F)F)C4)c3)cc12] | 0.02 | 0.02 |
| Example 45b | 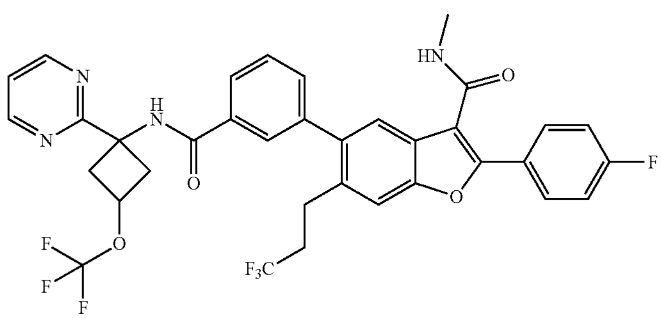 [SMILES: CNC(=O)c1c(-c2ccc(F)cc2)oc2cc(CCC(F)(F)F)c(-c3cccc(C(=O)NC4(c5ncccn5)CC(OC(F)(F)F)C4)c3)cc12] | 0.01 | 9.46E-03 |
| Example 46a | 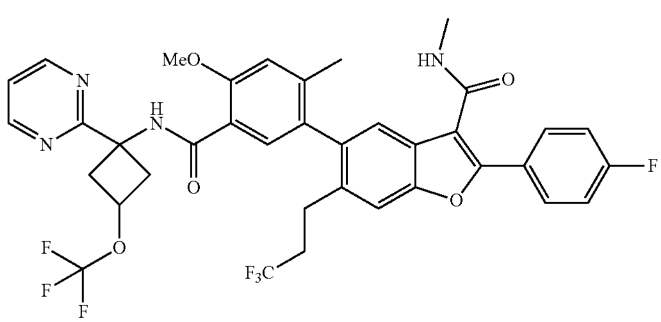 [SMILES: CNC(=O)c1c(-c2ccc(F)cc2)oc2cc(CCC(F)(F)F)c(-c3cc(C(=O)NC4(c5ncccn5)CC(OC(F)(F)F)C4)c(OC)cc3C)cc12] | | 0.04 |

| Example | Structure | IC$_{50}$ (μM) | EC$_{50}$ (μM) |
|---|---|---|---|
| Example 46b | 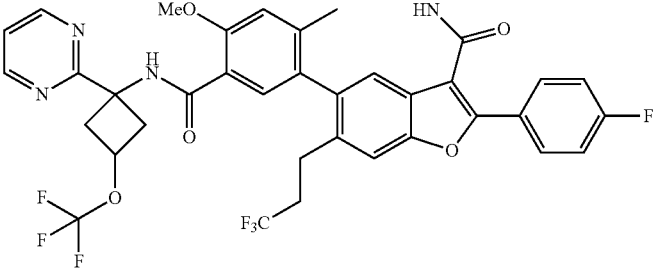 | | 0.08 |
| Example 47a | 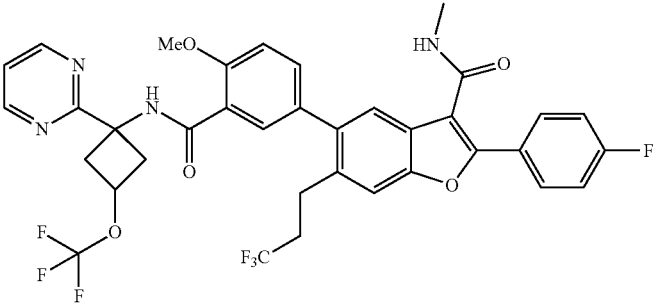 [SMILES: CNC(=O)c1c(-c2ccc(F)cc2)oc2cc(CCC(F)(F)F)c(-c3ccc(OC)c(C(=O)NC4(c5ncccn5)CC(OC(F)(F)F)C4)c3)cc12] | 0.02 | 0.01 |
| Example 47b | 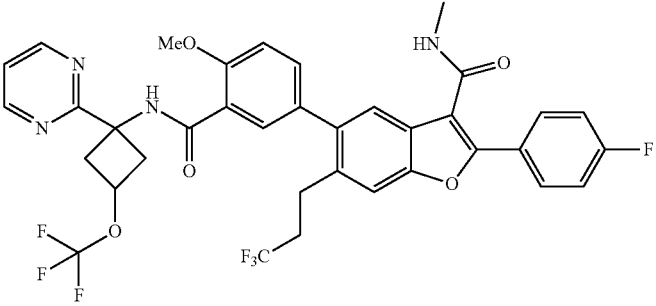 [SMILES: CNC(=O)c1c(-c2ccc(F)cc2)oc2cc(CCC(F)(F)F)c(-c3ccc(OC)c(C(=O)NC4(c5ncccn5)CC(OC(F)(F)F)C4)c3)cc12] | 0.01 | 0.01 |
| Example 48a | 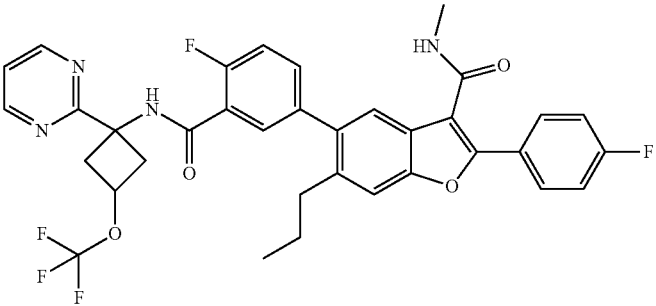 [SMILES: CCCc1cc2oc(-c3ccc(F)cc3)c(C(=O)NC)c2cc1-c1ccc(F)c(C(=O)NC2(c3ncccn3)CC(OC(F)(F)F)C2)c1] | | 0.02 |

-continued

| Example | Structure | IC$_{50}$ (μM) | EC$_{50}$ (μM) |
|---|---|---|---|
| Example 48b | 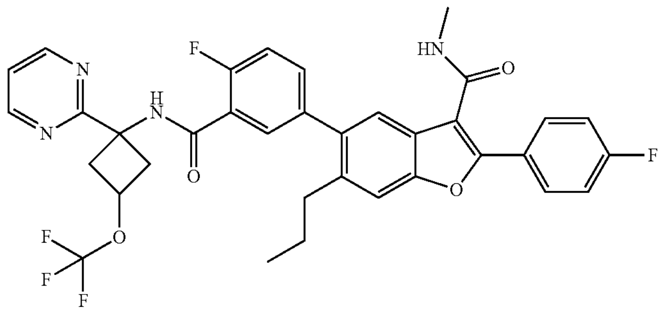 [SMILES: CCCc1cc2oc(-c3ccc(F)cc3)c(C(=O)NC)c2cc1-c1ccc(F)c(C(=O)NC2(c3ncccn3)CC(OC(F)(F)F)C2)c1] | 8.27E-03 | 0.01 |
| Example 49a | 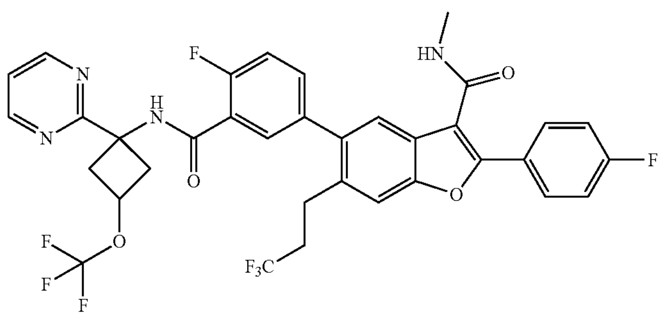 [SMILES: CNC(=O)c1c(-c2ccc(F)cc2)oc2cc(CCC(F)(F)F)c(-c3ccc(F)c(C(=O)NC4(c5ncccn5)CC(OC(F)(F)F)C4)c3)cc12] | | 0.02 |
| Example 49b | 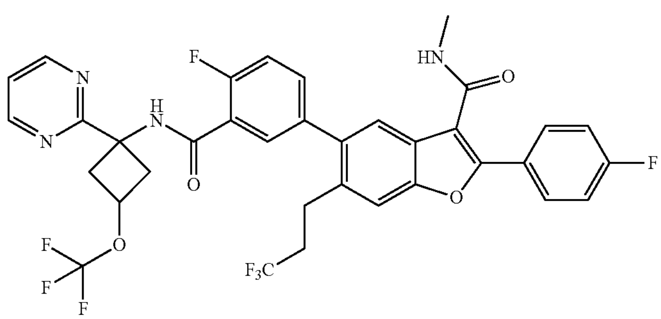 [SMILES: CNC(=O)c1c(-c2ccc(F)cc2)oc2cc(CCC(F)(F)F)c(-c3ccc(F)c(C(=O)NC4(c5ncccn5)CC(OC(F)(F)F)C4)c3)cc12] | 0.01 | 0.02 |
| Example 50a | 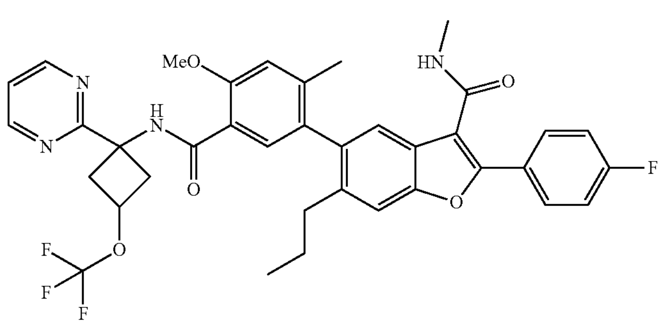 [SMILES: CCCc1cc2oc(-c3ccc(F)cc3)c(C(=O)NC)c2cc1-c1cc(C(=O)NC2(c3ncccn3)CC(OC(F)(F)F)C2)c(OC)cc1C] | | 0.12 |

| Example | Structure | IC₅₀ (μM) | EC₅₀ (μM) |
|---|---|---|---|
| Example 50b | 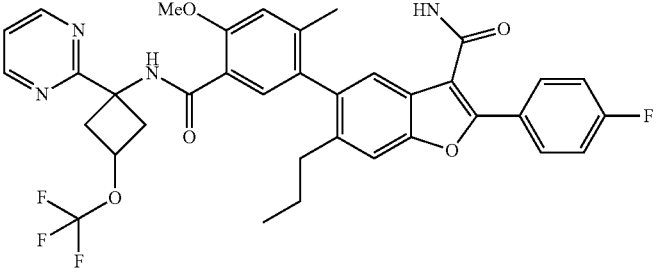 | | |
| Example 51a | 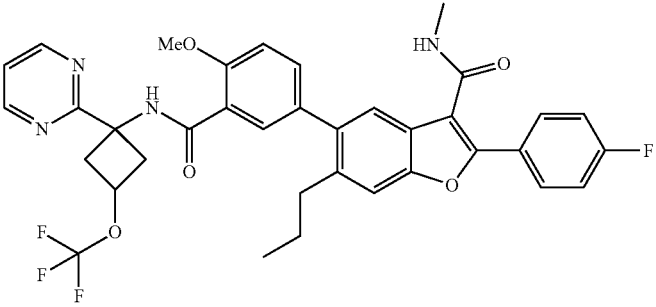 [SMILES: CCCc1cc2oc(-c3ccc(F)cc3)c(C(=O)NC)c2cc1-c1ccc(OC)c(C(=O)NC2(c3ncccn3)CC(OC(F)(F)F)C2)c1] | 0.05 | 0.02 |
| Example 51b | 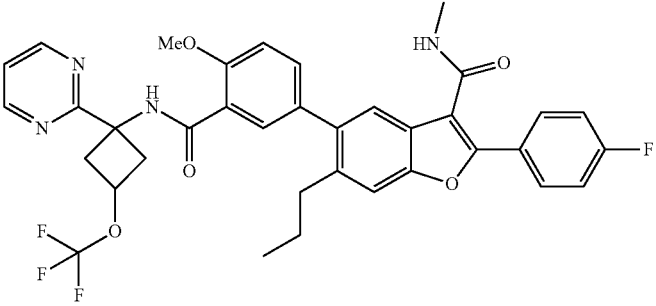 [SMILES: CCCc1cc2oc(-c3ccc(F)cc3)c(C(=O)NC)c2cc1-c1ccc(OC)c(C(=O)NC2(c3ncccn3)CC(OC(F)(F)F)C2)c1] | 0.02 | 0.01 |
| Example 53a | 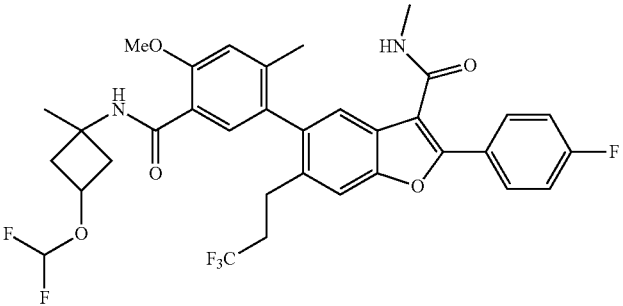 [SMILES: CNC(=O)c1c(-c2ccc(F)cc2)oc2cc(CCC(F)(F)F)c(-c3cc(C(=O)NC4(C)CC(OC(F)F)C4)c(OC)cc3C)cc12] | | 0.06 |

| Example | Structure | IC$_{50}$ (μM) | EC$_{50}$ (μM) |
|---|---|---|---|
| Example 53b | 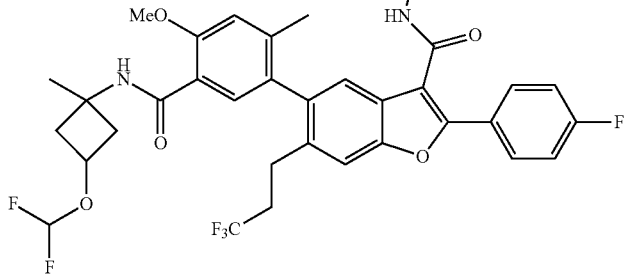 | | 0.06 |
| Example 55a | 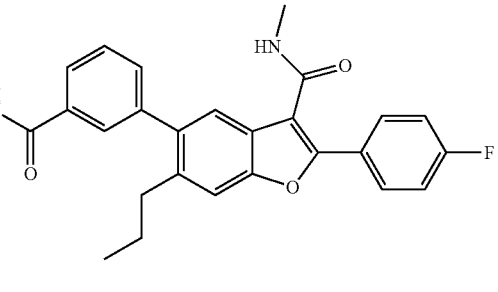 | | 0.03 |
| Example 55b | 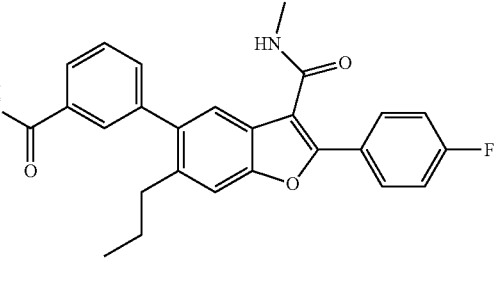 | | 0.03 |
| Example 57a | 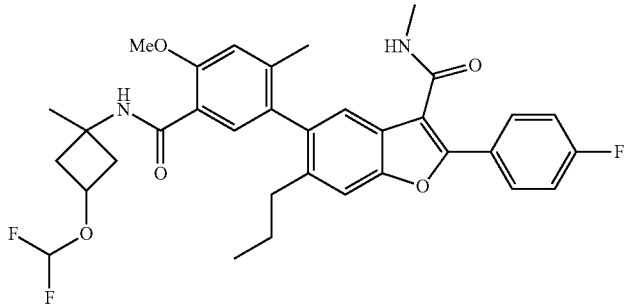 [SMILES: CCCc1cc2oc(-c3ccc(F)cc3)c(C(=O)NC)c2cc1-c1cc(C(=O)NC2(C)CC(OC(F)F)C2)c(OC)cc1C] | 0.01 | 0.05 |

-continued

| Example | Structure | IC$_{50}$ (µM) | EC$_{50}$ (µM) |
|---------|-----------|----------------|----------------|
| Example 57b | 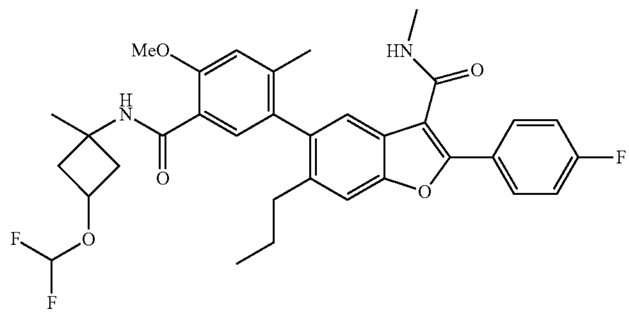 [SMILES: CCCc1cc2oc(-c3ccc(F)cc3)c(C(=O)NC)c2cc1-c1cc(C(=O)NC2(C)CC(OC(F)F)C2)c(OC)cc1C] | | 0.07 |
| Example 59a | 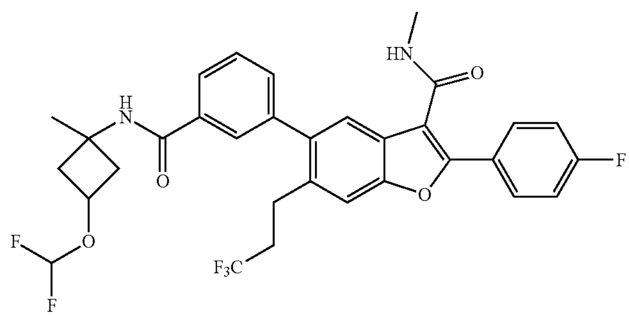 [SMILES: CNC(=O)c1c(-c2ccc(F)cc2)oc2cc(CCC(F)(F)F)c(-c3cccc(C(=O)NC4(C)CC(OC(F)F)C4)c3)cc12] | | 0.03 |
| Example 59b | 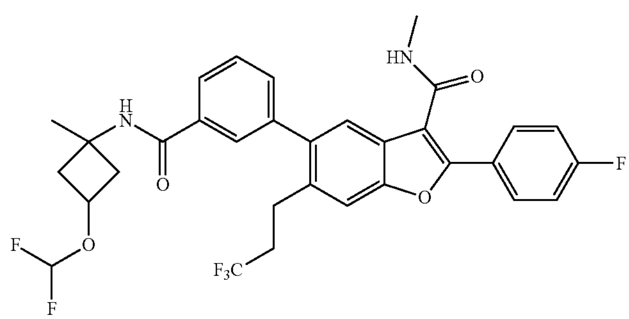 [SMILES: CNC(=O)c1c(-c2ccc(F)cc2)oc2cc(CCC(F)(F)F)c(-c3cccc(C(=O)NC4(C)CC(OC(F)F)C4)c3)cc12] | 0.01 | 0.02 |
| Example 61a | 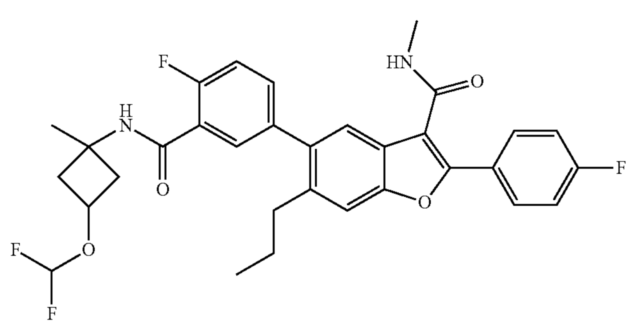 [SMILES: CCCc1cc2oc(-c3ccc(F)cc3)c(C(=O)NC)c2cc1-c1ccc(F)c(C(=O)NC2(C)CC(OC(F)F)C2)c1] | | 0.02 |

| Example | Structure | IC$_{50}$ (µM) | EC$_{50}$ (µM) |
|---|---|---|---|
| Example 61b | 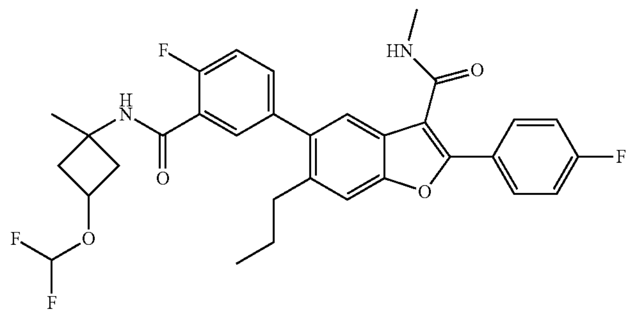 [SMILES: CCCc1cc2oc(-c3ccc(F)cc3)c(C(=O)NC)c2cc1-c1ccc(F)c(C(=O)NC2(C)CC(OC(F)F)C2)c1] | | 0.02 |
| Example 63a | 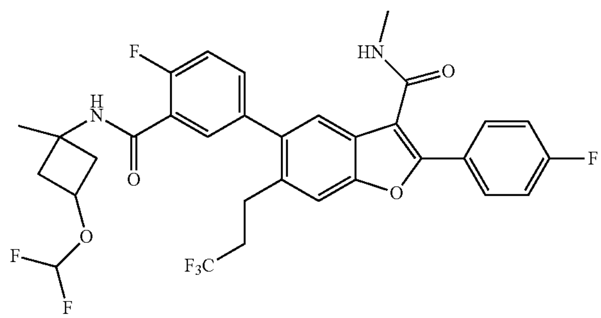 [SMILES: CNC(=O)c1c(-c2ccc(F)cc2)oc2cc(CCC(F)(F)F)c(-c3ccc(F)c(C(=O)NC4(C)CC(OC(F)F)C4)c3)cc12] | | 0.01 |
| Example 63b | 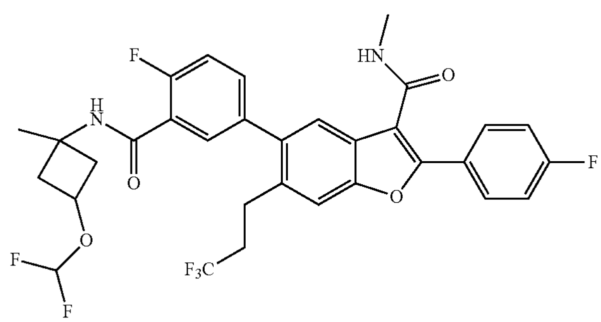 [SMILES: CNC(=O)c1c(-c2ccc(F)cc2)oc2cc(CCC(F)(F)F)c(-c3ccc(F)c(C(=O)NC4(C)CC(OC(F)F)C4)c3)cc12] | 3.03E-03 | 0.01 |
| Example 64a | 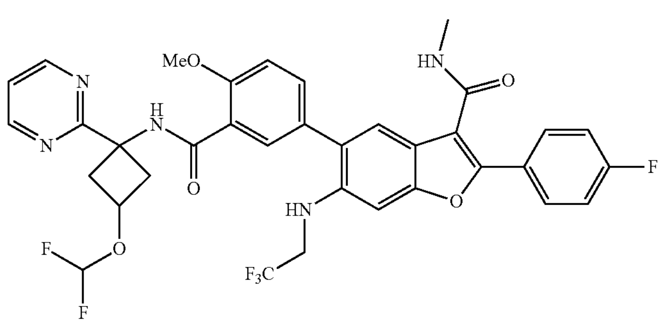 [SMILES: CNC(=O)c1c(-c2ccc(F)cc2)oc2cc(NCC(F)(F)F)c(-c3ccc(OC)c(C(=O)NC4(c5ncccn5)CC(OC(F)F)C4)c3)cc12] | 3.30E-03 | 4.23E-03 |

-continued

| Example | Structure | IC$_{50}$ (µM) | EC$_{50}$ (µM) |
|---|---|---|---|
| Example 64b | 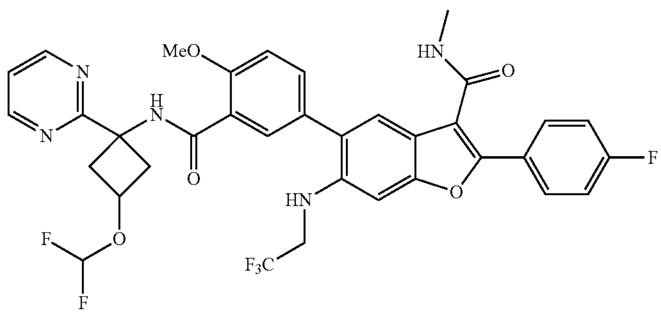 [SMILES: CNC(=O)c1c(-c2ccc(F)cc2)oc2cc(NCC(F)(F)F)c(-c3ccc(OC)c(C(=O)NC4(c5ncccn5)CC(OC(F)F)C4)c3)cc12] | 3.97E-03 | 5.97E-03 |
| Example 65a | 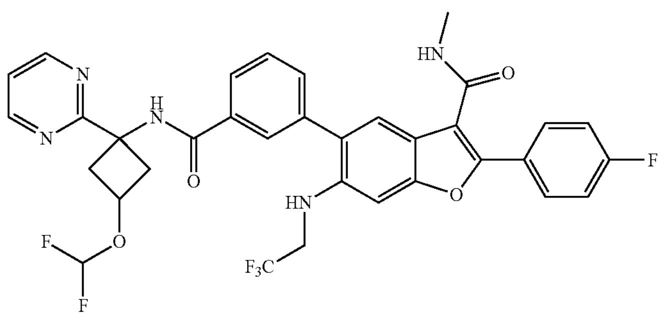 [SMILES: CNC(=O)c1c(-c2ccc(F)cc2)oc2cc(NCC(F)(F)F)c(-c3cccc(C(=O)NC4(c5ncccn5)CC(OC(F)F)C4)c3)cc12] | 4.55E-03 | 8.72E-03 |
| Example 65b | 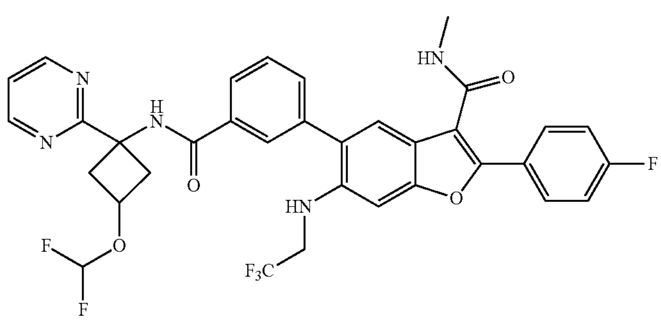 [SMILES: CNC(=O)c1c(-c2ccc(F)cc2)oc2cc(NCC(F)(F)F)c(-c3cccc(C(=O)NC4(c5ncccn5)CC(OC(F)F)C4)c3)cc12] | 4.73E-03 | 4.23E-03 |
| Example 66a | 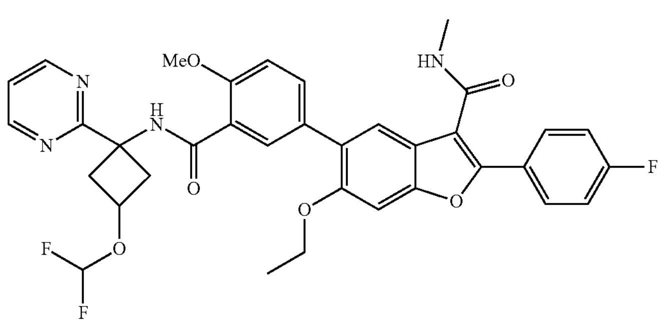 [SMILES: CCOc1cc2oc(-c3ccc(F)cc3)c(C(=O)NC)c2cc1-c1ccc(OC)c(C(=O)NC2(c3ncccn3)CC(OC(F)F)C2)c1] | 1.91E-03 | 4.05E-03 |

| Example | Structure | IC$_{50}$ (μM) | EC$_{50}$ (μM) |
|---|---|---|---|
| Example 66b | 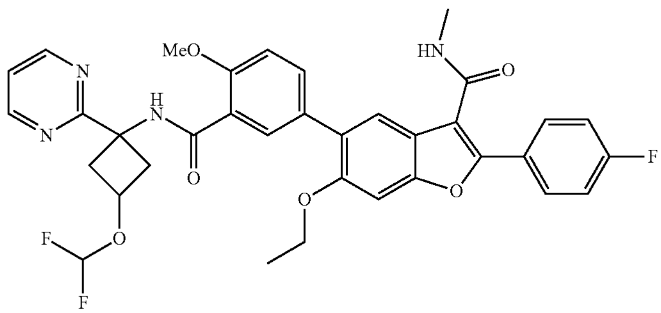 [SMILES: CCOc1cc2oc(-c3ccc(F)cc3)c(C(=O)NC)c2cc1-c1ccc(OC)c(C(=O)NC2(c3ncccn3)CC(OC(F)F)C2)c1] | 2.02E-03 | 4.39E-03 |
| Example 67a | 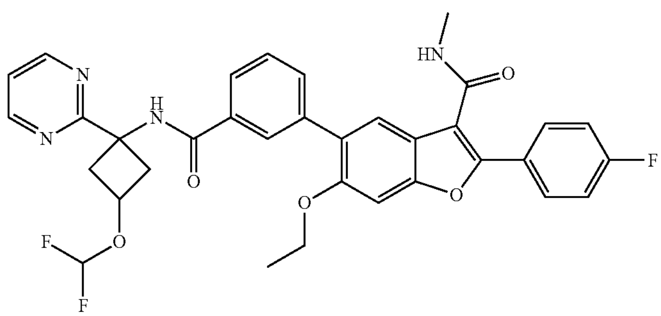 [SMILES: CCOc1cc2oc(-c3ccc(F)cc3)c(C(=O)NC)c2cc1-c1cccc(C(=O)NC2(c3ncccn3)CC(OC(F)F)C2)c1] | | 0.03 |
| Example 67b | 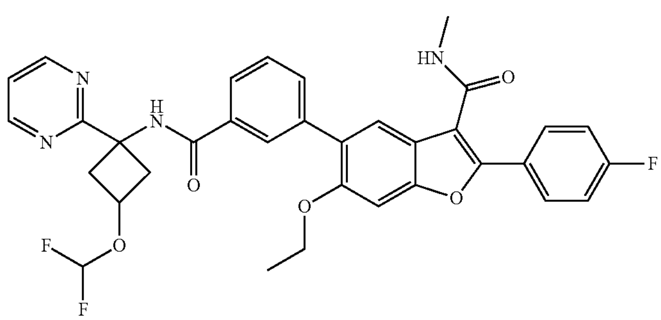 [SMILES: CCOc1cc2oc(-c3ccc(F)cc3)c(C(=O)NC)c2cc1-c1cccc(C(=O)NC2(c3ncccn3)CC(OC(F)F)C2)c1] | 2.11E-03 | 6.80E-03 |
| Example 70 | 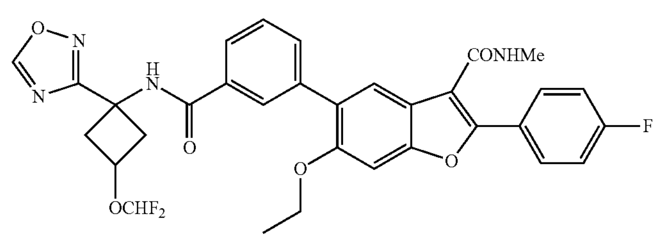 | | 6.47E-03 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

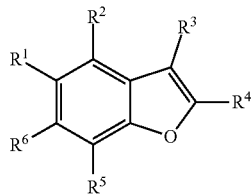

where:
R$^1$ is phenyl or pyridinyl and is substituted with 0-3 substituents selected from the group consisting of halo, alkyl, cycloalkyl, haloalkyl, alkoxy, or haloalkoxy, and wherein the phenyl or pyridinyl is also substituted with 1 CON(R$^9$)(R$^{10}$) substituent;
R$^2$ is hydrogen, halo, alkyl, or alkoxy;
R$^3$ is CON(R$^7$)(R$^8$);
R$^4$ is phenyl that is independently substituted with 0-2 halo, alkyl, or alkoxy or is para substituted with X—Ar$^1$;
R$^5$ is hydrogen, nitro, halo, alkyl, or alkoxy;
R$^6$ is hydrogen, alkyl, haloalkyl, alkoxy, haloalkoxy, or N(R$^{14}$)(R$^{15}$);
R$^7$ is alkyl;
R$^8$ is hydrogen;
R$^9$ is

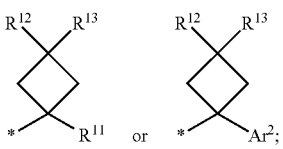

R$^{10}$ is hydrogen;
R$^{11}$ is alkyl;
R$^{12}$ is hydrogen, halo, hydroxy, alkoxy, or haloalkoxy;
R$^{13}$ is halo, hydroxy, alkoxy, or haloalkoxy;
or R$^{12}$ and R$^{13}$ taken together are carbonyl;
R$^{14}$ is hydrogen, alkyl, or haloalkyl;
R$^{15}$ is hydrogen, alkyl, haloalkyl, or alkylsulfonyl;
Ar$^1$ is phenyl or para-halophenyl;
Ar$^2$ is phenyl, pyridinyl, pyrazinyl, pyrimidinyl, pyrazolyl, isoxazolyl, isothiazolyl, imidazolyl, oxazolyl, thiazolyl, oxadiazolyl, thiadiazolyl, triazolyl, or tetrazolyl; and
X is —O— or NH—;
or a pharmaceutically acceptable salt thereof.

2. A compound of claim 1 where R$^1$ is phenyl substituted with 0-3 substituents selected from the group consisting of halo, alkyl, cycloalkyl, haloalkyl, alkoxy, and haloalkoxy, and wherein the phenyl is also substituted with 1 CON(R$^9$)(R$^{10}$) substituent; R$^2$ is hydrogen or halo; R$^3$ is CON(R$^7$)(R$^8$); R$^4$ is phenyl that is independently substituted with 0-1 halo; R$^5$ is hydrogen; R$^6$ is hydrogen, alkyl, haloalkyl, alkoxy, haloalkoxy, or N(R$^{14}$)(R$^{15}$); R$^7$ is alkyl; R$^8$ is hydrogen; R$^9$ is

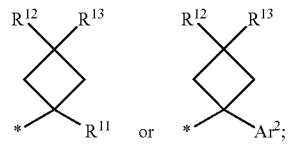

R$^{10}$ is hydrogen; R$^{11}$ is alkyl; R$^{12}$ is hydrogen, halo, hydroxy, alkoxy, or haloalkoxy; R$^{13}$ is halo, hydroxy, alkoxy, or haloalkoxy; or R$^{12}$ and R$^{13}$ taken together are carbonyl; R$^{14}$ is alkyl, or haloalkyl; R$^{15}$ is hydrogen or alkylsulfonyl; and Ar$^2$ is pyrimidinyl or oxadiazolyl; or a pharmaceutically acceptable salt thereof.

3. A compound of claim 2 where R$^1$ is phenyl substituted with 0-3 substituents selected from the group consisting of halo, alkyl, and alkoxy, and wherein the phenyl is also substituted with 1 CON(R$^9$)(R$^{10}$) substituent; R$^2$ is hydrogen or fluoro; R$^3$ is CON(R$^7$)(R$^8$); R$^4$ is phenyl that is independently substituted with 0-1 fluoro; R$^5$ is hydrogen; R$^6$ is hydrogen, alkyl, haloalkyl, alkoxy, haloalkoxy, or N(R$^7$)(R$^8$); R$^7$ is alkyl; R$^8$ is hydrogen; R$^9$ is

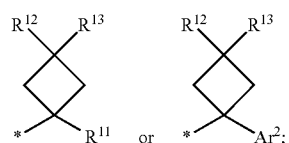

R$^{10}$ is hydrogen; R$^{11}$ is alkyl; R$^{12}$ is hydrogen, halo, hydroxy, alkoxy, or haloalkoxy; R$^{13}$ is halo, hydroxy, alkoxy, or haloalkoxy; or R$^{12}$ and R$^{13}$ taken together are carbonyl; R$^{14}$ is alkyl, or haloalkyl; R$^{15}$ is hydrogen or alkylsulfonyl; and Ar$^2$ is pyrimidinyl or oxadiazolyl; or a pharmaceutically acceptable salt thereof.

4. A compound of claim 1 where R$^1$ is phenyl substituted with 0-3 substituents selected from the group consisting of halo, alkyl, and alkoxy, and wherein the phenyl is also substituted with 1 CON(R$^9$)(R$^{10}$) substituent.

5. A compound of claim 1 where R$^2$ is hydrogen or halo.

6. A compound of claim 1 where R$^3$ is CON(R$^7$)(R$^8$); R$^7$ is methyl, and R$^8$ is hydrogen.

7. A compound of claim 1 where R$^9$ is

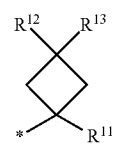

and R$^{11}$ is alkyl.

8. A compound of claim 1 where R$^9$ is

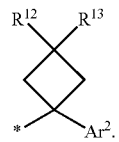

9. A compound of claim 1 where R$^{14}$ is haloalkyl and R$^{15}$ is hydrogen or where R$^{14}$ is alkyl and R$^{15}$ is alkylsulfonyl.

10. A compound of claim 1 where $Ar^2$ is pyrimidinyl or oxadiazolyl.
11. A compound of claim 1 selected from the group consisting of
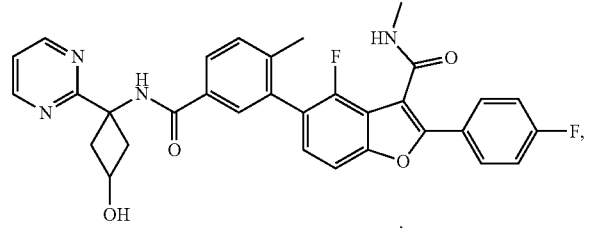
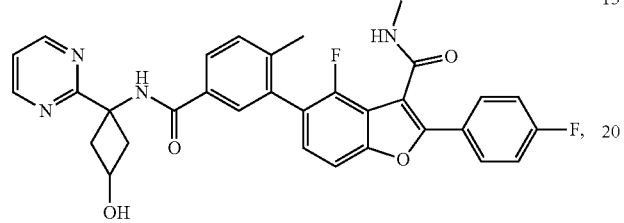
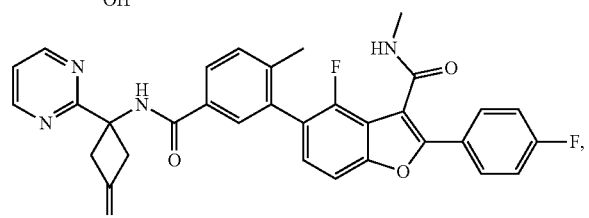
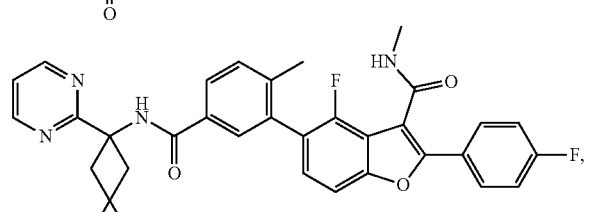
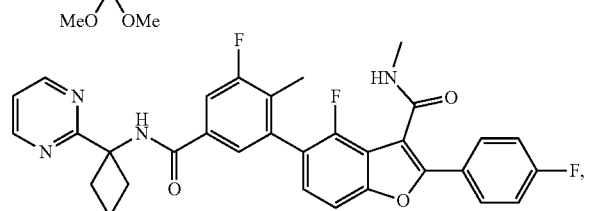
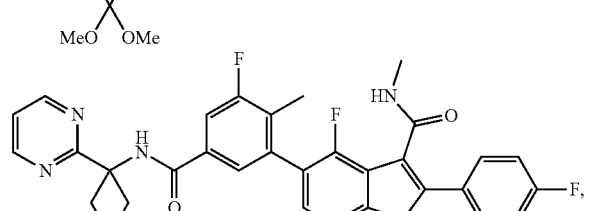
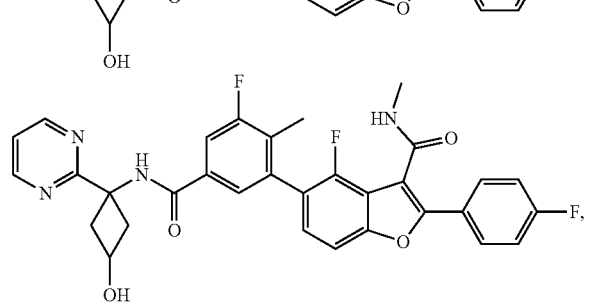
-continued
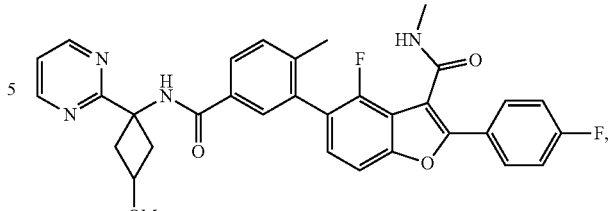
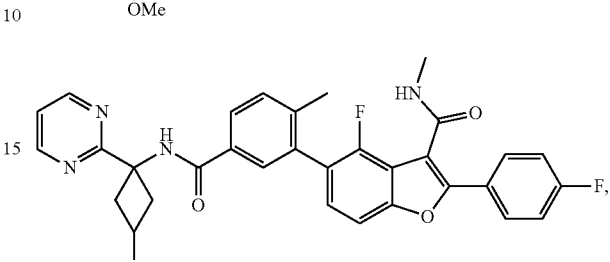
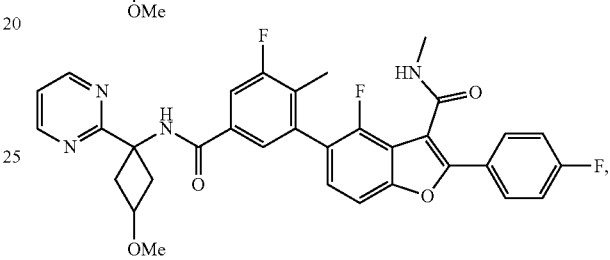
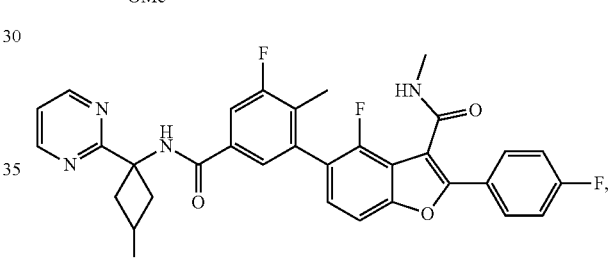
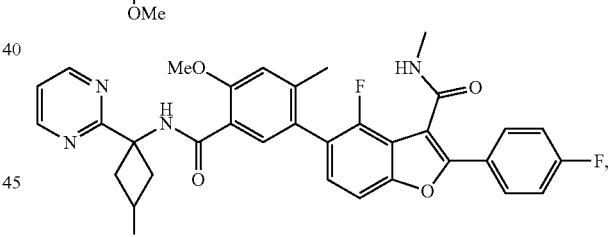
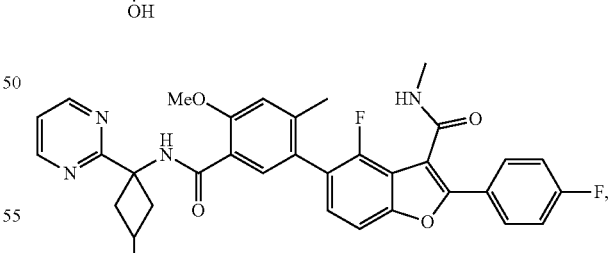
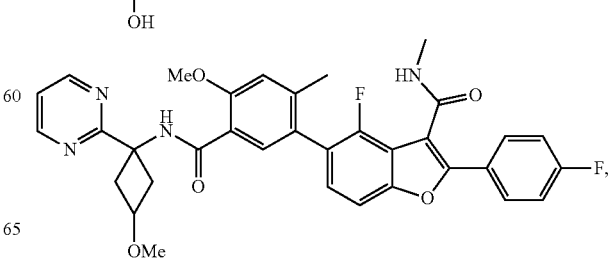

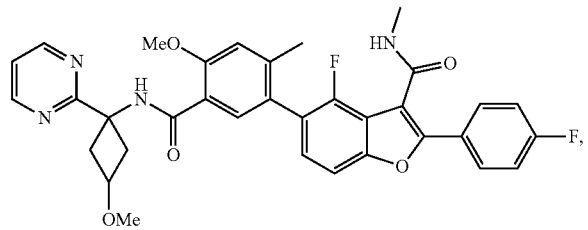
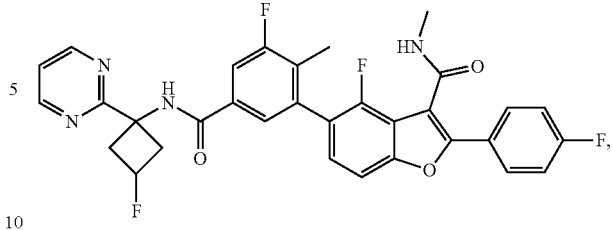
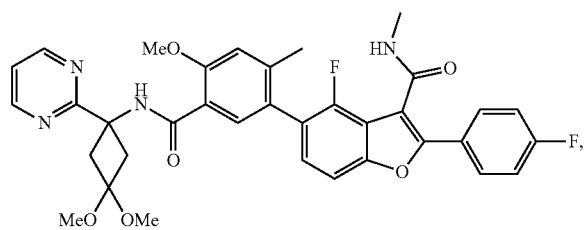
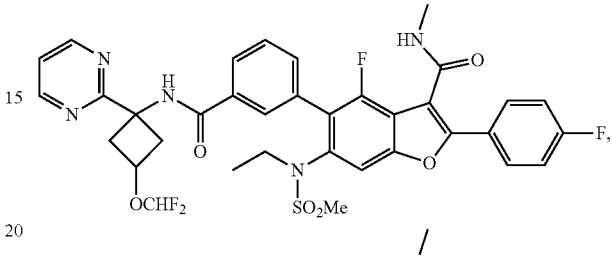
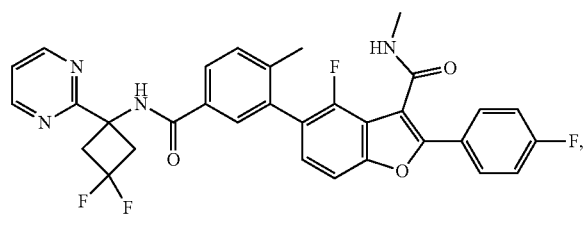
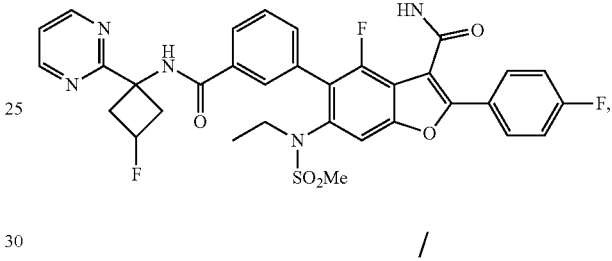
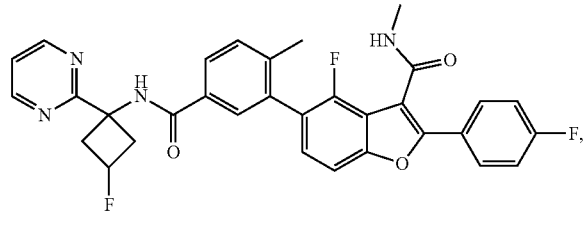
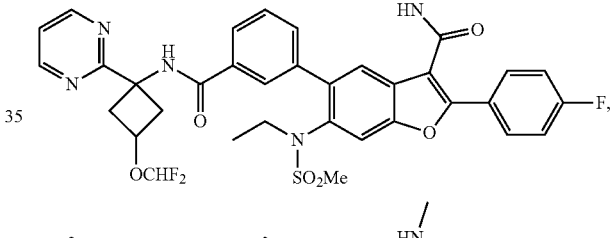
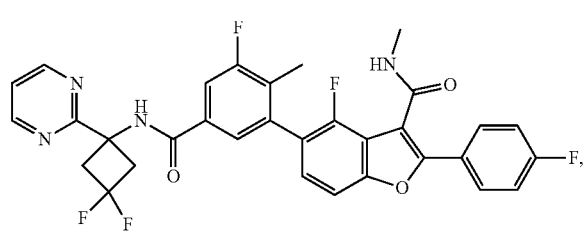
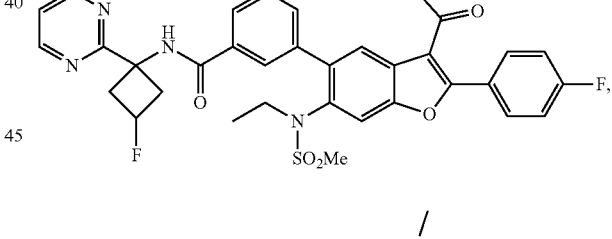
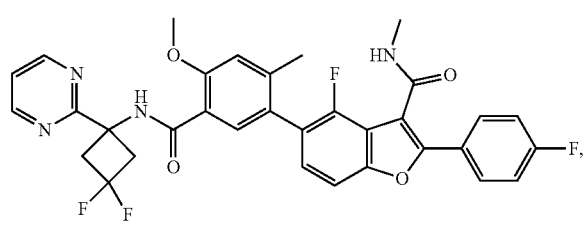
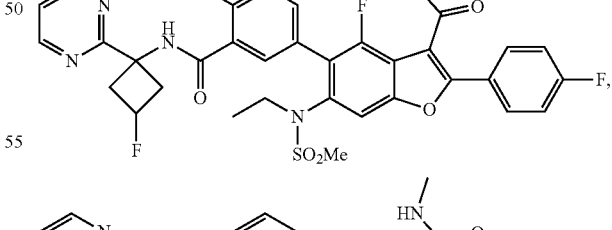
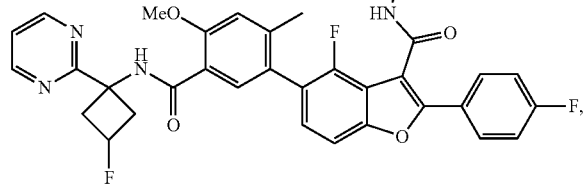
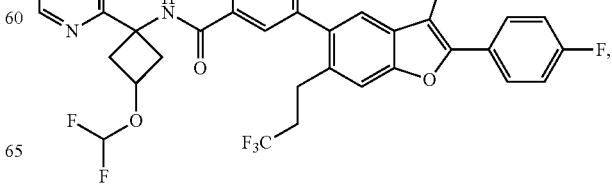

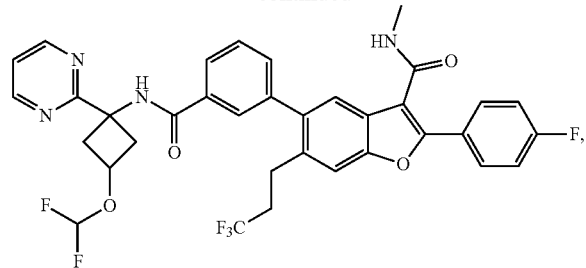
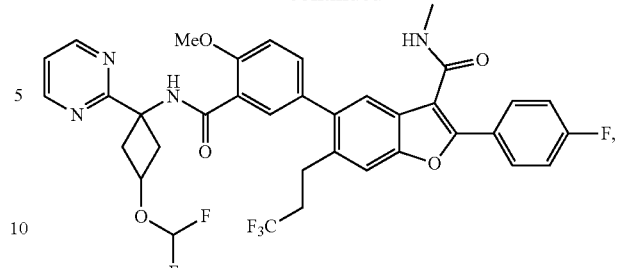
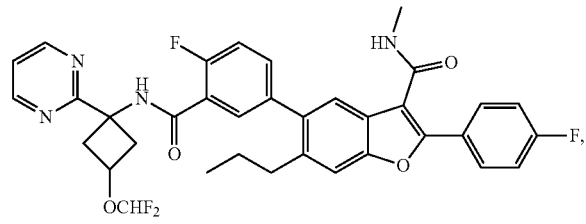
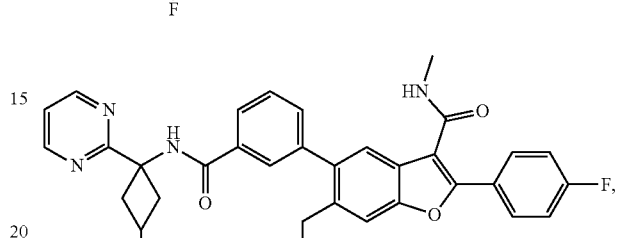
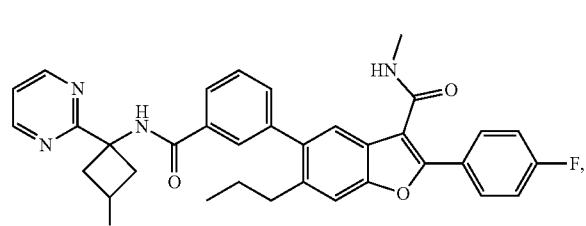
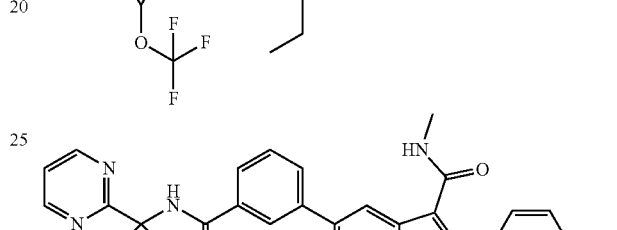
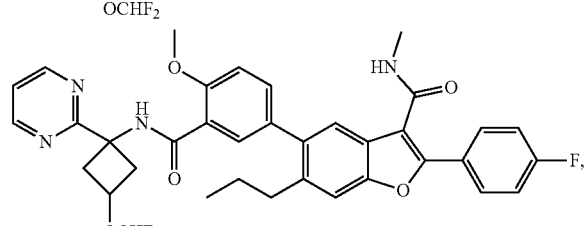
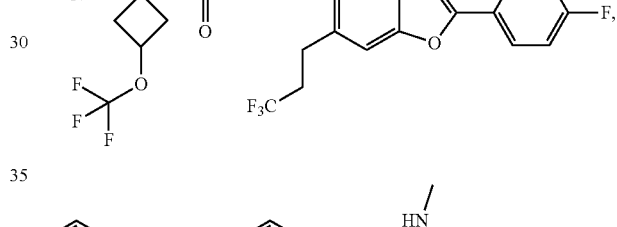
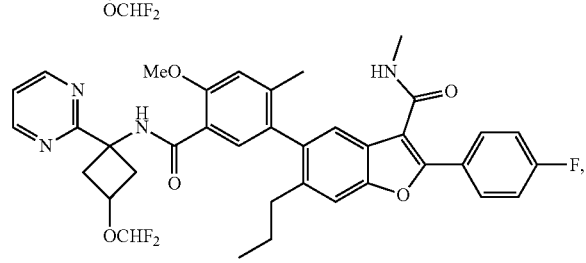
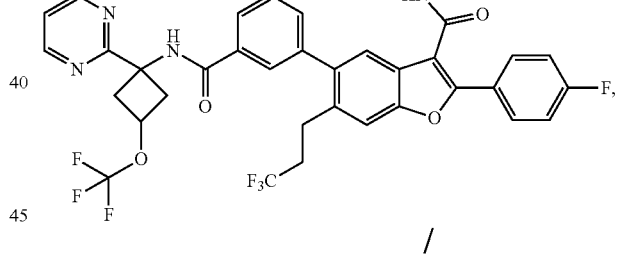
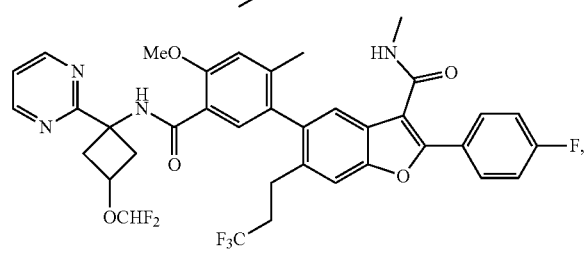
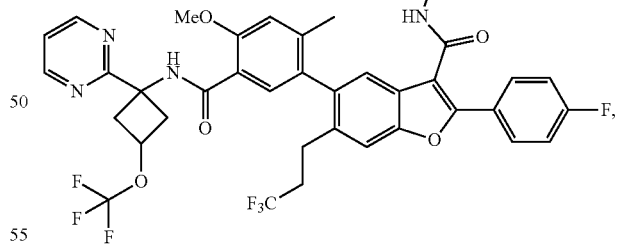
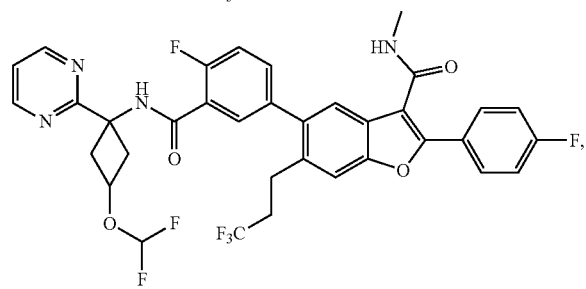
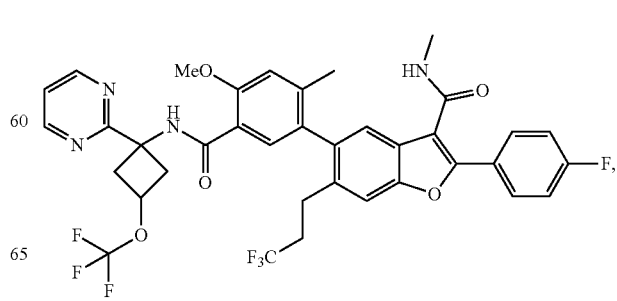

171
-continued
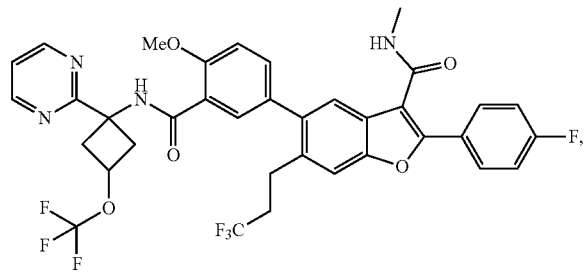
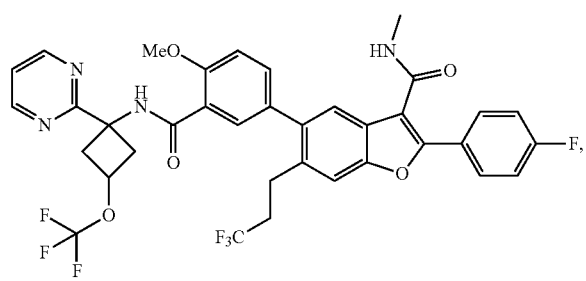
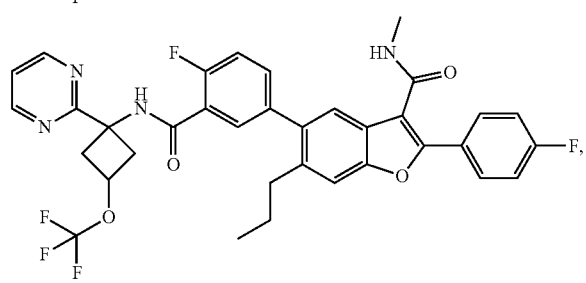
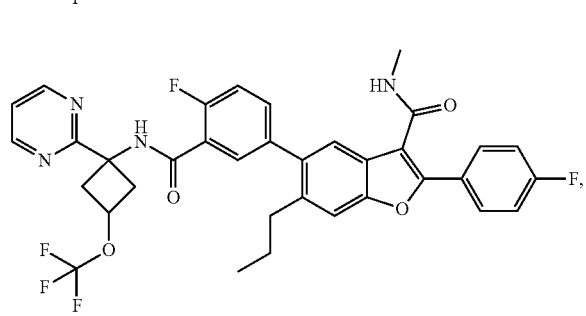
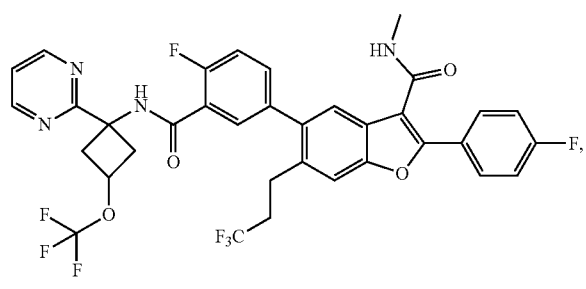
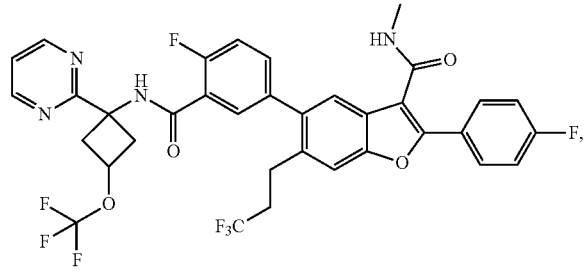
172
-continued
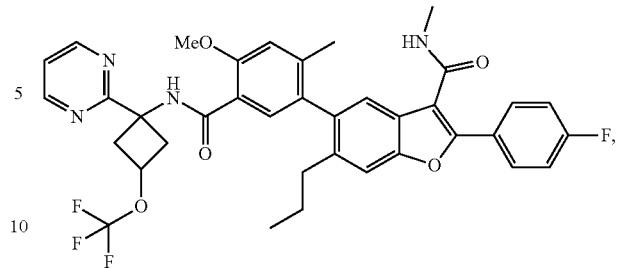
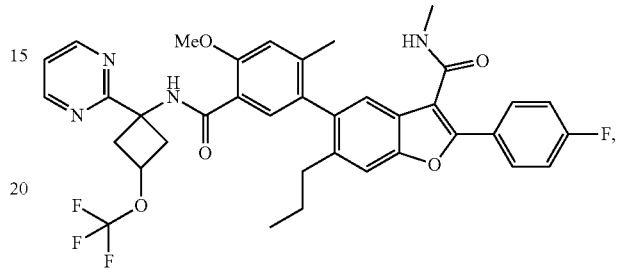
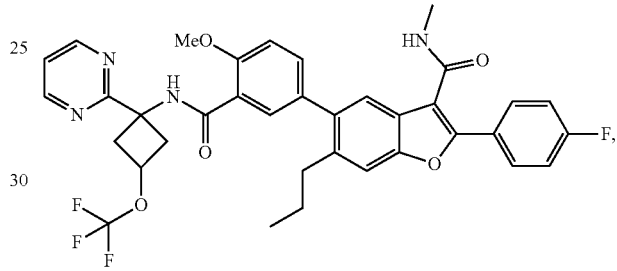
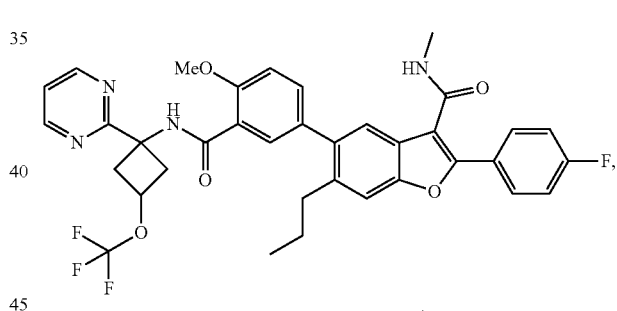
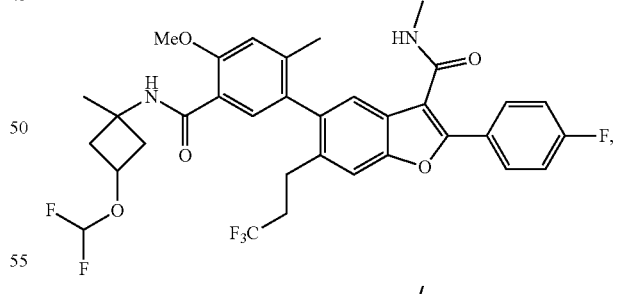
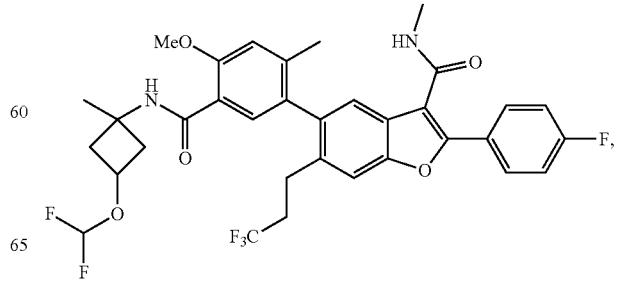

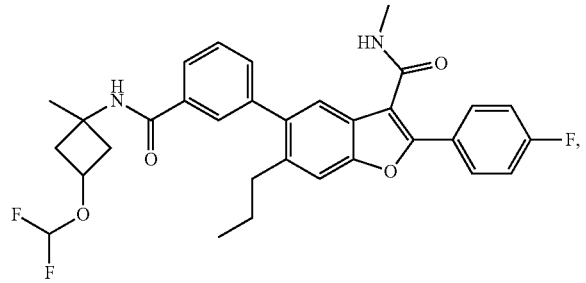
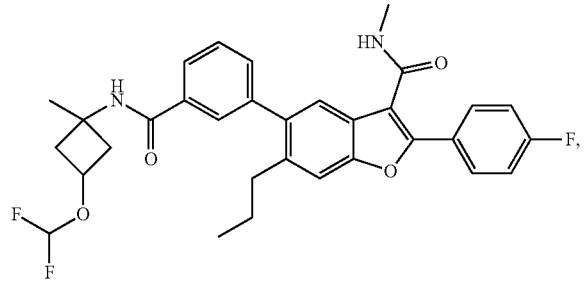
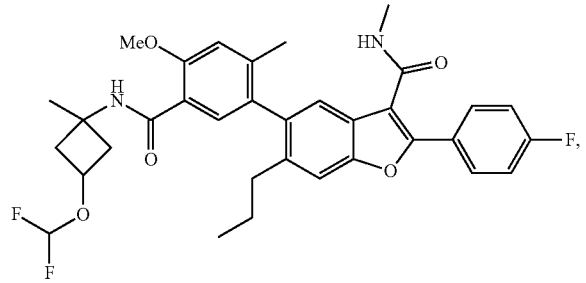
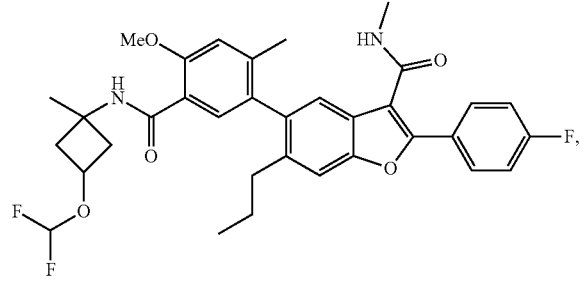
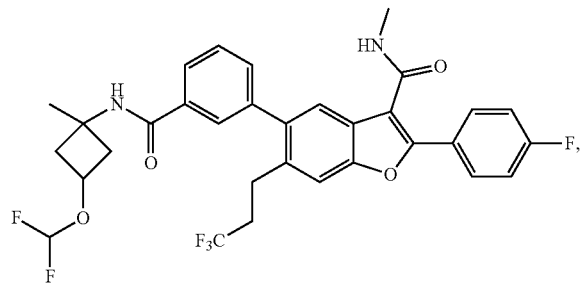
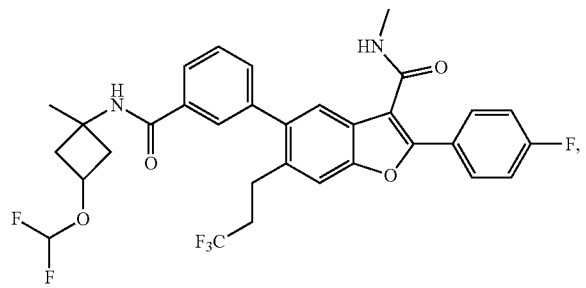
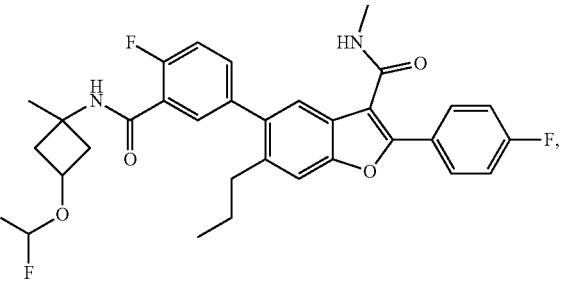
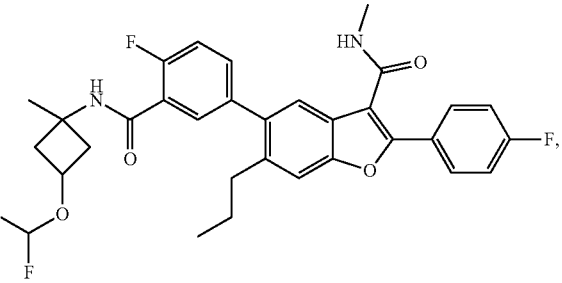
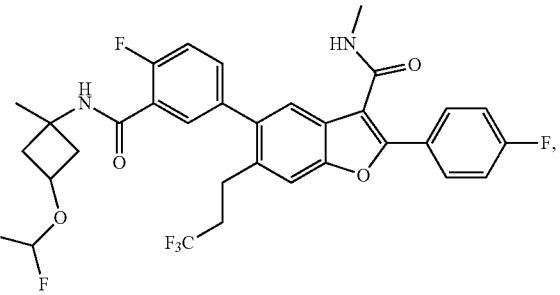
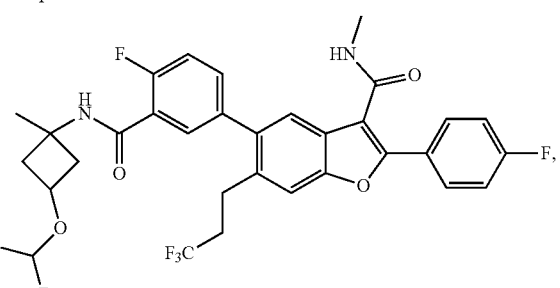
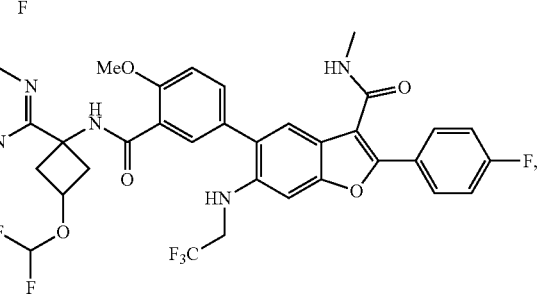
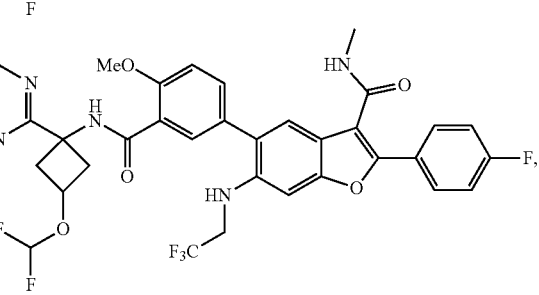

-continued
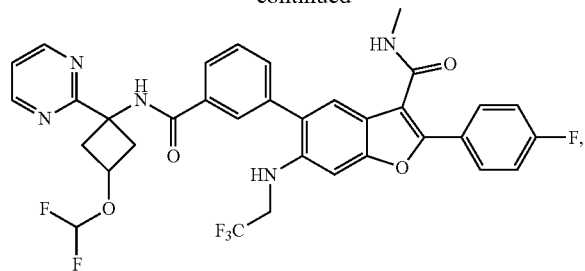
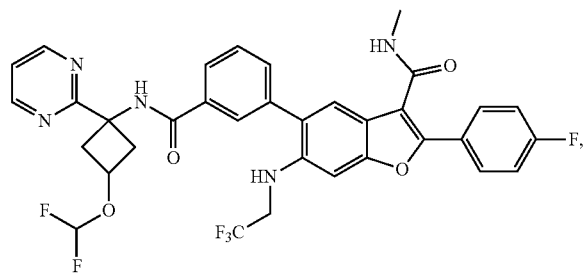
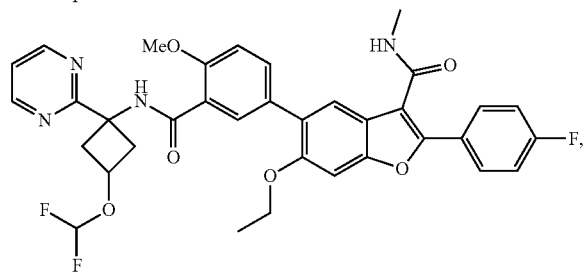
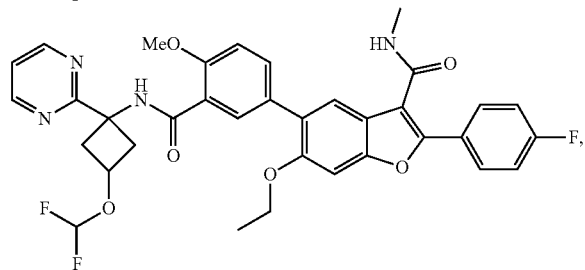
-continued
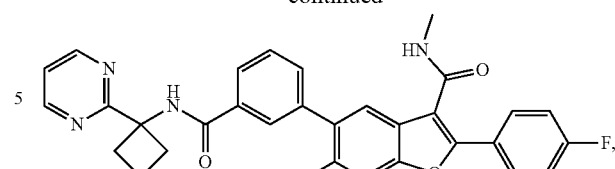
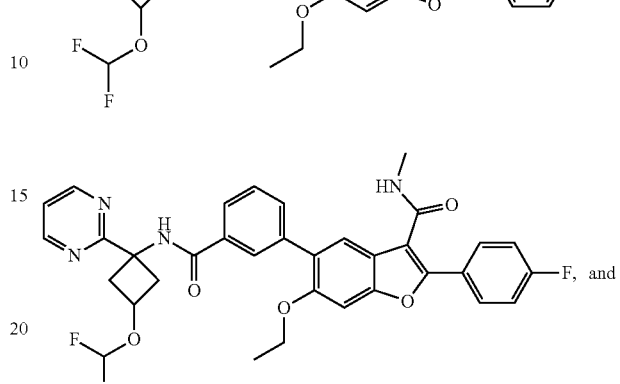
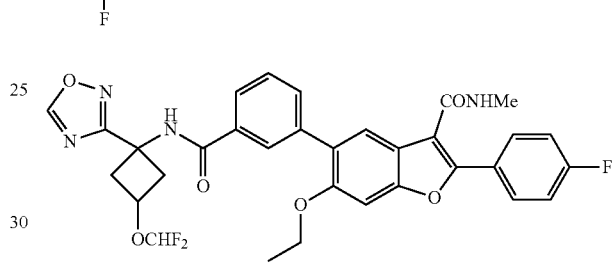
or a pharmaceutically acceptable salt thereof.
12. A composition comprising a compound of claim 1 or a pharmaceutically acceptable salt thereof and a pharmaceutically acceptable carrier.
13. A method of treating hepatitis C infection comprising administering a therapeutically effective amount of a compound of claim 1 to a patient.
* * * * *